US009587281B2

(12) United States Patent
Thakurta et al.

(10) Patent No.: US 9,587,281 B2
(45) Date of Patent: Mar. 7, 2017

(54) CEREBLON ISOFORMS AND THEIR USE AS BIOMARKERS FOR THERAPEUTIC TREATMENT

(71) Applicant: Celgene Corporation, Summit, NJ (US)

(72) Inventors: Anjan Thakurta, Basking Ridge, NJ (US); Anita Gandhi, Bernardsville, NJ (US); Michelle F. Waldman, Florham Park, NJ (US); Rajesh Chopra, Summit, NJ (US); Michael Amatangelo, Newtown, PA (US); Chad Bjorklund, Summit, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 14/621,298

(22) Filed: Feb. 12, 2015

(65) Prior Publication Data
US 2015/0152511 A1 Jun. 4, 2015

Related U.S. Application Data

(63) Continuation-in-part of application No. PCT/US2013/054663, filed on Aug. 13, 2013.

(60) Provisional application No. 61/683,134, filed on Aug. 14, 2012, provisional application No. 62/027,119, filed on Jul. 21, 2014.

(51) Int. Cl.
C12Q 1/68 (2006.01)
G01N 33/68 (2006.01)
G01N 33/574 (2006.01)
A61K 31/454 (2006.01)
A61K 31/517 (2006.01)
C07K 14/47 (2006.01)
A61K 31/5377 (2006.01)

(52) U.S. Cl.
CPC .......... C12Q 1/6886 (2013.01); A61K 31/454 (2013.01); A61K 31/517 (2013.01); A61K 31/5377 (2013.01); C07K 14/47 (2013.01); G01N 33/57496 (2013.01); G01N 33/6872 (2013.01); C12Q 2600/106 (2013.01); C12Q 2600/158 (2013.01); G01N 2333/4703 (2013.01); G01N 2800/52 (2013.01)

(58) Field of Classification Search
None
See application file for complete search history.

(56) References Cited

U.S. PATENT DOCUMENTS 3,536,809 A 10/1970 Applezweig
3,598,123 A 8/1971 Zaffaroni
3,845,770 A 11/1974 Theeuwes et al.
3,916,899 A 11/1975 Theeuwes et al.
4,008,719 A 2/1977 Theeuwes et al.
4,683,195 A 7/1987 Mullis et al.
4,810,643 A 3/1989 Souza
4,994,443 A 2/1991 Folkman et al.
4,999,291 A 3/1991 Souza
5,001,116 A 3/1991 Folkman et al.
5,059,595 A 10/1991 Le Grazie
5,073,543 A 12/1991 Marshall et al.
5,120,548 A 6/1992 McClelland et al.
5,134,127 A 7/1992 Stella et al.
5,229,496 A 7/1993 Deeley et al.
5,354,556 A 10/1994 Sparks et al.
5,391,485 A 2/1995 Deeley et al.
5,393,870 A 2/1995 Deeley et al.
5,441,050 A 8/1995 Thurston et al.
5,573,758 A 11/1996 Adorante et al.
5,580,755 A 12/1996 Souza
5,582,823 A 12/1996 Souza
5,591,767 A 1/1997 Mohr et al.
5,593,990 A 1/1997 D'Amato
5,629,327 A 5/1997 D'Amato
5,635,517 A 6/1997 Muller et al.
5,639,476 A 6/1997 Oshlack et al.
5,674,533 A 10/1997 Santus et al.
5,698,579 A 12/1997 Muller et al.
5,712,291 A 1/1998 D'Amato
5,733,566 A 3/1998 Lewis
5,798,368 A 8/1998 Muller et al.
5,874,448 A 2/1999 Muller et al.
5,877,200 A 3/1999 Muller
5,929,117 A 7/1999 Muller et al.
5,955,476 A 9/1999 Muller et al.
6,071,948 A 6/2000 D'Amato (Continued)

FOREIGN PATENT DOCUMENTS

EP 2 436 387 A1 4/2012
JP 11-504330 4/1994

(Continued)

OTHER PUBLICATIONS

Gerdes et al. (Front. Oncol. Dec. 18, 2014 doi: 10.3389/fonc.2014. 00366, pp. 1-12.*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Gandhi et al. (British J. Haematology Oct. 28, 2013, 164: 233-244).*
Ménard et al. (Blood Nov. 15, 2013 122:3107).*

(Continued)

Primary Examiner — Peter J Reddig
(74) Attorney, Agent, or Firm — Jones Day

(57) ABSTRACT

Provided herein are cereblon isoforms and methods of their use as biomarkers for treating a disease, disorder, or condition with a treatment compound, e.g., thalidomide, lenalidomide, pomalidomide, 3-(5-amino-2-methyl-4-oxoquinazolin-3(4H)-yl)-piperidine-2,6-dione, or (S)-3-(4-((4-(morpholinomethyl)benzyl)oxy)-1-oxoisoindolin-2-yl) piperidine-2,6-dione.

31 Claims, 15 Drawing Sheets

(56) References Cited

U.S. PATENT DOCUMENTS

| | | |
|---|---|---|
| 6,114,355 A | 9/2000 | D'Amato |
| 6,281,230 B1 | 8/2001 | Muller et al. |
| 6,316,471 B1 | 11/2001 | Muller et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,458,810 B1 | 10/2002 | Muller et al. |
| 6,476,052 B1 | 11/2002 | Muller et al. |
| 6,555,554 B2 | 4/2003 | Muller et al. |
| 6,927,024 B2 | 8/2005 | Dodge et al. |
| 7,091,353 B2 | 8/2006 | Robarge et al. |
| 7,101,663 B2 | 9/2006 | Godfrey et al. |
| 7,122,799 B2 | 10/2006 | Hsieh et al. |
| 7,186,507 B2 | 3/2007 | Bacallao et al. |
| 7,244,759 B2 | 7/2007 | Muller et al. |
| 7,393,862 B2 | 7/2008 | Zeldis |
| 7,468,363 B2 | 12/2008 | Zeldis |
| 7,635,700 B2 | 12/2009 | Muller et al. |
| 8,143,283 B1 | 3/2012 | D'Amato |
| 9,217,743 B2 | 12/2015 | Handa |
| 2002/0045643 A1 | 4/2002 | Muller et al. |
| 2003/0045552 A1 | 3/2003 | Robarge et al. |
| 2003/0096841 A1 | 5/2003 | Robarge et al. |
| 2004/0029832 A1 | 2/2004 | Zeldis |
| 2004/0220144 A1 | 11/2004 | Zeldis |
| 2006/0134767 A1 | 6/2006 | Buser-Doepner et al. |
| 2006/0188475 A1 | 8/2006 | Xu et al. |
| 2006/0205787 A1 | 9/2006 | Muller et al. |
| 2007/0015194 A1 | 1/2007 | Shohat et al. |
| 2007/0049618 A1 | 3/2007 | Muller et al. |
| 2007/0065888 A1 | 3/2007 | Ring et al. |
| 2007/0128636 A1 | 6/2007 | Baker et al. |
| 2008/0051379 A1 | 2/2008 | Lerner et al. |
| 2008/0280779 A1 | 11/2008 | Shaughnessy et al. |
| 2009/0023149 A1 | 1/2009 | Knudsen |
| 2009/0142297 A1 | 6/2009 | Muller et al. |
| 2009/0148853 A1 | 6/2009 | Schafer et al. |
| 2010/0021437 A1 | 1/2010 | Isacson et al. |
| 2010/0190656 A1 | 7/2010 | Li et al. |
| 2010/0284915 A1 | 11/2010 | Dai et al. |
| 2011/0070218 A1 | 3/2011 | Teichberg et al. |
| 2011/0196150 A1 | 8/2011 | Man et al. |
| 2011/0200998 A1 | 8/2011 | Weichselbaum et al. |
| 2011/0223157 A1 | 9/2011 | Schafer et al. |
| 2012/0035347 A1 | 2/2012 | Yver |
| 2012/0077741 A1 | 3/2012 | Delfani et al. |
| 2012/0134969 A1 | 5/2012 | Handa et al. |
| 2012/0192297 A1 | 7/2012 | Handa et al. |
| 2012/0230983 A1 | 9/2012 | Muller et al. |
| 2012/0322073 A1* | 12/2012 | Lopez-Girona ........ C07K 16/18 435/6.12 |
| 2013/0177644 A1 | 7/2013 | Zeldis |
| 2013/0302323 A1 | 11/2013 | Zeldis |
| 2014/0045843 A1 | 2/2014 | Schafer et al. |
| 2014/0051591 A1 | 2/2014 | O'Donnell et al. |
| 2014/0066480 A1 | 3/2014 | Stewart et al. |
| 2014/0162282 A1 | 6/2014 | Schafer et al. |

FOREIGN PATENT DOCUMENTS

| | | |
|---|---|---|
| WO | WO 93/18186 A1 | 9/1993 |
| WO | WO 98/03502 A1 | 1/1998 |
| WO | WO 98/54170 A1 | 3/1998 |
| WO | WO 02/059106 A1 | 8/2002 |
| WO | WO 2007/108968 A2 | 9/2007 |
| WO | WO 2009/075797 A2 | 6/2009 |
| WO | WO 2010/137547 A1 | 12/2010 |
| WO | WO 2011/049043 A1 | 4/2011 |
| WO | WO 2012/125405 A2 | 9/2012 |
| WO | WO 2012/125438 A1 | 9/2012 |
| WO | WO 2012/125459 A1 | 9/2012 |
| WO | WO 2012/125475 A1 | 9/2012 |
| WO | WO 2012/149299 A2 | 11/2012 |
| WO | WO 2012/153187 A1 | 11/2012 |
| WO | WO 2014/028445 A2 | 2/2014 |

OTHER PUBLICATIONS

Aitipamula et al. (Crystal Growth Des. 2012 12: 2147-5152).*
Vippagunta et al. (Advanced Drug Delivery Reviews, 2001, 48: 3-26).*
Gura (Science, 1997, 278:1041-1042).*
Aizawa et al., "mRNA distribution of the thalidomide binding protein cereblon in adult mouse brain," *Neurosci. Res.*, 69:343-347 (2011).
Akhurst, "Taking thalifomide out of rehab," *Nature Med.*, 16(4):370-372 (2010).
Altschul et al., "Gapped BLAST and PSI-BLAST: A new generation of protein database search programs," Nucleic Acid Res., 25(17):3389-3402 (1997).
Angers et al., "Molecular architecture and assembly of the DDB1-CUL4A ubiquitin ligase machinery," *Nature*, 443:590-593 (2006).
Anolik et al., "B cell reconstitution after rituximab treatment of lymphoma recapitulates B cell ontogeny," *Clin. Immunol.*, 122:139-145 (2007).
Ausubel et al. (eds.), *Short Protocols in Molecular Biology*, Fifth Edition, John Wiley and Sons, New York, Chapter 11 (2002).
Basel-Vanagaite et al., "The CC2D1A, a member fo a new gene family with C2 domains, is involved in autosomal recessive non-syndromic mental retardation," *J. Med. Genet.*, 43:203-210 (2006).
Basson, "Thalidomide's early effects," *Nature Med.*, 16(4):372 (2010).
Bea et al., "Diffuse large B-cell lymphoma subgroups have distinct genetic profiles that influence tumor biology and improve gene-expression-based survival prediction," *Blood*, 106(9):3183-3190 (2005).
Boyd et al., "High expression levels of the mammalian target of rapamycin inhibitor *DEPTOR* are predictive of response to thalidomide in myeloma," *Leukemia & Lymphoma*, 51(11):2126-2129 (2010).
Bruggermann et al., "Designer mice: the production of human antibody repertoires in transgenic animals," *Year Immunol.*, 7:33-40 (1993).
Burchiel et al., *Immunopharmacokinetics of Radiolabeled Antibodies and Their Fragments*, Masson Publishing, Inc., Chapter 13 (1982).
Burington et al., "Tumor cell gene expression changes following short-term in vivo exposure to single agent chemotherapeutics are related to survival in multiple myeloma," *Clin. Cancer Res.*, 14(15):4821-4829 (2008).
Cairns et al., "Regulation of cancer cell metabolism," *Nature Rev.*, 11:85-95 (2011).
*Cancer: Principles & Practice of Oncology*, Third Edition, J. B. Lippincott Co., Philadelphia, Pa, pp. 1843-1847 (1989).
Carstensen, *Drug Stability: Principles & Practices*, Second Edition, Marcel Dekker, New York, NY, pp. 379-380 (1995).
Cerny et al., "Advances in the treatment of non-Hodgkin's lymphoma," *Ann. Oncol.*, 13 Suppl., 4:211-216 (2002).
Chamberlain et al., "Structure of the human Cereblon-DDB1-lenalidomide complex reveals basis for responsiveness to thalidomide analogs," Nature Struct. Mol. Biol., 21(9):803-809 (2014).
Chang et al., "What is the functional role of the thalidomide binding protein cereblon," *Int. J. Biochem Mol. Biol.*, 2(3):287-294 (2011).
Chothia et al., "Structural determinants in the sequence of immunoglobulin variable domain," *J. Mol. Biol.*, 278:457-479 (1998).
Christian et al., "p62 (SQSTM1) and cyclic AMP phospodiesterase-4A4 (PDE4A4) locate to a novel, reversible protein aggregate with links to autophagy and proteasome degradation pathways," *Cellular Signaling*, 22:1576-1596 (2010).
Clarke et al., "Changing incidence of non-Hodgkin lymphomas in the United States," *Cancer*, 94(7):2015-2023 (2002).
Corral et al., "Immunomodulation by thalidomide and thalidomide analogues," *Ann. Rheum. Dis.*, 58:(Suppl I) 1117-1113 (1999).

(56) References Cited

OTHER PUBLICATIONS

Cuoco et al., "Microarray based analysis of an inherited terminal 3p26.3 deletion, containing only the CHL1 gene, from a normal father to his two affected children," *Orphanet J Rare Dis.*, 6:12 (2011).
Dufour-Rainfray et al., "Fetal exposure to teratogens: evidence of genes involved in autism," *Neurosci Biobehav Rev.*, (2011).
Emens et al., "Chemotherapy: friend of foe to cancer vaccines," *Curr. Opin. Mol. Ther.*, 3(1):77-84 (2001).
Ferraiuolo et al., "Microarray analysis of the cellular pathways involved in the adaptation to and progression of motor neuron injury in the SOD1 G93A mouse model of familial ALS," *J. Neurosci.*, 27(34):9201-9219 (2007).
Flemming, "Target indentification: Unravelling thalidomide teratogenicity," *Nature Rev. Drug Discov.*, 9:361 (2010).
Folkman et al., "Angiogenesis inhibition and tumor regression caused by heparin or a heparin fragment in the presence of cortisone," *Science*, 221:719-725 (1983).
Galustian et al., "Lenalidomide: a novel anticancer drug with multiple modalities," *Expert Opin. Pharmacother.*, 10(1):125-133 (2009).
Garshasbi et al., "A defect in the *TUSC3* gene is associated with autosomal recessive mental retardation," *Am. J. Hum. Genetics*, 82:1158-1164 (2008).
Genbank Accession No. NP_001166953; GI No. 291045198 (Nov. 24, 2013).
Genbank Accession No. NP_057386; GI No. 39545580 (Sep. 23, 2013).
Gladman et al., *Kelley's Textbook of Rheumatology*, 2 Vols. 6th Edition, W. B. Saunders Company, Chapter 71, pp. 1071-1073 (2001).
Gladman, "Current concepts in psoriatic arthritis," *Curr. Opin. Rheumatol.*, 14(4):361-366 (2002).
Heintel et al., "High Expression of the thalidomide-binding protein cereblon (CRBN) is associated with improved clinical response in patients with multiple myeloma treated with lenalidomide and dexamethasone," $53^{rd}$ *ASH Annual Meeting and Exposition*, Abstract 2879 (Dec. 10-13, 2011).
Hernandez et al., "Thalidomide modulates *Mycobacterium leprae*-induced NF-κB pathway and lower cytokine response," *Eur. J. Pharmacol.*, 670:272-279 (2011).
Higgins et al., "A mutation in a novel ATP-dependent Lon protease gene in a kindred with mild mental retardation," *Neurology* 63:1927-1931 (2004).
Higgins et al., "Candidate genes for recessive non-syndromic mentalretardation on chromosome 3p (MRT2A)," *Clin. Genet.*, 65:496-500 (2004).
Higgins et al., "Dysregulation of large-conductance $Ca^{2+}$—activated $K^+$channel expression in nonsyndromal mental retardation due to a cereblon p. R419X mutation," *Neurogenetics*, 9:219-223 (2008).
Higgins et al., "Temporal and spatial mouse brain expression of cereblon, an ionic channel regulator involved in human intelligence," *J. Neurogenetics*, 24:18-26 (2010).
Hohberger et al., "Cereblon is expressed in the retina and binds to voltage-gated chloride channels," *FEBS Lett.*, 583:633-637 (2009).
Ito et al., "Deciphering the mystery of thalidomide teratogenicity," *Congenital Anomalies*, 52:1-7 (2012).
Ito et al., "Identification of a primary target of thalidomide teratogenicity," *Science*, 327(5971):1345-1350 (2010).
Ito et al., "Teratogenic effects of thalidomide: molecular mechanisms," *Cell. Mol. Life Sci.*, 68(9):1569-1579 (2011).
Jakobovits et al., "Analysis of homozygous mutant chimeric mice: deletion of the immunoglobulin heavy-chain joining region blocks B-cell development and antibody production," *Proc. Natl. Acad. Sci., USA*, 90:2551-2555 (1993).
Jakobovits et al., "Germ-line transmission and expression of human-derived yeast artificial chromosome," *Nature*, 362(6417):255-258 (1993).

Jalkanen et al., "Cell surface proteoglycan of mouse mammary epithelial cells is shed by cleavage of its matrix-binding ectodomain from its membrane-associated domain," *J. Cell Biol.*, 105(6 Pt 2):3087-3096 (1987).
Jalkanen et al., "Heparan sulfate proteoglycans from mouse mammary epithelial cells: localization on the cell surface with a monoclonal antibody," *J. Cell Biol.*, 101(3):976-984 (1985).
Jemal et al., "Cancer Statistics," *CA Cancer J. Clin.*, 57:43-66 (2007).
Jo et al., "Identification and functional characterization of cereblon as a binding protein for large-conductance calcium-activated potassium channel in rat brain," *J. Neurochem.*, 94:1212-1224 (2005).
Jones et al., "Pharmaceutical cocrystals: an emerging approach to physical property enhancement," *MRS Bulletin* 31:875-879 (2006).
Kabat et al., "Attempts to locate complementarity-determining residues in the variable positions of light and heavy chains," *Ann. N.Y. Acad. Sci.*, 190:382-393 (1971).
Kantarci et al, "Identification of the genetic basis of nonsyndromic intellectual disability in large consanguineous families by exome sequencing," *Clin. Genet.*, 78(Suppl. 1):L03 (2010).
Kim et al., "Thalidomide: the tragedy of birth defects and the effective treatment of disease," *Toxicological Sci.*, 122(1):1-6 (2011).
Kim et al., "Use of absolute lymphocyte counts to predict response to chemotherapy and survival in diffuse large B-cell lymphoma," *J. Clin. Oncology*, ASCO Annual Meeting Proceedings Part I., 25(18S), Jun. 20 Supplement, p. 8082 (2007).
Knobloch et al., Apoptosis induction by thalidomide: critical for limb teratogenicity but therapeutic, *Current Mol. Pharmacol.*, 4:26-61 (2011).
Kohler et al., "Continuous cultures of fused cells secreting antibody of predefined specificity," *Nature*, 256:495-497 (1975).
Lee et al., "Cereblon inhibits proteasome activity by binding to the 20S core proteasome subunit beta type 4," *Biochem. Biophys. Res. Comm.*, 427:618-622 (2012).
Lee et al., "Embryopathic effects of thalidomide and its hydrolysis products in rabbit embryo culture: evidence for a prostaglandin H synthase (PHS)-dependent, reactive oxygen species (ROS)-mediated mechanism," *FASEB J.*, 25:2468-2483 (2011).
Lee et al., "Functional modulation of AMP-activated protein kinase by cereblon," *Biochimica Biophysica Acta*, 1813:448-455 (2011).
Lee et al., "Induction of cereblon by NF-E2-related factor 2 in neuroblastoma cells exposed to hypoxia-reoxygenation," *Biochem. Biophys. Res. Comm.*, 399:711-715 (2010).
Lee et al., "Resistance of CD-1 and *ogg1* DNA repair-deficient mice to thalidomide and hydrolysis product embryopathies in embryo culture," *Toxicological Sci.*, 122(1):146-156 (2011).
Lenz et al., "Molecular subtypes of diffuse large B-cell lymphoma arise by distinct genetic pathways," *Proc. Natl. Acad. Sci., USA*, 105(36): 13520-13525 (2008).
Lenz et al., "Oncogenic CARD11 mutations in human diffuse large B cell lymphoma," *Science*, 319(5870):1676-1679 (2008).
List et al., "The myelodysplastic syndromes: biology and implications for management," *J. Clin. Oncol.*, 8:1424-1441 (1990).
Lopez-Girona et al., "Cereblon is direct protein target for immunomodulatory and antiproliferative acttivities of lenalidomide and pomalidomide," *Leukemia*, 26:2326-2335 (2012).
Lopez-Girona et al., "Direct binding with cereblon mediates the antiproliferative and immunomodulatory action of lenalidomide and pomalidomide," $53^{rd}$ *ASH Annual Meeting and Exposition*, Abstract 738, 22 pages (Dec. 10-13, 2011).
Lowe et al., "The PDE IV family of calcium-independent phosphodiesterase enzymes," *Drugs of the Future*, 17(9):799-807 (1992).
Mardis et al., "Recurring mutations found by sequencing an acute myeloid leukemia genome," *N. Engl. J. Med.*, 361(11):1058-1066 (2009).
Marks et al., "By-passing immunization, human antibodies from V-gene libraries displayed on phage," *J. Mol. Biol.*, 222(3):581-597 (1991).
Marriott et al , "Immunotherapeutic and antitumor potential of thalidomide analogues," *Expert Opin. Biol. Ther.*, 1(4):1-8 (2001).

(56) References Cited

OTHER PUBLICATIONS

Martiniani et al., "Biological activity of lenalidomide and its underlying trherapeutic effects in multiple myeloma," *Adv. Hematol.*, 2012:842945.
*Medicine*, vol. 3, Dale and Federman, eds., Scientific American, Inc., New York , Chapter 12, Section IV and Section X (1998).
Mitchell et al., "Physical activity-associated gene expression signature in nonhuman primate motor cortex," *Obesity*, 20:692-698 (2012).
Muller et al., "Structural modifications of thalidomide produce analogs with enhanced tumor necrosis factor inhibitory activity," *J. Med. Chem.*, 39(17):3238-3240 (1996).
Muller et al., "Thalidomide analogs and PDE4 inhibition," *Bioorg. & Med. Chem. Lett.*, 8:2669-2674 (1998).
Neben et al., "High plasma basic fibroblast growth factor concentration is associated with response to thalidomide in progressive multiple myeloma," *Clin. Cancer Res.*, 7(9):2675-2681 (2001).
Ngo et al., "Oncogenically active MYD88 mutations in human lymphoma," *Nature*, 470(7332)115-119 (2011).
Offidani et al., "Serum C-reactive protein at diagnosis and response to therapy is the most powerful factor predicting outcome of multiple myeloma treated with thalidomide/anthracycline-based therapy," *Clin. Lymphoma & Myeloma*, 8(5):294-299 (2008).
Parsons et al., "An integrated genomic analysis of human glioblastoma multiforme," *Science*, 321:1807-1812 (2008).
Patent Cooperation Treaty, International Search Report for application PCT/US2013/054663, mailed Aug. 21, 2014.
Paul (ed) *Fundamental Immunology*, Second Edition, Raven Press, New York, pp. 332-336 (1989).
Penichet et al., "Antibody-cytokine fusion proteins for the therapy of cancer," *J. Immunol. Methods*, 284:91-101 (2001).
Plückthun, *The Pharmacology of Monoclonal Antibodies*, vol. 113, Springer Verlag, Berlin, pp. 269-315 (1994).
Rajadhyaksha et al., "Behavioral characterization of cereblon forebrain-specific conditional null mice: a model for human non-syndromic intellectual disability," *Behavioural Brain Res.*, 226:428-434 (2012).
Rajpal et al., "A novel panel of protein biomarkers for predicting response to thalidomide-based therapy in newly diagnosed multiple myeloma patients," *Proteomics*, 11(8):1391-1402 (2011).
Ren et al., "Oncogenic CUL4A determines the response to thalidomide treatment in prostate cancer," *J. Mol. Med.*, 90(10):1121-1132 (2012).
Ripa et al., "A linear model for the pharmacokinetics of azithromycin in healthy volunteers," *Chemother.*, 42:402-409 (1996).
Roitt et al., *Immunology*, Third Edition, Mosby, St. Louis, MO, 17.1-17.12 (1993).
Schultheiss et al., "Pharmaceutical cocrystals and their physicochemcial properties," *Cryst. Growth Des.*, 9(6):2950-2967 (2009).
Schütt et al., "Thalidomide in combination with dexamethasone for pretreated patients with multiple myeloma: serum level of soluble interleukin-2 receptor as a predictive factor for response rate and for survival," *Ann. Hematol.*, 84(9):594-600 (2005).
Shackelford et al., "The LKB1-AMPK pathway: metabolism and growth control in tumour suppression," *Nature Rev.*, 9:563-575 (2009).
Shan et al., "The role of cocrystals in pharmaceutical science," *Drug Discov. Today*, 13(9-10):440-446 (2008).
Sokka et al., "MRI-guieded gas bubble enhanced ultrasound heating in in vivo rabbit thigh," *Phys. Med. Biol.*, 48:223-241 (2003).
Stahnke et al., "Activation of apoptosis pathways in peripheral blood lymphocytes by in vivo chemotherapy," *Blood*, 98:3066-3073 (2001).
Staudt, "Gene expression profiling of lymphoid malignancies," *Ann. Rev. Med.*, 53:303-318 (2002).
Taylor et al., "A transgenic mouse that expresses a diversity of human sequence heavy and light chain immunoglobulins," *Nucleic Acids Res.*, 20(23):6287-6295 (1992).

Taylor et al., "Protamine is an inhibitor of angiogenesis," *Nature*, 297:307-312 (1982).
*The Merck Manual*, 17th Edition, Merck & Company, West Point, PA, pp. 448, 944-952 (1999).
Therasse et al., "New guidelines to evaluate the response to treatment in solid tumors," *J. Natl. Cancer Inst.*, 92(3):205-216 (2000).
Thome et al., "Antigen receptor signaling to NF-κb via CARMA1, BCL10, and MALT1," *Cold Spring Harb. Perspect. Biol.*, 2:a003004 (2010).
Tierney et al. (eds), *Current Medical Diagnosis & Treatment 1998*, 37th Edition, Appleton & Lange, Stamford, CT, p. 793 (1998).
Trask, "An overview of pharmaceutical cocrystals as intellectual property," *Mol. Pharm.*, 4(3):301-309 (2007).
Vishweshwar et al., "Pharmaceutical co-crystals," *J. Pharm. Sci.*, 95(3):499-516 (2006).
Wilson et al., "Novel disease targets and management approaches for diffuse large B-cell lymphoma," *Leukemia & Lymphoma*, 51(S1): 1-10 (2010).
Wu et al., "Screening and indentification of host factors interacting with UL14 of herpes simplex virus 1," *Med. Microbiol. Immunol.*, 200:203-208 (2011).
Xin et al., "Primary function analysis of human mental retardation related gene CRBN," *Mol. Biol. Rep.*, 35:251-256 (2008).
Yang et al., "Exploiting synthetic lethality for the therapy of ABC diffuse large B cell lymphoma," *Cancer Cell*, 21:723-737 (2012).
Zhu et al., "Molecular mechanism of action of immune-modulaotry drugs thalidomide, lenalidomide and pomalidomide in multiple myeloma," *Leukemia & Lymphoma*, 1-5 (2012).
Zhu et al., "Cereblon expression is required for the antimyeloma activity of lenalidomide and pomalidomide," *Blood*, 118(18):4771-4779 (2011).
Abnova, CRBN purified MaxPab mouse polyclonal antibody (B01P), Retrieved online <http://www.abnova.com/products/products_detail.asp?catalog_id=H00051185-B01P>, retrieved on Mar. 25, 2015.
Abrahams et al., "Methods used in the structure determination of bovine mitochondrial F1 ATPase," *Acta Crystallogr. D. Biol. Crystallogr.*, 52(Pt 1):30-42 (1996).
ADAPT, Paterson Institute for Cancer Research, probests for CRBN, printed Dec. 2, 2013.
Aitipamula et al., "Polymorphs, salts, and cocrystals: what's in a name?," *Cryst. Growth Des.*, 12:2147-2152 (2012).
Aklilu et al., "Depletion of normal B cells with rituximab as an adjunct to IL-2 therapy for renal cell carcinoma and melanoma," Annals Oncology, 15:1109-1114 (2004).
Ando et al., "Efficient transfection strategy for the spatiotemporal control of gene expression in zebrafish," Mar. Biotechnol. (NY), 8(3):295-303 (2006).
Androutsellis-Theotokis et al., "Targeting neural precursors in the adult brain rescues injured dopamine neurons," Proc. Natl. Acad. Sci. U.S.A., 106 (32): 13570-13575 (2009).
Angerer et al., in Genetic Engineering: Principles and Methods, Setlow and Hollaender, Eds., Plenum Press, New York, vol. 7, pp. 43-65 (1985).
Babin et al., "Zebrafish models of human motor neuron diseases: advantages and limitations," Prog. Neurobiol., 118:36-58 (2014).
Bartlett, "Regulation of neural stem cell differentiation in the forebrain," Immunol. Cell Biol., 76(5):414-418 (1998).
Basel-Vanagaite, "Genetics of autosomal recessive non-syndromic mental retardation: recent advances," Clin Genet. 72(3):167-74 (2007).
Becker et al. (2008) "Adult zebrafish as a model for successful central nervous system regeneration" Restorative Neurol. Neurosci. 26:71-80.
Bedford et al., "Ubiquitin-like protein conjugation and the ubiquitin-proteasome system as drug targets," Drug Discovery, 10:29-46 (2011).
Bilal et al., "Generation of a 3D model for human cereblon using comparative modeling," J. Bioinformatics Sequence Analysis, 5(1):10-15 (2013).
Bisht et al., "Brain drug delivery system: a comprehensive review on recent experimental and clinical findings," IJPSR, 2(4):792-806 (2011).

(56) References Cited

OTHER PUBLICATIONS

Bonnamain et al., "Neural stem/progenitor cells as promising candidates for regenerative therapy of the central nervous system," Frontiers in Cellular Neuroscience, 6: 17 (2012).
Bredesen et al., "Cell death in the nervous system," Nature, 443 (7113): 796-802 (2006).
Bustin et al., "Real-time reverse transcription PCT (qRT-PCR) and its potential use in clinical diagnosis," Clin. Sci., 109:365-379 (2005).
Carter et al., *Chemotherapy of Cancer*, 2$^{nd}$ edition, John Wiley & Sons, New York, NY, pp. 361-367 (1981).
Charoenfuprasert et al., "Identification of salt-inducible kinase 3 as a novel tumor antigen associated with tumorigenesis of ovarian cancer," Oncogene, 30: 3570-6584 (2011).
Chini et al., "The JAZ family of repressors is the missing link in jasmonate signalling," *Nature*, 448(7154):666-671 (2007).
Chow et al. Pharmacological Research, "In vivo drug-response in patients with leukemic non-Hodgkin's lymphomas is associated with in vitro chemosensitivity and gene expression profiling," 53: 49-61 (2006).
De Graaff et al., "Matrix methods for solving protein substructures of chlorine and sulfur from anomalous data," *Acta Crystallogr. D. Biol. Crystallogr.*, 57(Pt 12):1857-1862 (2001).
Duman et al., "Crystal structures of bacillus subtilis lon protease," *J. Mol. Biol.*, 401(4):653-670 (2010).
Emsley et al., "Features and development of Coot," *Acta Crystallogr. D. Biol. Crystallogr.*, 66(Pt 4):486-501 (2010).
Eve et al., "Single-agent lenalidomide in relapsed/refractory mantle cell lymphoma: results from a UK phase II study suggest activity and possible gender differences," *Br. J. Haematol.*, 159(2):154-163 (2012).
Fleisch et al., "Investigating regeneration and functional integration of CNS neurons: Lessons from zebrafish genetics and other fish species" Biochim. Biophys. Acta 1812:364-380 (2011).
Fukuchi, "Ligand-dependent degradation of Smad3 by a ubiquitin ligase complex of ROC1 and associated proteins," *Molecular Biology of The Cell*, 12(5):1431-1443 (2001).
Gall et al., "Nucleic acid hybridization in cytological preparations," Methods Enzymol., 21:470-480 (1981).
Gandhi et al., "Measuring cereblon as a biomarker of response or resistance to lenalidomide and pomalidomide requires use of standardized reagents and understanding of gene complexity," *Br. J. Haematol.*, 164(2):233-244 (2013).
Garshasbi et al., "Two independent mutations in the ZC3H14 gene are associated with non-syndromic autosomal recessive mental retardation," Medizinische Genetik, 22(1): 83 (2010).
Gerdes et al., "Emerging understanding of multiscale tumor heterogeneity," *Front. Oncol.*, 4:1-12 (2014).
Gupta D et al., "Adherence of Multiple Myeloma Cells to Bone Marrow Stromal Cells Up Regulates Vascular Endothelial Growth Factor Secretion: Therapeutic Applications," Leukemia, 2001, 15 (12): 1950-1961.
Gura, "Systems for identifying new drugs are often faulty," *Science*, 278:1041-1042 (1997).
He et al., "DDB1 functions as a linker to recruit receptor WD40 proteins to CUL4-ROC1 ubiquitin ligases," *Genes Dev.*, 20(21):2949-2954 (2006).
Hernandez-Ilizalitrurri et al., Higher Response to Lenalidomide in Relapsed/Refractory Diffuse Large B-Cell lymphoma in Nongerminal Center B-Cell Like Than in Germinal Center B-Cell Like Phenotype, Cancer, pp. 5058-5066 (2011).
Higa et al., "CUL4-DDB1 ubiquitin ligase interacts with multiple WD40-repeat proteins and regulates histone methylation," *Nat. Cell. Biol.*, 8(11):1277-1283 (2006).
Hsich et al., "Review: Critical issues in gene therapy for neurologic disease," Human Gene Ther., 13:579-604 (1998).
International Search Report for PCT/JP2010/058722 issued Jun. 22, 2010.

International Searching Authority, English Translation of International Preliminary Report on Patentability Issued in PCT/JP2010/058722 on Dec. 15, 2011.
Interntional Searching Authority, "International Search Report for International Application No. PCT/US2013/048510," (mailed Jun. 12, 2014).
Ito et al., "CRBN, a mental retardation-related protein, forms a novel E3 ubiquitin ligase complex with DDB1," Dai 80 Kai The Japanese Society Taikai, Dai 30 Kai The Molecular Biology Society of Japan Nenkai Godo Taikai Koen Yoshishu, pp. 4P-1011 (2007). English machine translation attached.
Ito et al., "Identification of a primary target of thalidomide teratogenicity," Science, 327:1-28 (2010).
Johansson, "Regeneration and plasticity in the brain and spinal cord," *J. Cereb. Blood Flow Metab.*, 27:1417-1430 (2007).
Kaiser, "First pass at cancer genome reveals complex landscape," *Science*, 313:1370 (2006).
Kallioniemi et al., "Comparative genomic hybridization for molecular cytogenetic analysis of solid tumors," Science 258:818-821 (1992).
Kamarch, "Fluorescence-activated cell sorting of hybrid and transfected cells," Methods Enzymol., 151:150-165 (1987).
Kim et al., Gene Expression Profiles for the Prediction of Progression-free Survival in Diffuse Large B Cell Lymphoma: Results of a DASL Assay, Annals of Hematology, 93 (3): 437-447 (2013).
Kishimoto et al., "Neuronal regeneration in zebrafish model of adult brain injury" Disease Models and Mechanisms 5:200-209 (2012).
Kobayashi et al., "Overexpression of the forebrain-specific homeobox gene six3 induces rostral forebrain enlargement in zebrafish," Development, 125:2973-2982 (1998).
Krontiris et al., *Internal Medicine*, 4$^{th}$ edition, Elsevier Science, Chapters 71-72, pp. 699-729 (1994).
Kumar et al., "Occurrence of Multiple Myeloma in Both Donor and Recipient After Bone Marrow Transplantation." American Journal of Hematology, 2002, 71: 227-228.
Lee et al., "Cereblon binding modulates AMP-activated protein kinase function," Journal of Neurochemistry, 115(WE03-03): 74 (2010).
Li et al., "A promiscuous alpha-helical motif anchors viral hijackers and substrate receptors to the CUL4-DDB1 ubiquitin ligase machinery," *Nat. Struct. Mol. Biol.*, 17(1):105-111 (2010).
Li et al., "The RIG-I-like receptor LGP2 recognizes the termini of double-stranded RNA," *J. Biol. Chem.*, 284(20):13881-13891 (2009).
Lopez-Girona et al., "Lenalidomide downregulates the cell survival factor, interferon regulatory factor-4, providing a potential mechanistic link for predicting response," *Br. J. Haematol.*, 154(3):325-336 (2011).
Lopez-Girona et al., "Direct binding with cereblon mediates the antiproliferative and immunomodulatory action of lenalidomide and pomalidomide," 53$^{rd}$ $^{ASH\ Annual\ Meeting\ and\ Exposition}$, Abstract 738 (Dec. 10-13, 2011).
Lu et al., "The structural basis of 5' triphosphate double-stranded RNA recognition by RIG-I C-terminal domain," *Structure*, 18(8):1032-1043 (2010).
Lu et al., "MaxiK channel partners: Physiological Impact," Journal of Physiology, 570 (1): 65-72 (2006).
Ludwig et al., "IMWG consensus on maintenance therapy in multiple myeloma," Blood, 119(3): 3003-15 (2012).
Magavi et al., "Induction of neurogenesis in the neocortex of adult mice," Nature, 405(6789): 951-955 (2000).
McCoy et al., "Phaser crystallographic software," *J. Appl. Crystallogr.*,40(Pt 4):658-674 (2007).
Ménard et al., Cereblon (CRBN) splicing could influence response to IMiDs : A new PCR strategy to easily detect and semi-quantify loss of the IMiDs binding domain, *Blood*, 122(21):3107 (2013).
Michalak et al., "Testis-derived microRNA profiles of African clawed frogs (*Xenopus*) and their sterile hybrids," Genomics, 91(2): 158-64 (2008).
Mochida et al., "Genetic basis of developmental malformations of the cerebral cortex," Arch. Neurol., 61:637-640 (2004).

(56) References Cited

OTHER PUBLICATIONS

Mullis et al., "Specific enzymatic amplification of DNA in vitro: the polymerase chain reaction," *Cold Spring Harbor Symp. Quant. Biol.*, 51:263-273 (1986).
Murshudov et al., "REFMAC5 for the refinement of macromolecular crystal structures," *Acta Crystallogr. D. Biol. Crystallogr.*, 67(Pt 4):355-367 (2011).
Nakamura et al., "Freud-1/Akil, a Novel PDK1-interacting Protein, Functions as a Scaffold to Activate the PDK1/Akt Pathway in Epidermal Growth Factor Signaling," *Mol. Cell. Biol.*, 28(19):5996-6009 (2008).
Nakatomi et al., (2002) "Regeneration of Hippocampal Pyramidal Neurons after Ischemic Brain Injury by Recruitment of Endogenous Neural Progenitors," Cell, 110 (4): 429-41 (2002).
Newman et al., "Assessment of the effectiveness of animal developmental toxicity testing for human safety," *Reprod. Toxicol.*, 7(4):359-390 (1993).
Oliver et al., "Immune stimulation in scleroderma patients treated with thalidomide," *Clin. Immunol.*, 97(2):109-120 (2000).
Otwinowski et al., "Processing of X-ray diffraction data collected in oscillation mode," *Methods Enzymol.*, 276:307-326 (1997).
Pannu et al., "Recent advances in the CRANK software suite for experimental phasing," *Acta Crystallogr. D.Biol. Crystallogr.*, 67(Pt 4):331-337 (2011).
Pannu et al., "The application of multivariate statistical techniques improves single-wavelength anomalous diffraction phasing," *Acta Crystallogr. D. Biol. Crystallogr.*, 60(Pt 1):22-27 (2004).
Parman et al., "Free radical-mediated oxidative DNA damage in the mechanism of thalidomide teratogenicity," *Nature Med.*, 5(5):582-585 (1999).
Petroski, "The ubiquitin system, disease, and drug discovery," *BMC Biochem.*, 9(Suppl. 1):S7 (2008).
Pohjola et al., "Terminal 3p deletions in two families—correlation between molecular karyotype and phenotype," American Journal of Medical Genetics, Part (2): 441-6 (2010).
Quach et al., "Mechanism of action of immunomodulatory drugs (IMiDS) in multiple myeloma," *Leukemia*, 24(1):22-32 (2010).
Rajkumar, "Multiple myeloma: 2012 update on diagnosis, risk-stratification, and management," Am J Hematol., 87(1):78-88 (2012).
Ramsay et al., "Chronic lymphocytic leukemia cells induce defective LFA-1-directed T-cell motility by altering Rho GTPase signaling that is reversible with lenalidomide," *Blood*, 121(14):2704-2714 (2013).
Ramsay et al., "Multiple inhibitory ligands induce impaired T-cell immunologic synapse function in chronic lymphocytic leukemia that can be blocked with lenalidomide: establishing a reversible immune evasion mechanism in human cancer," *Blood*, 120(7):1412-1421 (2012).
Razek et al., "Disorders of cortical formation: MR imaging features," *AJNR Am. J. Neuroradiol.*, 30:4-11 (2009).
Rehmann et al., "The rise, fall and subsequent triumph of thalidomide: Lessons learned in drug development," Ther Adv Hematol., 2(5):291-308 (2011).
Santana et al., "Can zebrafish be used as animal model to study Alzheimer's disease," Am. J. Neurodegener. Dis., 1(1):32-48 (2012).
Science Daily, "How many species on Earth? About 8.7 million, new estimate says," Retrieved online <http://www.sciencedaily.com/releases/2011/08/1108323180459.htm>, retrieved on Apr. 7, 2013.
Sheard et al., "Jasmonate perception by inositol-phosphate-potentiated COI1-JAZ co-receptor," *Nature*,468(7322):400-405 (2010).
Shestopalov et al., "Oligonucleotide-based tools for studying zebrafish development," Zebrafish, 7(1):31-40 (2010).
Stockdale, *Medicine*, vol. 3, Rubenstein and Federman, eds., Chapter 12, Section IV and Section X (1998).
Suzuki et al., "Stabe transgene expression from HSV amplicon ectors in the brain: potential involvement of immunoregulatory signals," Mol. Ther., 16(10):1727-1736 (2008).
Takada et al., "Protective effect of thalidomide against N-methyl-D-aspartate-induced retinal neurotoxicity," J Neurosci Res., 89(10):1596-604 (2011).
Tan et al., "Mechanism of auxin perception by the TIR1 ubiquitin ligase," *Nature*, 446(7136)640-645 (2007).
Thiel et al., "Small-molecule stabilization of protein-protein interactions: an underestimated concept in drug discovery?," *Angew Chem. Int. Ed. Engl.*, 51(9):2012-2018 (2012).
Thomas et al., "Progess and problems with the use of viral vectors for gene," Nat. Rev. Genet., 4(5):346-358 (2003).
Vallet et al., "Update on immunomodulatory drugs (IMiDs) in hematologic and solid malignancies," Expert Opinion on Pharmacotherapy, vol. 13, No. 4, pp. 473-494 (2012).
Vanhook, "Thalidomide Target Identified," Sci. Signal., vol. 3, Issue 113, p. ec82 (2010), abstract only.
Vippagunta et al., "Crystalline solids," *Adv. Drug Del. Rev.*, 48:3-26 (2001).
Wilen et al., "Strategies in optical resolutions," Tetrahedron, 33:2725-2736 (1977).
Wilen, Tables of Resolving Agents and Optical Resolutions, (E.L. Eliel, Ed.), University of Notre Dame Press, Notre Dame, IN, p. 268 (1972).
Willems, "Cognition genes on autosomes: The paradox," Clinical Genetics, 72(1): 9-12 (2007).
Wu, "Large-Conductance $Ca^{2+}$—Activated K+ Channels: Physiological Role and Pharmacology," Current medicinal Chemistry, 10(8): 649-661 (2003).
Yamazaki et al., "In vivo formation of a glutathione conjugate derived from thalidomide in humanized uPA-NOG mice," Chem Res Toxicol., 24(3):287-9 (2011).
Zhang et al., "PI3K/Akt signaling pathway is required for neuroprotection of thalidomide on hypoxic-ischemic cortical neurons in vitro," Brain Research, 1357: 157-65 (2010).

\* cited by examiner

FIG. 2

ATGGCCGGCGAAGGAGATCAGCAGGACGCTGCGCACAACATGGGCAACCACCTGCC
GCTCCTGCCTGCAGAGAGTGAGGAAGAAGATGAAATGGAAGTTGAAGACCAGGAT
AGTAAAGAAGCCAAAAAACCAAACATCATAAATTTTGACACCAGTCTGCCGACATC
ACATACATACCTAGGTGCTGATATGGAAGAATTTCATGGCAGGACTTTGCACGATG
ACGACAGCTGTCAGGTGATTCCAGTTCTTCCACAAGTGATGATGATCCTGATTCCCG
GACAGACATTACCTCTTCAGCTTTTTCACCCTCAAGAAGTCAGTATGGTGCGGAATT
TAATTCAGAAAGATAGAACCTTTGCTGTTCTTGCATACAGCAATGTACAGGAAAGG
GAAGCACAGTTTGGAACAACAGCAGAGATATATGCCTATCGAGAAGAACAGGATTT
TGGAATTGAGATAGTGAAAGTGAAAGCAATTGGAAGACAAAGGTTCAAAGTCCTTG
AGCTAAGAACACAGTCAGATGGAATCCAGCAAGCTAAAGTGCAAATTCTTCCCGAA
TGTGTGTTGCCTTCAACCATGTCTGCAGTTCAATTAGAATCCCTCAATAAGTGCCAG
ATATTTCCTTCAAAACCTGTCTCAAGAGAAGACCAATGTTCATATAAATGGTGGCAG
AAATACCAGAAGAGAAAGTTTCATTGTGCAAATCTAACTTCATGGCCTCGCTGGCTG
TATTCCTTATATGATGCTGAGACCTTAATGGACAGAATCAAGAAACAGCTACGTGA
ATGGGATGAAAATCTAAAAGATGATTCTCTTCCTTCAAATCCAATAGATTTTCTTA
CAGAGTAGCTGCTTGTCTTCCTATTGATGATGTATTGAGAATTCAGCTCCTTAAAATT
GGCAGTGCTATCCAGCGACTTCGCTGTGAATTAGACATTATGAATAAATGTACTTCC
CTTTGCTGTAAACAATGTCAAGAAACAGAAATAACAACCAAAAATGAAATATTCAG
TTTATCCTTATGTGGGCCGATGGCAGCTTATGTGAATCCTCATGGATATGTGCATGA
GACACTTACTGTGTATAAGGCTTGCAACTTGAATCTGATAGGCCGGCCTTCTACAGA
ACACAGCTGGTTTCCTGGGTATGCCTGGACTGTTGCCCAGTGTAAGATCTGTGCAAG
CCATATTGGATGGAAGTTTACGGCCACCAAAAAAGACATGTCACCTCAAAAATTTT
GGGGCTTAACGCGATCTGCTCTGTTGCCCACGATCCCAGACACTGAAGATGAAATA
AGTCCAGACAAAGTAATACTTTGCTTGTAA (SEQ ID NO: 1)

FIG. 3

ATGGCCGGCGAAGGAGATCAGCAGGACGCTGCGCACAACATGGGCAACCACCTGCC
GCTCCTGCCTGCAGAGAGTGAGGAAGAAGATGAAATGGAAGTTGAAGACCAGGAT
AGTAAAGAAGCCAAAAAACCAAACATCATAAATTTTGACACCAGTCTGCCGACATC
ACATACATACCTAGGTGCTGATATGGAAGAATTTCATGGCAGGACTTTGCACGATG
ACGACAGCTGTCAGGTGATTCCAGTTCTTCCACAAGTGATGATGATCCTGATTCCCG
GACAGACATTACCTCTTCAGCTTTTTCACCCTCAAGAAGTCAGTATGGTGCGGAATT
TAATTCAGAAAGATAGAACCTTTGCTGTTCTTGCATACAGCAATGTACAGGAAAGG
GAAGCACAGTTTGGAACAACAGCAGAGATATATGCCTATCGAGAAGAACAGGATTT
TGGAATTGAGATAGTGAAAGTGAAAGCAATTGGAAGACAAAGGTTCAAAGTCCTTG
AGCTAAGAACACAGTCAGATGGAATCCAGCAAGCTAAAGTGCAAATTCTTCCCGAA
TGTGTGTTGCCTTCAACCATGTCTGCAGTTCAATTAGAATCCCTCAATAAGTGCCAG
ATATTTCCTTCAAAACCTGTCTCAAGAGAAGACCAATGTTCATATAAATGGTGGCAG
AAATACCAGAAGAGAAAGTTTCATTGTGCAAATCTAACTTCATGGCCTCGCTGGCTG
TATTCCTTATATGATGCTGAGACCTTAATGGACAGAATCAAGAAACAGCTACGTGA
ATGGGATGAAAATCTAAAAGATGATTCTCTTCCTTCAAATCCAATAGATTTTTCTTA
CAGAGTAGCTGCTTGTCTTCCTATTGATGATGTATTGAGAATTCAGCTCCTTAAAATT
GGCAGTGCTATCCAGCGACTTCGCTGTGAATTAGACATTATGAATAAATGTACTTCC
CTTTGCTGTAAACAATGTCAAGAAACAGAAATAACAACCAAAAATGAAATATTCAG
GTATGCCTGGACTGTTGCCCAGTGTAAGATCTGTGCAAGCCATATTGGATGGAAGTT
TACGGCCACCAAAAAAGACATGTCACCTCAAAAATTTTGGGGCTTAACGCGATCTG
CTCTGTTGCCCACGATCCCAGACACTGAAGATGAAATAAGTCCAGACAAAGTAATA
CTTTGCTTGTAA (SEQ ID NO: 2)

FIG. 4

ATGGCCGGCGAAGGAGATCAGCAGGACGCTGCGCACAACATGGGCAACCACCTGCC
GCTCCTGCCTGCAGAGAGTGAGGAAGAAGATGAAATGGAAGTTGAAGACCAGGAT
AGTAAAGAAGCCAAAAAACCTGTCTCAAGAGAAGACCAATGTTCATATAAATGGTG
GCAGAAATACCAGAAGAGAAAGTTTCATTGTGCAAATCTAACTTCATGGCCTCGCT
GGCTGTATTCCTTATATGATGCTGAGACCTTAATGGACAGAATCAAGAAACAGCTAC
GTGAATGGGATGAAAATCTAAAAGATGATTCTCTTCCTTCAAATCCAATAGATTTTT
CTTACAGAGTAGCTGCTTGTCTTCCTATTGATGATGTATTGAGAATTCAGCTCCTTAA
AATTGGCAGTGCTATCCAGCGACTTCGCTGTGAATTAGACATTATGAATAAATGTAC
TTCCCTTTGCTGTAAACAATGTCAAGAAACAGAAATAACAACCAAAAATGAAATAT
TCAGTTTATCCTTATGTGGGCCGATGGCAGCTTATGTGAATCCTCATGGATATGTGC
ATGAGACACTTACTGTGTATAAGGCTTGCAACTTGAATCTGATAGGCCGGCCTTCTA
CAGAACACAGCTGGTTTCCTGGGTATGCCTGGACTGTTGCCCAGTGTAAGATCTGTG
CAAGCCATATTGGATGGAAGTTTACGGCCACCAAAAAAGACATGTCACCTCAAAAA
TTTTGGGGCTTAACGCGATCTGCTCTGTTGCCCACGATCCAGACACTGAAGATGAA
ATAAGTCCAGACAAAGTAATACTTTGCTTGTAA (SEQ ID NO: 3)

FIG. 5

ATGGCCGGCGAAGGAGATCAGCAGGACGCTGCGCACAACATGGGCAACCACCTGCC
GCTCCTGCCTGCAGAGAGTGAGGAAGAAGATGAAATGGAAGTTGAAGACCAGGAT
AGTAAAGAAGCCAAAAAACCAAACATCATAAATTTTGACACCAGTCTGCCGACATC
ACATACATACCTAGGTGCTGATATGGAAGAATTTCATGGCAGGACTTTGCACGATG
ACGACAGCTGTCAGGTGATTCCAGTTCTTCCACAAGTGATGATGATCCTGATTCCCG
GACAGACATTACCTCTTCAGCTTTTTCACCCTCAAGAAGTCAGTATGGTGCGGAATT
TAATTCAGAAAGATAGAACCTTTGCTGTAAACAATGTCAAGAAACAGAAATAACAA
CCAAAAATGAAATATTCAGTTTATCCTTATGTGGGCCGATGGCAGCTTATGTGAATC
CTCATGGATATGTGCATGAGACACTTACTGTGTATAAGGCTTGCAACTTGAATCTGA
TAGGCCGGCCTTCTACAGAACACAGCTGGTTTCCTGGGTATGCCTGGACTGTTGCCC
AGTGTAAGATCTGTGCAAGCCATATTGGATGGAAGTTTACGGCCACCAAAAAAGAC
ATGTCACCTCAAAAATTTTGGGGCTTAACGCGATCTGCTCTGTTGCCCACGATCCCA
GACACTGAAGATGAAATAAGTCCAGACAAAGTAATACTTTGCTTGTAA (SEQ ID NO: 4)

FIG. 6

ATGGCCGGCGAAGGAGATCAGCAGGACGCTGCGCACAACATGGGCAACCACCTGCC
GCTCCTGCCTGCAGAGAGTGAGGAAGAAGATGAAATGGAAGTTGAAGACCAGGAT
AGTAAAGAAGCCAAAAAACCAAACATCATAAATTTTGACACCAGTCTGCCGACATC
ACATACATACCTAGGTGCTGATATGGAAGAATTTCATGGCAGGACTTTGCACGATG
ACGACAGCTGTCAGGTGATTCCAGTTCTTCCACAAGTGATGATGATCCTGATTCCCG
GACAGACATTACCTCTTCAGCTTTTTCACCCTCAAGAAGTCAGTATGGTGCGGAATT
TAATTCAGAAAGATAGAACCTTTGCTGTTCTTGCATACAGCAATGTACAGGAAAGG
GAAGCACAGTTTGGAACAACAGCAGAGATATATGCCTATCGAGAAGAACAGGATTT
TGGAATTGATGATGTATTGAGAAAAGACATGTCACCTCAAAAATTTTGGGGCTTAAC
GCGATCTGCTCTGTTGCCCACGATCCCAGACACTGAAGATGAAATAAGTCCAGACA
AAGTAATACTTTGCTTGTAA (SEQ ID NO: 5)

FIG. 7

ATGGCCGGCGAAGGAGATCAGCAGGACGCTGCGCACAACATGGGCAACCACCTGCC
GCTCCTGCCTGCAGAGAGTGAGGAAGAAGATGAAATGGAAGTTGAAGACCAGGAT
AGTAAAGAAGCCaAAAAACCAAACATCATAAATTTTGACACCAGTCTGCCGACATC
ACATACATACCTAGGTGCTGATATGGAAGAATTTCATGGCAGGACTTTGCACGATG
ACGACAGCTGTCAGGTGATTCCAGTTCTTCCACAAGTGATGATGATCCTGATTCCCG
GACAGACATTACCTCTTCAGCTTTTTCACCCTCAAGAAGTCAGTATGGTGCGGAATT
TAATTCAAAAAAGACATGTCACCTCAAAAATTTTGGGGCTTAACGCGATCTGCTCTG
TTGCCCACGATCCCAGACACTGAAGATGAAATAAGTCCAGACAAAGTAATACTTTG
CTTGTAA (SEQ ID NO: 6)

FIG. 8

ATGGCCGGCGAAGGAGATCAGCAGGACGCTGCGCACAACATGAGCTTATGTGAATC
CTCATGGATATGTGCATGAGACACTTACTGTGTATAAGGCTTGCAACTTGAATCTGA
TAGGCCGGCCTTCTACAGAACACAGCTGGTTTCCTGGGTATGCCTGGACTGTTGCCC
AGTGTAAGATCTGTGCAAGCCATATTGGATGGAAGTTTACGGCCACCAAAAAAGAC
ATGTCACCTCAAAAATTTTGGGGCTTAACGCGATCTGCTCTGTTGCCCACGATCCCA
GACACTGAAGATGAAATAAGTCCAGACAAAGTAATACTTTGCTTGTAA (SEQ ID NO: 7)

FIG.11

ATGGCCGGCGAAGGAGATCAGCAGGACGCTGCGCACAACATGGGCAACCACCTGCC
GCTCCTGCCTGCAGAGAGTGAGGAAGAAGATGAAATGGAAGTTGAAGACCAGGAT
AGTAAAGAAGCCAAAAAACCAAACATCATAAATTTTGACACCAGTCTGCCGACATC
ACATACATACCTAGGTGCTGATATGGAAGAATTTCATGGCAGGACTTTGCACGATG
ACGACAGCTGTCAGGTGATTCCAGTTCTTCCACAAGTGATGATGATCCTGATTCCCG
GACAGACATTACCTCTTCAGCTTTTTCACCCTCAAGAAGTCAGTATGGTGCGGAATT
TAATTCAGAAGATAGAACCTTTGCTGTTCTTGCATACAGCAATGTACAGGAAAGG
GAAGCACAGTTTGGAACAACAGCAGAGATATATGCCTATCGAGAAGAACAGGATTT
TGGAATTGAGATAGTGAAAGTGAAAGCAATTGGAAGACAAAGGTTCAAAGTCCTTG
AGCTAAGAACACAGTCAGATGGAATCCAGCAAGCTAAAGTGCAAATTCTTCCCGAA
TGTGTGTTGCCTTCAACCATGTCTGCAGTTCAATTAGAATCCCTCAATAAGTGCCAG
ATATTTCCTTCAAAACCTGTCTCAAGAGAAGACCAATGTTCATATAAATGGTGGCAG
AAATACCAGAAGGAGACCTTAATGGACAGAATCAAGAAACAGCTACGTGAATGGG
ATGAAAATCTAAAGATGATTCTCTTCCTTCAAATCCAATAGATTTTCTTACAGAG
TAGCTGCTTGTCTTCCTATTGATGATGTATTGAGAATTCAGCTCCTTAAAATTGGCAG
TGCTATCCAGCGACTTCGCTGTGAATTAGACATTATGAATAAATGTACTTCCCTTTG
CTGTAAACAATGTCAAGAAACAGAAATAACAACCAAAAATGAAATATTCAGTTTAT
CCTTATGTGGGCCGATGGCAGCTTATGTGAATCCTCATGGATATGTGCATGAGACAC
TTACTGTGTATAAGGCTTGCAACTTGAATCTGATAGGCCGGCCTTCTACAGAACACA
GCTGGTTTCCTGGGTATGCCTGGACTGTTGCCCAGTGTAAGATCTGTGCAAGCCATA
TTGGATGGAAGTTTACGGCCACCAAAAAAGACATGTCACCTCAAAAATTTTGGGGC
TTAACGCGATCTGCTCTGTTGCCCACGATCCCAGACACTGAAGATGAAATAAGTCCA
GACAAAGTAATACTTTGCTTGTAA (SEQ ID NO: 13)

Assay Data:

FIG 15

CEREBLON ISOFORMS AND THEIR USE AS BIOMARKERS FOR THERAPEUTIC TREATMENT

1. CROSS REFERENCE TO RELATED APPLICATION

This application is a continuation-in-part application of International Application No. PCT/US2013/054663, filed Aug. 13, 2013, which claims the benefit of priority to U.S. Provisional Application No. 61/683,134, filed Aug. 14, 2012; and this application also claims the benefit of priority to U.S. Provisional Application No. 62/027,119, filed Jul. 21, 2014. The disclosure of each of these applications is incorporated herein by reference in its entirety.

2. FIELD

Provided herein are cereblon isoforms and methods of their use as biomarkers for treating a disease, disorder, or condition with a treatment compound, e.g., thalidomide, lenalidomide, pomalidomide, 3-(5-amino-2-methyl-4-oxoquinazolin-3(4H)-yl)piperidine-2,6-dione, or (S)-3-(4-((4-(morpholinomethyl)benzyl)oxy)-1-oxoisoindolin-2-yl)piperidine-2,6-dione.

3. BACKGROUND

Cereblon (CRBN), a component of the DDB1-CUL4a-Roc1 ubiquitin ligase complex, has been identified as a target of certain immunomodulatory compounds, e.g., thalidomide, lenalidomide, and pomalidomide (Lopez-Girona et al., *Leukemia* 2012). It is believed that the interactions of CRBN with the immunomodulatory compounds mediate their anti-proliferative effects in multiple myeloma (MM) cells (Lopez-Girona et al., *Leukemia* 2012; Zhu et al., *Blood* 2011, 118, Abstract 127).

The translated full-length CRBN protein contains 442 amino acid residues. It has been established that the C terminal region of CRBN binds the immunomodulatory compound, thalidomide, and that amino acid residues 374Y and 376W are critical for the binding of thalidomide to CRBN (Ito et al., *Science* 2010, 327, 1345-1350).

CRBN is encoded by a 25 kb gene on chromosome 6, consisting of 11 exons and 10 introns. Thus, alternative splicing process can potentially generate multiple functional proteins as well as variants of a protein from a single gene having different structural organization and functional activity. Truncated proteins that have lost interaction domains or critical functional amino acid residues may create non-functional or aberrant CRBN proteins that may interfere with the functions of the full-length CRBN protein and reduce or alter the therapeutic activity of a treatment compound that exerts its activity via its interactions with the full-length CRBN protein.

At least two isoforms of the protein cereblon (CRBN) exist, which are 442 and 441 amino acids long, respectively, and CRBN is conserved from plant to human. In humans, the CRBN gene has been identified as a candidate gene of an autosomal recessive nonsyndromic mental retardation (ARNSMR). See Higgins, J. J. et al., *Neurology,* 2004, 63:1927-1931. CRBN was initially characterized as an RGS-containing novel protein that interacted with a calcium-activated potassium channel protein (SLO1) in the rat brain, and was later shown to interact with a voltage-gated chloride channel (ClC-2) in the retina with AMPK1 and DDB1. See Jo, S. et al., *J. Neurochem,* 2005, 94:1212-1224; Hohberger B. et al., *FEBS Lett,* 2009, 583:633-637; Angers S. et al., *Nature,* 2006, 443:590-593. DDB1 was originally identified as a nucleotide excision repair protein that associates with damaged DNA binding protein 2 (DDB2). Its defective activity causes the repair defect in the patients with xeroderma pigmentosum complementation group E (XPE). DDB1 also appears to function as a component of numerous distinct DCX (DDB1-CUL4-X-box) E3 ubiquitin-protein ligase complexes which mediate the ubiquitination and subsequent proteasomal degradation of target proteins. CRBN has also been identified as a target for the development of therapeutic agents for diseases of the cerebral cortex. See WO 2010/137547 A1.

As a direct binding target of immunomodulatory agents, CRBN can thus potentially be used as a biomarker for a treatment with an immunomodulatory agent, such as thalidomide, lenalidomide, pomalidomide, 3-(5-amino-2-methyl-4-oxoquinazolin-3(4H)-yl)piperidine-2,6-dione, or (S)-3-(4-((4-(morpholinomethyl)-benzyl)oxy)-1-oxoisoindolin-2-yl)piperidine-2,6-dione.

4. SUMMARY

Provided herein is an isolated, synthetic, or recombinant polypeptide of an isoform of CRBN, which has a deletion of amino acid residues 126 to 175 (Δ126-175) or amino acid residues 176 to 228 (Δ176-228) in the full-length amino acid sequence of CRBN. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 3 of CRBN, which has a deletion of amino acids 58 to 175 (Δ58-175) in the full-length amino acid sequence of CRBN.

In another embodiment, the polypeptide is isoform 4 of CRBN, which has a deletion of amino acids 126 to 316 (Δ126-316) in the full-length amino acid sequence of CRBN.

In yet another embodiment, the polypeptide is isoform 5 of CRBN, which has deletions of amino acid residues 176 to 278 (Δ176-278) and amino acid residues 317 to 382 (Δ317-382) in the full-length amino acid sequence of CRBN.

In yet another embodiment, the polypeptide is isoform 6 of CRBN, which has a deletion of amino acids 126 to 382 (Δ126-382) in the full-length amino acid sequence of CRBN.

In still another embodiment, the polypeptide is isoform 7 of CRBN, which has a deletion of amino acids 23 to 338 (Δ23-338) in the full-length amino acid sequence of CRBN.

Also provided herein is an isolated, synthetic, or recombinant nucleic acid encoding an isoform of CRBN, wherein the isoform has a deletion of amino acid residues 126 to 175 (Δ126-175) or amino acid residues 176 to 228 (Δ176-228) in the full-length amino acid sequence of CRBN. In some embodiments, the polypeptide is an isolated polypeptide. In some embodiments, the polypeptide is a synthetic polypeptide. In some embodiments, the polypeptide is a recombinant polypeptide.

In one embodiment, the nucleic acid is one encoding isoform 3 of CRBN, wherein the isoform has a deletion of amino acids 58 to 175 (Δ58-175) in the full-length amino acid sequence of CRBN.

In another embodiment, the nucleic acid is one encoding isoform 4 of CRBN, wherein the isoform has a deletion of amino acids 126 to 316 (Δ126-316) in the full-length amino acid sequence of CRBN.

In yet another embodiment, the nucleic acid is one encoding isoform 5 of CRBN, wherein the isoform has deletions of amino acid residues 176 to 278 (Δ176-278) and amino acid residues 317 to 382 (Δ317-382) in the full-length amino acid sequence of CRBN.

In yet another embodiment, the nucleic acid is one encoding isoform 6 of CRBN, wherein the isoform has a deletion of amino acids 126 to 382 (Δ126-382) in the full-length amino acid sequence of CRBN.

In still another embodiment, the nucleic acid is one encoding isoform 7 of CRBN, wherein the isoform has a deletion of amino acids 23 to 338 (Δ23-338) in the full-length amino acid sequence of CRBN.

In some embodiments, provided herein is an isolated, synthetic, or recombinant polypeptide of an isoform of CRBN, wherein the isoform comprises an exon 6 deletion in the full-length amino acid sequence of CRBN. In some embodiments, the polypeptide is an isolated polypeptide of an isoform of CRBN, wherein the isoform comprises an exon 6 deletion in the full-length amino acid sequence of CRBN. In some embodiments, the polypeptide is a synthetic polypeptide of an isoform of CRBN, wherein the isoform comprises an exon 6 deletion in the full-length amino acid sequence of CRBN. In some embodiments, the polypeptide is a recombinant polypeptide of an isoform of CRBN, wherein the isoform comprises an exon 6 deletion in the full-length amino acid sequence of CRBN. In some embodiments, the isoform of CRBN comprises a single exon 6 deletion in the full-length amino acid sequence of CRBN, and wherein the isoform comprises exons 1-5 and 7-11. In some embodiments, the exon 6 of CRBN encodes 229-249 amino acid segment (SEQ ID NO: 8) of the full-length amino acid of CRBN (SEQ ID NO: 9). In some embodiments, the exon 6 of CRBN encodes 230-250 amino acid segment (SEQ ID NO: 8) of the full-length amino acid of CRBN (SEQ ID NO: 10).

Additionally provided herein is a method of identifying a subject who is likely to be responsive to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof; and b) comparing the level of the biomarker in the biological sample to a reference level of the biomarker;

wherein the subject is likely to be responsive to the treatment if the level of the biomarker in the biological sample from the subject is altered as compared to the reference level of the biomarker.

Further provided herein is a method of identifying a subject who is likely to be responsive to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof;

b) determining the level of the biomarker in a control sample; and c) comparing the level of the biomarker in the biological sample from the subject to the level of the biomarker in the control sample;

wherein the subject is likely to be responsive to the treatment if the level of the biomarker in the biological sample from the subject is altered as compared to the level of the biomarker in the control sample.

Provided herein is a method of identifying a subject who is likely to be responsive to a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and c) comparing the level of the biomarker in the biological sample to a reference level of the biomarker;

wherein the subject is likely to be responsive to the treatment if the level of the biomarker in the biological sample from the subject is altered as compared to the reference level of the biomarker.

Provided herein is a method of identifying a subject who is likely to be responsive to a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof;

c) determining the level of the biomarker in a control sample; and d) comparing the level of the biomarker in the biological sample from the subject to the level of the biomarker in the control sample;

wherein the subject is likely to be responsive to the treatment if the level of the biomarker in the biological sample from the subject is altered as compared to the level of the biomarker in the control sample.

Provided herein is a method of predicting the responsiveness of a subject to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof; and b) comparing the level of the biomarker in the biological sample to a reference level of the biomarker;

wherein the difference between the level of the biomarker in the biological sample from the subject and the reference level of the biomarker correlates with the responsiveness of the subject to the treatment.

Provided herein is a method of predicting the responsiveness of a subject to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof;

b) determining the level of the biomarker in a control sample; and c) comparing the level of the biomarker in the biological sample from the subject to the level of the biomarker in the control sample;

wherein the difference between the level of the biomarker in the biological sample from the subject and the level of the biomarker in the control sample correlates with the responsiveness of the subject to the treatment.

Provided herein is a method of predicting the responsiveness of a subject to a treatment of a disease, disorder, or condition with a treatment compound, comprising:
 a) obtaining a biological sample from the subject;
 b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and
 c) comparing the level of the biomarker in the biological sample to a reference level of the biomarker;
 wherein the difference between the level of the biomarker in the biological sample from the subject and the reference level of the biomarker correlates with the responsiveness of the subject to the treatment.

Provided herein is a method of predicting the responsiveness of a subject to a treatment of a disease, disorder, or condition with a treatment compound, comprising:
 a) obtaining a biological sample from the subject;
 b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof;
 c) determining the level of the biomarker in a control sample; and
 d) comparing the level of the biomarker in the biological sample from the subject to the level of the biomarker in the control sample;
 wherein the difference between the level of the biomarker in the biological sample from the subject and the level of the biomarker in the control sample correlates with the responsiveness of the subject to the treatment.

Provided herein is a method of monitoring the efficacy of a treatment of a disease, disorder, or condition in a subject treated with a treatment compound, comprising:
 a) obtaining a first biological sample from the subject;
 b) determining the level of a biomarker in the first biological sample, wherein the biomarker is an isoform of CRBN, in one embodiment, isoform 1, isoform 2, isoform 3, isoform 4, isoform 5, isoform 6, isoform 7, or a combination thereof;
 c) administering the treatment compound to the subject;
 d) thereafter obtaining a second biological sample from the subject;
 e) determining the level of the biomarker in the second biological sample, and
 f) comparing the levels of the biomarker in the first and second biological samples;
 wherein the subject is responsive to the treatment if the level of the biomarker in the second biological sample of the subject is altered as compared to the level of the biomarker in the first biological sample of the subject.

Provided herein is a method of monitoring the compliance of a subject with a treatment of a disease, disorder, or condition with a treatment compound, comprising:
 a) obtaining a biological sample from the subject;
 b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and
 c) comparing the level of the biomarker with the level of the biomarker in a control sample from the subject;
 wherein the change in the level of the biomarker in the biological sample in comparison with the level of the biomarker in the control sample indicates the compliance of the subject with the treatment.

Provided herein is a method of identifying a subject who is likely to be responsive to a treatment of a disease, disorder, or condition with a treatment compound, comprising:
 a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof; and
 b) comparing the level of the biomarker in the biological sample to a reference level of the biomarker;
 wherein the subject is likely to be responsive to the treatment if the level of the biomarker in the biological sample from the subject is higher than the reference level of the biomarker.

Provided herein is a method of identifying a subject who is likely to be responsive to a treatment of a disease, disorder, or condition with a treatment compound, comprising:
 a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof;
 b) determining the level of the biomarker in a control sample; and
 c) comparing the level of the biomarker in the biological sample from the subject to the level of the biomarker in the control sample;
 wherein the subject is likely to be responsive to the treatment if the level of the biomarker in the biological sample from the subject is higher than the level of the biomarker in the control sample.

Provided herein is a method of identifying a subject who is likely to be responsive to a treatment of a disease, disorder, or condition with a treatment compound, comprising:
 a) obtaining a biological sample from the subject;
 b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and
 c) comparing the level of the biomarker in the biological sample to a reference level of the biomarker;
 wherein the subject is likely to be responsive to the treatment if the level of the biomarker in the biological sample from the subject is higher than the reference level of the biomarker.

Provided herein is a method of identifying a subject who is likely to be responsive to a treatment of a disease, disorder, or condition with a treatment compound, comprising:
 a) obtaining a biological sample from the subject;
 b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof;
 c) determining the level of the biomarker in a control sample; and
 d) comparing the level of the biomarker in the biological sample from the subject to the level of the biomarker in the control sample;
 wherein the subject is likely to be responsive to the treatment if the level of the biomarker in the biological sample from the subject is higher than the level of the biomarker in the control sample.

Provided herein is a method of predicting the responsiveness of a subject to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof; and b) comparing the level of the biomarker in the biological sample to a reference level of the biomarker;

wherein an increased level of the biomarker in the biological sample from the subject in comparison with the reference level of the biomarker correlates with an increased responsiveness of the subject to the treatment.

Provided herein is a method of predicting the responsiveness of a subject to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof;

b) determining the level of the biomarker in a control sample; and c) comparing the level of the biomarker in the biological sample from the subject to the level of the biomarker in the control sample;

wherein an increased level of the biomarker in the biological sample from the subject in comparison with the level of the biomarker in the control sample correlates with an increased responsiveness of the subject to the treatment.

Provided herein is a method of predicting the responsiveness of a subject to a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and c) comparing the level of the biomarker in the biological sample to a reference level of the biomarker;

wherein an increased level of the biomarker in the biological sample from the subject in comparison with the reference level of the biomarker correlates with an increased responsiveness of the subject to the treatment.

Provided herein is a method of predicting the responsiveness of a subject to a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof;

c) determining the level of the biomarker in a control sample; and d) comparing the level of the biomarker in the biological sample from the subject to the level of the biomarker in the control sample;

wherein an increased level of the biomarker in the biological sample from the subject in comparison with the level of the biomarker in the control sample correlates with an increased responsiveness of the subject to the treatment.

Provided herein is a method of monitoring the efficacy of a treatment of a disease, disorder, or condition in a subject treated with a treatment compound, comprising:

a) obtaining a first biological sample from the subject;

b) determining the level of a biomarker in the first biological sample, wherein the biomarker is an isoform of CRBN, in one embodiment, isoform 1, isoform 2, isoform 3, isoform 4, isoform 5, isoform 6, isoform 7, or a combination thereof;

c) administering the treatment compound to the subject;

d) thereafter obtaining a second biological sample from the subject;

e) determining the level of the biomarker in the second biological sample, and f) comparing the levels of the biomarker in the first and second biological samples;

wherein an increased level of the biomarker in the second biological sample in comparison with the level of the biomarker in the first biological sample indicates that the subject is responsive to the treatment.

Provided herein is a method of monitoring the compliance of a subject with a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and c) comparing the level of the biomarker with the level of the biomarker in a control sample from the subject;

wherein an increased level of the biomarker in the biological sample in comparison with the level of the biomarker in the control sample indicates the compliance of the subject with the treatment.

Provided herein is a method of identifying a subject who is likely to be responsive to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof; and b) comparing the level of the biomarker in the biological sample to a reference level of the biomarker;

wherein the subject is likely to be responsive to the treatment if the level of the biomarker in the biological sample from the subject is lower than the reference level of the biomarker.

Provided herein is a method of identifying a subject who is likely to be responsive to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof;

b) determining the level of the biomarker in a control sample; and c) comparing the level of the biomarker in the biological sample from the subject to the level of the biomarker in the control sample;

wherein the subject is likely to be responsive to the treatment if the level of the biomarker in the biological sample from the subject is lower than the level of the biomarker in the control sample.

Provided herein is a method of identifying a subject who is likely to be responsive to a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and c) comparing the level of the biomarker in the biological sample to a reference level of the biomarker;

wherein the subject is likely to be responsive to the treatment if the level of the biomarker in the biological sample from the subject is lower than the reference level of the biomarker.

Provided herein is a method of identifying a subject who is likely to be responsive to a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof;

c) determining the level of the biomarker in a control sample; and d) comparing the level of the biomarker in the biological sample from the subject to the level of the biomarker in the control sample;

wherein the subject is likely to be responsive to the treatment if the level of the biomarker in the biological sample from the subject is lower than the level of the biomarker in the control sample.

Provided herein is a method of predicting the responsiveness of a subject to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof; and b) comparing the level of the biomarker in the biological sample to a reference level of the biomarker;

wherein a decreased level of the biomarker in the biological sample from the subject in comparison with the reference level of the biomarker correlates with an increased responsiveness of the subject to the treatment.

Provided herein is a method of predicting the responsiveness of a subject to a treatment of a disease, disorder, or condition with a treatment compound, comprising:

a) determining the level of a biomarker in a biological sample from the subject, wherein the biomarker is an isoform of CRBN, in one embodiment, isoform 1, isoform 2, isoform 3, isoform 4, isoform 5, isoform 6, isoform 7, or a combination thereof;

b) determining the level of the biomarker in a control sample; and c) comparing the level of the biomarker in the biological sample from the subject to the level of the biomarker in the control sample;

wherein a decreased level of the biomarker in the biological sample from the subject in comparison with the level of the biomarker in the control sample correlates with an increased responsiveness of the subject to the treatment.

Provided herein is a method of predicting the responsiveness of a subject to a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and c) comparing the level of the biomarker in the biological sample to a reference level of the biomarker;

wherein a decreased level of the biomarker in the biological sample from the subject in comparison with the reference level of the biomarker correlates with an increased responsiveness of the subject to the treatment.

Provided herein is a method of predicting the responsiveness of a subject to a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof;

c) determining the level of the biomarker in a control sample; and d) comparing the level of the biomarker in the biological sample from the subject to the level of the biomarker in the control sample;

wherein a decreased level of the biomarker in the biological sample from the subject in comparison with the level of the biomarker in the control sample correlates with an increased responsiveness of the subject to the treatment.

Provided herein is a method of monitoring the efficacy of a treatment of a disease, disorder, or condition in a subject treated with a treatment compound, comprising:

a) obtaining a first biological sample from the subject;

b) determining the level of a biomarker in the first biological sample, wherein the biomarker is an isoform of CRBN, in one embodiment, isoform 1, isoform 2, isoform 3, isoform 4, isoform 5, isoform 6, isoform 7, or a combination thereof;

c) administering the treatment compound to the subject;

d) thereafter obtaining a second biological sample from the subject;

e) determining the level of the biomarker in the second biological sample, and f) comparing the levels of the biomarker in the first and second biological samples;

wherein a decreased level of the biomarker in the second biological sample in comparison with the level of the biomarker in the first biological sample indicates that the subject is responsive to the treatment.

Provided herein is a method of monitoring the compliance of a subject with a treatment of a disease, disorder, or condition with a treatment compound, comprising:

a) obtaining a biological sample from the subject;

b) determining the level of a biomarker in the biological sample, wherein the biomarker is an isoform of CRBN, in one embodiment, isoform 1, isoform 2, isoform 3, isoform 4, isoform 5, isoform 6, isoform 7, or a combination thereof; and c) comparing the level of the biomarker with the level of the biomarker in a control sample from the subject;

wherein a decreased level of the biomarker in the biological sample in comparison with the level of the biomarker in the control sample indicates the compliance of the subject with the treatment.

Provided herein is a method of identifying a subject who is likely to be responsive to a treatment of a disease, disorder, or condition with a treatment compound, comprising:
a) obtaining a biological sample from the subject;
b) determining the level of an isoform of CRBN comprising an exon 6 deletion in the biological sample; and
c) diagnosing the subject as being likely to be responsive to a treatment of a disease, disorder, or condition with a treatment compound if the level of the isoform of CRBN comprising an exon 6 deletion present is determined to be less than a baseline level,
wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

Provided herein is a method of identifying a subject who is likely to be responsive to a treatment of a disease, disorder, or condition with a treatment compound, comprising:
a) obtaining a biological sample from the subject;
b) determining the level of an isoform of CRBN comprising an exon 6 deletion in the biological sample; and
c) diagnosing the subject as not being likely to be responsive to a treatment of a disease, disorder, or condition with a treatment compound if the level of the isoform of CRBN comprising an exon 6 deletion present in the biological sample is determined to be a baseline level,
wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

Provided herein is a method for determining whether a subject has a treatment compound-sensitive cancer wherein said method comprises
a) obtaining a cancer sample from the subject;
b) determining the level of an isoform of CRBN comprising an exon 6 deletion in the cancer sample;
c) diagnosing the subject as having a treatment compound-sensitive cancer if the isoform of CRBN comprising an exon 6 deletion was determined to be less than a baseline level in the cancer sample; and
d) administering an effective amount of the treatment compound to the subject diagnosed as having the treatment compound-sensitive cancer,
wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

In some embodiments, the cancer is multiple myeloma, lymphoma, melanoma or solid tumor. In some embodiments, the cancer is multiple myeloma. In some embodiments, the cancer is lymphoma. In some embodiments, the cancer is melanoma. In some embodiments, the cancer is solid tumor.

Provided herein is a method for treating a having or suspected of having a cancer, wherein said method comprising:
a) obtaining a cancer sample from the subject;
b) determining the level of an isoform of CRBN comprising an exon 6 deletion in the cancer sample;
c) diagnosing the subject as having a treatment compound-sensitive cancer if the isoform of CRBN comprising an exon 6 deletion was determined to be less than a baseline level in the cancer sample; and
d) administering an effective amount of the treatment compound to the subject diagnosed as having the treatment compound-sensitive cancer,
wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

Provided herein is a method of predicting the responsiveness of a subject to a treatment of a disease, disorder, or condition with a treatment compound, comprising:
a) obtaining a biological sample from the subject;
b) determining the level of an isoform of CRBN comprising an exon 6 deletion in the biological sample; and
c) diagnosing the subject as being likely to be responsive to a treatment of a disease, disorder, or condition with a treatment compound if the level of the isoform of CRBN comprising an exon 6 deletion is determined to be less than a baseline level,
wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

Provided herein is a method of predicting the responsiveness of a subject to a treatment of a disease, disorder, or condition with a treatment compound, comprising:
a) obtaining a biological sample from the subject;
b) determining the level of an isoform of CRBN comprising an exon 6 deletion in the biological sample; and
c) diagnosing the subject as not being likely to be responsive to a treatment of a disease, disorder, or condition with a treatment compound if the level of the isoform of CRBN comprising an exon 6 deletion present in the biological sample is determined to be a baseline level or higher than a baseline level,
wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

Provided herein is a method of monitoring the efficacy of a treatment of a disease, disorder, or condition in a subject treated with a treatment compound, comprising:
a) obtaining a first biological sample from the subject;
b) determining the level of an isoform of CRBN comprising an exon 6 deletion in the first biological sample;
d) administering an effective amount of the treatment compound to the subject;
e) obtaining a second biological sample from the subject; and
b) determining the level of the isoform of CRBN comprising an exon 6 deletion in the second biological sample;

wherein the subject develops resistance to the treatment compound when an increased level of the isoform of CRBN comprising an exon 6 is determined, and wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl) piperidine-2,6-dione a stereoisomer thereof, or a pharmaceutically acceptable salt, solvate, hydrate, co-crystal, clathrate, or polymorph thereof.

In some embodiments of the various methods provided herein, the method further comprises administering the treatment compound to the subject. In some embodiments, the method further comprises administering an effective amount of the treatment compound to the subject who is likely to be responsive to the treatment compound. In some embodiments, the method further comprises administering additional treatment compound to the subject.

In certain embodiments of the various methods provided herein, the isoform of CRBN comprising an exon 6 deletion comprises a single exon 6 deletion and comprises exons 1-5 and 7-11.

In certain embodiments of the various methods provided herein, the disease, disorder, or condition is a CRBN-mediated disease, disorder, or condition.

Provided herein is a probe for determining the level of a biomarker in a sample by hybridizing with a polynucleotide of the biomarker, wherein the biomarker is an isoform of CRBN, in one embodiment, isoform 1, isoform 2, isoform 3, isoform 4, isoform 5, isoform 6, isoform 7, or a combination thereof. In some embodiments, the biomarker is an isoform of CRBN comprising an exon 6 deletion. In some embodiment, the biomarker is an isoform of CRBN comprising exons 1-5 and 7-11. In certain embodiments, the level of the biomarker is used to select a subject for a treatment with a treatment compound, in one embodiment, an immunomodulatory compound; to predict or monitor the responsiveness of a subject to the treatment; or monitoring the compliance of a subject with the treatment. In certain embodiments, the probe is one that hybridizes with a splice junction of a polynucleotide of the biomarker. In certain embodiments, the probe is specific for detecting or quantitating an isoform of CRBN, in one embodiment, isoform 1, isoform 2, isoform 3, isoform 4, isoform 5, isoform 6, or isoform 7.

Provided herein is a probe for determining the level of a biomarker in a sample by hybridizing with an mRNA of the biomarker, wherein the biomarker is an isoform of CRBN, in one embodiment, isoform 1, isoform 2, isoform 3, isoform 4, isoform 5, isoform 6, isoform 7, or a combination thereof. In some embodiments, the biomarker is an isoform of CRBN comprising an exon 6 deletion. In some embodiment, the biomarker is an isoform of CRBN comprising exons 1-5 and 7-11. In certain embodiments, the level of the biomarker is used to select a subject for a treatment with a treatment compound, in one embodiment, an immunomodulatory compound; predict or monitor the responsiveness of a subject to the treatment; or monitor the compliance of a subject with the treatment. In certain embodiments, the probe is one that hybridizes with a splice junction of an mRNA of the biomarker. In certain embodiments, the probe is specific for detecting or quantitating an isoform of CRBN, in one embodiment, isoform 1, isoform 2, isoform 3, isoform 4, isoform 5, isoform 6, or isoform 7. In certain embodiments, the probe targets to exon 6 of CRBN. In some embodiments, the probe targets to a junction region between exon 6 and exon 7 of CRBN. In some embodiments, the probe targets to a junction region between exon 5 and exon 6 of CRBN.

Provided herein is an antibody for determining the level of a biomarker in a sample, wherein the biomarker is an isoform of CRBN, in one embodiment, isoform 1, isoform 2, isoform 3, isoform 4, isoform 5, isoform 6, isoform 7, or a combination thereof. In some embodiments, the biomarker is an isoform of CRBN comprising an exon 6 deletion. In some embodiment, the biomarker is an isoform of CRBN comprising exons 1-5 and 7-11. In certain embodiments, the level of the biomarker is used to select a subject for a treatment with a treatment compound, in one embodiment, an immunomodulatory compound; to predict or monitor the responsiveness of a subject to the treatment; or monitoring the compliance of a subject with the treatment. In certain embodiments, the antibody is one that binds to a splice junction of an isoform, in one embodiment, isoform 1, isoform 2, isoform 3, isoform 4, isoform 5, isoform 6, or isoform 7. In certain embodiments, the antibody is one that binds to a splice junction of an isoform of CRBN comprising an exon 6 deletion. In certain embodiments, the antibody is specific for detecting or quantitating an isoform of CRBN, in one embodiment, isoform 1, isoform 2, isoform 3, isoform 4, isoform 5, isoform 6, or isoform 7. In certain embodiments, the antibody is specific for detecting or quantitating an isoform of CRBN comprising an exon 6 deletion.

Provided herein is a kit for determining the level of a biomarker in a biological sample from a subject, wherein the biomarker is an isoform of CRBN, in one embodiment, isoform 1, isoform 2, isoform 3, isoform 4, isoform 5, isoform 6, isoform 7, or a combination thereof. Also provided herein is a kit for determining the level of a biomarker in a biological sample from a subject, wherein the biomarker is an isoform of CRBN comprising an exon 6 deletion. In certain embodiments, the level of the biomarker is used to select a subject for a treatment with a treatment compound, predict or monitor the responsiveness of a subject to the treatment; or monitor the compliance of a subject with the treatment.

5. DETAILED DESCRIPTION

The methods, probes, antibodies, and kits provided herein are based, in part, on the discovery that the change in the level of certain molecules (e.g., mRNAs, cDNA, or proteins) in a biological sample can be utilized as biomarkers to predict responsiveness of a subject having or suspected to have a disease, disorder, or condition to a treatment with a treatment compound, in one embodiment, an immunomodulatory compound, e.g., thalidomide, lenalidomide, pomalidomide, 3-(5-amino-2-methyl-4-oxoquinazolin-3 (4H)-yl)piperidine-2,6-dione, or (S)-3-(4-((4-(morpholinomethyl)-benzyl)oxy)-1-oxoisoindolin-2-yl)piperidine-2, 6-dione.

In certain embodiments, the methods provided herein are based on comparison of the level of a biomarker in a biological sample from a subject having or suspected to have a disease, disorder, or condition to a reference level of the biomarker or the level of the biomarker in a control sample. The biomarker level is used to determine or to predict, for example, the likelihood of the responsiveness of the subject to a treatment with a treatment compound, in one embodiment, an immunomodulatory compound, such as thalidomide, lenalidomide, pomalidomide, 3-(5-amino-2-methyl-4-oxoquinazolin-3 (4H)-yl)piperidine-2,6-dione, or (S)-3-(4-((4-(morpholinomethyl)-benzyl)oxy)-1-oxoisoindolin-2-yl) piperidine-2,6-dione.

5.1 BRIEF DESCRIPTION OF FIGURES

FIG. 2 illustrates a nucleic acid sequence (SEQ ID NO: 1) encoding isoform 1 of CRBN.

FIG. 3 illustrates a nucleic acid sequence (SEQ ID NO: 2) encoding isoform 2 of CRBN.

FIG. 4 illustrates a nucleic acid sequence (SEQ ID NO: 3) encoding isoform 3 of CRBN.

FIG. 5 illustrates a nucleic acid sequence (SEQ ID NO: 4) encoding isoform 4 of CRBN.

FIG. 6 illustrates a nucleic acid sequence (SEQ ID NO: 5) encoding isoform 5 of CRBN.

FIG. 7 illustrates a nucleic acid sequence (SEQ ID NO: 6) encoding isoform 6 of CRBN.

FIG. 8 illustrates a nucleic acid sequence (SEQ ID NO: 7) encoding isoform 7 of CRBN.

FIG. 11 illustrates a nucleic acid sequence (SEQ ID NO: 13) encoding an isoform of CRBN with a single exon 6 deletion.

FIG. 15 shows sequencing results of PCR products from MM1.S and MM1.S Pomalidomide Resistant cells.

5.2 DEFINITIONS

Figure 1:
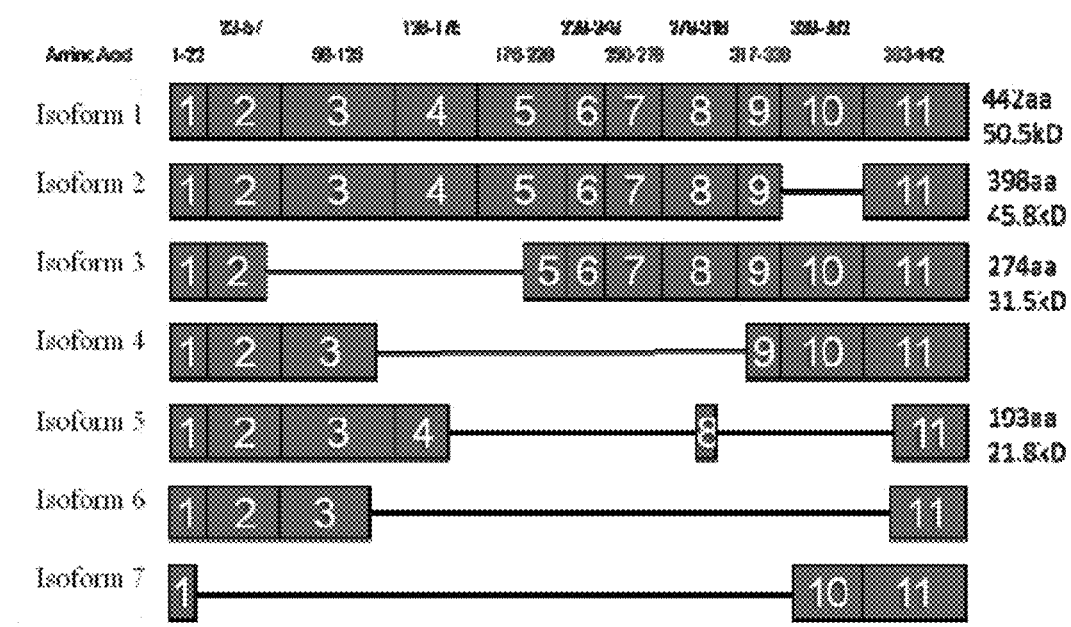
FIG. 1 illustrates seven isoforms of CRBN formed via alternative splicing.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The term "treat," "treating," or "treatment" refers to alleviating or abrogating a disease, or one or more of the symptoms associated with the disease; or alleviating or eradicating the cause(s) of the disease itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" of a compound refers to the amount of the compound that, when administered, is sufficient to prevent the development of, or alleviate to some extent, one or more of the symptoms of a disease, disorder, or condition being treated. The term also refers to the amount of the compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician. Furthermore, a therapeutically effective amount of a compound means an amount of a therapeutic agent, alone or in combination with other therapies, which provides a therapeutic benefit in the treatment or management of a disease, disorder, or condition. The term encompasses an amount of the compound that improves overall therapy, reduces, or avoids symptoms or causes of a disease, disorder, or condition, or enhances the therapeutic efficacy of another therapeutic agent.

The term "level" refers to the amount, accumulation, or rate of a biomarker molecule. A level can be represented, for example, by the amount or the rate of synthesis of a massager RNA (mRNA) encoded by a gene, the amount or the rate of synthesis of a polypeptide or protein encoded by a gene, the amount or the rate of synthesis of a biological molecule accumulated in a cell or biological fluid, or the biological activity of a biological molecule in a cell or biological fluid. The term "level" refers to an absolute amount of a molecule in a sample or to a relative amount of the molecule, determined under steady-state or non-steady-state conditions.

The term "responsiveness" or "responsive" when used in reference to a treatment refers to the degree of effectiveness of the treatment in lessening or decreasing the symptoms of a disease, disorder, or condition being treated. For example, the term "increased responsiveness" when used in reference to a treatment of a cell or a subject refers to an increase in the effectiveness in lessening or decreasing the symptoms of the disease when measured using any methods known in the art. In certain embodiments, the increase in the effectiveness is at least about 5%, at least about 10%, at least about 20%, at least about 30%, at least about 40%, or at least about 50%.

The terms "effective subject response" and "effective patient response" are used interchangeably, and refer to an increase in the therapeutic benefit to a subject in treating a disease, disorder, or condition. In certain embodiments, the increase is at least about 5%, at least about 10%, at least about 20%, at least about 30%, at least about 40%, or at least about 50%. An "effective subject tumor response" can be, for example, an about 5%, about 10%, about 25%, about 50%, or about 100% decrease in one or more physical symptoms of the disease or the tumor size.

The term "likelihood" refers to an increase in the probability of an event. The term "likelihood" when used in reference to the effectiveness of a subject's response to a treatment of a disease, disorder, or condition contemplates an increased probability that the symptoms of the disease, disorder, or condition will be lessened or decreased.

The term "predict" generally means to determine or tell in advance. When used to "predict" the effectiveness of the treatment of a disease, disorder, or condition, for example, the term "predict" can mean that the likelihood of the outcome of the treatment can be determined at the outset, before the treatment has begun, or before the treatment period has progressed substantially.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "polypeptide," "protein," or "peptide," as used herein interchangeably, refers to a polymer of two or more amino acids in a serial array, linked through one or more peptide bond(s). The term encompasses proteins, protein fragments, protein analogues, oligopeptides, and peptides. The amino acids of the polypeptide, protein, or peptide can be naturally occurring amino acids or synthetic amino acids (e.g., mimics of naturally occurring amino acids). The polypeptide, protein, or peptide can be made synthetically or purified from a biological sample. The polypeptide, protein, or peptide also encompasses modified polypeptides, proteins, and peptides, e.g., a glycopolypeptide, glycoprotein, or glycopeptide; or a lipopolypeptide, lipoprotein, or lipopeptide.

The term "antibody" refers to a polypeptide that specifically binds an epitope (e.g., an antigen). The term "antibody" is used herein in the broadest sense and covers fully assembled antibodies, antibody fragments which retain the ability to specifically bind to an antigen (e.g., Fab, $F(ab')_2$, Fv, and other fragments), single chain antibodies, di-antibodies, antibody chimeras, hybrid antibodies, bispecific antibodies, and humanized antibodies. The term "antibody" also covers both polyclonal and monoclonal antibodies.

The term "expressed" or "expression" refers to the transcription from a gene to give an RNA nucleic acid molecule, e.g., mRNA, at least complementary in part to a region of one of the two nucleic acid strands of the gene. The term "expressed" or "expression" as used herein also refers to the translation from an RNA molecule to give a protein, a polypeptide, or a portion thereof.

An mRNA that is "unregulated" generally refers to an increase in the level of expression of the mRNA in response to a given treatment or condition. An mRNA that is "downregulated" generally refers to a "decrease" in the level of expression of the mRNA in response to a given treatment or condition. In some situations, the mRNA level can remain unchanged upon a given treatment or condition. An mRNA from a subject sample can be "unregulated," i.e., the level of mRNA can be increased, for example, by about 5%, about 10%, about 20%, about 30%, about 40%, about 50%, about 60%, about 70%, about 90%, about 100%, about 200%, about 300%, about 500%, about 1,000%, about 5,000% or more of the comparative control mRNA level or a reference level. Alternatively, an mRNA can be "downregulated," i.e., the level of mRNA level can be decreased, for example, by about 99%, about 95%, about 90%, about 80%, about 70%, about 60%, about 50%, about 40%, about 30%, about 20%, about 10%, about 5%, about 2%, about 1% or less of the comparative control mRNA level or a reference level.

Similarly, the level of a polypeptide, protein, or peptide from a subject sample can be increased as compared to a control or a reference level. This increase can be about 5%, about 10%, about 20%, about 30%, about 40%, about 50%, about 60%, about 70%, about 90%, about 100%, about 200%, about 300%, about 500%, about 1,000%, about 5,000% or more of the comparative control protein level or a reference level. Alternatively, the level of a protein biomarker can be decreased. This decrease can be, for example, present at a level of about 99%, about 95%, about 90%, about 80%, about 70%, about 60%, about 50%, about 40%, about 30%, about 20%, about 10%, about 5%, about 2%, about 1% or less of the comparative control protein level or a reference level.

The terms "determining", "measuring", "evaluating", "assessing" and "assaying" are used interchangeably herein to refer to a form of measurement, including determining if an element is present or not. The measurement can be quantitative and/or qualitative determinations. "Assessing the presence of" can include determining the amount of something present, as well as determining whether it is present or absent.

The terms "nucleic acid" and "polynucleotide" are used interchangeably herein to refer to a polymer of nucleotides, e.g., deoxyribonucleotides or ribonucleotides, or compounds, which can hybridize with a naturally occurring nucleic acid in a sequence specific manner analogous to that of two naturally occurring nucleic acids, e.g., participating in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases. Such other heterocyclic bases include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. The term "analogue" of a "nucleic acid" or "polynucleotide" refers to a molecule having a structural feature that is recognized in the literature as being a mimetic, derivative, having an analogous structure, or other like terms, and includes, for example, a polynucleotide incorporating a non-natural nucleotide, a nucleotide mimetic such as a 2'-modified nucleoside, peptide nucleic acid, oligomeric nucleoside phosphonate, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g., if they produce a given or detectable level of signal in a hybridization assay. Portions of polynucleotides are complementary to each other if they follow conventional base-pairing rules, e.g., A pairs with T (or U) and G pairs with C, although small regions (e.g., less than about 3 bases) of mismatch, insertion, or deleted sequence may be present.

The term "sequence identity" or "identity" in the context of two nucleic acid sequences refers to the residues in the two sequences which are the same when aligned for maximum correspondence over a specified comparison window, and can take into consideration additions, deletions and substitutions.

The term "substantial identity" or "homologous" in their various grammatical forms in the context of polynucleotides generally means that a polynucleotide comprises a sequence that has a desired identity, for example, at least 60%, at least 70%, at least 80%, at least 90% and at least 95% sequence identity, compared to a reference sequence. Another indication that nucleotide sequences are substantially identical is if two molecules hybridize to each other under stringent conditions.

As used herein, the term "bound" can be used herein to indicate direct or indirect attachment. In the context of chemical structures, "bound" (or "bonded") may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

The terms "isolated" and "purified" refer to isolation of a substance (such as mRNA or protein) such that the substance comprises a substantial portion of the sample in which it resides, i.e., greater than the substance is typically found in its natural or un-isolated state. Typically, a substantial portion of the sample comprises, e.g., greater than about 1%, greater than about 2%, greater than about 5%, greater than about 10%, greater than about 20%, greater than about 50%, or more, usually up to about 90% to 100% of the sample. For example, a sample of an isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

The term "biological sample" as used herein refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include, but are not limited to, cell lysate, a cell culture, a cell line, a tissue, oral tissue, gastrointestinal tissue, an organ, an organelle, a biological fluid, a blood sample, a urine sample, a skin sample, and the like. In certain embodiments, biological samples include, but are not limited to, whole blood, partially purified blood, PBMCs, tissue biopsies, and the like.

The term "analyte" as used herein, refers to a known or unknown component of a sample.

The term "capture agent," as used herein, refers to an agent that binds an mRNA or protein through an interaction that is sufficient to permit the agent to bind and concentrate the mRNA or protein from a homogeneous mixture.

The term "probe," as used herein, refers to a capture agent that is directed to a specific target nucleic acid (e.g., mRNA) biomarker sequence. Accordingly, each probe of a probe set has a respective target nucleic acid (e.g., mRNA) biomarker. A probe/target nucleic acid duplex is a structure formed by hybridizing a probe to its target nucleic acid biomarker.

The term "nucleic acid probe" or "oligonucleotide probe" refers to a nucleic acid capable of binding to a target nucleic acid of complementary sequence, such as an mRNA biomarker, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. In certain embodiments, the probes are directly labeled with an isotope, chromophore, lumiphore, chromogen, or biotin. By assaying for the presence (or absence) of the probe, one can detect the presence (or absence) of a target nucleic acid biomarker of interest.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term "stringent assay conditions" generally refers to the combination of hybridization and wash conditions.

A "label" or a "detectable moiety" in reference to a nucleic acid, refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid can be detected by detecting the presence of the label bound to the nucleic acid.

The terms "polymerase chain reaction" or "PCR," as used herein, generally refers to a procedure wherein small amounts of a nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, NY, 1989).

The term "cycle number" or "CT" when used herein in reference to a PCR method, refers to the PCR cycle number at which the fluorescence level passes a given set threshold level. The CT measurement can be used, for example, to approximate levels of mRNA in an original sample. The CT measurement is often used in terms of "dCT" or the "difference in the CT" score, when the CT of one nucleic acid is subtracted from the CT of another nucleic acid.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "cereblon" or "CRBN" refers to a protein encoded by the CRBN gene in humans, or a variant thereof. The term "CRBN variant" is intended to include proteins substantially homologous to a native CRBN, i.e., proteins having one or more naturally or non-naturally occurring amino acid deletions, insertions, or substitutions (e.g., CRBN derivatives, homologs, and fragments), as compared to the amino acid sequence of a native CRBN. The amino acid sequence of a CRBN variant is at least about 80% identical, at least about 90% identical, or at least about 95% identical to a native CRBN.

The term "CRBN-mediated disease, disorder, or condition" refers to any disease, disorder, and/or condition that is completely or partially caused by or is the direct or indirect result of CRBN, or a substrate thereof.

The term "baseline level," when used in the context of CRBN expression, refers to the cumulative expression level of all isoforms of CRBN in a biological sample. For example, if there is only one isoform of CRBN present in a biological sample, this isoform of CRBN has a baseline level. If there are two equal amount isoforms of CRBN present in a biological sample, each isoform of CRBN is 50% of a baseline level.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning; A Laboratory Manual* (2d ed.), 1989; Glover, ed. *DNA Cloning*, Volumes I and II, 1985; Gait, ed., *Oligonucleotide Synthesis*, 1984; Hames & Higgins, eds. *Nucleic Acid Hybridization*, 1984; Hames &. Higgins, eds., *Transcription and Translation*, 1984; Freshney, ed., *Animal Cell Culture*, 1986; *Immobilized Cells and Enzymes*, IRL Press, 1986; *Immunochemical Methods in Cell and Molecular Biology* (Academic Press, London); Scopes, *Protein Purification: Principles and Practice* (2d ed.; Springer Verlag, N.Y.), 1987; and Weir and Blackwell, eds. *Handbook of Experimental Immunology*, Volumes I-IV, 1986.

5.3 CRBN ISOFORMS AND NUCLEIC ACID THEREOF

In one embodiment, provided herein is an isolated, synthetic, or recombinant polypeptide of an isoform of CRBN, wherein the isoform has a deletion of amino acid residues 126 to 175 (Δ1126-175) or amino acid residues 176 to 228 (Δ1176-228) in the full-length amino acid sequence of CRBN. In certain embodiments, the 126-175 and 176-228 amino acid segments are encoded by exons 4 and 5 of the CRBN gene, respectively. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 3 of CRBN, wherein the isoform has a deletion of amino acids 58 to 175 (Δ58-175) in the full-length amino acid sequence of CRBN. In certain embodiments, the 58-125 and 126-175 amino acid segments are encoded by exons 3 and 4 of the CRBN gene, respectively.

In another embodiment, the polypeptide is isoform 4 of CRBN, wherein the isoform has a deletion of amino acids 126 to 316 (Δ126-316) in the full-length amino acid sequence of CRBN. In certain embodiments, the 126-175, 176-228, 229-249, 250-278, and 279-316 amino acid segments are encoded by exons 4, 5, 6, 7, and 8 of the CRBN gene, respectively.

In yet another embodiment, the polypeptide is isoform 5 of CRBN, wherein the isoform has deletions of amino acid residues 176 to 278 (Δ176-278) and amino acid residues 317 to 382 (Δ317-382) in the full-length amino acid sequence of CRBN. In certain embodiments, the 176-228, 229-249, 250-278, 317-338, and 339-382 amino acid segments are encoded by exons 5, 6, 7, 9, and 10 of the CRBN gene, respectively.

In yet another embodiment, the polypeptide is isoform 6 of CRBN, wherein the isoform has a deletion of amino acids 126 to 382 (Δ126-382) in the full-length amino acid sequence of CRBN. In certain embodiments, the 126-175, 176-228, 229-249, 250-278, 279-316, 317-338, and 339-382 amino acid segments are encoded by exons 4, 5, 6, 7, 8, 9, and 10 of the CRBN gene, respectively.

In still another embodiment, the polypeptide is isoform 7 of CRBN, wherein the isoform has a deletion of amino acids 23 to 338 (Δ23-338) in the full-length amino acid sequence of CRBN. In certain embodiments, the 23-57, 56-125, 126-175, 176-228, 229-249, 250-278, 279-316, and 317-338 amino acid segments are encoded by exons 2, 3, 4, 5, 6, 7, 8, and 9 of the CRBN gene, respectively.

In another embodiment, provided herein is an isolated, synthetic, or recombinant polypeptide of an isoform of CRBN, wherein the isoform has a deletion of amino acid residues 23 to 57 (Δ23-57) in the full-length amino acid sequence of CRBN. In certain embodiments, the 23-57 amino acid segment is encoded by exon 2 of the CRBN gene. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant polypeptide of an isoform of CRBN, wherein the isoform has a deletion of amino acid residues 58 to 125 (Δ58-125) in the full-length amino acid sequence of CRBN. In certain embodiments, the 58-125 amino acid segment is encoded by exon 3 of the CRBN gene. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 3 of CRBN, wherein the isoform has a deletion of amino acids 58 to 175 (Δ58-175) in the full-length amino acid sequence of CRBN.

In another embodiment, the polypeptide is isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant polypeptide of an isoform of CRBN, wherein the isoform has a deletion of amino acid residues 126 to 175 (Δ1126-175) in the full-length amino acid sequence of CRBN. In certain embodiments, the 126-175 amino acid segment is encoded by exon 4 of the CRBN gene. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 3 of CRBN, wherein the isoform has a deletion of amino acids 58 to 175 (Δ58-175) in the full-length amino acid sequence of CRBN.

In another embodiment, the polypeptide is isoform 4 of CRBN, wherein the isoform has a deletion of amino acids 126 to 316 (Δ126-316) in the full-length amino acid sequence of CRBN.

In yet another embodiment, the polypeptide is isoform 6 of CRBN, wherein the isoform has a deletion of amino acids 126 to 382 (Δ126-382) in the full-length amino acid sequence of CRBN.

In still another embodiment, the polypeptide is isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant polypeptide of an isoform of CRBN, wherein the isoform has a deletion of amino acid residues 176 to 228 (Δ176-228) in the full-length amino acid sequence of CRBN. In certain embodiments, the 176-228 amino acid segment is encoded by exon 5 of the CRBN gene. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 4 of CRBN, wherein the isoform has a deletion of amino acids 126 to 316 (Δ126-316) in the full-length amino acid sequence of CRBN.

In another embodiment, the polypeptide is isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the polypeptide is isoform 6 of CRBN, wherein the isoform has a deletion of amino acids 126 to 382 (Δ126-382) in the full-length amino acid sequence of CRBN.

In still another embodiment, the polypeptide is isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant polypeptide of an isoform of CRBN, wherein the isoform has a deletion of amino acid residues 229 to 249 (Δ229-249) in the full-length amino acid sequence of CRBN. In some embodiments, the polypeptide is an isolated polypeptide. In some embodiments, the polypeptide is a synthetic polypeptide. In some embodiments, the polypeptide is a recombinant polypeptide. In certain embodiments, the 229-249 amino acid segment is encoded by exon 6 of the CRBN gene. The sequence of amino acid residues 229 to 249 encoded by exon 6 is RKFHCANLTSWPRWLYSLYDA (SEQ ID NO: 8). As recognized by those skilled in the art, there are at least two isoforms of full length CRBN. One CRBN isoform contains 441 amino acids (SEQ ID NO: 9), and in such CRBN isoform exon 6 is amino acid residues 229 to 249 (SEQ ID NO: 8).

(SEQ ID NO: 8)
MAGEGDQQDAAHNMGNHLPLLPESEEEDEMEVEDQDSKEAKKPNII

NFDTSLPTSHTYLGADMEEFHGRTLHDDDSCQVIPVLPQVMMILIPG

QTLPLQLFHPQEVSMVRNLIQKDRTFAVLAYSNVQEREAQFGTTAEI

YAYREEQDFGIEIVKVKAIGRQRFKVLELRTQSDGIQQAKVQILPECV

LPSTMSAVQLESLNKCQIFPSKPVSREDQCSYKWWQKYQKRKFHCA

NLTSWPRWLYSLYDA

(SEQ ID NO: 9)
ETLMDRIKKQLREWDENLKDDSLPSNPIDFSYRVAACLPIDDVLRIQL

LKIGSAIQRLRCELDIMNKCTSLCCKQCQETEITTKNEIFSLSLCGPMA

AYVNPHGYVHETLTVYKACNLNLIGRPSTEHSWFPGYAWTVAQCKI

CASHIGWKFTATKKDMSPQKFWGLTRSALLPTIPDTEDEISPDKVILCL

A second CRBN isoform contains 442 amino acids (SEQ ID NO: 10). The second CRBN isoform contains an additional amino acid residue Ala (the 23$^{rd}$ amino acid residue of SEQ ID NO: 10). This Ala is absent from the first CRBN isoform (SEQ ID NO: 9). Thus, in the second CRBN isoform exon 6 is amino acid residues 230 to 250 (SEQ ID NO: 8).

(SEQ ID NO: 8)
MAGEGDQQDAAHNMGNHLPLLPAESEEEDEMEVEDQDSKEAKKPN

IINFDTSLPTSHTYLGADMEEFHGRTLHDDDSCQVIPVLPQVMMILIP

GQTLPLQLFHPQEVSMVRNLIQKDRTFAVLAYSNVQEREAQFGTTAE

IYAYREEQDFGIEIVKVKAIGRQRFKVLELRTQSDGIQQAKVQILPEC

VLPSTMSAVQLESLNKCQIFPSKPVSREDQCSYKWWQKYQKRKFHC

ANLTSWPRWLYSLYDA

(SEQ ID NO: 10)
ETLMDRIKKQLREWDENLKDDSLPSNPIDFSYRVAACLPIDDVLRIQL

LKIGSAIQRLRCELDIMNKCTSLCCKQCQETEITTKNEIFSLSLCGPMA

AYVNPHGYVHETLTVYKACNLNLIGRPSTEHSWFPGYAWTVAQCKI

CASHIGWKFTATKKDMSPQKFWGLTRSALLPTIPDTEDEISPDKVILCL

As shown, in both full length isoforms, exon 6 has the same sequence: RKFHCANLTSWPRWLYSLYDA (SEQ ID NO: 8). Thus, it should be appreciated that when "exon 6" is referred to in the present disclosure, it means either amino acid residues 229 to 249 of SEQ ID NO: 9 or amino acid residues 230 to 250 of SEQ ID NO: 10 depending on the isoforms of CRBN protein. Similarly, "amino acid residues 229 to 249" and "amino acid residues 230 to 250" are used interchangeably, and should be understood to mean exon 6 of CRBN protein, having a sequence of SEQ ID NO: 8.

Figure 10:
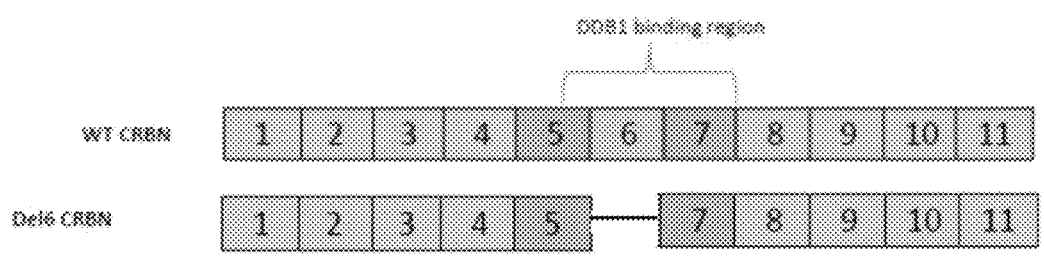
FIG. 10 illustrates the exons of wild type CRBN and an isoform of CRBN comprising an exon 6 deletion.

In one aspect, the present invention is partially based on the discovery that an isoform of CRBN comprising an exon 6 deletion and provides a mechanism for resistance to antiproliferative effects of immunomodulatory treatment compounds, such as pamalidomide. Thus, in some embodiments, provided herein is an isolated, synthetic, or recombinant polypeptide of an isoform of CRBN, wherein the isoform has a single exon 6 deletion in the full-length amino acid sequence of CRBN. In some embodiments, the polypeptide is an isolated polypeptide. In some embodiments, the polypeptide is a synthetic polypeptide. In some embodiments, the polypeptide is a recombinant polypeptide. As used in the present disclosure, the term "an isoform of CRBN comprising an exon 6 deletion" is an isoform of CRBN that contains only one exon deletion, and thus the rest of the exons (exons 1-5 and 7-11) of CRBN are present in the isoform, as illustrated in FIG. 10.

In some embodiments, exon 6 of CRBN encodes 229-249 amino acid segment (SEQ ID NO: 8) in a full length amino acid sequence of CRBN (SEQ ID NO: 9). The amino acid sequence having a single exon 6 deletion from the full length amino acid sequence of CRBN (SEQ ID NO: 9) is shown below:

(SEQ ID NO: 11)
MAGEGDQQDAAHNMGNHLPLLPESEEEDEMEVEDQDSKEAKKPNII

NFDTSLPTSHTYLGADMEEFHGRTLHDDDSCQVIPVLPQVMMILIPG

QTLPLQLFHPQEVSMVRNLIQKDRTFAVLAYSNVQEREAQFGTTAEI

YAYREEQDFGIEIVKVKAIGRQRFKVLELRTQSDGIQQAKVQILPECV

LPSTMSAVQLESLNKCQIFPSKPVSREDQCSYKWWQKYQKETLMDR

IKKQLREWDENLKDDSLPSNPIDFSYRVAACLPIDDVLRIQLLKIGSAI

QRLRCELDIMNKCTSLCCKQCQETEITTKNEIFSLSLCGPMAAYVNPH

-continued
GYVHETLTVYKACNLNLIGRPSTEHSWFPGYAWTVAQCKICASHIG

WKFTATKKDMSPQKFWGLTRSALLPTIPDTEDEISPDKVILCL

In some embodiments, exon 6 of CRBN encodes 230-250 amino acid segment (SEQ ID NO: 8) in a full length amino acid sequence of CRBN (SEQ ID NO: 10). The amino acid sequence having a single exon 6 deletion from the full length amino acid sequence of CRBN (SEQ ID NO: 10) is shown below:

(SEQ ID NO: 12)
MAGEGDQQDAAHNMGNHLPLLPAESEEEDEMEVEDQDSKEAKKPN

IINFDTSLPTSHTYLGADMEEFHGRTLHDDDSCQVIPVLPQVMMILIP

GQTLPLQLFHPQEVSMVRNLIQKDRTFAVLAYSNVQEREAQFGTTAE

IYAYREEQDFGIEIVKVKAIGRQRFKVLELRTQSDGIQQAKVQILPEC

VLPSTMSAVQLESLNKCQIFPSKPVSREDQCSYKWWQKYQKETLMD

RIKKQLREWDENLKDDSLPSNPIDFSYRVAACLPIDDVLRIQLLKIGS

AIQRLRCELDIMNKCTSLCCKQCQETEITTKNEIFSLSLCGPMAAYVN

PHGYVHETLTVYKACNLNLIGRPSTEHSWFPGYAWTVAQCKICASHI

GWKFTATKKDMSPQKFWGLTRSALLPTIPDTEDEISPDKVILCL

In one embodiment, the polypeptide is isoform 4 of CRBN, wherein the isoform has a deletion of amino acids 126 to 316 (Δ126-316) in the full-length amino acid sequence of CRBN.

In another embodiment, the polypeptide is isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the polypeptide is isoform 6 of CRBN, wherein the isoform has a deletion of amino acids 126 to 382 (Δ126-382) in the full-length amino acid sequence of CRBN.

In still another embodiment, the polypeptide is isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant polypeptide of an isoform of CRBN, wherein the isoform has a deletion of amino acid residues 250 to 278 (Δ250-278) in the full-length amino acid sequence of CRBN. In certain embodiments, the 250-278 amino acid segment is encoded by exon 7 of the CRBN gene. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 4 of CRBN, wherein the isoform has a deletion of amino acids 126 to 316 (Δ126-316) in the full-length amino acid sequence of CRBN.

In another embodiment, the polypeptide is isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the polypeptide is isoform 6 of CRBN, wherein the isoform has a deletion of amino acids 126 to 382 (Δ126-382) in the full-length amino acid sequence of CRBN.

In still another embodiment, the polypeptide is isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant polypeptide of an isoform of CRBN, wherein the isoform has a deletion of amino acid residues 279 to 316 (Δ279-316) in the full-length amino acid sequence of CRBN. In certain embodiments, the 279-316 amino acid segment is encoded by exon 8 of the CRBN gene. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 4 of CRBN, wherein the isoform has a deletion of amino acids 126 to 316 (Δ126-316) in the full-length amino acid sequence of CRBN.

In another embodiment, the polypeptide is isoform 6 of CRBN, wherein the isoform has a deletion of amino acids 126 to 382 (Δ126-382) in the full-length amino acid sequence of CRBN.

In yet another embodiment, the polypeptide is isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant polypeptide of an isoform of CRBN, wherein the isoform has a deletion of amino acid residues 317 to 338 (Δ317-338) in the full-length amino acid sequence of CRBN. In certain embodiments, the 317-338 amino acid segment is encoded by exon 9 of the CRBN gene. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 5 of CRBN, wherein the isoform has deletions of amino acids 176 to 278 (Δ176-278) and amino acids 317 to 382 (Δ317-382) in the full-length amino acid sequence of CRBN.

In another embodiment, the polypeptide is isoform 6 of CRBN, wherein the isoform has a deletion of amino acids 126 to 382 (Δ126-382) in the full-length amino acid sequence of CRBN.

In yet another embodiment, the polypeptide is isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant polypeptide of an isoform of CRBN, wherein the isoform has a deletion of amino acid residues 339 to 382 (Δ339-382) in the full-length amino acid sequence of CRBN. In certain embodiments, the 339-382 amino acid segment is encoded by exon 10 of the CRBN gene. In some embodiments, the polypeptide is an isolated polypeptide. In some embodiments, the polypeptide is a synthetic polypeptide. In some embodiments, the polypeptide is a recombinant polypeptide.

In one embodiment, the polypeptide is isoform 2 of CRBN, wherein the isoform has a deletion of amino acids 339 to 382 (Δ339-382) in the full-length amino acid sequence of CRBN.

In another embodiment, the polypeptide is isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the polypeptide is isoform 6 of CRBN, wherein the isoform has a deletion of amino acids 126 to 382 (Δ126-382) in the full-length amino acid sequence of CRBN.

In yet another embodiment, provided herein is an isolated, synthetic, or recombinant polypeptide of an isoform CRBN, comprising from about 100 to about 400 amino acid residues. In some embodiments, the polypeptide is an isolated polypeptide. In some embodiments, the polypeptide is a synthetic polypeptide. In some embodiments, the polypeptide is a recombinant polypeptide. In one embodiment, the polypeptide is isoform 2 of CRBN, which contains about 398 amino acid residues. In another embodiment, the polypeptide is isoform 3 of CRBN, which contains about 274 amino acid residues. In yet another embodiment, the polypeptide is isoform 4 of CRBN. In yet another embodiment, the polypeptide is isoform 5 of CRBN, which contains about 193 amino acid residues. In yet another embodiment, the polypeptide is isoform 6 of CRBN. In still another embodiment, the polypeptide is isoform 7 of CRBN.

In still another embodiment, provided herein is an isolated, synthetic, or recombinant polypeptide of an isoform of CRBN, comprising from about 100 to about 300 amino acid residues. In some embodiments, the polypeptide is an isolated polypeptide. In some embodiments, the polypeptide is a synthetic polypeptide. In some embodiments, the polypeptide is a recombinant polypeptide. In one embodiment, the polypeptide is isoform 3 of CRBN, which contains about 274 amino acid residues. In another embodiment, the polypeptide is isoform 4 of CRBN. In yet another embodiment, the polypeptide is isoform 5 of CRBN, which contains about 193 amino acid residues. In yet another embodiment, the polypeptide is isoform 6 of CRBN. In still another embodiment, the polypeptide is isoform 7 of CRBN.

In one embodiment, provided herein is an isolated, synthetic, or recombinant nucleic acid encoding an isoform of CRBN provided herein. In some embodiments, provided herein is an isolated nucleic acid encoding an isoform of CRBN provided herein. In some embodiments, provided herein is a synthetic nucleic acid encoding an isoform of CRBN provided herein. In some embodiments, provided herein is a recombinant nucleic acid encoding an isoform of CRBN provided herein.

Thus, in one embodiment, provided herein is an isolated, synthetic, or recombinant nucleic acid encoding an isoform of CRBN, wherein the isoform has a deletion of amino acid residues 126 to 175 (Δ1126-175) or amino acid residues 176 to 228 (Δ176-228) in the full-length amino acid sequence of CRBN. In certain embodiments, the 126-175 and 176-228 amino acid segments are encoded by exons 4 and 5 of the CRBN gene, respectively.

In one embodiment, the nucleic acid is one encoding isoform 3 of CRBN, wherein the isoform has a deletion of amino acids 58 to 175 (Δ58-175) in the full-length amino acid sequence of CRBN.

In another embodiment, the nucleic acid is one encoding isoform 4 of CRBN, wherein the isoform has a deletion of amino acids 126 to 316 (Δ126-316) in the full-length amino acid sequence of CRBN.

In yet another embodiment, the nucleic acid is one encoding isoform 5 of CRBN, wherein the isoform has deletions of amino acid residues 176 to 278 (Δ176-278) and amino acid residues 317 to 382 (Δ317-382) in the full-length amino acid sequence of CRBN.

In yet another embodiment, the nucleic acid is one encoding isoform 6 of CRBN, wherein the isoform has a deletion of amino acids 126 to 382 (Δ126-382) in the full-length amino acid sequence of CRBN.

In still another embodiment, the nucleic acid is one encoding isoform 7 of CRBN, wherein the isoform has a deletion of amino acids 23 to 338 (Δ23-338) in the full-length amino acid sequence of CRBN.

In another embodiment, provided herein is an isolated, synthetic, or recombinant nucleic acid encoding an isoform of CRBN, wherein the isoform has a deletion of amino acid residues 23 to 57 (Δ23-57) in the full-length amino acid sequence of CRBN. In certain embodiments, the 23-57 amino acid segment is encoded by exon 2 of the CRBN gene.

In one embodiment, the nucleic acid is one encoding the nucleic acid is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant nucleic acid encoding an isoform of CRBN, wherein the isoform has a deletion of amino acid residues 58 to 125 (Δ58-125) in the full-length amino acid sequence of CRBN. In certain embodiments, the 58-125 amino acid segment is encoded by exon 3 of the CRBN gene.

In one embodiment, the nucleic acid is one encoding isoform 3 of CRBN, wherein the isoform has a deletion of amino acids 58 to 175 (Δ58-175) in the full-length amino acid sequence of CRBN.

In another embodiment, the nucleic acid is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant nucleic acid encoding an isoform of CRBN, wherein the isoform has a deletion of amino acid residues 126 to 175 (Δ126-175) in the full-length amino acid sequence of CRBN. In certain embodiments, the 126-175 amino acid segment is encoded by exon 4 of the CRBN gene.

In one embodiment, the nucleic acid is one encoding isoform 3 of CRBN, wherein the isoform has a deletion of amino acids 58 to 175 (Δ58-175) in the full-length amino acid sequence of CRBN.

In another embodiment, the nucleic acid is one encoding isoform 4 of CRBN, wherein the isoform has a deletion of amino acids 126 to 316 (Δ126-316) in the full-length amino acid sequence of CRBN.

In yet another embodiment, the nucleic acid is one encoding isoform 6 of CRBN, wherein the isoform has a deletion of amino acids 126 to 382 (Δ126-382) in the full-length amino acid sequence of CRBN.

In still another embodiment, the nucleic acid is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant nucleic acid encoding of an isoform of CRBN, wherein the isoform has a deletion of amino acid residues 176 to 228 (Δ176-228) in the full-length amino acid sequence of CRBN. In certain embodiments, the 176-228 amino acid segment is encoded by exon 5 of the CRBN gene.

In one embodiment, the nucleic acid is one encoding isoform 4 of CRBN, wherein the isoform has a deletion of amino acids 126 to 316 (Δ126-316) in the full-length amino acid sequence of CRBN.

In another embodiment, the nucleic acid is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the nucleic acid is one encoding isoform 6 of CRBN, wherein the isoform has a deletion of amino acids 126 to 382 (Δ126-382) in the full-length amino acid sequence of CRBN.

In still another embodiment, the nucleic acid is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant nucleic acid encoding an isoform of CRBN, wherein the isoform has a deletion of amino acid residues 229 to 249 (Δ229-249) (SEQ ID NO: 8) in the full-length amino acid sequence of CRBN. In certain embodiments, the 229-249 amino acid segment is encoded by exon 6 of the CRBN gene.

In yet another embodiment, provided herein is an isolated, synthetic, or recombinant nucleic acid encoding an isoform of CRBN comprising an exon 6 deletion in the full-length amino acid sequence of CRBN. In some embodiments, exon 6 of CRBN encodes 229-249 amino acid segment of a full length isoform of CRBN having a sequence of SEQ ID NO: 9. In some embodiments, exon 6 of CRBN encodes 230-250 amino acid segment of a full length isoform of CRBN having a sequence of SEQ ID NO: 10.

In one embodiment, the nucleic acid is one encoding isoform 4 of CRBN, wherein the isoform has a deletion of amino acids 126 to 316 (Δ126-316) in the full-length amino acid sequence of CRBN.

In another embodiment, the nucleic acid is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the nucleic acid is one encoding isoform 6 of CRBN, wherein the isoform has a deletion of amino acids 126 to 382 (Δ126-382) in the full-length amino acid sequence of CRBN.

In still another embodiment, the nucleic acid is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant nucleic acid encoding an isoform of CRBN, wherein the isoform has a deletion of amino acid residues 250 to 278 (Δ250-278) in the full-length amino acid sequence of CRBN. In certain embodiments, the 250-278 amino acid segment is encoded by exon 7 of the CRBN gene.

In one embodiment, the nucleic acid is one encoding isoform 4 of CRBN, wherein the isoform has a deletion of amino acids 126 to 316 (Δ126-316) in the full-length amino acid sequence of CRBN.

In another embodiment, the nucleic acid is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the nucleic acid is one encoding isoform 6 of CRBN, wherein the isoform has a deletion of amino acids 126 to 382 (Δ126-382) in the full-length amino acid sequence of CRBN.

In still another embodiment, the nucleic acid is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant nucleic acid encoding an isoform of CRBN, wherein the isoform has a deletion of amino acid residues 279 to 316 (Δ279-316) in the full-length amino acid sequence of CRBN. In certain embodiments, the 279-316 amino acid segment is encoded by exon 8 of the CRBN gene.

In one embodiment, the nucleic acid is one encoding isoform 4 of CRBN, wherein the isoform has a deletion of amino acids 126 to 316 (Δ126-316) in the full-length amino acid sequence of CRBN.

In another embodiment, the nucleic acid is one encoding isoform 6 of CRBN, wherein the isoform has a deletion of amino acids 126 to 382 (Δ126-382) in the full-length amino acid sequence of CRBN.

In yet another embodiment, the nucleic acid is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant nucleic acid encoding an isoform of CRBN, wherein the isoform has a deletion of amino acid residues 317 to 338 (Δ317-338) in the full-length amino acid sequence of CRBN. In certain embodiments, the 317-338 amino acid segment is encoded by exon 9 of the CRBN gene.

In one embodiment, the nucleic acid is one encoding isoform 5 of CRBN, wherein the isoform has deletions of amino acids 176 to 278 (Δ176-278) and amino acids 317 to 382 (Δ317-382) in the full-length amino acid sequence of CRBN.

In another embodiment, the nucleic acid is one encoding isoform 6 of CRBN, wherein the isoform has a deletion of amino acids 126 to 382 (Δ126-382) in the full-length amino acid sequence of CRBN.

In yet another embodiment, the nucleic acid is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant nucleic acid encoding an isoform of CRBN, wherein the isoform has a deletion of amino acid residues 339 to 382 (Δ339-382) in the full-length amino acid sequence of CRBN. In certain embodiments, the 339-382 amino acid segment is encoded by exon 10 of the CRBN gene.

In one embodiment, the nucleic acid is one encoding isoform 2 of CRBN, wherein the isoform has a deletion of amino acids 339 to 382 (Δ339-382) in the full-length amino acid sequence of CRBN.

In another embodiment, the nucleic acid is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the nucleic acid is one encoding isoform 6 of CRBN, wherein the isoform has a deletion of amino acids 126 to 382 (Δ126-382) in the full-length amino acid sequence of CRBN.

In yet another embodiment, provided herein is an isolated, synthetic, or recombinant nucleic acid encoding an isoform CRBN, comprising from about 300 to about 1200 base pairs. In one embodiment, the nucleic acid is one encoding isoform 2 of CRBN, which contains about 1197 base pairs. In another embodiment, the nucleic acid is one encoding isoform 3 of CRBN, which contains about 825 base pairs. In yet another embodiment, the nucleic acid is one encoding isoform 4 of CRBN. In yet another embodiment, the nucleic acid is one encoding isoform 5 of CRBN, which contains about 582 base pairs. In yet another embodiment, the nucleic acid is one encoding isoform 6 of CRBN. In still another embodiment, the nucleic acid is one encoding isoform 7 of CRBN.

In still another embodiment, provided herein is an isolated, synthetic, or recombinant nucleic acid encoding an isoform of CRBN, comprising from about 300 to about 900 base pairs. In one embodiment, the nucleic acid is one encoding isoform 3 of CRBN, which contains about 825 base pairs. In another embodiment, the nucleic acid is one encoding isoform 4 of CRBN. In yet another embodiment, the nucleic acid is one encoding isoform 5 of CRBN, which contains about 582 base pairs. In yet another embodiment, the nucleic acid is one encoding isoform 6 of CRBN. In still another embodiment, the nucleic acid is one encoding isoform 7 of CRBN.

In certain embodiments, the nucleic acid is a DNA. In certain embodiments, the nucleic acid is an RNA. In certain embodiments, the nucleic acid is a cDNA. In certain embodiments, the nucleic acid is an mRNA.

Thus, in one embodiment, provided herein is an isolated, synthetic, or recombinant DNA encoding an isoform of CRBN, wherein the isoform has a deletion of amino acid residues 126 to 175 (Δ1126-175) or amino acid residues 176 to 228 (Δ1176-228) in the full-length amino acid sequence of CRBN. In certain embodiments, the 126-175 and 176-228 amino acid segments are encoded by exons 4 and 5 of the CRBN gene, respectively.

In one embodiment, the DNA is one encoding isoform 3 of CRBN, wherein the isoform has a deletion of amino acids 58 to 175 (Δ58-175) in the full-length amino acid sequence of CRBN.

In another embodiment, the DNA is one encoding isoform 4 of CRBN, wherein the isoform has a deletion of amino acids 126 to 316 (Δ126-316) in the full-length amino acid sequence of CRBN.

In yet another embodiment, the DNA is one encoding isoform 5 of CRBN, wherein the isoform has deletions of amino acid residues 176 to 278 (Δ176-278) and amino acid residues 317 to 382 (Δ317-382) in the full-length amino acid sequence of CRBN.

In yet another embodiment, the DNA is one encoding isoform 6 of CRBN, wherein the isoform has a deletion of amino acids 126 to 382 (Δ126-382) in the full-length amino acid sequence of CRBN.

In still another embodiment, the DNA is one encoding isoform 7 of CRBN, wherein the isoform has a deletion of amino acids 23 to 338 (Δ23-338) in the full-length amino acid sequence of CRBN.

In another embodiment, provided herein is an isolated, synthetic, or recombinant DNA encoding an isoform of CRBN, wherein the isoform has a deletion of amino acid residues 23 to 57 (Δ23-57) in the full-length amino acid sequence of CRBN. In certain embodiments, the 23-57 amino acid segment is encoded by exon 2 of the CRBN gene.

In one embodiment, the DNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant DNA encoding an isoform of CRBN, wherein the isoform has a deletion of amino acid residues 58 to 125 (Δ58-125) in the full-length amino acid sequence of CRBN. In certain embodiments, the 58-125 amino acid segment is encoded by exon 3 of the CRBN gene.

In one embodiment, the DNA is one encoding isoform 3 of CRBN, wherein the isoform has a deletion of amino acids 58 to 175 (Δ58-175) in the full-length amino acid sequence of CRBN.

In another embodiment, the DNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant DNA encoding an isoform of CRBN, wherein the isoform has a deletion of amino acid residues 126 to 175 (Δ126-175) in the full-length amino acid sequence of CRBN. In certain embodiments, the 126-175 amino acid segment is encoded by exon 4 of the CRBN gene.

In one embodiment, the DNA is one encoding isoform 3 of CRBN, wherein the isoform has a deletion of amino acids 58 to 175 (Δ58-175) in the full-length amino acid sequence of CRBN.

In another embodiment, the DNA is one encoding isoform 4 of CRBN, wherein the isoform has a deletion of amino acids 126 to 316 (Δ126-316) in the full-length amino acid sequence of CRBN.

In yet another embodiment, the DNA is one encoding isoform 6 of CRBN, wherein the isoform has a deletion of amino acids 126 to 382 (Δ126-382) in the full-length amino acid sequence of CRBN.

In still another embodiment, the DNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant DNA encoding of an isoform of CRBN, wherein the isoform has a deletion of amino acid residues 176 to 228 (Δ176-228) in the full-length amino acid sequence of CRBN. In certain embodiments, the 176-228 amino acid segment is encoded by exon 5 of the CRBN gene.

In one embodiment, the DNA is one encoding isoform 4 of CRBN, wherein the isoform has a deletion of amino acids 126 to 316 (Δ126-316) in the full-length amino acid sequence of CRBN.

In another embodiment, the DNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the DNA is one encoding isoform 6 of CRBN, wherein the isoform has a deletion of amino acids 126 to 382 (Δ126-382) in the full-length amino acid sequence of CRBN.

In still another embodiment, the DNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant DNA encoding an isoform of CRBN, wherein the isoform has a deletion of amino acid residues 229 to 249 (Δ229-249) (SEQ ID NO: 8) in the full-length amino acid sequence of CRBN. In certain embodiments, the 229-249 amino acid segment is encoded by exon 6 of the CRBN gene.

In yet another embodiment, provided herein is an isolated, synthetic, or recombinant DNA encoding an isoform of CRBN comprising an exon 6 deletion in the full-length amino acid sequence of CRBN. In some embodiments, the full-length amino acid sequence of CRBN has a sequence of SEQ ID NO: 9, and the isoform of CRBN comprising an exon 6 deletion in the full-length amino acid sequence of CRBN has a sequence of SEQ ID NO: 11. In some embodiments, the full-length amino acid sequence of CRBN has a sequence of SEQ ID NO: 10, and the isoform of CRBN comprising an exon 6 deletion in the full-length amino acid sequence of CRBN has a sequence of SEQ ID NO: 12.

In one embodiment, the DNA is one encoding isoform 4 of CRBN, wherein the isoform has a deletion of amino acids 126 to 316 (Δ126-316) in the full-length amino acid sequence of CRBN.

In another embodiment, the DNA is one encoding isoform 5 of CRBN, wherein the isoform has deletions of amino acids 176 to 278 (Δ1176-278) and amino acids 317 to 382 (Δ1317-382) in the full-length amino acid sequence of CRBN.

In yet another embodiment, the DNA is one encoding isoform 6 of CRBN, wherein the isoform has a deletion of amino acids 126 to 382 (Δ126-382) in the full-length amino acid sequence of CRBN.

In still another embodiment, the DNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant DNA encoding an isoform of CRBN, wherein the isoform has a deletion of amino acid residues 250 to 278 (Δ250-278) in the full-length amino acid sequence of CRBN. In certain embodiments, the 250-278 amino acid segment is encoded by exon 7 of the CRBN gene.

In one embodiment, the DNA is one encoding isoform 4 of CRBN, wherein the isoform has a deletion of amino acids 126 to 316 (Δ126-316) in the full-length amino acid sequence of CRBN.

In another embodiment, the DNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the DNA is one encoding isoform 6 of CRBN, wherein the isoform has a deletion of amino acids 126 to 382 (Δ126-382) in the full-length amino acid sequence of CRBN.

In still another embodiment, the DNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant DNA encoding an isoform of CRBN, wherein the isoform has a deletion of amino acid residues 279 to 316(Δ279-316) in the full-length amino acid sequence of CRBN. In certain embodiments, the 279-316 amino acid segment is encoded by exon 8 of the CRBN gene.

In one embodiment, the DNA is one encoding isoform 4 of CRBN, wherein the isoform has a deletion of amino acids 126 to 316 (Δ126-316) in the full-length amino acid sequence of CRBN.

In another embodiment, the DNA is one encoding isoform 6 of CRBN, wherein the isoform has a deletion of amino acids 126 to 382 (Δ126-382) in the full-length amino acid sequence of CRBN.

In yet another embodiment, the DNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant DNA encoding an isoform of CRBN, wherein the isoform has a deletion of amino acid residues 317 to 338 (Δ317-338) in the full-length amino acid sequence of CRBN. In certain embodiments, the 317-338 amino acid segment is encoded by exon 9 of the CRBN gene.

In one embodiment, the DNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In another embodiment, the DNA is one encoding isoform 6 of CRBN, wherein the isoform has a deletion of amino acids 126 to 382 (Δ126-382) in the full-length amino acid sequence of CRBN.

In yet another embodiment, the DNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant DNA encoding an isoform of CRBN, wherein the isoform has a deletion of amino acid residues 339 to 382 (Δ339-382) in the full-length amino acid sequence of CRBN. In certain embodiments, the 339-382 amino acid segment is encoded by exon 10 of the CRBN gene.

In one embodiment, the DNA is one encoding isoform 2 of CRBN, wherein the isoform has a deletion of amino acids 339 to 382 (Δ339-382) in the full-length amino acid sequence of CRBN.

In another embodiment, the DNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the DNA is one encoding isoform 6 of CRBN, wherein the isoform has a deletion of amino acids 126 to 382 (Δ126-382) in the full-length amino acid sequence of CRBN.

In yet another embodiment, provided herein is an isolated, synthetic, or recombinant DNA encoding an isoform CRBN, comprising from about 300 to about 1200 base pairs. In one embodiment, the DNA is one encoding isoform 2 of CRBN, which contains about 1197 base pairs. In another embodiment, the DNA is one encoding isoform 3 of CRBN, which contains about 825 base pairs. In yet another embodiment, the DNA is one encoding isoform 4 of CRBN. In yet another embodiment, the DNA is one encoding isoform 5 of CRBN, which contains about 582 base pairs. In yet another embodiment, the DNA is one encoding isoform 6 of CRBN. In still another embodiment, the DNA is one encoding isoform 7 of CRBN.

In still another embodiment, provided herein is an isolated, synthetic, or recombinant DNA encoding an isoform of CRBN, comprising from about 300 to about 900 base pairs. In one embodiment, the DNA is one encoding isoform 3 of CRBN, which contains about 825 base pairs. In another embodiment, the DNA is one encoding isoform 4 of CRBN. In yet another embodiment, the DNA is one encoding isoform 5 of CRBN, which contains about 582 base pairs. In yet another embodiment, the DNA is one encoding isoform 6 of CRBN. In still another embodiment, the DNA is one encoding isoform 7 of CRBN.

In one embodiment, provided herein is an isolated, synthetic, or recombinant cDNA encoding an isoform of CRBN, wherein the isoform has a deletion of amino acid residues 126 to 175 (Δ126-175) or amino acid residues 176 to 228 (Δ176-228) in the full-length amino acid sequence of CRBN. In certain embodiments, the 126-175 and 176-228 amino acid segments are encoded by exons 4 and 5 of the CRBN gene, respectively.

In one embodiment, the cDNA is one encoding isoform 3 of CRBN, wherein the isoform has a deletion of amino acids 58 to 175 (Δ58-175) in the full-length amino acid sequence of CRBN.

In another embodiment, the cDNA is one encoding isoform 4 of CRBN, wherein the isoform has a deletion of amino acids 126 to 316 (Δ126-316) in the full-length amino acid sequence of CRBN.

In yet another embodiment, the cDNA is one encoding isoform 5 of CRBN, wherein the isoform has deletions of amino acid residues 176 to 278 (Δ176-278) and amino acid residues 317 to 382 (Δ317-382) in the full-length amino acid sequence of CRBN.

In yet another embodiment, the cDNA is one encoding isoform 6 of CRBN, wherein the isoform has a deletion of amino acids 126 to 382 (Δ126-382) in the full-length amino acid sequence of CRBN.

In still another embodiment, the cDNA is one encoding isoform 7 of CRBN, wherein the isoform has a deletion of amino acids 23 to 338 (Δ23-338) in the full-length amino acid sequence of CRBN.

In another embodiment, provided herein is an isolated, synthetic, or recombinant cDNA encoding an isoform of CRBN, wherein the isoform has a deletion of amino acid residues 23 to 57 (Δ23-57) in the full-length amino acid sequence of CRBN. In certain embodiments, the 23-57 amino acid segment is encoded by exon 2 of the CRBN gene.

In one embodiment, the cDNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant cDNA encoding an isoform of CRBN, wherein the isoform has a deletion of amino acid residues 58 to 125 (Δ58-125) in the full-length amino acid sequence of CRBN. In certain embodiments, the 58-125 amino acid segment is encoded by exon 3 of the CRBN gene.

In one embodiment, the cDNA is one encoding isoform 3 of CRBN, wherein the isoform has a deletion of amino acids 58 to 175 (Δ58-175) in the full-length amino acid sequence of CRBN.

In another embodiment, the cDNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant cDNA encoding an isoform of CRBN, wherein the isoform has a deletion of amino acid residues 126 to 175 (Δ1126-175) in the full-length amino acid sequence of CRBN. In certain embodiments, the 126-175 amino acid segment is encoded by exon 4 of the CRBN gene.

In one embodiment, the cDNA is one encoding isoform 3 of CRBN, wherein the isoform has a deletion of amino acids 58 to 175 (Δ58-175) in the full-length amino acid sequence of CRBN.

In another embodiment, the cDNA is one encoding isoform 4 of CRBN, wherein the isoform has a deletion of amino acids 126 to 316 (Δ126-316) in the full-length amino acid sequence of CRBN.

In yet another embodiment, the cDNA is one encoding isoform 6 of CRBN, wherein the isoform has a deletion of amino acids 126 to 382 (Δ126-382) in the full-length amino acid sequence of CRBN.

In still another embodiment, the cDNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant cDNA encoding of an isoform of CRBN, wherein the isoform has a deletion of amino acid residues 176 to 228 (Δ176-228) in the full-length amino acid sequence of CRBN. In certain embodiments, the 176-228 amino acid segment is encoded by exon 5 of the CRBN gene.

In one embodiment, the cDNA is one encoding isoform 4 of CRBN, wherein the isoform has a deletion of amino acids 126 to 316 (Δ126-316) in the full-length amino acid sequence of CRBN.

In another embodiment, the cDNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the cDNA is one encoding isoform 6 of CRBN, wherein the isoform has a deletion of amino acids 126 to 382 (Δ126-382) in the full-length amino acid sequence of CRBN.

In still another embodiment, the cDNA is one encoding isoform 7 of CRBN, wherein the isoform has a deletion of amino acids 23 to 338 (Δ123-338) in the full-length amino acid sequence of CRBN.

In yet another embodiment, provided herein is an isolated, synthetic, or recombinant cDNA encoding an isoform of CRBN, wherein the isoform has a deletion of amino acid residues 229 to 249 (Δ1229-249) (SEQ ID NO: 8) in the full-length amino acid sequence of CRBN. In certain embodiments, the 229-249 amino acid segment is encoded by exon 6 of the CRBN gene.

In yet another embodiment, provided herein is an isolated, synthetic, or recombinant cDNA encoding an isoform of CRBN comprising an exon 6 deletion in the full-length amino acid sequence of CRBN. In some embodiments, the full-length amino acid sequence of CRBN has a sequence of SEQ ID NO: 9, and the isoform of CRBN comprising an exon 6 deletion in the full-length amino acid sequence of CRBN has a sequence of SEQ ID NO: 11. In some embodiments, the full-length amino acid sequence of CRBN has a sequence of SEQ ID NO: 10, and the isoform of CRBN comprising an exon 6 deletion in the full-length amino acid sequence of CRBN has a sequence of SEQ ID NO: 12.

In one embodiment, the cDNA is one encoding isoform 4 of CRBN, wherein the isoform has a deletion of amino acids 126 to 316 (Δ126-316) in the full-length amino acid sequence of CRBN.

In another embodiment, the cDNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the cDNA is one encoding isoform 6 of CRBN, wherein the isoform has a deletion of amino acids 126 to 382 (Δ126-382) in the full-length amino acid sequence of CRBN.

In still another embodiment, the cDNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant cDNA encoding an isoform of CRBN, wherein the isoform has a deletion of amino acid residues 250 to 278 (Δ250-278) in the full-length amino acid sequence of CRBN. In certain embodiments, the 250-278 amino acid segment is encoded by exon 7 of the CRBN gene.

In one embodiment, the cDNA is one encoding isoform 4 of CRBN, wherein the isoform has a deletion of amino acids 126 to 316 (Δ126-316) in the full-length amino acid sequence of CRBN.

In another embodiment, the cDNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the cDNA is one encoding isoform 6 of CRBN, wherein the isoform has a deletion of amino acids 126 to 382 (Δ126-382) in the full-length amino acid sequence of CRBN.

In still another embodiment, the cDNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant cDNA encoding an isoform of CRBN, wherein the isoform has a deletion of amino acid residues 279 to 316 (Δ279-316) in the full-length amino acid sequence of CRBN. In certain embodiments, the 279-316 amino acid segment is encoded by exon 8 of the CRBN gene.

In one embodiment, the cDNA is one encoding isoform 4 of CRBN, wherein the isoform has a deletion of amino acids 126 to 316 (Δ126-316) in the full-length amino acid sequence of CRBN.

In another embodiment, the cDNA is one encoding isoform 6 of CRBN, wherein the isoform has a deletion of amino acids 126 to 382 (Δ126-382) in the full-length amino acid sequence of CRBN.

In yet another embodiment, the cDNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant cDNA encoding an isoform of CRBN, wherein the isoform has a deletion of amino acid residues 317 to 338 (Δ317-338) in the full-length amino acid sequence of CRBN. In certain embodiments, the 317-338 amino acid segment is encoded by exon 9 of the CRBN gene.

In one embodiment, the cDNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In another embodiment, the cDNA is one encoding isoform 6 of CRBN, wherein the isoform has a deletion of amino acids 126 to 382 (Δ126-382) in the full-length amino acid sequence of CRBN.

In yet another embodiment, the cDNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant cDNA encoding an isoform of CRBN, wherein the isoform has a deletion of amino acid residues 339 to 382 (Δ339-382) in the full-length amino acid sequence of CRBN. In certain embodiments, the 339-382 amino acid segment is encoded by exon 10 of the CRBN gene.

In one embodiment, the cDNA is one encoding isoform 2 of CRBN, wherein the isoform has a deletion of amino acids 339 to 382 (Δ339-382) in the full-length amino acid sequence of CRBN.

In another embodiment, the cDNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the cDNA is one encoding isoform 6 of CRBN, wherein the isoform has a deletion of amino acids 126 to 382 (Δ126-382) in the full-length amino acid sequence of CRBN.

In yet another embodiment, provided herein is an isolated, synthetic, or recombinant cDNA encoding an isoform CRBN, comprising from about 300 to about 1200 base pairs. In one embodiment, the cDNA is one encoding isoform 2 of CRBN, which contains about 1197 base pairs. In another embodiment, the cDNA is one encoding isoform 3 of CRBN, which contains about 825 base pairs. In yet another embodiment, the cDNA is one encoding isoform 4 of CRBN. In yet another embodiment, the cDNA is one encoding isoform 5 of CRBN, which contains about 582 base pairs. In yet another embodiment, the cDNA is one encoding isoform 6 of CRBN. In still another embodiment, the cDNA is one encoding isoform 7 of CRBN.

In still another embodiment, provided herein is an isolated, synthetic, or recombinant cDNA encoding an isoform of CRBN, comprising from about 300 to about 900 base pairs. In one embodiment, the cDNA is one encoding isoform 3 of CRBN, which contains about 825 base pairs. In another embodiment, the cDNA is one encoding isoform 4 of CRBN. In yet another embodiment, the cDNA is one encoding isoform 5 of CRBN, which contains about 582 base pairs. In yet another embodiment, the cDNA is one encoding isoform 6 of CRBN. In still another embodiment, the cDNA is one encoding isoform 7 of CRBN.

In one embodiment, provided herein is an isolated, synthetic, or recombinant RNA encoding an isoform of CRBN, wherein the isoform has a deletion of amino acid residues 126 to 175 (Δ126-175) or amino acid residues 176 to 228 (Δ176-228) in the full-length amino acid sequence of CRBN. In certain embodiments, the 126-175 and 176-228 amino acid segments are encoded by exons 4 and 5 of the CRBN gene, respectively.

In one embodiment, the RNA is one encoding isoform 3 of CRBN, wherein the isoform has a deletion of amino acids 58 to 175 (Δ58-175) in the full-length amino acid sequence of CRBN.

In another embodiment, the RNA is one encoding isoform 4 of CRBN, wherein the isoform has a deletion of amino acids 126 to 316 (Δ126-316) in the full-length amino acid sequence of CRBN.

In yet another embodiment, the RNA is one encoding isoform 5 of CRBN, wherein the isoform has deletions of amino acid residues 176 to 278 (Δ176-278) and amino acid residues 317 to 382 (Δ317-382) in the full-length amino acid sequence of CRBN.

In yet another embodiment, the RNA is one encoding isoform 6 of CRBN, wherein the isoform has a deletion of amino acids 126 to 382 (Δ126-382) in the full-length amino acid sequence of CRBN.

In still another embodiment, the RNA is one encoding isoform 7 of CRBN, wherein the isoform has a deletion of amino acids 23 to 338 (Δ23-338) in the full-length amino acid sequence of CRBN.

In another embodiment, provided herein is an isolated, synthetic, or recombinant RNA encoding an isoform of CRBN, wherein the isoform has a deletion of amino acid residues 23 to 57 (Δ23-57) in the full-length amino acid sequence of CRBN. In certain embodiments, the 23-57 amino acid segment is encoded by exon 2 of the CRBN gene.

In one embodiment, the RNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant RNA encoding an isoform of CRBN, wherein the isoform has a deletion of amino acid residues 58 to 125 (Δ58-125) in the full-length amino acid sequence of CRBN. In certain embodiments, the 58-125 amino acid segment is encoded by exon 3 of the CRBN gene.

In one embodiment, the RNA is one encoding isoform 3 of CRBN, wherein the isoform has a deletion of amino acids 58 to 175 (Δ58-175) in the full-length amino acid sequence of CRBN.

In another embodiment, the RNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant RNA encoding an isoform of CRBN, wherein the isoform has a deletion of amino acid residues 126 to 175 (Δ126-175) in the full-length amino acid sequence of CRBN. In certain embodiments, the 126-175 amino acid segment is encoded by exon 4 of the CRBN gene.

In one embodiment, the RNA is one encoding isoform 3 of CRBN, wherein the isoform has a deletion of amino acids 58 to 175 (Δ58-175) in the full-length amino acid sequence of CRBN.

In another embodiment, the RNA is one encoding isoform 4 of CRBN, wherein the isoform has a deletion of amino acids 126 to 316 (Δ126-316) in the full-length amino acid sequence of CRBN.

In yet another embodiment, the RNA is one encoding isoform 6 of CRBN, wherein the isoform has a deletion of amino acids 126 to 382 (Δ126-382) in the full-length amino acid sequence of CRBN.

In still another embodiment, the RNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant RNA encoding of an isoform of CRBN, wherein the isoform has a deletion of amino acid residues 176 to 228 (Δ176-228) in the full-length amino acid sequence of CRBN. In certain embodiments, the 176-228 amino acid segment is encoded by exon 5 of the CRBN gene.

In one embodiment, the RNA is one encoding isoform 4 of CRBN, wherein the isoform has a deletion of amino acids 126 to 316 (Δ126-316) in the full-length amino acid sequence of CRBN.

In another embodiment, the RNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the RNA is one encoding isoform 6 of CRBN, wherein the isoform has a deletion of amino acids 126 to 382 (Δ126-382) in the full-length amino acid sequence of CRBN.

In still another embodiment, the RNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant RNA encoding an isoform of CRBN, wherein the isoform has a deletion of amino acid residues 229 to 249 (Δ229-249) (SEQ ID NO: 8) in the full-length amino acid sequence of CRBN. In certain embodiments, the 229-249 amino acid segment is encoded by exon 6 of the CRBN gene.

In yet another embodiment, provided herein is an isolated, synthetic, or recombinant RNA encoding an isoform of CRBN comprising an exon 6 deletion in the full-length amino acid sequence of CRBN. In some embodiments, the full-length amino acid sequence of CRBN has a sequence of SEQ ID NO: 9, and the isoform of CRBN comprising an exon 6 deletion in the full-length amino acid sequence of CRBN has a sequence of SEQ ID NO: 11. In some embodiments, the full-length amino acid sequence of CRBN has a sequence of SEQ ID NO: 10, and the isoform of CRBN comprising an exon 6 deletion in the full-length amino acid sequence of CRBN has a sequence of SEQ ID NO: 12.

In one embodiment, the RNA is one encoding isoform 4 of CRBN, wherein the isoform has a deletion of amino acids 126 to 316 (Δ126-316) in the full-length amino acid sequence of CRBN.

In another embodiment, the RNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the RNA is one encoding isoform 6 of CRBN, wherein the isoform has a deletion of amino acids 126 to 382 (Δ126-382) in the full-length amino acid sequence of CRBN.

In still another embodiment, the RNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant RNA encoding an isoform of CRBN, wherein the isoform has a deletion of amino acid residues 250 to 278 (Δ250-278) in the full-length amino acid sequence of CRBN. In certain embodiments, the 250-278 amino acid segment is encoded by exon 7 of the CRBN gene.

In one embodiment, the RNA is one encoding isoform 4 of CRBN, wherein the isoform has a deletion of amino acids 126 to 316 (Δ126-316) in the full-length amino acid sequence of CRBN.

In another embodiment, the RNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the RNA is one encoding isoform 6 of CRBN, wherein the isoform has a deletion of amino acids 126 to 382 (Δ126-382) in the full-length amino acid sequence of CRBN.

In still another embodiment, the RNA is one encoding isoform 7 of CRBN, wherein the isoform has a deletion of amino acids 23 to 338 (Δ123-338) in the full-length amino acid sequence of CRBN.

In yet another embodiment, provided herein is an isolated, synthetic, or recombinant RNA encoding an isoform of CRBN, wherein the isoform has a deletion of amino acid residues 279 to 316(Δ279-316) in the full-length amino acid sequence of CRBN. In certain embodiments, the 279-316 amino acid segment is encoded by exon 8 of the CRBN gene.

In one embodiment, the RNA is one encoding isoform 4 of CRBN, wherein the isoform has a deletion of amino acids 126 to 316 (Δ126-316) in the full-length amino acid sequence of CRBN.

In another embodiment, the RNA is one encoding isoform 6 of CRBN, wherein the isoform has a deletion of amino acids 126 to 382 (Δ126-382) in the full-length amino acid sequence of CRBN.

In yet another embodiment, the RNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant RNA encoding an isoform of CRBN, wherein the isoform has a deletion of amino acid residues 317 to 338 (Δ317-338) in the full-length amino acid sequence of CRBN. In certain embodiments, the 317-338 amino acid segment is encoded by exon 9 of the CRBN gene.

In one embodiment, the RNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In another embodiment, the RNA is one encoding isoform 6 of CRBN, wherein the isoform has a deletion of amino acids 126 to 382 (Δ126-382) in the full-length amino acid sequence of CRBN.

In yet another embodiment, the RNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant RNA encoding an isoform of CRBN, wherein the isoform has a deletion of amino acid residues 339 to 382 (Δ339-382) in the full-length amino acid sequence of CRBN. In certain embodiments, the 339-382 amino acid segment is encoded by exon 10 of the CRBN gene.

In one embodiment, the RNA is one encoding isoform 2 of CRBN, wherein the isoform has a deletion of amino acids 339 to 382 (Δ339-382) in the full-length amino acid sequence of CRBN.

In another embodiment, the RNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the RNA is one encoding isoform 6 of CRBN, wherein the isoform has a deletion of amino acids 126 to 382 (Δ126-382) in the full-length amino acid sequence of CRBN.

In yet another embodiment, provided herein is an isolated, synthetic, or recombinant RNA encoding an isoform CRBN, comprising from about 300 to about 1200 bases. In one embodiment, the RNA is one encoding isoform 2 of CRBN, which contains about 1194 bases. In another embodiment, the RNA is one encoding isoform 3 of CRBN, which contains about 822 bases. In yet another embodiment, the RNA is one encoding isoform 4 of CRBN. In yet another embodiment, the RNA is one encoding isoform 5 of CRBN, which contains about 579 bases. In yet another embodiment, the RNA is one encoding isoform 6 of CRBN. In still another embodiment, the RNA is one encoding isoform 7 of CRBN.

In still another embodiment, provided herein is an isolated, synthetic, or recombinant RNA encoding an isoform of CRBN, comprising from about 300 to about 900 bases. In one embodiment, the RNA is one encoding isoform 3 of CRBN, which contains about 822 bases. In another embodiment, the RNA is one encoding isoform 4 of CRBN. In yet another embodiment, the RNA is one encoding isoform 5 of CRBN, which contains about 579 bases. In yet another embodiment, the RNA is one encoding isoform 6 of CRBN. In still another embodiment, the RNA is one encoding isoform 7 of CRBN.

In one embodiment, provided herein is an isolated, synthetic, or recombinant mRNA encoding an isoform of CRBN, wherein the isoform has a deletion of amino acid residues 126 to 175 (Δ1126-175) or amino acid residues 176 to 228 (Δ1176-228) in the full-length amino acid sequence of CRBN. In certain embodiments, the 126-175 and 176-228 amino acid segments are encoded by exons 4 and 5 of the CRBN gene, respectively.

In one embodiment, the mRNA is one encoding isoform 3 of CRBN, wherein the isoform has a deletion of amino acids 58 to 175 (Δ58-175) in the full-length amino acid sequence of CRBN.

In another embodiment, the mRNA is one encoding isoform 4 of CRBN, wherein the isoform has a deletion of amino acids 126 to 316 (Δ126-316) in the full-length amino acid sequence of CRBN.

In yet another embodiment, the mRNA is one encoding isoform 5 of CRBN, wherein the isoform has deletions of amino acid residues 176 to 278 (Δ176-278) and amino acid residues 317 to 382 (Δ317-382) in the full-length amino acid sequence of CRBN.

In yet another embodiment, the mRNA is one encoding isoform 6 of CRBN, wherein the isoform has a deletion of amino acids 126 to 382 (Δ126-382) in the full-length amino acid sequence of CRBN.

In still another embodiment, the mRNA is one encoding isoform 7 of CRBN, wherein the isoform has a deletion of amino acids 23 to 338 (Δ23-338) in the full-length amino acid sequence of CRBN.

In another embodiment, provided herein is an isolated, synthetic, or recombinant mRNA encoding an isoform of CRBN, wherein the isoform has a deletion of amino acid residues 23 to 57 (Δ23-57) in the full-length amino acid sequence of CRBN. In certain embodiments, the 23-57 amino acid segment is encoded by exon 2 of the CRBN gene.

In one embodiment, the mRNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant mRNA encoding an isoform of CRBN, wherein the isoform has a deletion of amino acid residues 58 to 125 (Δ58-125) in the full-length amino acid sequence of CRBN. In certain embodiments, the 58-125 amino acid segment is encoded by exon 3 of the CRBN gene.

In one embodiment, the mRNA is one encoding isoform 3 of CRBN, wherein the isoform has a deletion of amino acids 58 to 175 (Δ58-175) in the full-length amino acid sequence of CRBN.

In another embodiment, the mRNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant mRNA encoding an isoform of CRBN, wherein the isoform has a deletion of amino acid residues 126 to 175 (Δ126-175) in the full-length amino acid sequence of CRBN. In certain embodiments, the 126-175 amino acid segment is encoded by exon 4 of the CRBN gene.

In one embodiment, the mRNA is one encoding isoform 3 of CRBN, wherein the isoform has a deletion of amino acids 58 to 175 (Δ58-175) in the full-length amino acid sequence of CRBN.

In another embodiment, the mRNA is one encoding isoform 4 of CRBN, wherein the isoform has a deletion of amino acids 126 to 316 (Δ126-316) in the full-length amino acid sequence of CRBN.

In yet another embodiment, the mRNA is one encoding isoform 6 of CRBN, wherein the isoform has a deletion of amino acids 126 to 382 (Δ126-382) in the full-length amino acid sequence of CRBN.

In still another embodiment, the mRNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant mRNA encoding of an isoform of CRBN, wherein the isoform has a deletion of amino acid residues 176 to 228 (Δ176-228) in the full-length amino acid sequence of CRBN. In certain embodiments, the 176-228 amino acid segment is encoded by exon 5 of the CRBN gene.

In one embodiment, the mRNA is one encoding isoform 4 of CRBN, wherein the isoform has a deletion of amino acids 126 to 316 (Δ126-316) in the full-length amino acid sequence of CRBN.

In another embodiment, the mRNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the mRNA is one encoding isoform 6 of CRBN, wherein the isoform has a deletion of amino acids 126 to 382 (Δ126-382) in the full-length amino acid sequence of CRBN.

In still another embodiment, the mRNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant mRNA encoding an isoform of CRBN, wherein the isoform has a deletion of amino acid residues 229 to 249 (Δ229-249) (SEQ ID NO: 8) in the full-length amino acid sequence of CRBN. In certain embodiments, the 229-249 amino acid segment is encoded by exon 6 of the CRBN gene.

In yet another embodiment, provided herein is an isolated, synthetic, or recombinant mRNA encoding an isoform of CRBN comprising an exon 6 deletion in the full-length amino acid sequence of CRBN. In some embodiments, the 229-249 amino acid segment is encoded by exon 6 of the CRBN gene. In some embodiments, the 230-250 amino acid segment is encoded by exon 6 of the CRBN gene.

In one embodiment, the mRNA is one encoding isoform 4 of CRBN, wherein the isoform has a deletion of amino acids 126 to 316 (Δ126-316) in the full-length amino acid sequence of CRBN.

In another embodiment, the mRNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the mRNA is one encoding isoform 6 of CRBN, wherein the isoform has a deletion of amino acids 126 to 382 (Δ126-382) in the full-length amino acid sequence of CRBN.

In still another embodiment, the mRNA is one encoding isoform 7 of CRBN, wherein the isoform has a deletion of amino acids 23 to 338 (Δ123-338) in the full-length amino acid sequence of CRBN.

In yet another embodiment, provided herein is an isolated, synthetic, or recombinant mRNA encoding an isoform of CRBN, wherein the isoform has a deletion of amino acid residues 250 to 278 (Δ1250-278) in the full-length amino acid sequence of CRBN. In certain embodiments, the 250-278 amino acid segment is encoded by exon 7 of the CRBN gene.

In one embodiment, the mRNA is one encoding isoform 4 of CRBN, wherein the isoform has a deletion of amino acids 126 to 316 (Δ126-316) in the full-length amino acid sequence of CRBN.

In another embodiment, the mRNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the mRNA is one encoding isoform 6 of CRBN, wherein the isoform has a deletion of amino acids 126 to 382 (Δ126-382) in the full-length amino acid sequence of CRBN.

In still another embodiment, the mRNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant mRNA encoding an isoform of CRBN, wherein the isoform has a deletion of amino acid residues 279 to 316 (Δ279-316) in the full-length amino acid sequence of CRBN. In certain embodiments, the 279-316 amino acid segment is encoded by exon 8 of the CRBN gene.

In one embodiment, the mRNA is one encoding isoform 4 of CRBN, wherein the isoform has a deletion of amino acids 126 to 316 (Δ126-316) in the full-length amino acid sequence of CRBN.

In another embodiment, the mRNA is one encoding isoform 6 of CRBN, wherein the isoform has a deletion of amino acids 126 to 382 (Δ126-382) in the full-length amino acid sequence of CRBN.

In yet another embodiment, the mRNA is one encoding isoform 7 of CRBN, wherein the isoform has a deletion of amino acids 23 to 338 (Δ123-338) in the full-length amino acid sequence of CRBN.

In yet another embodiment, provided herein is an isolated, synthetic, or recombinant mRNA encoding an isoform of CRBN, wherein the isoform has a deletion of amino acid residues 317 to 338 (Δ317-338) in the full-length amino acid sequence of CRBN. In certain embodiments, the 317-338 amino acid segment is encoded by exon 9 of the CRBN gene.

In one embodiment, the mRNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In another embodiment, the mRNA is one encoding isoform 6 of CRBN, wherein the isoform has a deletion of amino acids 126 to 382 (Δ126-382) in the full-length amino acid sequence of CRBN.

In yet another embodiment, the mRNA is one encoding isoform 7 of CRBN, wherein the isoform has a deletion of amino acids 23 to 338 (Δ23-338) in the full-length amino acid sequence of CRBN.

In yet another embodiment, provided herein is an isolated, synthetic, or recombinant mRNA encoding an isoform of CRBN, wherein the isoform has a deletion of amino acid residues 339 to 382 (Δ339-382) in the full-length amino acid sequence of CRBN. In certain embodiments, the 339-382 amino acid segment is encoded by exon 10 of the CRBN gene.

In one embodiment, the mRNA is one encoding isoform 2 of CRBN, wherein the isoform has a deletion of amino acids 339 to 382 (Δ339-382) in the full-length amino acid sequence of CRBN.

In another embodiment, the mRNA is one encoding isoform 5 of CRBN, wherein the isoform has deletions of amino acids 176 to 278 (Δ176-278) and amino acids 317 to 382 (Δ317-382) in the full-length amino acid sequence of CRBN.

In yet another embodiment, the mRNA is one encoding isoform 6 of CRBN, wherein the isoform has a deletion of amino acids 126 to 382 (Δ126-382) in the full-length amino acid sequence of CRBN.

In yet another embodiment, provided herein is an isolated, synthetic, or recombinant mRNA encoding an isoform CRBN, comprising from about 300 to about 1200 bases. In one embodiment, the mRNA is one encoding isoform 2 of CRBN, which contains about 1194 bases. In another embodiment, the mRNA is one encoding isoform 3 of CRBN, which contains about 822 bases. In yet another embodiment, the mRNA is one encoding isoform 4 of CRBN. In yet another embodiment, the mRNA is one encoding isoform 5 of CRBN, which contains about 579 bases. In yet another embodiment, the mRNA is one encoding isoform 6 of CRBN. In still another embodiment, the mRNA is one encoding isoform 7 of CRBN.

In still another embodiment, provided herein is an isolated, synthetic, or recombinant mRNA encoding an isoform of CRBN, comprising from about 300 to about 900 bases. In one embodiment, the mRNA is one encoding isoform 3 of CRBN, which contains about 822 bases. In another embodiment, the mRNA is one encoding isoform 4 of CRBN. In yet another embodiment, the mRNA is one encoding isoform 5 of CRBN, which contains about 579 bases. In yet another embodiment, the mRNA is one encoding isoform 6 of CRBN. In still another embodiment, the mRNA is one encoding isoform 7 of CRBN.

In one embodiment, provided herein is an isolated, synthetic, or recombinant nucleic acid comprising SEQ ID NO: 1 (FIG. 2).

In another embodiment, provided herein is an isolated, synthetic, or recombinant nucleic acid comprising SEQ ID NO: 2 (FIG. 3).

In yet another embodiment, provided herein is an isolated, synthetic, or recombinant nucleic acid comprising SEQ ID NO: 3 (FIG. 4).

In yet another embodiment, provided herein is an isolated, synthetic, or recombinant nucleic acid comprising SEQ ID NO: 4 (FIG. 5).

In yet another embodiment, provided herein is an isolated, synthetic, or recombinant nucleic acid comprising SEQ ID NO: 5 (FIG. 6).

In yet another embodiment, provided herein is an isolated, synthetic, or recombinant nucleic acid comprising SEQ ID NO: 6 (FIG. 7).

In still another embodiment, provided herein is an isolated, synthetic, or recombinant nucleic acid comprising SEQ ID NO: 7 (FIG. 8).

In still another embodiment, provided herein is an isolated, synthetic, or recombinant nucleic acid comprising SEQ ID NO: 13 (FIG. 11).

5.4 BIOMARKERS

A biological marker or "biomarker" is a substance, the change and/or the detection of which indicates a particular biological state, such as, for example, the responsiveness of a disease to a given treatment, e.g., a treatment with a treatment compound, in one embodiment, an immunomodulatory compound, e.g., thalidomide, lenalidomide, pomalidomide, 3-(5-amino-2-methyl-4-oxoquinazolin-3 (4H)-yl)piperidine-2,6-dione, or (S)-3-(4-((4-(morpholinomethyl)benzyl)oxy)-1-oxoisoindolin-2-yl)piperidine-2,6-dione.

In certain embodiments, the biomarker is an isoform of CRBN. In certain embodiments, the biomarker is isoform 1, 2, 3, 4, 5, 6, 7, or 8 of CRBN, or a combination thereof. In certain embodiments, the biomarker is isoform 2, 3, 4, 5, 6, 7, or 8 of CRBN, or a combination thereof. In certain embodiments, the biomarker is isoform 3, 4, 5, 6, 7, or 8 of CRBN, or a combination thereof. In certain embodiments, the biomarker is an isoform of CRBN comprising an exon 6 deletion. In certain embodiments, the biomarker comprises exons 1-5 and 7-11. In certain embodiments, the isoform of CRBN comprising an exon 6 deletion comprises a sequence set forth in SEQ ID NO: 11. In certain embodiments, the isoform of CRBN comprising an exon 6 deletion comprises a sequence set forth in SEQ ID NO: 12. In certain embodiments, the isoform of CRBN comprising an exon 6 deletion consists of a sequence set forth in SEQ ID NO: 11. In certain embodiments, the isoform of CRBN comprising an exon 6 deletion consists of a sequence set forth in SEQ ID NO: 12.

In certain embodiments, the biomarker is isoform 1 of CRBN. In certain embodiments, the biomarker is isoform 2 of CRBN. In certain embodiments, the biomarker is isoform 3 of CRBN. In certain embodiments, the biomarker is isoform 4 of CRBN. In certain embodiments, the biomarker is isoform 5 of CRBN. In certain embodiments, the biomarker is isoform 6 of CRBN. In certain embodiments, the biomarker is isoform 7 of CRBN.

In certain embodiments, the biomarker is a nucleic acid encoding an isoform of CRBN. In certain embodiments, the biomarker is a nucleic acid encoding isoform 1, 2, 3, 4, 5, 6, 7, or 8 of CRBN, or a combination thereof. In certain embodiments, the biomarker is a nucleic acid encoding isoform 2, 3, 4, 5, 6, 7, or 8 of CRBN, or a combination thereof. In certain embodiments, the biomarker is a nucleic acid encoding isoform 3, 4, 5, 6, 7, or 8 of CRBN, or a combination thereof. In certain embodiments, the biomarker is a nucleic acid encoding an isoform of CRBN comprising an exon 6 deletion.

In certain embodiments, the biomarker is a nucleic acid encoding isoform 1 of CRBN. In certain embodiments, the biomarker is a nucleic acid encoding isoform 2 of CRBN. In certain embodiments, the biomarker is a nucleic acid encoding isoform 3 of CRBN. In certain embodiments, the biomarker is a nucleic acid encoding isoform 4 of CRBN. In certain embodiments, the biomarker is a nucleic acid encoding isoform 5 of CRBN. In certain embodiments, the biomarker is a nucleic acid encoding isoform 6 of CRBN. In certain embodiments, the biomarker is a nucleic acid encoding isoform 7 of CRBN.

In certain embodiments, the biomarker is a DNA encoding an isoform of CRBN. In certain embodiments, the biomarker is a DNA encoding isoform 1, 2, 3, 4, 5, 6, 7, or 8 of CRBN, or a combination thereof. In certain embodiments, the biomarker is a DNA encoding isoform 2, 3, 4, 5, 6, 7, or 8 of CRBN, or a combination thereof. In certain embodiments, the biomarker is a DNA encoding isoform 3, 4, 5, 6, 7, or 8 of CRBN, or a combination thereof. In certain embodiments, the biomarker is a DNA encoding an isoform of CRBN comprising an exon 6 deletion.

In certain embodiments, the biomarker is a DNA encoding isoform 1 of CRBN. In certain embodiments, the biomarker is a DNA encoding isoform 2 of CRBN. In certain embodiments, the biomarker is a DNA encoding isoform 3 of CRBN. In certain embodiments, the biomarker is a DNA encoding isoform 4 of CRBN. In certain embodiments, the biomarker is a DNA encoding isoform 5 of CRBN. In certain embodiments, the biomarker is a DNA encoding isoform 6 of CRBN. In certain embodiments, the biomarker is a DNA encoding isoform 7 of CRBN.

In certain embodiments, the biomarker is a cDNA encoding an isoform of CRBN. In certain embodiments, the biomarker is a cDNA encoding isoform 1, 2, 3, 4, 5, 6, 7, or 8 of CRBN, or a combination thereof. In certain embodiments, the biomarker is a cDNA encoding isoform 2, 3, 4, 5, 6, 7, or 8 of CRBN, or a combination thereof. In certain embodiments, the biomarker is a cDNA encoding isoform 3, 4, 5, 6, 7, or 8 of CRBN, or a combination thereof. In certain embodiments, the biomarker is a cDNA encoding an isoform of CRBN comprising an exon 6 deletion.

In certain embodiments, the biomarker is a cDNA encoding isoform 1 of CRBN. In certain embodiments, the biomarker is a cDNA encoding isoform 2 of CRBN. In certain embodiments, the biomarker is a cDNA encoding isoform 3 of CRBN. In certain embodiments, the biomarker is a cDNA encoding isoform 4 of CRBN. In certain embodiments, the biomarker is a cDNA encoding isoform 5 of CRBN. In certain embodiments, the biomarker is a cDNA encoding isoform 6 of CRBN. In certain embodiments, the biomarker is a cDNA encoding isoform 7 of CRBN.

In certain embodiments, the biomarker is an RNA encoding an isoform of CRBN. In certain embodiments, the biomarker is an RNA encoding isoform 1, 2, 3, 4, 5, 6, 7, or 8 of CRBN, or a combination thereof. In certain embodiments, the biomarker is an RNA of isoform 2, 3, 4, 5, 6, 7, or 8 encoding CRBN, or a combination thereof. In certain embodiments, the biomarker is an RNA of isoform 3, 4, 5, 6, 7, or 8 encoding CRBN, or a combination thereof. In certain embodiments, the biomarker is an RNA encoding an isoform of CRBN comprising an exon 6 deletion.

In certain embodiments, the biomarker is an RNA encoding isoform 1 of CRBN. In certain embodiments, the biomarker is an RNA encoding isoform 2 of CRBN. In certain embodiments, the biomarker is an RNA encoding isoform 3 of CRBN. In certain embodiments, the biomarker is an RNA encoding isoform 4 of CRBN. In certain embodiments, the biomarker is an RNA encoding isoform 5 of CRBN. In certain embodiments, the biomarker encoding an RNA of isoform 6 of CRBN. In certain embodiments, the biomarker encoding an RNA of isoform 7 of CRBN.

In certain embodiments, the biomarker is an mRNA encoding an isoform of CRBN. In certain embodiments, the biomarker is an mRNA encoding isoform 1, 2, 3, 4, 5, 6, 7, or 8 of CRBN, or a combination thereof. In certain embodiments, the biomarker is an mRNA of isoform 2, 3, 4, 5, 6, 7, or 8 encoding CRBN, or a combination thereof. In certain embodiments, the biomarker is an mRNA of isoform 3, 4, 5, 6, 7, or 8 encoding CRBN, or a combination thereof. In certain embodiment, the biomarker is an mRNA encoding an isoform of CRBN comprising an exon 6 deletion.

In certain embodiments, the biomarker is an mRNA encoding isoform 1 of CRBN. In certain embodiments, the biomarker is an mRNA encoding isoform 2 of CRBN. In certain embodiments, the biomarker is an mRNA encoding isoform 3 of CRBN. In certain embodiments, the biomarker is an mRNA encoding isoform 4 of CRBN. In certain embodiments, the biomarker is an mRNA encoding isoform 5 of CRBN. In certain embodiments, the biomarker encoding an mRNA of isoform 6 of CRBN. In certain embodiments, the biomarker encoding an mRNA of isoform 7 of CRBN.

In one embodiment, the biomarker comprises SEQ ID NO: 1 (FIG. 2). In another embodiment, the biomarker comprises SEQ ID NO: 2 (FIG. 3). In yet another embodiment, the biomarker comprises SEQ ID NO: 3 (FIG. 4). In yet another embodiment, the biomarker comprises SEQ ID NO: 4 (FIG. 5). In yet another embodiment, the biomarker comprises SEQ ID NO: 5 (FIG. 6). In yet another embodiment, the biomarker comprises SEQ ID NO: 6 (FIG. 7). In still another embodiment, provided biomarker comprises SEQ ID NO: 7 (FIG. 8). In still another embodiment, provided biomarker comprises SEQ ID NO: 13 (FIG. 11).

In certain embodiments, the level of a biomarker provided herein correlates with or is indicative of the responsiveness of a subject having a disease or condition to a treatment with a treatment compound, in one embodiment, an immunomodulatory compound, e.g., thalidomide, lenalidomide, pomalidomide, 3-(5-amino-2-methyl-4-oxoquinazolin-3(4H)-yl)piperidine-2,6-dione, or (S)-3-(4-((4-(morpholinomethyl)-benzyl)oxy)-1-oxoisoindolin-2-yl)piperidine-2,6-dione.

In certain embodiments, the reference level of the biomarker is one that a treatment decision is made based on whether a subject has the level of a biomarker provided here that is altered as compared to the reference level of the biomarker. A subject who has a level of the biomarker that is altered as compared to the reference level of the biomarker has a different probability of responsiveness to the treatment than a subject who has a level of the biomarker the same as the reference level of the biomarker.

In certain embodiments, the reference level of the biomarker is one that a treatment decision is made based on whether a subject has the level of a biomarker provided here above the reference level of the biomarker. In certain embodiments, the reference level of the biomarker is one that a treatment decision is made based on whether a subject has the level of a biomarker provided here below the reference level of the biomarker. A subject who has a level of the biomarker higher than the reference level of the biomarker has a different probability of responsiveness to the treatment than a subject who has a level of the biomarker lower than the reference level of the biomarker.

In certain embodiments, the reference level of the biomarker is measured simultaneously with the level of the biomarker in the biological sample from the subject. In certain embodiments, the reference level of the biomarker is predetermined.

In certain embodiments, the level of the biomarker in a control sample is one that a treatment decision is made based on whether a subject has the level of a biomarker provided here that is altered as compared to the level of the biomarker in the control sample. A subject who has a level of the biomarker that is altered as compared to the level of the biomarker in the control sample has a different probability of responsiveness to the treatment than a subject who has a level of the biomarker the same as the level of the biomarker in the control sample.

In certain embodiments, the level of the biomarker in the control sample is one that a treatment decision is made based on whether a subject has the level of a biomarker provided here above the level of the biomarker in the control sample. In certain embodiments, the level of the biomarker in the control sample is one that a treatment decision is made based on whether a subject has the level of a biomarker provided here below the level of the biomarker in the control sample. A subject who has a level of the biomarker higher than the level of the biomarker in the control sample has a different probability of responsiveness to the treatment than a subject who has a level of the biomarker lower than the level of the biomarker in the control sample.

In certain embodiments, the level of the biomarker in the control sample is measured simultaneously with the level of the biomarker in the biological sample from the subject. In certain embodiments, the level of the biomarker in the control sample is predetermined.

In certain embodiments, the biomarkers provided herein are determined individually. In certain embodiments, two or more of the biomarkers provided herein are determined simultaneously.

5.4.1 Use of CRBN Isoforms for Identifying a Subject for a Treatment

In one embodiment, provided herein is a method of identifying a subject who is likely to be responsive to a treatment with a treatment compound, comprising:

a) determining the level of a biomarker in a biological sample from the subject; and b) comparing the level of the biomarker in the biological sample to a reference level of the biomarker;

wherein the subject is likely to be responsive to the treatment if the level of the biomarker in the biological sample from the subject is altered as compared to the reference level of the biomarker.

In another embodiment, provided herein is a method of identifying a subject who is likely to be responsive to a treatment with a treatment compound, comprising:

a) determining the level of a biomarker in a biological sample from the subject; and b) determining the level of the biomarker in a control sample; and c) comparing the level of the biomarker in the biological sample from the subject to the level of the biomarker in the control sample;

wherein the subject is likely to be responsive to the treatment if the level of the biomarker in the biological sample from the subject is altered as compared to the level of the biomarker in the control sample.

In yet another embodiment, provided herein is a method of identifying a subject who is likely to be responsive to a treatment with a treatment compound, comprising:

a) obtaining a biological sample from the subject;

b) determining the level of a biomarker in the biological sample; and c) comparing the level of the biomarker in the biological sample to a reference level of the biomarker;

wherein the subject is likely to be responsive to the treatment if the level of the biomarker in the biological sample from the subject is altered as compared to the reference level of the biomarker.

In yet another embodiment, provided herein is a method of identifying a subject who is likely to be responsive to a treatment with a treatment compound, comprising:

a) obtaining a biological sample from the subject;

b) determining the level of a biomarker in the biological sample;

c) determining the level of the biomarker in a control sample; and d) comparing the level of the biomarker in the biological sample from the subject to the level of the biomarker in the control sample;

wherein the subject is likely to be responsive to the treatment if the level of the biomarker in the biological sample from the subject is altered as compared to the reference level of the biomarker.

In yet another embodiment, provided herein is a method of identifying a subject who is likely to be responsive to a treatment with a treatment compound, comprising:

a) determining the level of a biomarker in a biological sample from the subject; and b) comparing the level of the biomarker in the biological sample to a reference level of the biomarker;

wherein the subject is likely to be responsive to the treatment if the level of the biomarker in the biological sample from the subject is higher than the reference level of the biomarker.

In another embodiment, provided herein is a method of identifying a subject who is likely to be responsive to a treatment with a treatment compound, comprising:

a) determining the level of a biomarker in a biological sample from the subject; and b) determining the level of the biomarker in a control sample; and c) comparing the level of the biomarker in the biological sample from the subject to the level of the biomarker in the control sample;

wherein the subject is likely to be responsive to the treatment if the level of the biomarker in the biological sample from the subject is higher than the level of the biomarker in the control sample.

In yet another embodiment, provided herein is a method of identifying a subject who is likely to be responsive to a treatment with a treatment compound, comprising:
  a) obtaining a biological sample from the subject;
  b) determining the level of a biomarker in the biological sample; and
  c) comparing the level of the biomarker in the biological sample to a reference level of the biomarker;
  wherein the subject is likely to be responsive to the treatment if the level of the biomarker in the biological sample from the subject is higher than the reference level of the biomarker.

In yet another embodiment, provided herein is a method of identifying a subject who is likely to be responsive to a treatment with a treatment compound, comprising:
  a) obtaining a biological sample from the subject;
  b) determining the level of a biomarker in the biological sample;
  c) determining the level of the biomarker in a control sample; and
  d) comparing the level of the biomarker in the biological sample from the subject to the level of the biomarker in the control sample;
  wherein the subject is likely to be responsive to the treatment if the level of the biomarker in the biological sample from the subject is higher than the reference level of the biomarker.

In yet another embodiment, provided herein is a method of identifying a subject who is likely to be responsive to a treatment with a treatment compound, comprising:
  a) determining the level of a biomarker in a biological sample from the subject; and
  b) comparing the level of the biomarker in the biological sample to a reference level of the biomarker;
  wherein the subject is likely to be responsive to the treatment if the level of the biomarker in the biological sample from the subject is lower than the reference level of the biomarker.

In another embodiment, provided herein is a method of identifying a subject who is likely to be responsive to a treatment with a treatment compound, comprising:
  a) determining the level of a biomarker in a biological sample from the subject; and
  b) determining the level of the biomarker in a control sample; and
  c) comparing the level of the biomarker in the biological sample from the subject to the level of the biomarker in the control sample;
  wherein the subject is likely to be responsive to the treatment if the level of the biomarker in the biological sample from the subject is lower than the level of the biomarker in the control sample.

In yet another embodiment, provided herein is a method of identifying a subject who is likely to be responsive to a treatment with a treatment compound, comprising:
  a) obtaining a biological sample from the subject;
  b) determining the level of a biomarker in the biological sample; and
  c) comparing the level of the biomarker in the biological sample to a reference level of the biomarker;
  wherein the subject is likely to be responsive to the treatment if the level of the biomarker in the biological sample from the subject is lower than the reference level of the biomarker.

In still another embodiment, provided herein is a method of identifying a subject who is likely to be responsive to a treatment with a treatment compound, comprising:
  a) obtaining a biological sample from the subject;
  b) determining the level of a biomarker in the biological sample;
  c) determining the level of the biomarker in a control sample; and
  d) comparing the level of the biomarker in the biological sample from the subject to the level of the biomarker in the control sample;
  wherein the subject is likely to be responsive to the treatment if the level of the biomarker in the biological sample from the subject is lower than the reference level of the biomarker.

In certain embodiments of the various methods provided herein, the biomarker is an isoform of CRBN comprising an exon 6 deletion. Thus, in some embodiments, provided herein is a method of identifying a subject who is likely to be responsive to a treatment of a disease, disorder, or condition with a treatment compound, comprising:
  a) obtaining a biological sample from the subject;
  b) determining the level of an isoform of CRBN comprising an exon 6 deletion in the biological sample; and
  c) diagnosing the subject as being likely to be responsive to a treatment of a disease, disorder, or condition with the treatment compound if the level of the isoform of CRBN comprising an exon 6 deletion present is determined to be less than a baseline level;
  wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl) piperidine-2,6-dione a stereoisomer thereof, or a pharmaceutically acceptable salt, solvate, hydrate, co-crystal, clathrate, or polymorph thereof.

In some embodiments, provided herein is a method of identifying a subject who is likely to be responsive to a treatment of a disease, disorder, or condition with a treatment compound, comprising:
  a) obtaining a biological sample from the subject;
  b) determining the level of an isoform of CRBN comprising an exon 6 deletion in the biological sample; and
  c) diagnosing the subject as not being likely to be responsive to a treatment of a disease, disorder, or condition with the treatment compound if the level of the isoform of CRBN comprising an exon 6 deletion present in the biological sample is determined to be a baseline level,
  wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl) piperidine-2,6-dione a stereoisomer thereof, or a pharmaceutically acceptable salt, solvate, hydrate, co-crystal, clathrate, or polymorph thereof.

In some embodiments, provided herein is a method for determining whether a subject has a treatment compound-sensitive cancer wherein said method comprises
  a) obtaining a cancer sample from the subject;
  b) determining the level of an isoform of CRBN comprising an exon 6 deletion in the cancer sample;
  c) diagnosing the subject as having a treatment compound-sensitive cancer if the level of the isoform of CRBN comprising an exon 6 deletion was determined to be less than a baseline level in the cancer sample; and
  d) administering an effective amount of the treatment compound to the subject diagnosed as having the treatment compound-sensitive cancers;
  wherein the treatment compound is thalidomide, lenalidomide, pomalidomide, 3-(5-amino-2-methyl-4-oxo-4H- quinazolin-3-yl)-piperidine-2,6-dione, or (S)-3-(4-((4-(morpholinomethyl)benzyl)oxy)-1-oxoisoindolin-2-yl) piperidine-2,6-dione a stereoisomer thereof, or a pharmaceutically acceptable salt, solvate, hydrate, co-crystal, clathrate, or polymorph thereof.

In certain embodiments, the biomarker is a polypeptide of a CRBN isoform.

In certain embodiments, the reference level is determined from a disease-free sample from the same subject. In certain embodiments, the reference level is determined from a disease-free sample from a group of subjects.

In certain embodiments, the reference level is determined simultaneously with the level of the biomarker in the biological sample from the subject. In certain embodiments, the reference level is determined independently from the level of the biomarker in the biological sample from the subject.

In certain embodiments, the control sample is a disease-free sample from the same subject. In certain embodiments, the control sample is a disease-free sample from a group of subjects.

In certain embodiments, the level of the biomarker in the control sample is determined simultaneously with the level of the biomarker in the biological sample from the subject. In certain embodiments, the level of the biomarker in the control sample is determined independently from the level of the biomarker in the biological sample from the subject.

In certain embodiments of various methods provided herein, the method further comprises administering an effective amount of the treatment compound to the subject likely to be responsive to the treatment compound. In some embodiments, the method further comprises administering an effective amount of the treatment compound to the subject having a treatment compound sensitive cancer.

In certain embodiments, the methods provided herein are coupled with a treatment with a treatment compound, in one embodiment, an immunomodulatory compound, e.g., thalidomide, lenalidomide, pomalidomide, 3-(5-amino-2-methyl-4-oxoquinazolin-3(4H)-yl)piperidine-2,6-dione, or (S)-3-(4-((4-(morpholinomethyl)-benzyl)oxy)-1-oxoisoindolin-2-yl)piperidine-2,6-dione.

In certain embodiments, the treatment compound is administered to a patient as a dose of from about 0.1 mg per day to about 100 mg per day. In other embodiments, the treatment compound is administered to a patient as a dose of between about 0.5 mg per day to about 100 mg per day. In other embodiments, the treatment compound is administered to a patient as a dose of between about 0.5 mg per day to about 20 mg per day. In other embodiments, the treatment compound is administered to a patient as a dose of between about 5 mg per day to about 25 mg per day. In some embodiments, the treatment compound is administered to a patient as a dose of between about 0.5 mg per day to about 10 mg per day. In certain embodiments, the treatment compound is administered to a patient as a dose of between about 0.5 mg per day to about 100 mg per day.

In other embodiments, the treatment compound is administered at a dose of about 0.1 mg, 0.5 mg, 1 mg, 1.5 mg, 2 mg, 2.5 mg, 3 mg, 3.5 mg, 4.0 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 20 mg, 25 mg, 30 mg, 35 mg, 40 mg, 45 mg, 50 mg, 60 mg, 70 mg, 80 mg, 90 mg or 100 mg per day.

In some embodiments, the treatment compound is administered once daily. In some embodiments, the treatment compound is administered twice daily. In certain embodiments, the treatment compound is cyclically administered to a patient. Cycling therapy involves the administration of an active agent for a period of time, followed by a rest for a period of time, and repeating this sequential administration. Accordingly, in some embodiments, about 0.5 mg per day to about 100 mg per day of the treatment compound is administered on days 1-12 of a repeated 28 day cycle. In a specific embodiment, 25 mg of the treatment compound is administered once a day on days 1-12 of a repeated 28 day cycle.

It is understood that specific dose levels of a treatment compound described for any particular subject depends upon a variety of factors including the activity of the specific compound employed, the age, body weight, general health, sex, and diet of the patient, the time of administration, the rate of excretion, the treatment compound combination, and the severity of the tumor being treated and form of administration. In it also understand that one of ordinary skill in the art can readily determine the appropriate dose of the treatment compound based on these factors. Treatment dosages generally may be titrated to optimize safety and efficacy.

A treatment compound can be administered by any route of administration known in the art, such as oral, intravenous, subcutaneous, or intramucosal administration. In one embodiment, lenalidomide or a stereoisomer thereof; or a pharmaceutically acceptable salt, solvate, hydrate, co-crystal, clathrate thereof; or a polymorph thereof, is administered to a patient orally. In one embodiment, thalidomide or a stereoisomer thereof; or a pharmaceutically acceptable salt, solvate, hydrate, co-crystal, clathrate thereof; or a polymorph thereof, is administered to a patient orally. In one embodiment, pomalidomide or a stereoisomer thereof; or a pharmaceutically acceptable salt, solvate, hydrate, co-crystal, clathrate thereof; or a polymorph thereof, is administered to a patient orally. In one embodiment, lenalidomide or a stereoisomer thereof; or a pharmaceutically acceptable salt, solvate, hydrate, co-crystal, clathrate thereof; or a polymorph thereof, is administered to a patient orally. In one embodiment, 3-(5-amino-2-methyl-4-oxoquinazolin-3(4H)-yl)piperidine-2,6-dione or a stereoisomer thereof; or a pharmaceutically acceptable salt, solvate, hydrate, co-crystal, clathrate thereof; or a polymorph thereof, is administered to a patient orally. In one embodiment, (S)-3-(4-((4-(morpholinomethyl)benzyl)oxy)-1-oxoisoindolin-2-yl)piperidine-2,6-dione or a stereoisomer thereof; or a pharmaceutically acceptable salt, solvate, hydrate, co-crystal, clathrate thereof; or a polymorph thereof, is administered to a patient orally. The oral dosage form can be a tablet or a capsule. In some embodiments, the dosage form is a tablet. In some other embodiments, the dosage for is a capsule.

Thus, in one embodiment, provided herein is a method of a treatment with a treatment compound, comprising:
(i) identifying a subject who is likely to be responsive to the treatment compound, comprising:
a) determining the level of a biomarker in a biological sample from the subject; and
b) comparing the level of the biomarker in the biological sample to a reference level of the biomarker; wherein the subject is likely to be responsive to the treatment if the level of the biomarker in the biological sample from the subject is altered as compared to the reference level of the biomarker; and
(ii) administering a therapeutically effective amount of the treatment compound to the subject identified to be likely to be responsive to the treatment.

In another embodiment, provided herein is a method of a treatment with a treatment compound, comprising:
(i) identifying a subject who is likely to be responsive to the treatment compound, comprising:

a) determining the level of a biomarker in a biological sample from the subject;
b) determining the level of the biomarker in a control sample; and
c) comparing the level of the biomarker in the biological sample from the subject to the level of the biomarker in the control sample; wherein the subject is likely to be responsive to the treatment if the level of the biomarker in the biological sample from the subject is altered as compared to the level of the biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
  a) obtaining a biological sample from the subject;
  b) determining the level of a biomarker in the biological sample; and
  c) comparing the level of the biomarker in the biological sample to a reference level of the biomarker; wherein the subject is likely to be responsive to the treatment if the level of the biomarker in the biological sample from the subject is altered as compared to the reference level of the biomarker; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
  a) obtaining a biological sample from the subject;
  b) determining the level of a biomarker in the biological sample;
  c) determining the level of the biomarker in a control sample; and
  d) comparing the level of the biomarker in the biological sample from the subject to the level of the biomarker in the control sample; wherein the subject is likely to be responsive to the treatment if the level of the biomarker in the biological sample from the subject is altered as compared to the level of the biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
  a) determining the level of a biomarker in a biological sample from the subject; and
  b) comparing the level of the biomarker in the biological sample to a reference level of the biomarker; wherein the subject is likely to be responsive to the treatment if the level of the biomarker in the biological sample from the subject is higher than the reference level of the biomarker; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
  a) determining the level of a biomarker in a biological sample from the subject;
  b) determining the level of the biomarker in a control sample; and
  c) comparing the level of the biomarker in the biological sample from the subject to the level of the biomarker in the control sample; wherein the subject is likely to be responsive to the treatment if the level of the biomarker in the biological sample from the subject is higher than the level of the biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
  a) obtaining a biological sample from the subject;
  b) determining the level of a biomarker in the biological sample; and
  c) comparing the level of the biomarker in the biological sample to a reference level of the biomarker; wherein the subject is likely to be responsive to the treatment if the level of the biomarker in the biological sample from the subject is higher than the reference level of the biomarker; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
  a) obtaining a biological sample from the subject;
  b) determining the level of a biomarker in the biological sample;
  c) determining the level of the biomarker in a control sample; and
  d) comparing the level of the biomarker in the biological sample from the subject to the level of the biomarker in the control sample; wherein the subject is likely to be responsive to the treatment if the level of the biomarker in the biological sample from the subject is higher than the level of the biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
  a) determining the level of a biomarker in a biological sample from the subject; and
  b) comparing the level of the biomarker in the biological sample to a reference level of the biomarker; wherein the subject is likely to be responsive to the treatment if the level of the biomarker in the biological sample from the subject is lower than the reference level of the biomarker; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) determining the level of a biomarker in a biological sample from the subject;
b) determining the level of the biomarker in a control sample; and
c) comparing the level of the biomarker in the biological sample from the subject to the level of the biomarker in the control sample; wherein the subject is likely to be responsive to the treatment if the level of the biomarker in the biological sample from the subject is lower than the level of the biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) obtaining a biological sample from the subject;
b) determining the level of a biomarker in the biological sample; and
c) comparing the level of the biomarker in the biological sample to a reference level of the biomarker; wherein the subject is likely to be responsive to the treatment if the level of the biomarker in the biological sample from the subject is lower than the reference level of the biomarker; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) obtaining a biological sample from the subject;
b) determining the level of a biomarker in the biological sample;
c) determining the level of the biomarker in a control sample; and
d) comparing the level of the biomarker in the biological sample from the subject to the level of the biomarker in the control sample; wherein the subject is likely to be responsive to the treatment if the level of the biomarker in the biological sample from the subject is lower than the level of the biomarker in the control sample; and
(ii) administering a therapeutically effective amount of the treatment compound to the subject identified to be likely to be responsive to the treatment.

In yet another embodiment, provided herein is a method for treating a having or suspected of having a cancer, wherein said method comprising:
a) obtaining a cancer sample from the subject;
b) determining the level of an isoform of CRBN comprising an exon 6 deletion in the cancer sample;
c) diagnosing the subject as having the treatment compound-sensitive cancer if the level of the isoform of CRBN comprising an exon 6 deletion was determined to be less than a baseline level in the cancer sample; and
d) administering an effective amount of the treatment compound to the subject diagnosed as having the treatment compound-sensitive cancer;
wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl) piperidine-2,6-dione a stereoisomer thereof, or a pharmaceutically acceptable salt, solvate, hydrate, co-crystal, clathrate, or polymorph thereof.

In some embodiments of the various methods provided herein, the isoform of CRBN comprising an exon 6 deletion contains a single exon 6 deletion and contains exons 1-5 and 7-11.

In some embodiments of the various methods provided herein, the disease, disorder, or condition is a CRBN-mediated disease, disorder, or condition.

In some embodiments of the various methods provided herein, the subject has multiple myeloma, lymphoma, melanoma or solid tumor. In some embodiments, the subject has multiple myeloma. In other embodiments, the subject has lymphoma. In yet other embodiments, the subject has melanoma. In yet other embodiments, the subject has solid tumor.

In some embodiments of the various methods provided herein, the determining the level of an isoform of CRBN comprising an exon 6 deletion in the cancer sample determines presence (or absence) of the isoform of CRBN comprising an exon 6 deletion. In some embodiments, the isoform of CRBN comprising an exon 6 deletion is determined to be the only isoform of CRBN in the sample.

In some embodiments of the various methods provided herein, the subject is diagnosed as having a treatment compound-sensitive cancer if the level of the isoform of CRBN comprising an exon 6 deletion present in the biological sample is determined to be less than 10%, 20%, 30%, 40%, 50%, 60%, 70%, 80% or 90% of the baseline level. In other embodiments of the various methods provided herein, the subject is diagnosed as having a treatment compound-sensitive cancer if the isoform of CRBN comprising an exon 6 deletion is absent from the cancer sample.

In some embodiments of the various methods provided herein, the determining the level of the isoform of CRBN comprising an exon 6 deletion is performed by contacting the sample with an isolated antibody that immunospecifically binds to an epitope in the CRBN, wherein the epitope has the amino acid sequence SEQ ID NO: 8. The SEQ ID NO: 8 represents the amino acid sequence of exon 6 of CRBN. The isoform of CRBN comprising an exon 6 deletion cannot be detected with such an antibody, and thus the antibody can be used in the present method to detect the presence or determine the level of the isoform of CRBN comprising an exon 6 deletion.

In other embodiments of the various methods provided herein, the methods provided herein further include purifying CRBN protein and isoforms thereof from the sample. The purified CRBN proteins and isoforms thereof can be subjected to various assays for determining the level (e.g., quantitating) or presence of the isoform of CRBN comprising an exon 6 deletion. In some embodiments, such assay includes measuring the size of the purified CRBN proteins and isoforms thereof. In other embodiments, the purified/enriched CRBN proteins and isoforms thereof can be sequenced, and thereby determining presence or the level of the isoform of CRBN comprising an exon 6 deletion. In yet other embodiments, the sequencing purified CRBN protein and isoforms thereof. includes use of mass spectrometry or An Edmandegradation reaction. Other methods for protein sequencing and/or characterization known in the art may also be used in the present disclosure for determining the presence or the level of the isoform of CRBN comprising an exon 6 deletion.

In other embodiments of the various methods provided herein, the methods provided herein further include extracting mRNA from the biological sample. Thus, in some embodiments, the method provided herein can determine the level of the isoform of CRBN comprising an exon 6 deletion by determining the presence or the level of mRNA of exon 6 of CRBN using a polymerase chain reaction (PCR). In some embodiments, the PCR is a reverse transcriptase PCR (RT-PCR).

Various primer designs in a RT-PCR can be used to determine the presence or the level of exon 6 of CRBN in a sample in some embodiments of the various methods provided herein. For example, in some embodiments, one primer used in the PCR represents a sequence within exon 7 of CRBN, and a second PCR primer has a 5' portion and a 3' portion, the 5' portion representing a sequence within exon 6 of CRBN, the 3' portion presenting a sequence within exon 7 of CRBN. Because the second primer is complementary to a junction region between exon 6 and exon 7, the presence of PCR products with proper size indicates the presence of exon 6 before exon 7. In some embodiments, one primer used in the PCR represents a sequence within exon 7 of CRBN, and a second PCR primer has a 5' portion and a 3' portion, the 5' portion representing a sequence within exon 5 of CRBN, the 3' portion presenting a sequence within exon 7 of CRBN. Because the second primer is complementary to a junction region between exon 5 and exon 7, the presence of PCR products with proper size indicates the presence of exon 5 right before exon 7 and absence of exon 6. Similarly, in some embodiments, one primer represents a sequence within exon 5, and a second primer represents a sequence at junction between exon 5 and exon 6, and thus presence of PCR products with proper size indicates the presence of exon 6 after exon 5. In some embodiments, one primer represents a sequence within exon 5, and a second primer represents a sequence at junction between exon 5 and exon 7, and thus presence of PCR products with proper size indicates the presence of exon 7 right after exon 5 and absence of exon 6.

In yet other embodiments of the various methods provided herein, the methods provided herein further comprise generating cDNA from the mRNA. Thus, the cDNA can be subjected to various assays for determining the level (e.g., quantitating) or presence of the isoform of CRBN comprising an exon 6 deletion. In some embodiments, the determining the level of the isoform of CRBN comprising an exon 6 deletion in is performed by a polymerase chain reaction (PCR) using cDNA as templates.

Similarly to the primer designs for RT-PCR described above, various primer designs can be used to determine the presence or the level of exon 6 of CRBN in a sample using cDNA as templates in some embodiments of the various methods provided herein. In some embodiments, one primer used in the PCR represents a sequence within exon 7 of CRBN, and a second PCR primer has a 5' portion and a 3' portion, the 5' portion representing a sequence within exon 6 of CRBN, the 3' portion presenting a sequence within exon 7 of CRBN. The presence of PCR products with proper size indicates the presence of exon 6 before exon 7. In some embodiments, one primer used in the PCR represents a sequence within exon 7 of CRBN, and a second PCR primer has a 5' portion and a 3' portion, the 5' portion representing a sequence within exon 5 of CRBN, the 3' portion presenting a sequence within exon 7 of CRBN. The presence of PCR products with proper size indicates the presence of exon 5 right before exon 7 and absence of exon 6. In other embodiments, one primer represents a sequence within exon 5, and a second primer represents a sequence at junction between exon 5 and exon 6, and thus presence of PCR products with proper size indicates the presence of exon 6 after exon 5. In some embodiments, one primer represents a sequence within exon 5, and a second primer represents a sequence at junction between exon 5 and exon 7, and thus presence of PCR products with proper size indicates the presence of exon 7 right after exon 5 and absence of exon 6. In one embodiment, a first primer has a sequence of 5'-GCAGAAATACCAGAAGGAGACCTTA-3' (SEQ ID NO: 14), and a second primer has a sequence of 5'-GCGAAGTCGCTGGATAGCA-3' (SEQ ID NO:15).

In yet other embodiments of the various methods provided herein, the methods provided herein can use a probe to detect the presence of exon 6 in a nucleic acid sample, e.g., mRNA and cDNA, prepared from a subject. Thus, in some embodiments, determining the level of the isoform of CRBN comprising an exon 6 deletion is performed using a probe targeting a nucleic acid sequence presenting CRBN. In some embodiments, the probe comprises a nucleic acid sequence complementary to a region of exon 6 of CRBN. In some embodiments, the probe comprises a nucleic acid sequence complementary to a sequence representing a junction region between exon 6 of CRBN and exon 7 of CRBN. In some embodiments, the probe comprises a nucleic acid sequence complementary to a sequence representing a junction region between exon 5 of CRBN and exon 6 of CRBN.

Nucleic acid representing CRBN or isoforms thereof can be used for determining the presence or the level of the isoforms of CRBN comprising an exon 6 deletion, e.g., by sequencing. Thus, in some embodiments of the various methods provided herein, the methods provided herein further include enriching a target nucleic acid from the cancer sample, wherein the target nucleic acid represents CRBN or isoforms thereof. In some embodiments, the target nucleic acid is a DNA. In some embodiments, the target nucleic acid is a mRNA. In other embodiments, cDNA is generated from the enriched mRNA and can be subjected to sequencing analysis.

In yet other embodiments of the various methods provided herein, the methods provided herein further include sequencing the target nucleic acid, and thereby determining the presence or the level of the isoform of CRBN with a single exon 6 deletion. In some embodiments, the sequencing the target nucleic acid includes use of sequencing by synthesis, sequencing by ligation, or sequencing by hybridization. Other sequencing methods known in the art can also be used in the present methods.

In some embodiments of the various methods provided herein, the treatment compound is pomalidomide. In other embodiments of the various methods provided herein, the treatment compound is thalidomide. In other embodiments of the various methods provided herein, the treatment compound is lenalidomide. In yet other embodiments of the various methods provided herein, the treatment compound is 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione. In a specific embodiment of the various methods provided herein, the subject has multiple myeloma and the treatment compound is pomalidomide.

In certain embodiments, the biomarkers are used to identify a subject who is likely to be responsive to a treatment with thalidomide, lenalidomide, pomalidomide, 3-(5-amino- 2-methyl-4-oxoquinazolin-3(4H)-yl)piperidine-2,6-dione, or (S)-3-(4-(4-(morpholinomethyl)benzyl)oxy)-1-oxoisoindolin-2-yl)piperidine-2,6-dione. In certain embodiments, the biomarkers are used to identify a subject who is likely to be responsive to treatment by thalidomide. In certain embodiments, the biomarkers are used to identify a subject who is likely to be responsive to treatment by lenalidomide. In certain embodiments, the biomarkers are used to identify a subject who is likely to be responsive to treatment by pomalidomide. In certain embodiments, the biomarkers are used to identify a subject who is likely to be responsive to treatment by 3-(5-amino-2-methyl-4-oxoquinazolin-3(4H)-yl)piperidine-2,6-dione. In certain embodiments, the biomarkers are used to identify a subject who is likely to be responsive to treatment by (S)-3-(4-((4-(morpholinomethyl)benzyl)oxy)-1-oxoisoindolin-2-yl)piperidine-2,6-dione.

5.4.2 Use of CRBN Isoforms for Predicting the Efficacy of a Treatment

In one embodiment, provided herein is a method of predicting the responsiveness of a subject to a treatment with a treatment compound, comprising:
a) determining the level of a biomarker in a biological sample from the subject; and
b) comparing the level of the biomarker in the biological sample to a reference level of the biomarker,
wherein the difference between the level of the biomarker in the biological sample from the subject and the reference level correlates with an increased responsiveness of the subject to the treatment.

In another embodiment, provided herein is a method of predicting the responsiveness of a subject to a treatment with a treatment compound, comprising:
a) determining the level of a biomarker in a biological sample from the subject;
b) determining the level of the biomarker in a control sample; and
c) comparing the level of the biomarker in the biological sample from the subject to the level of the biomarker in the control sample;
wherein the difference between the level of the biomarker in the biological sample from the subject and the level of the biomarker in the control sample correlates with an increased responsiveness of the subject to the treatment.

In yet another embodiment, provided herein is a method of predicting the responsiveness of a subject to a treatment with a treatment compound, comprising:
a) obtaining a biological sample from the subject;
b) determining the level of a biomarker in the biological sample; and
c) comparing the level of the biomarker in the biological sample to a reference level of the biomarker;
wherein the difference between the level of the biomarker in the biological sample from the subject and the reference level correlates with an increased responsiveness of the subject to the treatment.

In yet another embodiment, provided herein is a method of predicting the responsiveness of a subject to a treatment with a treatment compound, comprising:
a) obtaining a biological sample from the subject;
b) determining the level of a biomarker in the biological sample;
c) determining the level of the biomarker in a control sample; and
d) comparing the level of the biomarker in the biological sample from the subject to the level of the biomarker in the control sample;
wherein the difference between the level of the biomarker in the biological sample from the subject and the level of the biomarker in the control sample correlates with an increased responsiveness of the subject to the treatment.

In yet another embodiment, provided herein is a method of predicting the responsiveness of a subject to a treatment with a treatment compound, comprising:
a) determining the level of a biomarker in a biological sample from the subject; and
b) comparing the level of the biomarker in the biological sample to a reference level of the biomarker,
wherein an increased level of the biomarker in the biological sample from the subject in comparison with the reference level of the biomarker correlates with an increased responsiveness of the subject to the treatment.

In yet another embodiment, provided herein is a method of predicting the responsiveness of a subject to a treatment with a treatment compound, comprising:
a) determining the level of a biomarker in a biological sample from the subject;
b) determining the level of the biomarker in a control sample; and
c) comparing the level of the biomarker in the biological sample from the subject to the level of the biomarker in the control sample;
wherein an increased level of the biomarker in the biological sample from the subject in comparison with the level of the biomarker in the control sample correlates with an increased responsiveness of the subject to the treatment.

In yet another embodiment, provided herein is a method of predicting the responsiveness of a subject to a treatment with a treatment compound, comprising:
a) obtaining a biological sample from the subject;
b) determining the level of a biomarker in the biological sample; and
c) comparing the level of the biomarker in the biological sample to a reference level of the biomarker;
wherein an increased level of the biomarker in the biological sample from the subject in comparison with the reference level of the biomarker correlates with an increased responsiveness of the subject to the treatment.

In yet another embodiment, provided herein is a method of predicting the responsiveness of a subject to a treatment with a treatment compound, comprising:
a) obtaining a biological sample from the subject;
b) determining the level of a biomarker in the biological sample;
c) determining the level of the biomarker in a control sample; and
d) comparing the level of the biomarker in the biological sample from the subject to the level of the biomarker in the control sample;
wherein an increased level of the biomarker in the biological sample from the subject in comparison with the level of the biomarker in the control sample correlates with an increased responsiveness of the subject to the treatment.

In yet another embodiment, provided herein is a method of predicting the responsiveness of a subject to a treatment with a treatment compound, comprising:
a) determining the level of a biomarker in a biological sample from the subject; and
b) comparing the level of the biomarker in the biological sample to a reference level of the biomarker,
wherein a decreased level of the biomarker in the biological sample from the subject in comparison with the reference level of the biomarker correlates with an increased responsiveness of the subject to the treatment.

In yet another embodiment, provided herein is a method of predicting the responsiveness of a subject to a treatment with a treatment compound, comprising:
 a) determining the level of a biomarker in a biological sample from the subject;
 b) determining the level of the biomarker in a control sample; and
 c) comparing the level of the biomarker in the biological sample from the subject to the level of the biomarker in the control sample;
 wherein a decreased level of the biomarker in the biological sample from the subject in comparison with the level of the biomarker in the control sample correlates with an increased responsiveness of the subject to the treatment.

In yet another embodiment, provided herein is a method of predicting the responsiveness of a subject to a treatment with a treatment compound, comprising:
 a) obtaining a biological sample from the subject;
 b) determining the level of a biomarker in the biological sample; and
 c) comparing the level of the biomarker in the biological sample to a reference level of the biomarker;
 wherein a decreased level of the biomarker in the biological sample from the subject in comparison with the reference level of the biomarker correlates with an increased responsiveness of the subject to the treatment.

In still another embodiment, provided herein is a method of predicting the responsiveness of a subject to a treatment with a treatment compound, comprising:
 a) obtaining a biological sample from the subject;
 b) determining the level of a biomarker in the biological sample;
 c) determining the level of the biomarker in a control sample; and
 d) comparing the level of the biomarker in the biological sample from the subject to the level of the biomarker in the control sample;
 wherein a decreased level of the biomarker in the biological sample from the subject in comparison with the level of the biomarker in the control sample correlates with an increased responsiveness of the subject to the treatment.

In some embodiments, provided herein is a method of predicting the responsiveness of a subject to a treatment of a disease, disorder, or condition with a treatment compound, comprising:
 a) obtaining a biological sample from the subject;
 b) determining the level of an isoform of CRBN comprising an exon 6 deletion in the biological sample; and
 c) diagnosing the subject as being likely to be responsive to a treatment of a disease, disorder, or condition with the treatment compound if the level of the isoform of CRBN comprising an exon 6 deletion is determined to be less than a baseline level;
 wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

In some embodiments, provided herein is a method of predicting the responsiveness of a subject to a treatment of a disease, disorder, or condition with a treatment compound, comprising:
 a) obtaining a biological sample from the subject;
 b) determining the level of an isoform of CRBN comprising an exon 6 deletion in the biological sample; and
 c) diagnosing the subject as not being likely to be responsive to a treatment of a disease, disorder, or condition with the treatment compound if the level of the isoform of CRBN comprising an exon 6 deletion present in the biological sample is determined to be a baseline level;
 wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

In one embodiment, provided herein is a method of monitoring the efficacy of a treatment of a disease, disorder, or condition in a subject treated with a treatment compound, comprising:
 a) obtaining a first biological sample from the subject;
 b) determining the level of a biomarker in the first biological sample;
 c) administering the treatment compound to the subject;
 d) thereafter obtaining a second biological sample from the subject;
 e) determining the level of the biomarker in the second biological sample, and
 f) comparing the levels of the biomarker in the first and second biological samples;
 wherein the subject is responsive to the treatment if the level of the biomarker in the second biological sample of the subject is altered as compared to the level of the biomarker in the first biological sample of the subject.

In another embodiment, provided herein is a method of monitoring the efficacy of a treatment of a disease, disorder, or condition in a subject treated with a treatment compound, comprising:
 a) obtaining a first biological sample from the subject;
 b) determining the level of a biomarker in the first biological sample;
 c) administering the treatment compound to the subject;
 d) thereafter obtaining a second biological sample from the subject;
 e) determining the level of the biomarker in the second biological sample, and
 f) comparing the levels of the biomarker in the first and second biological samples;
 wherein an increased level of the biomarker in the second biological sample in comparison with the level of the biomarker in the first biological sample indicates that the subject is responsive to the treatment.

In yet another embodiment, provided herein is a method of monitoring the efficacy of a treatment of a disease, disorder, or condition in a subject treated with a treatment compound, comprising:
 a) obtaining a first biological sample from the subject;
 b) determining the level of a biomarker in the first biological sample;
 c) administering the treatment compound to the subject;
 d) thereafter obtaining a second biological sample from the subject;
 e) determining the level of the biomarker in the second biological sample, and
 f) comparing the levels of the biomarker in the first and second biological samples;
 wherein a decreased level of the biomarker in the second biological sample in comparison with the level of the biomarker in the first biological sample indicates that the subject is responsive to the treatment.

As shown in Examples 6.3-6.5, an isoform of CRBN comprising an exon 6 is detected in acquired pomalidomide resistant cancer cells but is absent in the parent cancer cells where the pomalidomide resistant cancer cells are derived from. Thus, the monitoring the expression level of the isoform of CRBN comprising an exon 6 deletion provides a tool for monitoring the efficacy of a treatment to a subject. Thus, in some embodiments, provided herein is a method of monitoring the efficacy of a treatment of a disease, disorder, or condition in a subject treated with a treatment compound, comprising:
  a) obtaining a first biological sample from the subject;
  b) determining the level of an isoform of CRBN comprising an exon 6 deletion in the first biological sample;
  d) administering an effective amount of the treatment compound to the subject;
  e) obtaining a second biological sample from the subject; and
  b) determining the level of the isoform of CRBN comprising an exon 6 deletion in the second biological sample;
  wherein the subject develops resistance to the treatment compound when an increased level of the isoform of CRBN comprising an exon 6 is determined, and
  wherein the treatment compound is thalidomide, lenalidomide, pomalidomide, 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione a stereoisomer thereof, or a pharmaceutically acceptable salt, solvate, hydrate, co-crystal, clathrate, or polymorph thereof.

In one embodiment, provided herein is a method of monitoring the compliance of a subject with a treatment of a disease, disorder, or condition with a treatment compound, comprising:
  a) obtaining a biological sample from the subject;
  b) determining the level of a biomarker in the biological sample; and
  c) comparing the level of the biomarker with the level of the biomarker in a control sample from the subject;
  wherein the change in the level of the biomarker in the biological sample in comparison with the level of the biomarker in the control sample indicates the compliance of the subject with the treatment.

In another embodiment, provided herein is a method of monitoring the compliance of a subject with a treatment of a disease, disorder, or condition with a treatment compound, comprising:
  a) obtaining a biological sample from the subject;
  b) determining the level of a biomarker in the biological sample; and
  c) comparing the level of the biomarker with the level of the biomarker in a control sample from the subject;
  wherein an increased level of the biomarker in the biological sample in comparison with the level of the biomarker in the control sample indicates the compliance of the subject with the treatment.

In yet another embodiment, provided herein is a method of monitoring the compliance of a subject with a treatment of a disease, disorder, or condition with a treatment compound, comprising:
  a) obtaining a biological sample from the subject;
  b) determining the level of a biomarker in the biological sample; and
  c) comparing the level of the biomarker with the level of the biomarker in a control sample from the subject;
  wherein a decreased level of the biomarker in the biological sample in comparison with the level of the biomarker in the control sample indicates the compliance of the subject with the treatment.

In certain embodiments of various methods provided herein, the method further comprises administering an effective amount of the treatment compound to the subject, e.g., the subject predicted to be responsive to the treatment compound. In certain embodiments, the methods provided herein are coupled with a treatment with a treatment compound, in one embodiment, an immunomodulatory compound, e.g., thalidomide, lenalidomide, pomalidomide, 3-(5-amino-2-methyl-4-oxoquinazolin-3(4H)-yl)piperidine-2,6-dione, or (S)-3-(4-((4-(morpholinomethyl)-benzyl)oxy)-1-oxoisoindolin-2-yl)piperidine-2,6-dione.

In certain embodiments, the treatment compound is administered to a patient as a dose of from about 0.1 mg per day to about 100 mg per day. In other embodiments, the treatment compound is administered to a patient as a dose of between about 0.5 mg per day to about 100 mg per day. In other embodiments, the treatment compound is administered to a patient as a dose of between about 0.5 mg per day to about 20 mg per day. In other embodiments, the treatment compound is administered to a patient as a dose of between about 5 mg per day to about 25 mg per day. In some embodiments, the treatment compound is administered to a patient as a dose of between about 0.5 mg per day to about 10 mg per day. In certain embodiments, the treatment compound is administered to a patient as a dose of between about 0.5 mg per day to about 100 mg per day.

In other embodiments, the treatment compound is administered at a dose of about 0.1 mg, 0.5 mg, 1 mg, 1.5 mg, 2 mg, 2.5 mg, 3 mg, 3.5 mg, 4.0 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 20 mg, 25 mg, 30 mg, 35 mg, 40 mg, 45 mg, 50 mg, 60 mg, 70 mg, 80 mg, 90 mg or 100 mg per day.

In some embodiments, the treatment compound is administered once daily. In some embodiments, the treatment compound is administered twice daily. In certain embodiments, the treatment compound is cyclically administered to a patient. Cycling therapy involves the administration of an active agent for a period of time, followed by a rest for a period of time, and repeating this sequential administration. Accordingly, in some embodiments, about 0.5 mg per day to about 100 mg per day of the treatment compound is administered on days 1-12 of a repeated 28 day cycle. In a specific embodiment, 25 mg of the treatment compound is administered once a day on days 1-12 of a repeated 28 day cycle.

It is understood that specific dose levels of a treatment compound described for any particular subject depends upon a variety of factors including the activity of the specific compound employed, the age, body weight, general health, sex, and diet of the patient, the time of administration, the rate of excretion, the treatment compound combination, and the severity of the tumor being treated and form of administration. In it also understand that one of ordinary skill in the art can readily determine the appropriate dose of the treatment compound based on these factors. Treatment dosages generally may be titrated to optimize safety and efficacy.

A treatment compound can be administered by any route of administration known in the art, such as oral, intravenous, subcutaneous, or intramucosal administration. In one embodiment, lenalidomide or a stereoisomer thereof; or a pharmaceutically acceptable salt, solvate, hydrate, co-crystal, clathrate thereof; or a polymorph thereof, is administered to a patient orally. In one embodiment, thalidomide or a stereoisomer thereof; or a pharmaceutically acceptable salt, solvate, hydrate, co-crystal, clathrate thereof; or a polymorph thereof, is administered to a patient orally. In one embodiment, pomalidomide or a stereoisomer thereof; or a pharmaceutically acceptable salt, solvate, hydrate, co-crystal, clathrate thereof; or a polymorph thereof, is administered to a patient orally. In one embodiment, lenalidomide or a stereoisomer thereof; or a pharmaceutically acceptable salt, solvate, hydrate, co-crystal, clathrate thereof; or a polymorph thereof, is administered to a patient orally. In one embodiment, 3-(5-amino-2-methyl-4-oxoquinazolin-3(4H)-yl)piperidine-2,6-dione or a stereoisomer thereof; or a pharmaceutically acceptable salt, solvate, hydrate, co-crystal, clathrate thereof; or a polymorph thereof, is administered to a patient orally. In one embodiment, (S)-3-(4-((4-(morpholinomethyl)benzyl)oxy)-1-oxoisoindolin-2-yl)piperidine-2,6-dione or a stereoisomer thereof; or a pharmaceutically acceptable salt, solvate, hydrate, co-crystal, clathrate thereof; or a polymorph thereof, is administered to a patient orally. The oral dosage form can be a tablet or a capsule. In some embodiments, the dosage form is a tablet. In some other embodiments, the dosage for is a capsule.

In some embodiments of the various methods provided herein, the isoform of CRBN comprising an exon 6 deletion contains a single exon 6 deletion and contains exons 1-5 and 7-11.

In some embodiments of the various methods provided herein, the disease, disorder, or condition is a CRBN-mediated disease, disorder, or condition.

In some embodiments of the various methods provided herein, the subject has multiple myeloma, lymphoma, melanoma or solid tumor. In some embodiments, the subject has multiple myeloma. In other embodiments, the subject has lymphoma. In yet other embodiments, the subject has melanoma. In yet other embodiments, the subject has solid tumor.

In some embodiments of the various methods provided herein, the determining the level of an isoform of CRBN comprising an exon 6 deletion in the cancer sample determines presence (or absence) of the isoform of CRBN comprising an exon 6 deletion. In some embodiments, the isoform of CRBN comprising an exon 6 deletion is determined to be the only isoform of CRBN in the sample.

In some embodiments of the various methods provided herein, the subject is diagnosed as having a treatment compound-sensitive cancer if the level of the isoform of CRBN comprising an exon 6 deletion present in the biological sample is determined to be less than 10%, 20%, 30%, 40%, 50%, 60%, 70%, 80% or 90% of the baseline level. In other embodiments of the various methods provided herein, the subject is diagnosed as having a treatment compound-sensitive cancer if the isoform of CRBN comprising an exon 6 deletion is absent from the cancer sample.

In some embodiments of the various methods provided herein, the determining the level of the isoform of CRBN comprising an exon 6 deletion is performed by contacting the sample with an isolated antibody that immunospecifically binds to an epitope in the CRBN, wherein the epitope has the amino acid sequence SEQ ID NO: 8. The SEQ ID NO: 8 represents the amino acid sequence of exon 6 of CRBN. The isoform of CRBN comprising an exon 6 deletion cannot be detected with such an antibody, and thus the antibody can be used in the present method to detect the presence or determine the level of the isoform of CRBN comprising an exon 6 deletion.

In other embodiments of the various methods provided herein, the methods provided herein further include purifying CRBN protein and isoforms thereof from the sample. The purified CRBN proteins and isoforms thereof can be subjected to various assays for determining the level (e.g., quantitating) or presence of the isoform of CRBN comprising an exon 6 deletion. In some embodiments, such assay includes measuring the size of the purified CRBN proteins and isoforms thereof. In some embodiments, the purified/enriched CRBN proteins and isoforms thereof can be sequenced, and thereby determining presence or the level of the isoform of CRBN comprising an exon 6 deletion. In some embodiments, the sequencing purified CRBN protein and isoforms thereof includes use of mass spectrometry or An Edmandegradation reaction. Other methods for protein sequencing and/or characterization known in the art may also be used in the present disclosure for determining the presence or the level of the isoform of CRBN comprising an exon 6 deletion.

In other embodiments of the various methods provided herein, the methods provided herein further include extracting mRNA from the biological sample. Thus, in some embodiments, the method provided herein can determine the level of the isoform of CRBN comprising an exon 6 deletion by determining the presence or the level of mRNA of exon 6 of CRBN using a polymerase chain reaction (PCR). In some embodiments, the PCR is a RT-PCR.

Various primer designs in a RT-PCR can be used to determine the presence or the level of exon 6 of CRBN in a sample in some embodiments of the various methods provided herein. For example, in some embodiments, one primer used in the PCR represents a sequence within exon 7 of CRBN, and a second PCR primer has a 5' portion and a 3' portion, the 5' portion representing a sequence within exon 6 of CRBN, the 3' portion presenting a sequence within exon 7 of CRBN. Because the second primer is complementary to a junction region between exon 6 and exon 7, the presence of PCR products with proper size indicates the presence of exon 6 before exon 7. In some embodiments, one primer used in the PCR represents a sequence within exon 7 of CRBN, and a second PCR primer has a 5' portion and a 3' portion, the 5' portion representing a sequence within exon 5 of CRBN, the 3' portion presenting a sequence within exon 7 of CRBN. Because the second primer is complementary to a junction region between exon 5 and exon 7, the presence of PCR products with proper size indicates the presence of exon 5 right before exon 7 and absence of exon 6. Similarly, in some embodiments, one primer represents a sequence within exon 5, and a second primer represents a sequence at junction between exon 5 and exon 6, and thus presence of PCR products with proper size indicates the presence of exon 6 after exon 5. In some embodiments, one primer represents a sequence within exon 5, and a second primer represents a sequence at junction between exon 5 and exon 7, and thus presence of PCR products with proper size indicates the presence of exon 7 right after exon 5 and absence of exon 6.

In yet other embodiments of the various methods provided herein, the methods provided herein further comprise generating cDNA from the mRNA. Thus, the cDNA can be subjected to various assays for determining the level (e.g., quantitating) or presence of the isoform of CRBN comprising an exon 6 deletion. In some embodiments, the determining the level of the isoform of CRBN comprising an exon 6 deletion in is performed by a polymerase chain reaction (PCR) using cDNA as templates.

Similarly to the primer designs for RT-PCR described above, various primer designs can be used to determine the presence or the level of exon 6 of CRBN in a sample using cDNA as templates in some embodiments of the various methods provided herein. In some embodiments, one primer used in the PCR represents a sequence within exon 7 of CRBN, and a second PCR primer has a 5' portion and a 3' portion, the 5' portion representing a sequence within exon 6 of CRBN, the 3' portion presenting a sequence within exon 7 of CRBN. The presence of PCR products with proper size indicates the presence of exon 6 before exon 7. In some embodiments, one primer used in the PCR represents a sequence within exon 7 of CRBN, and a second PCR primer has a 5' portion and a 3' portion, the 5' portion representing a sequence within exon 5 of CRBN, the 3' portion presenting a sequence within exon 7 of CRBN. The presence of PCR products with proper size indicates the presence of exon 5 right before exon 7 and absence of exon 6. In other embodiments, one primer represents a sequence within exon 5, and a second primer represents a sequence at junction between exon 5 and exon 6, and thus presence of PCR products with proper size indicates the presence of exon 6 after exon 5. In some embodiments, one primer represents a sequence within exon 5, and a second primer represents a sequence at junction between exon 5 and exon 7, and thus presence of PCR products with proper size indicates the presence of exon 7 right after exon 5 and absence of exon 6. In one embodiment, a first primer has a sequence of 5'-GCAGAAATACCAGAAGGAGACCTTA-3' (SEQ ID NO: 14), and a second primer has a sequence of 5'-GCGAAGTCGCTGGATAGCA-3' (SEQ ID NO:15).

In yet other embodiments of the various methods provided herein, the methods provided herein can use a probe to detect the presence of exon 6 in a nucleic acid sample, e.g., mRNA and cDNA, prepared from a subject. Thus, in some embodiments, determining the level of the isoform of CRBN comprising an exon 6 deletion is performed using a probe targeting a nucleic acid sequence presenting CRBN. In some embodiments, the probe comprises a nucleic acid sequence complementary to a region of exon 6 of CRBN. In some embodiments, the probe comprises a nucleic acid sequence complementary to a sequence representing a junction region between exon 6 of CRBN and exon 7 of CRBN. In some embodiments, the probe comprises a nucleic acid sequence complementary to a sequence representing a junction region between exon 5 of CRBN and exon 6 of CRBN.

Nucleic acid representing CRBN or isoforms thereof can be used for determining the presence or the level of the isoforms of CRBN comprising an exon 6 deletion, e.g., by sequencing. Thus, in some embodiments of the various methods provided herein, the methods provided herein further include enriching a target nucleic acid from the cancer sample, wherein the target nucleic acid represents CRBN or isoforms thereof. In some embodiments, the target nucleic acid is a DNA. In some embodiments, the target nucleic acid is a mRNA. In other embodiments, cDNA is generated from the enriched mRNA and can be subjected to sequencing analysis.

In yet other embodiments of the various methods provided herein, the methods provided herein further include sequencing the target nucleic acid, and thereby determining the presence or the level of the isoform of CRBN with a single exon 6 deletion. In some embodiments, the sequencing the target nucleic acid includes use of sequencing by synthesis, sequencing by ligation, or sequencing by hybridization. Other sequencing methods known in the art can also be used in the present methods.

In some embodiments of the various methods provided herein, the treatment compound is pomalidomide. In other embodiments of the various methods provided herein, the treatment compound is thalidomide. In other embodiments of the various methods provided herein, the treatment compound is lenalidomide. In yet other embodiments of the various methods provided herein, the treatment compound is 3-(5-amino-2-methyl-4-oxo-4H-quinazolin-3-yl)-piperidine-2,6-dione, or (S)-3-(4-((4-(morpholinomethyl)benzyl)oxy)-1-oxoisoindolin-2-yl)piperidine-2,6-dione. In a specific embodiment of the various methods provided herein, the subject has multiple myeloma and the treatment compound is pomalidomide.

In certain embodiments, the biomarker is a polypeptide of a CRBN isoform.

In certain embodiments, the control sample is a disease-free sample from the same subject. In certain embodiments, the control sample is a disease-free sample from a group of subjects.

In certain embodiments, the level of the biomarker in a control sample is determined simultaneously with the level of the biomarker in the biological sample from the subject. In certain embodiments, the level of the biomarker in a control sample is determined independently from the level of the biomarker in the biological sample from the subject.

In certain embodiments, the biomarkers are used to predict the responsiveness of a subject to a treatment with thalidomide, lenalidomide, pomalidomide, 3-(5-amino-2-methyl-4-oxoquinazolin-3(4H)-yl)piperidine-2,6-dione, or (S)-3-(4-(4-(morpholinomethyl)benzyl)oxy)-1-oxoisoindolin-2-yl)piperidine-2,6-dione. In certain embodiments, the biomarkers are used to predict the responsiveness of a subject to a treatment with thalidomide. In certain embodiments, the biomarkers are used to predict the responsiveness of a subject to a treatment with lenalidomide. In certain embodiments, the biomarkers are used to predict the responsiveness of a subject to a treatment with pomalidomide. In certain embodiments, the biomarkers are used to predict the responsiveness of a subject to a treatment 3-(5-amino-2-methyl-4-oxoquinazolin-3(4H)-yl)piperidine-2,6-dione. In certain embodiments, the biomarkers are used to predict the responsiveness of a subject to a treatment (S)-3-(4-((4-(morpholinomethyl)benzyl)oxy)-1-oxoisoindolin-2-yl)piperidine-2,6-dione.

In certain embodiments, the level of the biomarker is measured in an in vitro assay to predict the responsiveness of a subject to a treatment with a treatment compound, comprising obtaining a sample of cells from the subject, culturing the cells in the presence (or absence) of the treatment compound, and determining the level of the biomarker in the cells, wherein the difference between the level of the biomarker in the cells treated with the treatment compound in comparison with the level of the biomarker in the untreated cells indicates the likelihood of responsiveness of the subject to the treatment compound.

In certain embodiments, the level of the biomarker is measured in an in vitro assay to predict the responsiveness of a subject to a treatment with a treatment compound, comprising obtaining a sample of cells from the subject, culturing the cells in the presence (or absence) of the treatment compound, and determining the level of the biomarker in the cells, wherein an increased level of the biomarker in the cells treated with the treatment compound in comparison with the level of the biomarker in the untreated cells indicates the likelihood of responsiveness of the subject to the treatment compound.

In certain embodiments, the level of the biomarker is measured in an in vitro assay to predict the responsiveness of a subject to a treatment with a treatment compound, comprising obtaining a sample of cells from the subject, culturing the cells in the presence (or absence) of the treatment compound, and determining the level of the biomarker in the cells, wherein a decreased level of the biomarker in the cells treated with the treatment compound in comparison with the level of the biomarker in the untreated cells indicates the likelihood of responsiveness of the subject to the treatment compound.

5.4.3 Use of mRNAs Encoding CRBN Isoforms as Biomarkers for Identifying a Subject for a Treatment In one embodiment, provided herein is a method of identifying a subject who is likely to be responsive to a treatment with a treatment compound, comprising:

a) determining the level of an mRNA encoding a CRBN isoform as a biomarker in a biological sample from the subject; and b) comparing the level of the mRNA biomarker in the biological sample to a reference level of the mRNA biomarker;

wherein the subject is likely to be responsive to the treatment if the level of the mRNA biomarker in the biological sample from the subject is altered as compared to the reference level of the mRNA biomarker.

In another embodiment, provided herein is a method of identifying a subject who is likely to be responsive to a treatment with a treatment compound, comprising:

a) determining the level of an mRNA encoding a CRBN isoform as a biomarker in a biological sample from the subject; and b) determining the level of the mRNA biomarker in a control sample; and c) comparing the level of the mRNA biomarker in the biological sample from the subject to the level of the mRNA biomarker in the control sample;

wherein the subject is likely to be responsive to the treatment if the level of the mRNA biomarker in the biological sample from the subject is altered as compared to the level of the mRNA biomarker in the control sample.

In yet another embodiment, provided herein is a method of identifying a subject who is likely to be responsive to a treatment with a treatment compound, comprising:

a) obtaining a biological sample from the subject;

b) determining the level of an mRNA encoding a CRBN isoform as a biomarker in the biological sample; and c) comparing the level of the mRNA biomarker in the biological sample to a reference level of the mRNA biomarker;

wherein the subject is likely to be responsive to the treatment if the level of the mRNA biomarker in the biological sample from the subject is altered as compared to the reference level of the mRNA biomarker.

In yet another embodiment, provided herein is a method of identifying a subject who is likely to be responsive to a treatment with a treatment compound, comprising:

a) obtaining a biological sample from the subject;

b) determining the level of an mRNA encoding a CRBN isoform as a biomarker in the biological sample;

c) determining the level of the mRNA biomarker in a control sample; and d) comparing the level of the mRNA biomarker in the biological sample from the subject to the level of the mRNA biomarker in the control sample;

wherein the subject is likely to be responsive to the treatment if the level of the mRNA biomarker in the biological sample from the subject is altered as compared to the reference level of the mRNA biomarker.

In yet another embodiment, provided herein is a method of identifying a subject who is likely to be responsive to a treatment with a treatment compound, comprising:

a) determining the level of an mRNA encoding a CRBN isoform as a biomarker in a biological sample from the subject; and b) comparing the level of the mRNA biomarker in the biological sample to a reference level of the mRNA biomarker;

wherein the subject is likely to be responsive to the treatment if the level of the mRNA biomarker in the biological sample from the subject is higher than the reference level of the mRNA biomarker.

In another embodiment, provided herein is a method of identifying a subject who is likely to be responsive to a treatment with a treatment compound, comprising:

a) determining the level of an mRNA encoding a CRBN isoform as a biomarker in a biological sample from the subject; and b) determining the level of the mRNA biomarker in a control sample; and c) comparing the level of the mRNA biomarker in the biological sample from the subject to the level of the mRNA biomarker in the control sample;

wherein the subject is likely to be responsive to the treatment if the level of the mRNA biomarker in the biological sample from the subject is higher than the level of the mRNA biomarker in the control sample.

In yet another embodiment, provided herein is a method of identifying a subject who is likely to be responsive to a treatment with a treatment compound, comprising:

a) obtaining a biological sample from the subject;

b) determining the level of an mRNA encoding a CRBN isoform as a biomarker in the biological sample; and c) comparing the level of the mRNA biomarker in the biological sample to a reference level of the mRNA biomarker;

wherein the subject is likely to be responsive to the treatment if the level of the mRNA biomarker in the biological sample from the subject is higher than the reference level of the mRNA biomarker.

In yet another embodiment, provided herein is a method of identifying a subject who is likely to be responsive to a treatment with a treatment compound, comprising:

a) obtaining a biological sample from the subject;

b) determining the level of an mRNA encoding a CRBN isoform as a biomarker in the biological sample;

c) determining the level of the mRNA biomarker in a control sample; and d) comparing the level of the mRNA biomarker in the biological sample from the subject to the level of the mRNA biomarker in the control sample;

wherein the subject is likely to be responsive to the treatment if the level of the mRNA biomarker in the biological sample from the subject is higher than the reference level of the mRNA biomarker.

In yet another embodiment, provided herein is a method of identifying a subject who is likely to be responsive to a treatment with a treatment compound, comprising:

a) determining the level of an mRNA encoding a CRBN isoform as a biomarker in a biological sample from the subject; and b) comparing the level of the mRNA biomarker in the biological sample to a reference level of the mRNA biomarker;

wherein the subject is likely to be responsive to the treatment if the level of the mRNA biomarker in the biological sample from the subject is lower than the reference level of the mRNA biomarker.

In another embodiment, provided herein is a method of identifying a subject who is likely to be responsive to a treatment with a treatment compound, comprising:
- a) determining the level of an mRNA encoding a CRBN isoform as a biomarker in a biological sample from the subject; and
- b) determining the level of the mRNA biomarker in a control sample; and
- c) comparing the level of the mRNA biomarker in the biological sample from the subject to the level of the mRNA biomarker in the control sample;

wherein the subject is likely to be responsive to the treatment if the level of the mRNA biomarker in the biological sample from the subject is lower than the level of the mRNA biomarker in the control sample.

In yet another embodiment, provided herein is a method of identifying a subject who is likely to be responsive to a treatment with a treatment compound, comprising:
- a) obtaining a biological sample from the subject;
- b) determining the level of an mRNA encoding a CRBN isoform as a biomarker in the biological sample; and
- c) comparing the level of the mRNA biomarker in the biological sample to a reference level of the mRNA biomarker;

wherein the subject is likely to be responsive to the treatment if the level of the mRNA biomarker in the biological sample from the subject is lower than the reference level of the mRNA biomarker.

In still another embodiment, provided herein is a method of identifying a subject who is likely to be responsive to a treatment with a treatment compound, comprising:
- a) obtaining a biological sample from the subject;
- b) determining the level of an mRNA encoding a CRBN isoform as a biomarker in the biological sample;
- c) determining the level of the mRNA biomarker in a control sample; and
- d) comparing the level of the mRNA biomarker in the biological sample from the subject to the level of the mRNA biomarker in the control sample;

wherein the subject is likely to be responsive to the treatment if the level of the mRNA biomarker in the biological sample from the subject is lower than the reference level of the mRNA biomarker.

In certain embodiments, the reference level is determined from a disease-free sample from the same subject. In certain embodiments, the reference level is determined from a disease-free sample from a group of subjects.

In certain embodiments, the reference level is determined simultaneously with the level of the mRNA biomarker in the biological sample from the subject. In certain embodiments, the reference level is determined independently from the level of the mRNA biomarker in the biological sample from the subject.

In certain embodiments, the control sample is a disease-free sample from the same subject. In certain embodiments, the control sample is a disease-free sample from a group of subjects.

In certain embodiments, the level of the mRNA biomarker in the control sample is determined simultaneously with the level of the mRNA biomarker in the biological sample from the subject. In certain embodiments, the level of the mRNA biomarker in the control sample is determined independently from the level of the mRNA biomarker in the biological sample from the subject.

In certain embodiments, the methods provided herein are coupled with a treatment with a treatment compound, in one embodiment, an immunomodulatory compound, e.g., thalidomide, lenalidomide, pomalidomide, 3-(5-amino-2-methyl-4-oxoquinazolin-3(4H)-yl)piperidine-2,6-dione, or (S)-3-(4-((4-(morpholinomethyl)-benzyl)oxy)-1-oxoisoindolin-2-yl)piperidine-2,6-dione.

Thus, in one embodiment, provided herein is a method of a treatment with a treatment compound, comprising:
- (i) identifying a subject who is likely to be responsive to the treatment compound, comprising:
  - a) determining the level of an mRNA encoding a CRBN isoform as a biomarker in a biological sample from the subject; and
  - b) comparing the level of the mRNA biomarker in the biological sample to a reference level of the mRNA biomarker; wherein the subject is likely to be responsive to the treatment if the level of the mRNA biomarker in the biological sample from the subject is altered as compared to the reference level of the mRNA biomarker; and
- (ii) administering a therapeutically effective amount of the treatment compound to the subject identified to be likely to be responsive to the treatment.

In another embodiment, provided herein is a method of a treatment with a treatment compound, comprising:
- (i) identifying a subject who is likely to be responsive to the treatment compound, comprising:
  - a) determining the level of an mRNA encoding a CRBN isoform as a biomarker in a biological sample from the subject;
  - b) determining the level of the mRNA biomarker in a control sample; and
  - c) comparing the level of the mRNA biomarker in the biological sample from the subject to the level of the mRNA biomarker in the control sample; wherein the subject is likely to be responsive to the treatment if the level of the mRNA biomarker in the biological sample from the subject is altered as compared to the level of the mRNA biomarker in the control sample; and
- (ii) administering a therapeutically effective amount of the treatment compound to the subject identified to be likely to be responsive to the treatment.

In yet another embodiment, provided herein is a method of a treatment with a treatment compound, comprising:
- (i) identifying a subject who is likely to be responsive to the treatment compound, comprising:
  - a) obtaining a biological sample from the subject;
  - b) determining the level of an mRNA encoding a CRBN isoform as a biomarker in the biological sample; and
  - c) comparing the level of the mRNA biomarker in the biological sample to a reference level of the mRNA biomarker; wherein the subject is likely to be responsive to the treatment if the level of the mRNA biomarker in the biological sample from the subject is altered as compared to the reference level of the mRNA biomarker; and
- (ii) administering a therapeutically effective amount of the treatment compound to the subject identified to be likely to be responsive to the treatment.

In yet another embodiment, provided herein is a method of a treatment with a treatment compound, comprising:
- (i) identifying a subject who is likely to be responsive to the treatment compound, comprising:
  - a) obtaining a biological sample from the subject;
  - b) determining the level of an mRNA encoding a CRBN isoform as a biomarker in the biological sample;

c) determining the level of the mRNA biomarker in a control sample; and
d) comparing the level of the mRNA biomarker in the biological sample from the subject to the level of the mRNA biomarker in the control sample; wherein the subject is likely to be responsive to the treatment if the level of the mRNA biomarker in the biological sample from the subject is altered as compared to the level of the mRNA biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) determining the level of an mRNA encoding a CRBN isoform as a biomarker in a biological sample from the subject; and
b) comparing the level of the mRNA biomarker in the biological sample to a reference level of the mRNA biomarker; wherein the subject is likely to be responsive to the treatment if the level of the mRNA biomarker in the biological sample from the subject is higher than the reference level of the mRNA biomarker; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) determining the level of an mRNA encoding a CRBN isoform as a biomarker in a biological sample from the subject;
b) determining the level of the mRNA biomarker in a control sample; and
c) comparing the level of the mRNA biomarker in the biological sample from the subject to the level of the mRNA biomarker in the control sample; wherein the subject is likely to be responsive to the treatment if the level of the mRNA biomarker in the biological sample from the subject is higher than the level of the mRNA biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) obtaining a biological sample from the subject;
b) determining the level of an mRNA encoding a CRBN isoform as a biomarker in the biological sample; and
c) comparing the level of the mRNA biomarker in the biological sample to a reference level of the mRNA biomarker; wherein the subject is likely to be responsive to the treatment if the level of the mRNA biomarker in the biological sample from the subject is higher than the reference level of the mRNA biomarker; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) obtaining a biological sample from the subject;
b) determining the level of an mRNA encoding a CRBN isoform as a biomarker in the biological sample;
c) determining the level of the mRNA biomarker in a control sample; and
d) comparing the level of the mRNA biomarker in the biological sample from the subject to the level of the mRNA biomarker in the control sample; wherein the subject is likely to be responsive to the treatment if the level of the mRNA biomarker in the biological sample from the subject is higher than the level of the mRNA biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) determining the level of an mRNA encoding a CRBN isoform as a biomarker in a biological sample from the subject; and
b) comparing the level of the mRNA biomarker in the biological sample to a reference level of the mRNA biomarker; wherein the subject is likely to be responsive to the treatment if the level of the mRNA biomarker in the biological sample from the subject is lower than the reference level of the mRNA biomarker; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) determining the level of an mRNA encoding a CRBN isoform as a biomarker in a biological sample from the subject;
b) determining the level of the mRNA biomarker in a control sample; and
c) comparing the level of the mRNA biomarker in the biological sample from the subject to the level of the mRNA biomarker in the control sample; wherein the subject is likely to be responsive to the treatment if the level of the mRNA biomarker in the biological sample from the subject is lower than the level of the mRNA biomarker in the control sample; and
(ii) administering a therapeutically effective amount of the treatment compound to the subject identified to be likely to be responsive to the treatment.

In yet another embodiment, provided herein is a method of a treatment with a treatment compound, comprising:
(i) identifying a subject who is likely to be responsive to the treatment compound, comprising:
a) obtaining a biological sample from the subject;
b) determining the level of an mRNA encoding a CRBN isoform as a biomarker in the biological sample; and
c) comparing the level of the mRNA biomarker in the biological sample to a reference level of the mRNA biomarker; wherein the subject is likely to be responsive to the treatment if the level of the mRNA biomarker in the biological sample from the subject is lower than the reference level of the mRNA biomarker; and (ii) administering a therapeutically effective amount of the treatment compound to the subject identified to be likely to be responsive to the treatment.

In yet another embodiment, provided herein is a method of a treatment with a treatment compound, comprising:

(i) identifying a subject who is likely to be responsive to the treatment compound, comprising:
　a) obtaining a biological sample from the subject;
　b) determining the level of an mRNA encoding a CRBN isoform as a biomarker in the biological sample;
　c) determining the level of the mRNA biomarker in a control sample; and
　d) comparing the level of the mRNA biomarker in the biological sample from the subject to the level of the mRNA biomarker in the control sample; wherein the subject is likely to be responsive to the treatment if the level of the mRNA biomarker in the biological sample from the subject is lower than the level of the mRNA biomarker in the control sample; and (ii) administering a therapeutically effective amount of the treatment compound to the subject identified to be likely to be responsive to the treatment.

In certain embodiments, the mRNA biomarkers are used to identify a subject who is likely to be responsive to a treatment with thalidomide, lenalidomide, pomalidomide, 3-(5-amino-2-methyl-4-oxoquinazolin-3(4H)-yl)piperidine-2,6-dione, or (S)-3-(4-((4-(morpholinomethyl)benzyl)oxy)-1-oxoisoindolin-2-yl)piperidine-2,6-dione. In certain embodiments, the mRNA biomarkers are used to identify a subject who is likely to be responsive to treatment by thalidomide. In certain embodiments, the mRNA biomarkers are used to identify a subject who is likely to be responsive to treatment by lenalidomide. In certain embodiments, the mRNA biomarkers are used to identify a subject who is likely to be responsive to treatment by pomalidomide. In certain embodiments, the mRNA biomarkers are used to identify a subject who is likely to be responsive to treatment by 3-(5-amino-2-methyl-4-oxoquinazolin-3(4H)-yl)piperidine-2,6-dione. In certain embodiments, the mRNA biomarkers are used to identify a subject who is likely to be responsive to treatment by (S)-3-(4-((4-(morpholinomethyl)-benzyl)oxy)-1-oxoisoindolin-2-yl)piperidine-2,6-dione.

5.4.4 Use of mRNAs Encoding CRBN Isoforms as Biomarkers for Predicting the Efficacy of a Treatment In one embodiment, provided herein is a method of predicting the responsiveness of a subject to a treatment with a treatment compound, comprising:
　a) determining the level of an mRNA encoding a CRBN isoform as a biomarker in a biological sample from the subject; and
　b) comparing the level of the mRNA biomarker in the biological sample to a reference level of the mRNA biomarker,
　wherein the difference between the level of the mRNA biomarker in the biological sample from the subject and the reference level correlates with an increased responsiveness of the subject to the treatment.

In another embodiment, provided herein is a method of predicting the responsiveness of a subject to a treatment with a treatment compound, comprising:

a) determining the level of an mRNA encoding a CRBN isoform as a biomarker in a biological sample from the subject;
　b) determining the level of the mRNA biomarker in a control sample; and
　c) comparing the level of the mRNA biomarker in the biological sample from the subject to the level of the mRNA biomarker in the control sample;
　wherein the difference between the level of the mRNA biomarker in the biological sample from the subject and the level of the mRNA biomarker in the control sample correlates with an increased responsiveness of the subject to the treatment.

In yet another embodiment, provided herein is a method of predicting the responsiveness of a subject to a treatment with a treatment compound, comprising:
　a) obtaining a biological sample from the subject;
　b) determining the level of an mRNA encoding a CRBN isoform as a biomarker in the biological sample; and
　c) comparing the level of the mRNA biomarker in the biological sample to a reference level of the mRNA biomarker;
　wherein the difference between the level of the mRNA biomarker in the biological sample from the subject and the reference level correlates with an increased responsiveness of the subject to the treatment.

In yet another embodiment, provided herein is a method of predicting the responsiveness of a subject to a treatment with a treatment compound, comprising:
　a) obtaining a biological sample from the subject;
　b) determining the level of an mRNA encoding a CRBN isoform as a biomarker in the biological sample;
　c) determining the level of the mRNA biomarker in a control sample; and
　d) comparing the level of the mRNA biomarker in the biological sample from the subject to the level of the mRNA biomarker in the control sample;
　wherein the difference between the level of the mRNA biomarker in the biological sample from the subject and the level of the mRNA biomarker in the control sample correlates with an increased responsiveness of the subject to the treatment.

In yet another embodiment, provided herein is a method of predicting the responsiveness of a subject to a treatment with a treatment compound, comprising:
　a) determining the level of an mRNA encoding a CRBN isoform as a biomarker in a biological sample from the subject; and
　b) comparing the level of the mRNA biomarker in the biological sample to a reference level of the mRNA biomarker,
　wherein an increased level of the mRNA biomarker in the biological sample from the subject in comparison with the reference level of the mRNA biomarker correlates with an increased responsiveness of the subject to the treatment.

In yet another embodiment, provided herein is a method of predicting the responsiveness of a subject to a treatment with a treatment compound, comprising:
　a) determining the level of an mRNA encoding a CRBN isoform as a biomarker in a biological sample from the subject;
　b) determining the level of the mRNA biomarker in a control sample; and
　c) comparing the level of the mRNA biomarker in the biological sample from the subject to the level of the mRNA biomarker in the control sample;

wherein an increased level of the mRNA biomarker in the biological sample from the subject in comparison with the level of the mRNA biomarker in the control sample correlates with an increased responsiveness of the subject to the treatment.

In yet another embodiment, provided herein is a method of predicting the responsiveness of a subject to a treatment with a treatment compound, comprising:
 a) obtaining a biological sample from the subject;
 b) determining the level of an mRNA encoding a CRBN isoform as a biomarker in the biological sample; and
 c) comparing the level of the mRNA biomarker in the biological sample to a reference level of the mRNA biomarker;
wherein an increased level of the mRNA biomarker in the biological sample from the subject in comparison with the reference level of the mRNA biomarker correlates with an increased responsiveness of the subject to the treatment.

In yet another embodiment, provided herein is a method of predicting the responsiveness of a subject to a treatment with a treatment compound, comprising:
 a) obtaining a biological sample from the subject;
 b) determining the level of an mRNA encoding a CRBN isoform as a biomarker in the biological sample;
 c) determining the level of the mRNA biomarker in a control sample; and
 d) comparing the level of the mRNA biomarker in the biological sample from the subject to the level of the mRNA biomarker in the control sample;
wherein an increased level of the mRNA biomarker in the biological sample from the subject in comparison with the level of the mRNA biomarker in the control sample correlates with an increased responsiveness of the subject to the treatment.

In yet another embodiment, provided herein is a method of predicting the responsiveness of a subject to a treatment with a treatment compound, comprising:
 a) determining the level of an mRNA encoding a CRBN isoform as a biomarker in a biological sample from the subject; and
 b) comparing the level of the mRNA biomarker in the biological sample to a reference level of the mRNA biomarker,
wherein a decreased level of the mRNA biomarker in the biological sample from the subject in comparison with the reference level of the mRNA biomarker correlates with an increased responsiveness of the subject to the treatment.

In yet another embodiment, provided herein is a method of predicting the responsiveness of a subject to a treatment with a treatment compound, comprising:
 a) determining the level of an mRNA encoding a CRBN isoform as a biomarker in a biological sample from the subject;
 b) determining the level of the mRNA biomarker in a control sample; and
 c) comparing the level of the mRNA biomarker in the biological sample from the subject to the level of the mRNA biomarker in the control sample;
wherein a decreased level of the mRNA biomarker in the biological sample from the subject in comparison with the level of the mRNA biomarker in the control sample correlates with an increased responsiveness of the subject to the treatment.

In yet another embodiment, provided herein is a method of predicting the responsiveness of a subject to a treatment with a treatment compound, comprising:
 a) obtaining a biological sample from the subject;
 b) determining the level of an mRNA encoding a CRBN isoform as a biomarker in the biological sample; and
 c) comparing the level of the mRNA biomarker in the biological sample to a reference level of the mRNA biomarker;
wherein a decreased level of the mRNA biomarker in the biological sample from the subject in comparison with the reference level of the mRNA biomarker correlates with an increased responsiveness of the subject to the treatment.

In still another embodiment, provided herein is a method of predicting the responsiveness of a subject to a treatment with a treatment compound, comprising:
 a) obtaining a biological sample from the subject;
 b) determining the level of an mRNA encoding a CRBN isoform as a biomarker in the biological sample;
 c) determining the level of the mRNA biomarker in a control sample; and
 d) comparing the level of the mRNA biomarker in the biological sample from the subject to the level of the mRNA biomarker in the control sample;
wherein a decreased level of the mRNA biomarker in the biological sample from the subject in comparison with the level of the mRNA biomarker in the control sample correlates with an increased responsiveness of the subject to the treatment.

In one embodiment, provided herein is a method of monitoring the efficacy of a treatment of a disease, disorder, or condition in a subject treated with a treatment compound, comprising:
 a) obtaining a first biological sample from the subject;
 b) determining the level of an mRNA encoding a CRBN isoform as a biomarker in the first biological sample;
 c) administering the treatment compound to the subject;
 d) thereafter obtaining a second biological sample from the subject;
 e) determining the level of the mRNA biomarker in the second biological sample, and
 f) comparing the levels of the mRNA biomarker in the first and second biological samples;
wherein the subject is responsive to the treatment if the level of the mRNA biomarker in the second biological sample of the subject is altered as compared to the level of the mRNA biomarker in the first biological sample of the subject.

In another embodiment, provided herein is a method of monitoring the efficacy of a treatment of a disease, disorder, or condition in a subject treated with a treatment compound, comprising:
 a) obtaining a first biological sample from the subject;
 b) determining the level of an mRNA encoding a CRBN isoform as a biomarker in the first biological sample;
 c) administering the treatment compound to the subject;
 d) thereafter obtaining a second biological sample from the subject;
 e) determining the level of the mRNA biomarker in the second biological sample, and
 f) comparing the levels of the mRNA biomarker in the first and second biological samples;
wherein an increased level of the mRNA biomarker in the second biological sample in comparison with the level of the mRNA biomarker in the first biological sample indicates that the subject is responsive to the treatment.

In yet another embodiment, provided herein is a method of monitoring the efficacy of a treatment of a disease, disorder, or condition in a subject treated with a treatment compound, comprising:

a) obtaining a first biological sample from the subject;

b) determining the level of an mRNA encoding a CRBN isoform as a biomarker in the first biological sample;

c) administering the treatment compound to the subject;

d) thereafter obtaining a second biological sample from the subject;

e) determining the level of the mRNA biomarker in the second biological sample, and f) comparing the levels of the mRNA biomarker in the first and second biological samples;

wherein a decreased level of the mRNA biomarker in the second biological sample in comparison with the level of the mRNA biomarker in the first biological sample indicates that the subject is responsive to the treatment.

In one embodiment, provided herein is a method of monitoring the compliance of a subject with a treatment of a disease, disorder, or condition with a treatment compound, comprising:

a) obtaining a biological sample from the subject;

b) determining the level of an mRNA encoding a CRBN isoform as a biomarker in the biological sample; and c) comparing the level of the mRNA biomarker with the level of the mRNA biomarker in a control sample from the subject;

wherein the change in the level of the mRNA biomarker in the biological sample in comparison with the level of the mRNA biomarker in the control sample indicates the compliance of the subject with the treatment.

In another embodiment, provided herein is a method of monitoring the compliance of a subject with a treatment of a disease, disorder, or condition with a treatment compound, comprising:

a) obtaining a biological sample from the subject;

b) determining the level of an mRNA encoding a CRBN isoform as a biomarker in the biological sample; and c) comparing the level of the mRNA biomarker with the level of the mRNA biomarker in a control sample from the subject;

wherein an increased level of the mRNA biomarker in the biological sample in comparison with the level of the mRNA biomarker in the control sample indicates the compliance of the subject with the treatment.

In yet another embodiment, provided herein is a method of monitoring the compliance of a subject with a treatment of a disease, disorder, or condition with a treatment compound, comprising:

a) obtaining a biological sample from the subject;

b) determining the level of an mRNA encoding a CRBN isoform as a biomarker in the biological sample; and c) comparing the level of the mRNA biomarker with the level of the mRNA biomarker in a control sample from the subject;

wherein a decreased level of the mRNA biomarker in the biological sample in comparison with the level of the mRNA biomarker in the control sample indicates the compliance of the subject with the treatment.

In certain embodiments, the control sample is a disease-free sample from the same subject. In certain embodiments, the control sample is a disease-free sample from a group of subjects.

In certain embodiments, the level of the mRNA biomarker in a control sample is determined simultaneously with the level of the mRNA biomarker in the biological sample from the subject. In certain embodiments, the level of the mRNA biomarker in a control sample is determined independently from the level of the mRNA biomarker in the biological sample from the subject.

In certain embodiments, the mRNA biomarkers are used to predict the responsiveness of a subject to a treatment with thalidomide, lenalidomide, pomalidomide, 3-(5-amino-2-methyl-4-oxoquinazolin-3(4H)-yl)piperidine-2,6-dione, or (S)-3-(4-(4-(morpholinomethyl)benzyl)oxy)-1-oxoisoindolin-2-yl)piperidine-2,6-dione. In certain embodiments, the mRNA biomarkers are used to predict the mRNA responsiveness of a subject to a treatment with thalidomide. In certain embodiments, the mRNA biomarkers are used to predict the responsiveness of a subject to a treatment with lenalidomide. In certain embodiments, the mRNA biomarkers are used to predict the responsiveness of a subject to a treatment with pomalidomide. In certain embodiments, the mRNA biomarkers are used to predict the responsiveness of a subject to a treatment with 3-(5-amino-2-methyl-4-oxoquinazolin-3(4H)-yl)piperidine-2,6-dione. In certain embodiments, the mRNA biomarkers are used to predict the responsiveness of a subject to a treatment with (S)-3-(4-((4-(morpholinomethyl)benzyl)oxy)-1-oxoisoindolin-2-yl)piperidine-2,6-dione.

In certain embodiments, the level of the mRNA biomarker is measured in an in vitro assay to predict the responsiveness of a subject to a treatment with a treatment compound, comprising obtaining a sample of cells from the subject, culturing the cells in the presence (or absence) of the treatment compound, and determining the level of the mRNA biomarker in the cells, wherein the difference between the level of the mRNA biomarker in the cells treated with the treatment compound in comparison with the level of the mRNA biomarker in the untreated cells indicates the likelihood of responsiveness of the subject to the treatment compound.

In certain embodiments, the level of the mRNA biomarker is measured in an in vitro assay to predict the responsiveness of a subject to a treatment with a treatment compound, comprising obtaining a sample of cells from the subject, culturing the cells in the presence (or absence) of the treatment compound, and determining the level of the mRNA biomarker in the cells, wherein an increased level of the mRNA biomarker in the cells treated with the treatment compound in comparison with the level of the mRNA biomarker in the untreated cells indicates the likelihood of responsiveness of the subject to the treatment compound.

In certain embodiments, the level of the mRNA biomarker is measured in an in vitro assay to predict the responsiveness of a subject to a treatment with a treatment compound, comprising obtaining a sample of cells from the subject, culturing the cells in the presence (or absence) of the treatment compound, and determining the level of the mRNA biomarker in the cells, wherein a decreased level of the mRNA biomarker in the cells treated with the treatment compound in comparison with the level of the mRNA biomarker in the untreated cells indicates the likelihood of responsiveness of the subject to the treatment compound.

5.5 METHODS OF DETECTING BIOMARKER LEVELS

5.5.1 Methods of Detecting mRNA Levels of Biomarkers

The levels of mRNAs of the biomarkers can be detected or quantified by any methods known in the art. Exemplary detecting or quantitating methods include, but are not limited to, northern blots, ribonuclease protection assays, and PCR-based methods. When the biomarker is an mRNA molecule, the mRNA sequence or a fragment thereof can be used to prepare a probe that is at least partially complementary. The probe can then be used to detect the mRNA sequence in a sample, using any methods known in the art, including, not limited to PCR-based methods, Northern blotting, or a dipstick assay.

In certain embodiments, the detecting or quantitating method is a northern blot, ribonuclease protection assay, or a PCR-based method. In certain embodiments, the detecting or quantitating method is a northern blot. In certain embodiments, the detecting or quantitating method is a ribonuclease protection assay. In certain embodiments, the detecting or quantitating method is a PCR-based method. In certain embodiments, the detecting or quantitating method is qRT-PCR.

Any suitable assay platform can be used to determine the presence of the mRNA in a sample. For example, an assay may be in the form of a dipstick, a membrane, a chip, a disk, a test strip, a filter, a microsphere, a slide, a multiwell plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The mRNAs can be labeled, if desired, to make a population of labeled mRNAs. In general, a sample can be labeled using methods that are well known in the art (e.g., using an RNA ligase or terminal transferase, or by labeling the RNA backbone). See e.g., Ausubel et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y. In certain embodiments, the sample is labeled with a fluorescent label. Exemplary fluorescent dyes include, but are not limited to, xanthene dyes, fluorescein dyes, rhodamine dyes, fluorescein isothiocyanate (FITC), 6-carboxyfluorescein (FAM), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine 6G (R6G5 or G5), 6-carboxyrhodamine 6G (R6G6 or G6), rhodamine 110, cyanine dyes (e.g., Cy3, Cy5, and Cy7 dyes), Alexa dyes (e.g., Alexa-fluor-555), coumarin, diethylaminocoumarin, umbelliferone; benzimide dyes (e.g., Hoechst 33258), phenanthridine dyes (e.g., Texas red), ethidium dyes, acridine dyes, carbazole dyes, phenoxazine dyes, porphyrin dyes, polymethine dyes, BODIPY dyes, quinoline dyes, pyrene, fluorescein chlorotriazinyl, R110, Eosin, JOE, R6G, tetramethylrhodamine, lissamine, ROX, and napthofluorescein.

In certain embodiments, nucleic acid probes may be present in specific, addressable locations on a solid support; each corresponding to at least a portion of mRNA sequences of a biomarker.

In certain embodiments, an mRNA assay comprises the steps of 1) obtaining surface-bound probes for one or more biomarkers; 2) hybridizing a population of mRNAs to the surface-bound probes under conditions sufficient to provide for specific binding; (3) removing unbound nucleic acids in the hybridization step; and (4) detecting the hybridized mRNAs.

Hybridization can be carried out under suitable hybridization conditions, which may vary in stringency as desired. Typical conditions are sufficient to produce probe/target complexes on a solid surface between complementary binding members, i.e., between surface-bound probes and complementary mRNAs in a sample.

In certain embodiments, stringent hybridization conditions are used. Standard hybridization techniques (e.g., under conditions sufficient to provide for specific binding of target mRNAs in the sample to the probes) are described in Kallioniemi et al., *Science* 258:818-821 (1992) and WO 93/18186, the disclosure of each which is incorporated herein by reference in its entirety. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol. 7, pages 43-65 (Plenum Press, New York 1985). Selection of appropriate conditions, including temperature, salt concentration, polynucleotide concentration, hybridization time, and stringency of washing conditions, depends on experimental design, including the source of a sample, the identity of capture agents, the degree of complementarity expected, etc.

After the mRNA hybridization procedure, the surface bound polynucleotides are washed to remove unbound nucleic acids. Washing may be performed using any convenient washing protocol. In certain embodiments, the washing conditions are stringent. The hybridization of the target mRNAs to the probes is then detected using standard techniques.

5.5.2 PCR-Based Methods of Detecting mRNA Levels

In certain embodiments, the mRNA level of a biomarker is determined using a PCR-based method. Examples of PCR assays can be found in U.S. Pat. No. 6,927,024, the disclosure of which is incorporated by reference herein in its entirety. Examples of RT-PCR methods can be found in U.S. Pat. No. 7,122,799, the disclosure of which is incorporated by reference herein in its entirety. Examples of fluorescent in situ PCR methods can be found in U.S. Pat. No. 7,186,507, the disclosure of which is incorporated by reference herein in its entirety.

In certain embodiments, real-time reverse transcription-PCR (qRT-PCR) is used for both the detection and quantification of mRNAs (Bustin et al., *Clin. Sci.*, 2005, 109, 365-379). Quantitative results obtained by qRT-PCR are generally more informative than qualitative data. Examples of qRT-PCR-based methods can be found in U.S. Pat. No. 7,101,663, the disclosure of which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as Applied Biosystems 7500, are available commercially. The reagents for real-time PCR, such as TaqMan Sequence Detection chemistry, are also commercially available.

To determine the cycle number at which the fluorescence signal associated with a particular amplicon accumulation crosses the threshold (referred to as CT), the data can be analyzed, for example, using a 7500 Real-Time PCR System Sequence Detection software v1.3, using the comparative CT relative quantification calculation method. Using this method, the output is expressed as a fold-change in expression levels. In some embodiments, the threshold level can be selected to be automatically determined by the software. In some embodiments, the threshold level is set to be above the baseline, but sufficiently low to be within the exponential growth region of an amplification curve.

5.5.3 Methods of Detecting Polypeptide or Protein Biomarkers

The levels of the protein biomarkers provided herein can be detected or quantified by any methods known in the art. In certain embodiments, antibody-based methods are used. In certain embodiments, the detecting or quantitating method is immunoblotting (western blot), an enzyme-linked immunosorbent assay (ELISA), immunohistochemistry, flow cytometry, a cytometric bead array, or mass spectroscopy.

In certain embodiments, the detecting or quantitating method is immunoblotting (western blot). In certain embodiments, the detecting or quantitating method is an enzyme-linked immunosorbent assay (ELISA). In certain embodiments, the detecting or quantitating method is a direct ELISA. In certain embodiments, the detecting or quantitating method is an indirect ELISA. In certain embodiments, the detecting or quantitating method is an sandwich ELISA. In certain embodiments, the detecting or quantitating method is immunohistochemistry. In certain embodiments, the detecting or quantitating method is flow cytometry. In certain embodiments, the detecting or quantitating method is a cytometric bead array. In certain embodiments, the detecting or quantitating method is mass spectroscopy.

5.6 KITS FOR DETECTING BIOMARKER LEVELS

In certain embodiments, provided herein is a kit for detecting the mRNA levels of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample.

5.7 TREATMENT COMPOUNDS

In one embodiment, the treatment compound is an immunomodulatory compound.

As used herein and unless otherwise indicated, the term "immunomodulatory compound" refers to a compound that inhibits LPS induced monocyte TNF-α, IL-1β, IL-12, IL-6, MIP-1α, MCP-1, GM-CSF, G-CSF, and/or COX-2 production. In certain embodiments, the immunomodulatory compound is an IMIDS® compound.

Exemplary immunomodulatory compounds include, but are not limited to, N-{[2-(2,6-dioxo(3-piperidyl)-1,3-dioxoisoindolin-4-yl]methyl}cyclopropylcarboxamide; 3-[2-(2,6-dioxopiperidin-3-yl)-1,3-dioxo-2,3-dihydro-1H-isoindol-4-ylmethyl]-1,1-dimethylurea; (−)-3-(3,4-dimethoxyphenyl)-3-(1-oxo-1,3-dihydroisoindol-2-yl)-propionamide; (+)-3-(3,4-dimethoxyphenyl)-3-(1-oxo-1,3-dihydroisoindol-2-yl)-propionamide; (−)-{2-[1-(3-ethoxy-4-methoxyphenyl)-2-methylsulfonylethyl]-4-acetylaminoisoindoline-1,3-dione}; (+)-{2-[1-(3-ethoxy-4-methoxyphenyl)-2-methylsulfonylethyl]-4-acetylaminoisoindoline-1,3-dione}; difluoromethoxy SelCIDs; 1-phthalimido-1-(3,4-diethoxyphenyl)ethane; 3-(3,4-dimethoxyphenyl)-3-(3,5-dimethoxyphenyl)acrylonitrile; 1-oxo-2-(2,6-dioxopiperidin-3-yl)-4-aminoisoindoline; 1,3-dioxo-2-(2,6-dioxopiperidin-3-yl)-4-aminoisoindoline; 4-amino-2-(3-methyl-2,6-dioxopiperidine-3-yl)isoindole-1,3-dione; 3-(3-acetoamidophthalimido)-3-(3-ethoxy-4-methoxyphenyl)-N-hydroxypropionamide; 1-oxo-2-(2,6-dioxopiperidin-3-yl)-4-methylisoindoline; cyclopropyl-N-{2-[(1S)-1-(3-ethoxy-4-methoxyphenyl)-2-(methylsulfonyl)ethyl]-3-oxoisoindoline-4-yl}carboxamide; substituted 2-(3-hydroxy-2,6-dioxopiperidin-5-yl)isoindoline; N-[2-(2,6-dioxopiperidin-3-yl)-1,3-dioxo-2,3-dihydro-1H-isoindol-5-ylmethyl]-4-trifluoromethoxybenzamide; (S)-4-chloro-N-((2-(3-methyl-2,6-dioxopiperidin-3-yl)-1,3-dioxoisoindolin-5-yl)methyl)benzamide; pyridine-2-carboxylic acid [2-[(3S)-3-methyl-2,6-dioxopiperidin-3-yl]-1,3-dioxo-2,3-dihydro-1H-isoindol-5-ylmethyl]amide; (S)—N-((2-(3-methyl-2,6-dioxopiperidin-3-yl)-1,3-dioxoisoindolin-5-yl)methyl)-4-(trifluoromethyl)benzamide; and 3-(2,5-dimethyl-4-oxo-4H-quinazolin-3-yl)piperidine-2,6-dione.

Exemplary immunomodulatory compounds include, but are not limited to, cyano and carboxy derivatives of substituted styrenes, including, but not limited to, those disclosed in U.S. Pat. No. 5,929,117; 1-oxo-2-(2,6-dioxo-3-fluoropiperidin-3-yl)isoindolines and 1,3-dioxo-2-(2,6-dioxo-3-fluoropiperidine-3-yl)isoindolines, including, but not limited to, those described in U.S. Pat. Nos. 5,874,448 and 5,955,476; tetra substituted 2-(2,6-dioxopiperdin-3-yl)-1-oxoisoindolines, including, but not limited to, those described in U.S. Pat. No. 5,798,368; 1-oxo- and 1,3-dioxo-2-(2,6-dioxopiperidin-3-yl)isoindolines (e.g., 4-methyl derivatives of thalidomide); substituted 2-(2,6-dioxopiperidin-3-yl)phthalimides, and substituted 2-(2,6-dioxopiperidin-3-yl)-1-oxoisoindoles, including, but not limited to, those disclosed in U.S. Pat. Nos. 5,635,517, 6,281,230, 6,316,471, 6,403,613, 6,476,052, and 6,555,554; 1-oxo- and 1,3-dioxoisoindolines substituted in the 4- or 5-position of the indoline ring (e.g., 4-(4-amino-1,3-dioxoisoindoline-2-yl)-4-carbamoylbutanoic acid), including, but not limited to, those described in U.S. Pat. No. 6,380,239; isoindoline-1-one and isoindoline-1,3-dione substituted in the 2-position of the indoline ring with 2,6-dioxo-3-hydroxypiperidin-5-yl (e.g., 2-(2,6-dioxo-3-hydroxy-5-fluoropiperidin-5-yl)-4-aminoisoindolin-1-one), including, but not limited to, those described in U.S. Pat. No. 6,458,810; non-polypeptide cyclic amides, including, but not limited to, those disclosed in U.S. Pat. Nos. 5,698,579 and 5,877,200; and isoindole-imide compounds, including, but not limited to, those described in U.S. Pat. App. Pub. Nos. 2003/0045552 and 2003/0096841, and International Pub. No. WO 02/059106.

The disclosure of each of the patents and patent application publications identified herein is incorporated herein by reference in its entirety.

Various immunomodulatory compounds provided herein contain one or more chiral centers, and can exist as mixtures of enantiomers (e.g., racemic mixtures) or mixtures of diastereomers. The methods provided herein encompass the use of stereomerically pure forms of such compounds as well as mixtures of those forms. For example, mixtures comprising equal or unequal amounts of the enantiomers of a particular immunomodulatory compound may be used in methods provided herein. These isomers may be asymmetrically synthesized or resolved using standard techniques, such as chiral columns or chiral resolving agents. See, Jacques et al., *Enantiomers, Racemates and Resolutions* (Wiley-Interscience, New York, 1981); Wilen et al., *Tetrahedron* 1977, 33, 2725-2736; Eliel, *Stereochemistry of Carbon Compounds* (McGraw-Hill, NY, 1962); and Wilen, *Tables of Resolving Agents and Optical Resolutions* p. 268 (Eliel, Ed., Univ. of Notre Dame Press, Notre Dame, Ind., 1972).

In certain embodiments, the immunomodulatory compound is an 1-oxo- or 1,3-dioxo-2-(2,6-dioxopiperidin-3-yl)-isoindoline substituted with amino in the benzo ring, including, but not limited to, those described in U.S. Pat. No. 5,635,517, the disclosure of which is incorporated herein by reference in its entirety.

In certain embodiments, the immunomodulatory compound is a compound of Formula I:

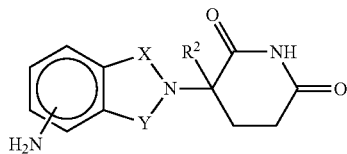

I wherein one of X and Y is C=O, the other of X and Y is C=O or CH$_2$, and R$^2$ is hydrogen or C$_{1-4}$ alkyl, in one embodiment, methyl.

In certain embodiments, the immunomodulatory compound is:

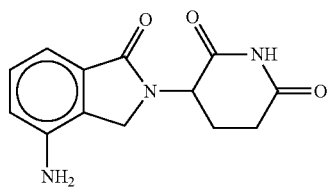

1-oxo-2-(2,6-dioxopiperidin-3-yl)-4-aminoisoindoline (lenalidomide);

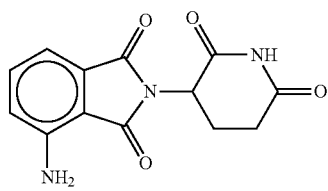

1,3-dioxo-2-(2,6-dioxopiperidin-3-yl)-4-aminoisoindoline (pomalidomide); or

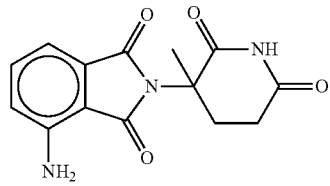

1,3-dioxo-2-(3-methyl-2,6-dioxopiperidin-3-yl)-4-aminoisoindole, or an optically pure isomer thereof.

In certain embodiments, the immunomodulatory compound is a substituted 2-(2,6-dioxopiperidin-3-yl)phthalimide or substituted 2-(2,6-dioxopiperidin-3-yl)-1-oxoisoindole, including, but not limited to, those described in U.S. Pat. Nos. 6,281,230; 6,316,471; 6,335,349; and 6,476,052; and International Pub. No. WO 98/03502; the disclosure of each of which is incorporated herein by reference in its entirety.

In certain embodiments, the immunomodulatory compound has the formula:

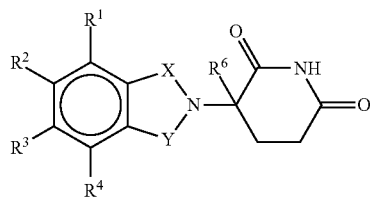

wherein:
one of X and Y is C=O and the other of X and Y is C=O or CH$_2$;
(i) each of R$^1$, R$^2$, R$^3$, and R$^4$ is independently halo, C$_{1-4}$ alkyl, or C$_{1-4}$ alkoxy; or
(ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or C$_{1-8}$ alkyl; and
R$^6$ is hydrogen, C$_{1-8}$ alkyl, benzyl, or halo;
provided that R$^6$ is other than hydrogen if X and Y are C=O and (i) each of R$^1$, R$^2$, R$^3$, and R$^4$ is fluoro or (ii) one of R$^1$, R$^2$, R$^3$, and R$^4$ is amino.

In certain embodiments, the immunomodulatory compound has the formula

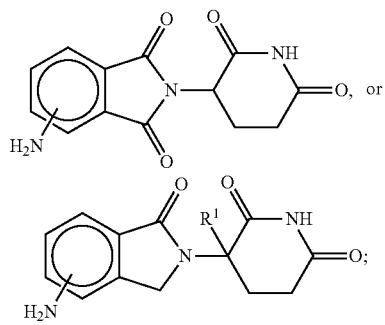

wherein R$^1$ is hydrogen or methyl.

In certain embodiments, the immunomodulatory compound is enantiomerically pure (e.g. optically pure (R)- or (S)-enantiomers).

In certain embodiments, the immunomodulatory compound is an isoindole-imide, including, but not limited to, those disclosed in U.S. Pat. No. 7,091,353, U.S. Pat. Pub. No. 2003/0045552, and International Pub. No. WO 02/059106, the disclosure of each of which is incorporated herein by reference in its entirety.

In certain embodiments, the immunomodulatory compound is a compound of Formula II:

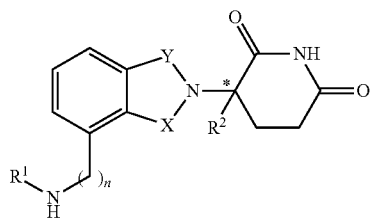

or a pharmaceutically acceptable salt, hydrate, solvate, clathrate, enantiomer, diastereomer, racemate, or mixture of stereoisomers thereof, wherein:

one of X and Y is C=O and the other is $CH_2$ or C=O;

$R^1$ is H, $C_{1-8}$ alkyl, $C_{3-7}$ cycloalkyl, $C_{2-8}$ alkenyl, $C_{2-8}$ alkynyl, benzyl, $C_{6-14}$ aryl, $C_{0-4}$ alkyl-heterocyclyl, $C_{0-4}$ alkyl-heteroaryl, —C(O)$R^3$, —C(S)$R^3$, —C(O)O$R^4$, $C_{1-8}$ alkyl-N($R^6$)$_2$, $C_{1-8}$ alkyl-O$R^5$, $C_{1-8}$ alkyl-C(O)O$R^5$, —C(O)NH$R^3$, —C(S)NH$R^3$, —C(O)N$R^3R^{3'}$, —C(S)N$R^3R^{3'}$, or $C_{1-8}$ alkyl-O(CO)$R^5$;

$R^2$ is H, F, benzyl, $C_{1-8}$ alkyl, $C_{2-8}$ alkenyl, or $C_{2-8}$ alkynyl;

$R^3$ and $R^{3'}$ are each independently $C_{1-8}$ alkyl, $C_{3-7}$ cycloalkyl, $C_{2-8}$ alkenyl, $C_{2-8}$ alkynyl, benzyl, $C_{6-14}$ aryl, $C_{0-4}$ alkyl-heterocyclyl, $C_{0-4}$ alkyl-heteroaryl, $C_{0-8}$ alkyl-N($R^6$)$_2$, $C_{1-8}$ alkyl-O$R^5$, $C_{1-8}$ alkyl-C(O)O$R^5$, $C_{1-8}$ alkyl-O(CO)$R^5$, or —C(O)O$R^5$;

$R^4$ is $C_{1-8}$ alkyl, $C_{2-8}$ alkenyl, $C_{2-8}$ alkynyl, $C_{1-4}$ alkyl-O$R^5$, benzyl, $C_{6-14}$ aryl, $C_{0-4}$ alkyl-heterocyclyl, or $C_{0-4}$ alkyl-heteroaryl;

$R^5$ is $C_{1-8}$ alkyl, $C_{2-8}$ alkenyl, $C_{2-8}$ alkynyl, benzyl, $C_{6-14}$ aryl, or heteroaryl; each occurrence of $R^6$ is independently H, $C_{1-8}$ alkyl, $C_{2-8}$ alkenyl, $C_{2-8}$ alkynyl, benzyl, $C_{6-14}$ aryl, heteroaryl, or $C_{0-8}$ alkyl-C(O)O—$R^5$; or the $R^6$ groups join to heterocyclyl; and n is 0 or 1;

* represents a chiral center.

In certain embodiments, in Formula II, n is 0, $R^1$ is $C_{3-7}$ cycloalkyl, $C_{2-8}$ alkenyl, $C_{2-8}$ alkynyl, benzyl, $C_{6-14}$ aryl, $C_{0-4}$ alkyl-heterocyclyl, $C_{0-4}$ alkyl-heteroaryl, —C(O)$R^3$, —C(O)O$R^4$, $C_{1-8}$ alkyl-N($R^6$)$_2$, $C_{1-8}$ alkyl-O$R^5$, $C_{1-8}$ alkyl-C(O)O$R^5$, —C(S)NH$R^3$, or $C_{1-8}$ alkyl-O(CO)$R^5$; $R^2$ is H or $C_{1-8}$ alkyl; and $R^3$ is $C_{1-8}$ alkyl, $C_{3-7}$ cycloalkyl, $C_{2-8}$ alkenyl, $C_{2-8}$ alkynyl, benzyl, $C_{6-14}$ aryl, $C_{0-4}$ alkyl-heterocyclyl, $C_{0-4}$ alkyl-heteroaryl, $C_{5-8}$ alkyl-N($R^6$)$_2$; $C_{0-8}$ alkyl-NH—C(O)O—$R^5$; $C_{1-8}$ alkyl-O$R^5$, $C_{1-8}$ alkyl-C(O)O$R^5$, $C_{1-8}$ alkyl-O(CO)$R^5$, or —C(O)O$R^5$; and the other variables are each as defined herein.

In certain embodiments, in Formula II, $R^2$ is H or $C_{1-4}$ alkyl.

In certain embodiments, in Formula II, $R^1$ is $C_{1-8}$ alkyl or benzyl.

In certain embodiments, in Formula II, $R^1$ is H, $C_{1-8}$ alkyl, benzyl, $CH_2OCH_3$, $CH_2CH_2OCH_3$, or

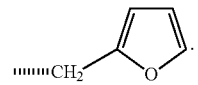

In certain embodiments, in Formula II, $R^1$ is

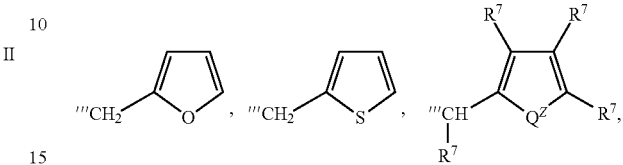

wherein $Q^Z$ is O or S, and each occurrence of $R^7$ is independently H, $C_{1-8}$ alkyl, $C_{3-7}$ cycloalkyl, $C_{2-8}$ alkenyl, $C_{2-8}$ alkynyl, benzyl, $C_{6-14}$ aryl, halogen, $C_{0-4}$ alkyl-heterocyclyl, $C_{0-4}$ alkyl-heteroaryl, $C_{0-8}$ alkyl-N($R^6$)$_2$, $C_{1-8}$ alkyl-O$R^5$, $C_{1-8}$ alkyl-C(O)O$R^5$, $C_{1-8}$ alkyl-O(CO)$R^5$, or —C(O)O$R^5$; or adjacent occurrences of $R^7$ can be taken together to form a bicyclic heteroaryl, heterocyclyl, or $C_{6-14}$ aryl ring.

In certain embodiments, in Formula II, $R^1$ is —C(O)$R^3$.

In certain embodiments, in Formula II, $R^3$ is $C_{0-4}$ alkyl-heteroaryl, $C_{1-8}$ alkyl, $C_{6-14}$ aryl, or $C_{0-4}$ alkyl-O$R^5$.

In certain embodiments, in Formula II, the heteroaryl is pyridyl, furyl, or thienyl.

In certain embodiments, in Formula II, $R^1$ is —C(O)O$R^4$.

In certain embodiments, in Formula II, the H of —C(O)NHC(O)— can be replaced with $C_{1-4}$ alkyl, $C_{6-14}$ aryl, or benzyl.

In certain embodiments, the immunomodulatory compounds include, but are not limited to, [2-(2,6-dioxopiperidin-3-yl)-1,3-dioxo-2,3-dihydro-1H-isoindol-4-ylmethyl] amide; (2-(2,6-dioxopiperidin-3-yl)-1,3-dioxo-2,3-dihydro-1H-isoindol-4-ylmethyl)carbamic acid tert-butyl ester; 4-(aminomethyl)-2-(2,6-dioxo(3-piperidyl))-isoindoline-1,3-dione; N-(2-(2,6-dioxopiperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}-cyclopropylcarboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl) pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)-carboxamide.

In certain embodiments, the immunomodulatory compounds encompass isoindole-imides as described in U.S. Pat. No. 6,395,754; U.S. Pat. App. Pub. No. 2002/0045643;

and International Pub. No. WO 98/54170; the disclosure of each of which is incorporated herein by reference in its entirety.

In certain embodiments, the immunomodulatory compound is a compound of Formula III:

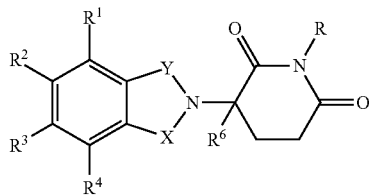

III or a pharmaceutically acceptable salt, hydrate, solvate, clathrate, enantiomer, diastereomer, racemate, and mixture of stereoisomers thereof, wherein:
  one of X and Y is C=O and the other is $CH_2$ or C=O;
  R is H or $CH_2OCOR'$;
  (i) each of $R^1$, $R^2$, $R^3$, and $R^4$ is independently halo, $C_{1-4}$ alkyl or $C_{1-4}$ alkoxy; or (ii) one of $R^1$, $R^2$, $R^3$, and $R^4$ is nitro or —$NHR^5$ and the remaining of $R^1$, $R^2$, $R^3$, and $R^4$ are hydrogen;
  $R^5$ is hydrogen or $C_{1-8}$ alkyl;
  $R^6$ is hydrogen, $C_{1-8}$ alkyl, benzyl, chloro, or fluoro;
  R' is —$R^7$—$CHR^{10}$—$N(R^8R^9)$;
  $R^7$ is m-phenylene, p-phenylene, or —$(C_nH_{2n})$—, where n is an integer of 0, 1, 2, 3, or 4;
  each of $R^8$ and $R^9$ is independently hydrogen or $C_{1-8}$ alkyl; or $R^8$ and $R^9$ taken together are tetramethylene, pentamethylene, hexamethylene, or —$CH_2CH_2X^1CH_2CH_2$—, where $X^1$ is –O—, —S—, or —NH—; and
  $R^{10}$ is hydrogen, $C_{1-8}$ alkyl, or phenyl.
  * represents a chiral center.

In certain embodiments, the immunomodulatory compound has the formula:

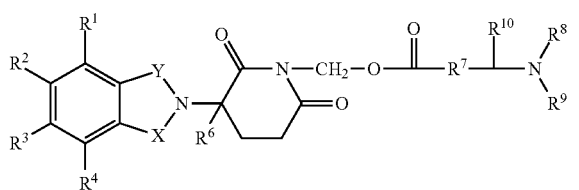

wherein:
  one of X and Y is C=O and the other of X and Y is C=O or $CH_2$;
  (i) each of $R^1$, $R^2$, $R^3$, and $R^4$ is independently halo, $C_{1-4}$ alkyl, or $C_{1-4}$ alkoxy; or (ii) one of $R^1$, $R^2$, $R^3$, and $R^4$ is —$NHR^5$ and the remaining of $R^1$, $R^2$, $R^3$, and $R^4$ are hydrogen;
  $R^5$ is hydrogen or $C_{1-8}$ alkyl;
  $R^6$ is hydrogen, $C_{1-8}$ alkyl, benzyl, chloro, or fluoro;
  $R^7$ is m-phenylene, p-phenylene, or —$(C_nH_{2n})$—, where n is an integer of 0, 1, 2, 3, or 4;
  each of $R^8$ and $R^9$ is independently hydrogen or $C_{1-8}$ alkyl; or $R^8$ and $R^9$ taken together are tetramethylene, pentamethylene, hexamethylene, or —$CH_2X^1CH_2CH_2$—, where $X^1$ is —O—, —S—, or —NH—; and
  $R^{10}$ is hydrogen, $C_{1-8}$ alkyl, or phenyl.

In certain embodiments, the immunomodulatory compound has the formula:

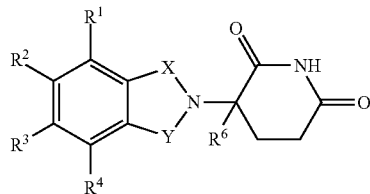

wherein:
  one of X and Y is C=O and the other of X and Y is C=O or $CH_2$;
  (i) each of $R^1$, $R^2$, $R^3$, and $R^4$ is independently halo, $C_{1-4}$ alkyl, or $C_{1-4}$ alkoxy; or (ii) one of $R^1$, $R^2$, $R^3$, and $R^4$ is nitro or a protected amino and the remaining of $R^1$, $R^2$, $R^3$, and $R^4$ are hydrogen; and
  $R^6$ is hydrogen, $C_{1-8}$ alkyl, benzyl, chloro, or fluoro.

In certain embodiments, the immunomodulatory compound has the formula:

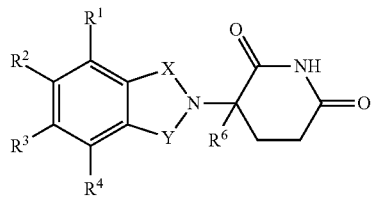

wherein:
  one of X and Y is C=O and the other of X and Y is C=O or $CH_2$;
  (i) each of $R^1$, $R^2$, $R^3$, and $R^4$ is independently halo, $C_{1-4}$ alkyl, or $C_{1-4}$ alkoxy; or (ii) one of $R^1$, $R^2$, $R^3$, and $R^4$ is —$NHR^5$ and the remaining of $R^1$, $R^2$, $R^3$, and $R^4$ are hydrogen;
  $R^5$ is hydrogen, $C_{1-8}$ alkyl, or —CO—$R^7$—$CH(R^{10})$ $NR^8R^9$, where each of $R^7$, $R^8$, $R^9$, and $R^{10}$ is as herein defined; and
  $R^6$ is $C_{1-8}$ alkyl, benzyl, chloro, or fluoro.

In certain embodiments, the immunomodulatory compound has the formula:

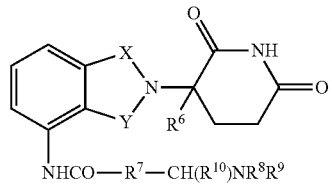

NHCO—$R^7$—$CH(R^{10})NR^8R^9$ wherein:
  one of X and Y is C=O and the other of X and Y is C=O or $CH_2$;
  $R^6$ is hydrogen, $C_{1-8}$ alkyl, benzyl, chloro, or fluoro;
  $R^7$ is m-phenylene, p-phenylene or —$(C_nH_{2n})$—, where n is an integer of 0, 1, 2, 3, or 4;
  each of $R^8$ and $R^9$ is independently hydrogen or $C_{1-8}$ alkyl; or $R^8$ and $R^9$ taken together are tetramethylene, pentamethylene, hexamethylene, or —$CH_2CH_2$ X¹CH₂CH₂—, where X¹ is —O—, —S—, or —NH—; and R¹⁰ is hydrogen, $C_{1-8}$ alkyl, or phenyl.

In certain embodiments, the immunomodulatory compound is a 1-oxo-2-(2,6-dioxo-3-fluoropiperidin-3-yl)isoindoline or 1,3-dioxo-2-(2,6-dioxo-3-fluoropiperidine-3-yl)-isoindoline, including, but not limited to, those described in U.S. Pat. Nos. 5,874,448 and 5,955,476, the disclosure of each of which is incorporated herein by reference in its entirety.

In certain embodiments, the immunomodulatory compound has the formula:

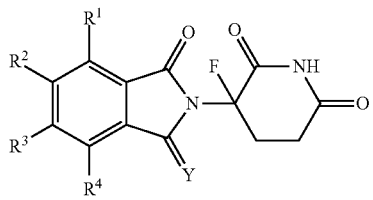

wherein:
Y is oxygen or H₂; and
each of R¹, R², R³, and R⁴ is independently hydrogen, halo, $C_{1-4}$ alkyl, $C_{1-4}$ alkoxy, or amino.

In certain embodiments, the immunomodulatory compound is a tetra substituted 2-(2,6-dioxopiperdin-3-yl)-1-oxoisoindoline, including, but not limited to, those described in U.S. Pat. No. 5,798,368, the disclosure of which is incorporated herein by reference in its entirety.

In certain embodiments, the immunomodulatory compound has the formula:

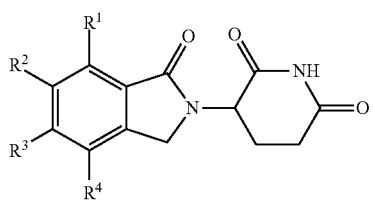

wherein each of R¹, R², R³, and R⁴ is independently halo, $C_{1-4}$ alkyl, or $C_{1-4}$ alkoxy.

In certain embodiments, the immunomodulatory compound is a 1-oxo or 1,3-dioxo-2-(2,6-dioxopiperidin-3-yl) isoindoline, including, but not limited to, those disclosed in U.S. Pat. No. 6,403,613, the disclosure of which is incorporated herein by reference in its entirety.

In certain embodiments, the immunomodulatory compound has the formula:

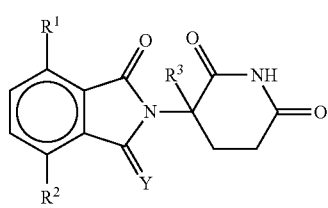

wherein:
Y is oxygen or H₂;
R¹ and R² are each independently halo, $C_{1-8}$ alkyl, $C_{1-8}$ alkoxy, $C_{1-8}$ alkylamino, di($C_{1-8}$ alkyl)amino, cyano, or carbamoyl; and
R³ is hydrogen, $C_{1-8}$ alkyl, or benzyl.

In certain embodiments, the immunomodulatory compound has the formula:

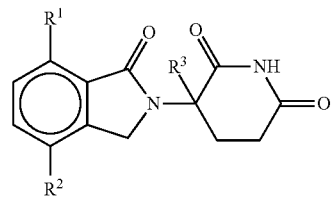

wherein:
one of R¹ and R² is halo, $C_{1-4}$ alkyl, $C_{1-4}$ alkoxy, di($C_{1-4}$ alkyl)amino, cyano, or carbamoyl; the other of R¹ and R² is independently hydrogen, halo, $C_{1-4}$ alkyl, $C_{1-4}$ alkoxy, $C_{1-4}$ alkylamino, di($C_{1-4}$ alkyl)amino, cyano, or carbamoyl; and
R³ is hydrogen, $C_{1-4}$ alkyl, or benzyl.

In certain embodiments, the immunomodulatory compound is 1-oxo-2-(2,6-dioxopiperidin-3-yl)-4-methylisoindoline.

In certain embodiments, the immunomodulatory compound has the formula:

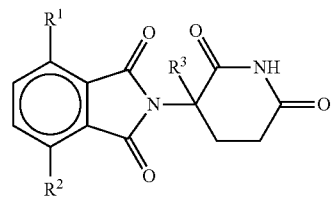

wherein:
one of R¹ and R² is halo, $C_{1-4}$ alkyl, $C_{1-4}$ alkoxy, di($C_{1-4}$ alkyl)amino, cyano, or carbamoyl; the other of R¹ and R² is independently hydrogen, halo, $C_{1-4}$ alkyl, $C_{1-4}$ alkoxy, $C_{1-4}$ alkylamino, di($C_{1-4}$ alkyl)amino, cyano, or carbamoyl; and
R³ is hydrogen, $C_{1-4}$ alkyl, or benzyl.

In certain embodiments, the immunomodulatory compound is a 1-oxo or 1,3-dioxoisoindolines substituted in the 4- or 5-position of the indoline ring, including, but not limited to, those described in U.S. Pat. Nos. 6,380,239 and 7,244,759, the disclosure of each of which is incorporated herein by reference in its entirety.

In certain embodiments, the immunomodulatory compound has the formula:

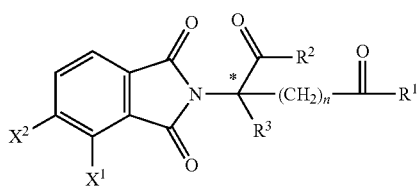

wherein:
one of X¹ and X² is amino, nitro, $C_{1-6}$ alkyl, or —NH—Z; and the other of X¹ or X² is hydrogen;
R¹ and R² are each independently hydroxy or —NH—Z;
R³ is hydrogen, $C_{1-6}$ alkyl, halo, or $C_{1-6}$ haloalkyl;

Z is hydrogen, $C_{6-14}$ aryl, $C_{1-6}$ alkyl, formyl, or $C_{1-6}$ acyl; and n is an integer of 0, 1, or 2;

provided that if $X^1$ is amino, and n is 1 or 2, then $R^1$ and $R^2$ are not both hydroxyl;

* designates a chiral center, when —$COR^2$ and —$(CH_2)_n COR^1$ are different.

In certain embodiments, the immunomodulatory compound has the formula:

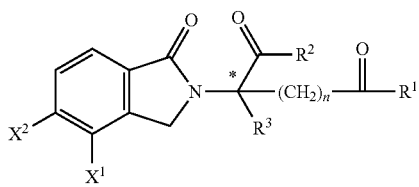

wherein:
one of $X^1$ and $X^2$ is amino, nitro, $C_{1-6}$ alkyl, or —NH—Z; and the other of $X^1$ or $X^2$ is hydrogen;

$R^1$ and $R^2$ are each independently hydroxy or —NH—Z;

$R^3$ is $C_{1-6}$ alkyl, halo, or hydrogen;

Z is hydrogen, $C_{6-14}$ aryl, $C_{1-6}$ alkyl, or $C_{1-6}$ acyl; and n is an integer of 0, 1, or 2;

* designates a chiral center, when —$COR^2$ and —$(CH_2)_n COR^1$ are different.

In certain embodiments, the immunomodulatory compound is 2-(4-amino-1-oxo-1,3-dihydroisoindol-2-yl)-4-carbamoylbutyric acid or 4-(4-amino-1-oxo-1,3-dihydroisoindol-2-yl)-4-cabamoylbutyric acid, or a pharmaceutically acceptable salt, solvate, protreatment compound, or a stereoisomer thereof:

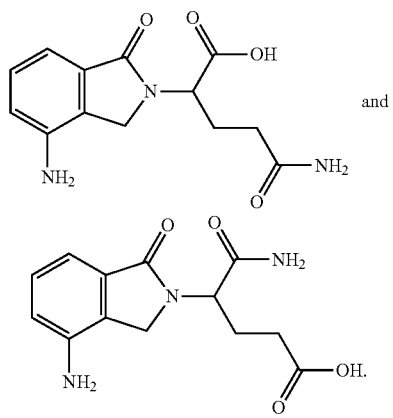

In certain embodiments, the immunomodulatory compound has the formula:

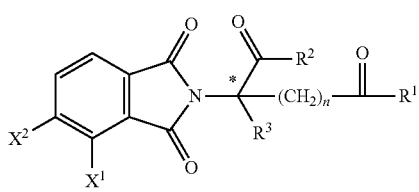

or a pharmaceutically acceptable salt thereof; wherein:
one of $X^1$ and $X^2$ is amino, nitro, $C_{1-6}$ alkyl, or —NH—Z; and the other of $X^1$ or $X^2$ is hydrogen;

$R^1$ and $R^2$ are independently hydroxy or —NH—Z;

$R^3$ is $C_{1-6}$ alkyl, halo, or hydrogen;

Z is hydrogen, $C_{6-14}$ aryl, $C_{1-6}$ alkyl, or $C_{1-6}$ acyl; and n is an integer of 0, 1, or 2;

* designates a chiral center, when —$COR^2$ and —$(CH_2)_n COR^1$ are different.

In certain embodiments, the immunomodulatory compound is 4-carbamoyl-4-{4-[(furan-2-yl-methyl)-amino]-1,3-dioxo-1,3-dihydroisoindol-2-yl}butyric acid, 4-carbamoyl-2-{4-[(furan-2-yl-methyl)amino]-1,3-dioxo-1,3-dihydroisoindol-2-yl}butyric acid, 2-{4-[(furan-2-yl-methyl)-amino]-1,3-dioxo-1,3-dihydroisoindol-2-yl}-4-phenylcarbamoylbutyric acid, or 2-{4-[(furan-2-yl-methyl)-amino]-1,3-dioxo-1,3-dihydroisoindol-2-yl}pentanedioic acid, or a pharmaceutically acceptable salt, solvate, protreatment compound, or stereoisomer thereof:

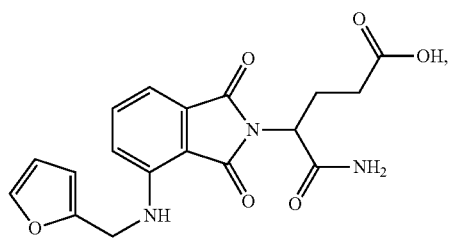

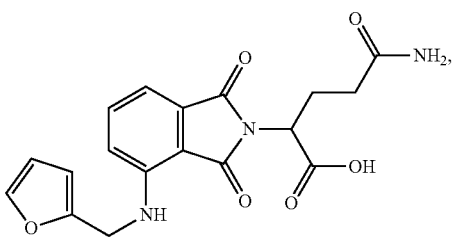

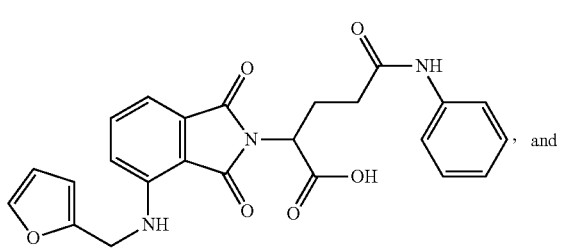

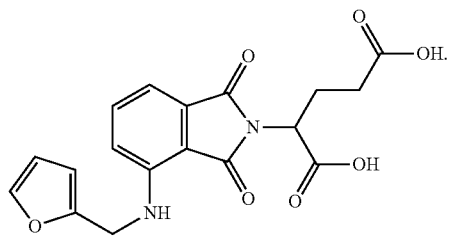

In certain embodiments, the immunomodulatory compound has the formula:

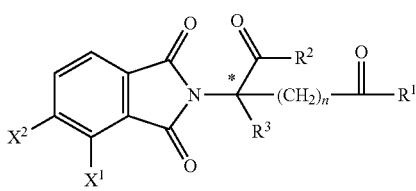

wherein:
one of $X^1$ and $X^2$ is nitro or —NH—Z; and the other of $X^1$ or $X^2$ is hydrogen;
$R^1$ and $R^2$ are each independently hydroxy or —NH—Z;
$R^3$ is $C_{1-6}$ alkyl, halo, or hydrogen;
Z is hydrogen, phenyl, $C_{1-6}$ acyl, or $C_{1-6}$ alkyl; and
n is an integer of 0, 1, or 2;
* designates a chiral center, when —$COR^2$ and —$(CH_2)_n COR^1$ are different.

In certain embodiments, the immunomodulatory compound has the formula:

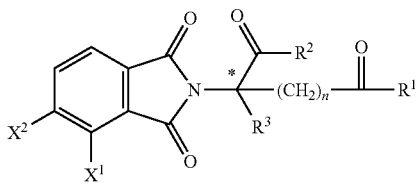

wherein:
one of $X^1$ and $X^2$ is $C_{1-6}$ alkyl; and the other of $X^1$ or $X^2$ is hydrogen;
$R^1$ and $R^2$ are each independently hydroxy or —NH—Z;
$R^3$ is $C_{1-6}$ alkyl, halo, or hydrogen;
Z is hydrogen, phenyl, $C_{1-6}$ acyl, or $C_{1-6}$ alkyl; and
n is an integer of 0, 1, or 2;
* designates a chiral center, when —$COR^2$ and —$(CH_2)_n COR^1$ are different.

In certain embodiments, the immunomodulatory compound is an isoindoline-1-one or isoindoline-1,3-dione substituted in the 2-position with 2,6-dioxo-3-hydroxypiperidin-5-yl, including, but not limited to, those described in U.S. Pat. No. 6,458,810, the disclosure of which is incorporated herein by reference in its entirety.

In certain embodiments, the immunomodulatory compound has the formula:

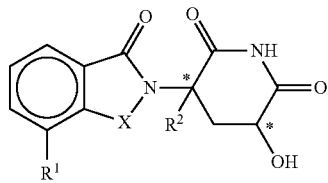

wherein:
X is —C(O)— or —$CH_2$—;
$R^1$ is $C_{1-8}$ alkyl or —$NHR^3$;
$R^2$ is hydrogen, $C_{1-8}$ alkyl, or halogen;
$R^3$ is hydrogen; $C_{1-8}$ alkyl, unsubstituted or substituted with $C_{1-8}$ alkoxy, halo, amino, or $C_{1-4}$ alkylamino; $C_{3-18}$ cycloalkyl; phenyl, unsubstituted or substituted with $C_{1-8}$ alkyl, $C_{1-8}$ alkoxy, halo, amino, or $C_{1-4}$ alkylamino; benzyl, unsubstituted or substituted with $C_{1-8}$ alkyl, $C_{1-8}$ alkoxy, halo, amino, or $C_{1-8}$ alkylamino; or —$COR^4$; and
$R^4$ is hydrogen; $C_{1-8}$ alkyl, unsubstituted or substituted with $C_{1-8}$ alkoxy, halo, amino, or $C_{1-8}$ alkylamino; $C_{3-18}$ cycloalkyl; phenyl, unsubstituted or substituted with $C_{1-8}$ alkyl, $C_{1-8}$ alkoxy, halo, amino, or $C_{1-8}$ alkylamino; or benzyl, unsubstituted or substituted with $C_{1-8}$ alkyl, $C_{1-8}$ alkoxy, halo, amino, or $C_{1-8}$ alkylamino;
* designates a chiral center.

In one embodiment, the immunomodulatory compound is a compound of Formula (IV):

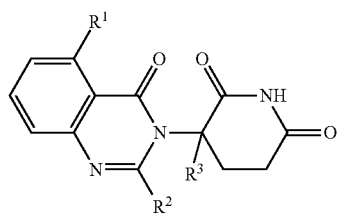

or a pharmaceutically acceptable salt, solvate, or stereoisomer thereof, wherein:
$R^1$ is (i) hydrogen; (ii) halo; (iii) —$(CH_2)$—OH; (iv) $C_{1-6}$ alkyl, optionally substituted with one or more halo; (v) $C_{1-6}$ alkoxy, optionally substituted with one or more halo; or (vi) —$(CH_2)$—$NHR^a$;
$R^a$ is:
hydrogen;
$C_{1-6}$ alkyl, optionally substituted with one or more halo;
—$(CH_2)_n$—$C_{6-14}$ aryl;
—C(O)—$(CH_2)_n$—$C_{6-14}$ aryl or —C(O)—$(CH_2)_n$-heteroaryl; wherein the aryl or heteroaryl is optionally substituted with one or more of: halo; —$SCF_3$; $C_{1-6}$ alkyl, itself optionally substituted with one or more halo; or $C_{1-6}$ alkoxy, itself optionally substituted with one or more halo;
—C(O)—$C_{1-8}$ alkyl, wherein the alkyl is optionally substituted with one or more halo;
—C(O)—$(CH_2)_n$—$C_{3-10}$ cycloalkyl;
—C(O)—$(CH_2)_n$—$NR^bR^c$, wherein $R^b$ and $R^c$ are each independently hydrogen;
$C_{1-6}$ alkyl, optionally substituted with one or more halo;
$C_{1-6}$ alkoxy, optionally substituted with one or more halo; or
$C_{6-14}$ aryl, optionally substituted with one or more of halo; $C_{1-6}$ alkyl, itself optionally substituted with one or more halo; or $C_{1-6}$ alkoxy, itself optionally substituted with one or more halo;
—C(O)—$(CH_2)_n$—O—$C_{1-6}$ alkyl; or
—C(O)—$(CH_2)_n$—O—$(CH_2)_n$—$C_{6-14}$ aryl;
$R^2$ is hydrogen; —$(CH_2)$—OH; phenyl; —O—$C_{1-6}$ alkyl; or $C_{1-6}$ alkyl, optionally substituted with one or more halo;
$R^3$ is hydrogen; or $C_{1-6}$ alkyl, optionally substituted with one or more halo; and
n is 0, 1, or 2.

In another embodiment, the immunomodulatory compound is a compound of Formula (V):

(V)

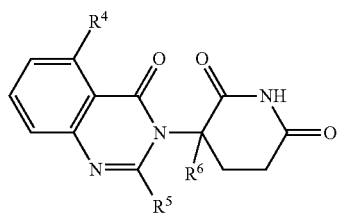

or a pharmaceutically acceptable salt, solvate, or stereoisomer thereof, wherein:
- $R^4$ is hydrogen; halo; —(CH$_2$)$_n$OH; C$_{1-6}$ alkyl, optionally substituted with one or more halo; or C$_{1-6}$ alkoxy, optionally substituted with one or more halo;
- $R^5$ is hydrogen; —(CH$_2$)—OH; phenyl; —O—C$_{1-6}$ alkyl; or C$_{1-6}$ alkyl, optionally substituted with one or more halo;
- $R^6$ is hydrogen; or C$_{1-6}$ alkyl, optionally substituted with one or more halo; and
- n is 0, 1, or 2.

In Formula V, in one embodiment, $R^4$ is hydrogen; in another embodiment, $R^4$ is halo; in yet another embodiment, $R^4$ is C$_{1-6}$ alkyl, optionally substituted with one or more halo; in yet another embodiment, $R^4$ is —(CH$_2$)—OH or hydroxyl; and in still another embodiment, $R^4$ is C$_{1-6}$ alkoxy, optionally substituted with one or more halo.

In Formula V, in one embodiment, $R^5$ is hydrogen; in another embodiment, $R^5$ is —(CH$_2$)—OH or hydroxyl; in yet another embodiment, $R^5$ is phenyl; in yet another embodiment, $R^5$ is —O—C$_{1-6}$ alkyl, optionally substituted with one or more halo; and in still another embodiment, $R^5$ is C$_{1-6}$ alkyl, optionally substituted with one or more halo.

In Formula V, in one embodiment, $R^6$ is hydrogen; and in another embodiment, $R^6$ is C$_{1-6}$ alkyl, optionally substituted with one or more halo.

In Formula V, in one embodiment, n is 0; in another embodiment, n is 1; and in still another embodiment, n is 2.

The immunomodulatory compounds of Formula V encompass any of the combinations of $R^4$, $R^5$, $R^6$ and n as described herein.

In Formula V, in one embodiment, $R^4$ is methyl; in another embodiment, $R^4$ is methoxy; in yet another embodiment, $R^4$ is —CF$_3$; and in still another embodiment, $R^4$ is F or Cl.

In Formula V, in one embodiment, $R^5$ is methyl; and in another embodiment, $R^5$ is —CF$_3$.

In certain embodiments, the immunomodulatory compound is selected from:

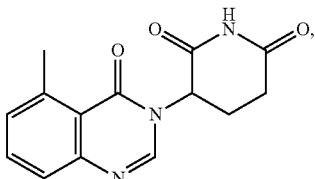

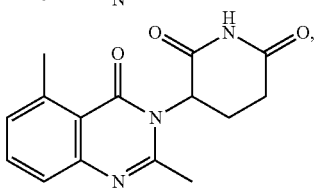

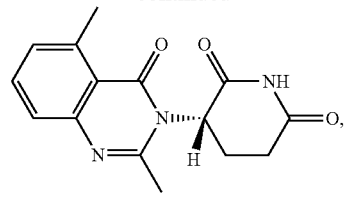

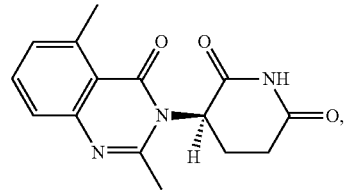

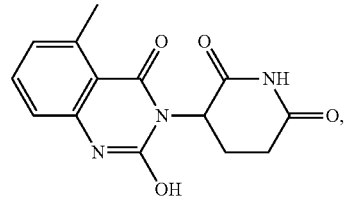

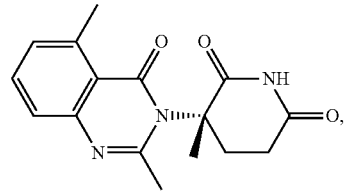

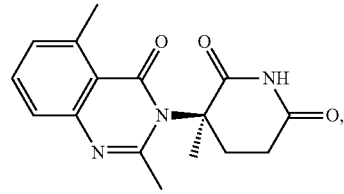

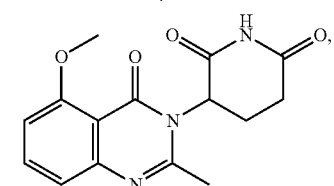

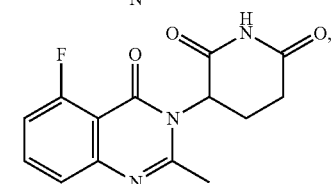

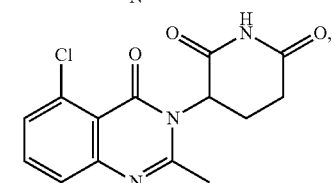

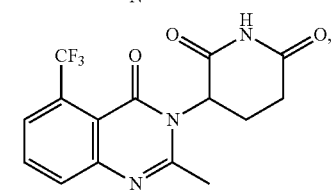

-continued

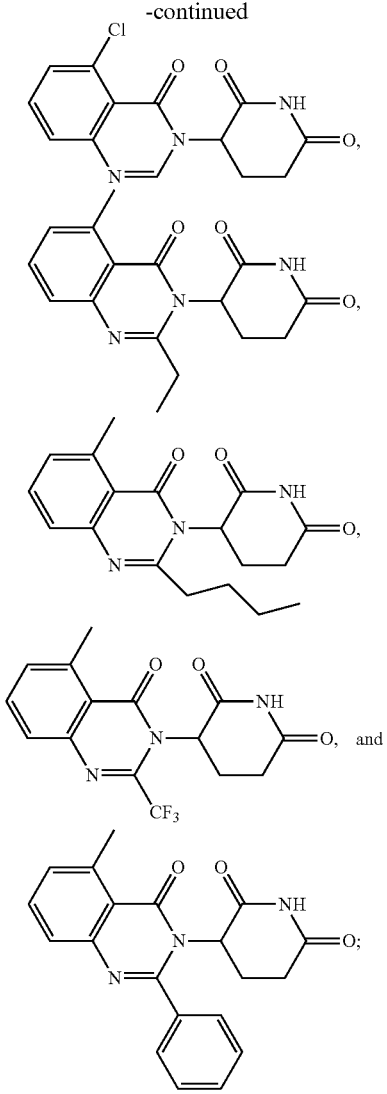

and pharmaceutically acceptable salts, solvates, and stereoisomers thereof.

In yet another embodiment, the immunomodulatory compound is a compound of Formula (VI):

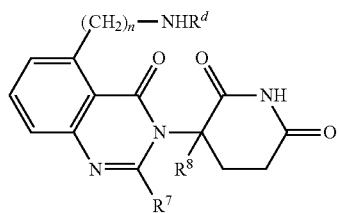

(VI)

or a pharmaceutically acceptable salt, solvate, or a stereoisomer thereof, wherein:

$R^d$ is:
hydrogen;
$C_{1-6}$ alkyl, optionally substituted with one or more halo;
—C(O)—$C_{1-8}$ alkyl, wherein the alkyl is optionally substituted with one or more halo;
—C(O)—$(CH_2)_n$—$C_{3-10}$ cycloalkyl;
—C(O)—$(CH_2)_n$—$NR^eR^f$, wherein $R^e$ and $R^f$ are each independently: hydrogen; $(C_1-C_6)$alkyl, optionally substituted with one or more halo; or $(C_1-C_6)$alkoxy, optionally substituted with one or more halo; or
—C(O)—$(CH_2)_n$—O—$C_{1-6}$ alkyl;

$R^7$ is hydrogen; —$(CH_2)$—OH; phenyl; —O—$C_{1-6}$ alkyl; or $C_{1-6}$ alkyl, optionally substituted with one or more halo;

$R^8$ is hydrogen; or $C_{1-6}$ alkyl, optionally substituted with one or more halo; and n is 0, 1, or 2.

In Formula VI, in one embodiment, $R^d$ is hydrogen; in another embodiment, $R^d$ is $C_{1-6}$ alkyl, optionally substituted with one or more halo; in yet another embodiment, $R^d$ is —C(O)—$C_{1-8}$ alkyl; in yet another embodiment, $R^d$ is —C(O)—$(CH_2)_n$—$C_{3-10}$ cycloalkyl; in yet another embodiment, $R^d$ is —C(O)—$(CH_2)_n$—$NR^eR^f$, wherein $R^e$ and $R^f$ are as described herein; and in still another embodiment, $R^d$ is —C(O)—$(CH_2)_n$—O—$(CH_2)_n$—$C_{1-6}$ alkyl.

In Formula VI, in one embodiment, $R^7$ is hydrogen; in another embodiment, $R^7$ is —$(CH_2)$—OH or hydroxyl; in yet another embodiment, $R^7$ is phenyl; in yet another embodiment, $R^7$ is —O—$C_{1-6}$ alkyl, optionally substituted with one or more halo; and in still another embodiment, $R^7$ is $C_{1-6}$ alkyl, optionally substituted with one or more halo.

In Formula VI, in one embodiment, $R^8$ is hydrogen; and in another embodiment, $R^8$ is $C_{1-6}$ alkyl, optionally substituted with one or more halo.

In Formula VI, in one embodiment, n is 0; in another embodiment, n is 1; and in still another embodiment, n is 2.

The immunomodulatory compounds of Formula VI encompass any of the combinations of $R^d$, $R^7$, $R^8$ and n described herein.

In Formula VI, in one embodiment, $R^7$ is methyl; in another embodiment, $R^d$ is —C(O)—$C_{1-6}$ alkyl; in yet another embodiment, $R^d$ is $NH_2$; and in still another embodiment, $R^d$ is —C(O)—$CH_2$—O—$C_{1-6}$ alkyl.

In certain embodiments, the immunomodulatory compound is selected from:

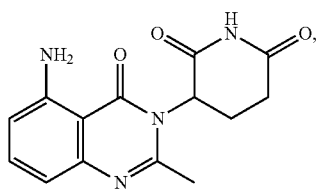

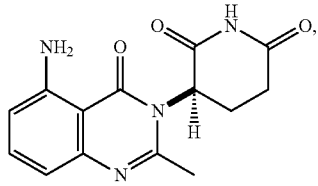

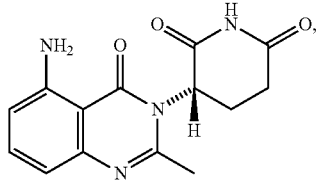

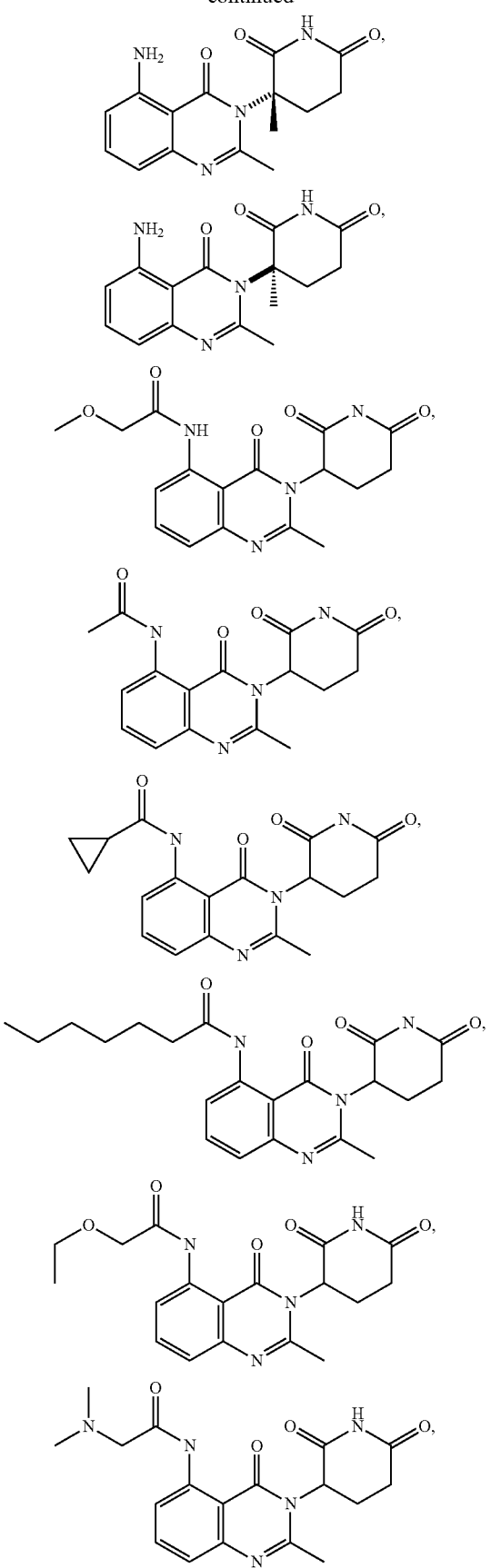
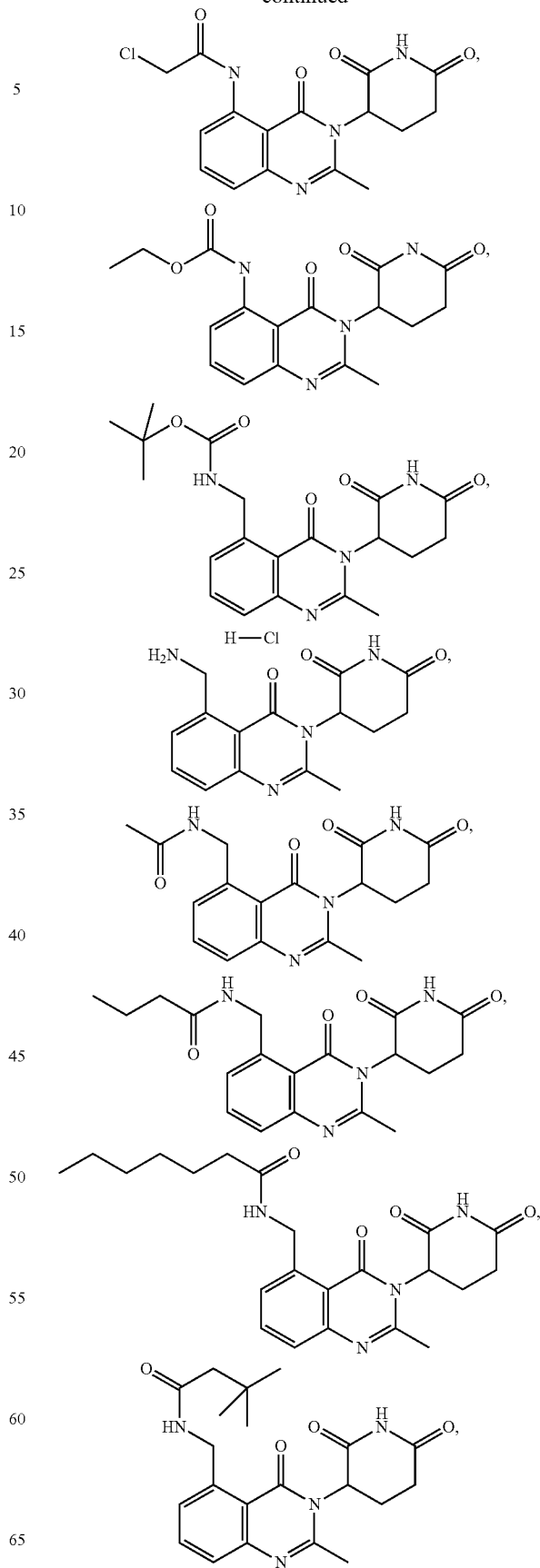

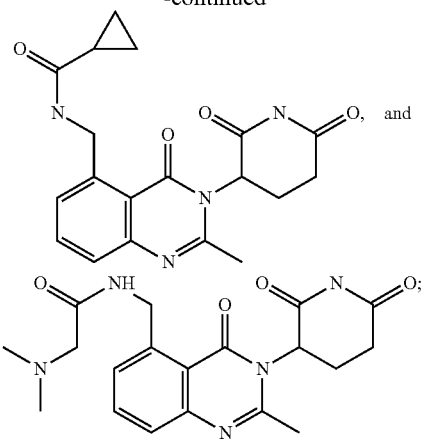

In yet another embodiment, the immunomodulatory compound is a compound of Formula (VII):

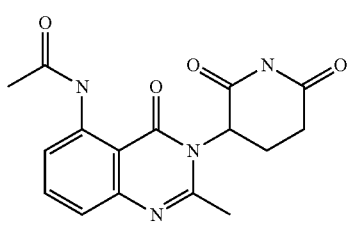

(VII)

or a pharmaceutically acceptable salt, solvate, or a stereoisomer thereof, wherein:

$R^g$ is:
- —$(CH_2)_n$—$C_{6-14}$ aryl;
- —C(O)—$(CH_2)_n$—$C_{6-14}$ aryl) or —C(O)—$(CH_2)_n$-heteroaryl, wherein the aryl or heteroaryl is optionally substituted with one or more of halo; —$SCF_3$; $C_{1-6}$ alkyl, itself optionally substituted with one or more halo; or ($C_{1-6}$ alkoxy, itself optionally substituted with one or more halo;
- —C(O)—$(CH_2)_n$—$NHR^h$, wherein $R^h$ is $C_{6-14}$ aryl, optionally substituted with one or more of: halo; $C_{1-6}$ alkyl, itself optionally substituted with one or more halo; or $C_{1-6}$ alkoxy, itself optionally substituted with one or more halo; or
- —C(O)—$(CH_2)_n$—O—$(CH_2)_n$—$C_{6-14}$ aryl;

$R^9$ is hydrogen; —$(CH_2)_n OH$; phenyl; —O—$C_{1-6}$ alkyl; or $C_{1-6}$ alkyl, optionally substituted with one or more halo;

$R^{10}$ is hydrogen; or $C_{1-6}$ alkyl, optionally substituted with one or more halo; and n is 0, 1, or 2.

In Formula VII, in one embodiment, $R^g$ is —$(CH_2)_n$—$C_{6-14}$ aryl; in another embodiment, $R^g$ is —C(O)—$(CH_2)_n$—$C_{6-14}$ aryl or —C(O)—$(CH_2)_n$-heteroaryl, wherein the aryl or heteroaryl is optionally substituted as described above; in yet another embodiment, $R^g$ is —C(O)—$(CH_2)_n$—$NHR^h$, wherein $R^h$ is $C_{6-14}$ aryl, optionally substituted as described above; and in still another embodiment, $R^g$ is —C(O)—$(CH_2)_n$—O—$(CH_2)_n$—$C_{6-14}$ aryl.

In Formula VII, in one embodiment, $R^9$ is hydrogen; in another embodiment, $R^9$ is —$(CH_2)$—OH or hydroxyl; in yet another embodiment, $R^9$ is phenyl; in yet another embodiment, $R^9$ is —O—$C_{1-6}$ alkyl, optionally substituted with one or more halo; and in still another embodiment, $R^9$ is $C_{1-6}$ alkyl, optionally substituted with one or more halo.

In Formula VII, in one embodiment, $R^{10}$ is hydrogen; and in another embodiment, $R^{10}$ is $C_{1-6}$ alkyl, optionally substituted with one or more halo.

In Formula VII, in one embodiment, n is 0; in another embodiment, n is 1; and in still another embodiment, n is 2.

The immunomodulatory compounds of Formula VII encompass any of the combinations of $R^g$, $R^9$, $R^{10}$ and n described herein.

In Formula VII, in one embodiment, $R^9$ is methyl; in another embodiment, $R^g$ is —C(O)-phenyl or —C(O)—$CH_2$-phenyl, wherein the phenyl is optionally substituted with methyl, —$CF_3$, and/or halo; and in still another embodiment, $R^g$ is —C(O)—NH-phenyl, wherein the phenyl is optionally substituted with methyl, —$CF_3$, and/or halo.

In certain embodiments, the immunomodulatory compound is selected from:

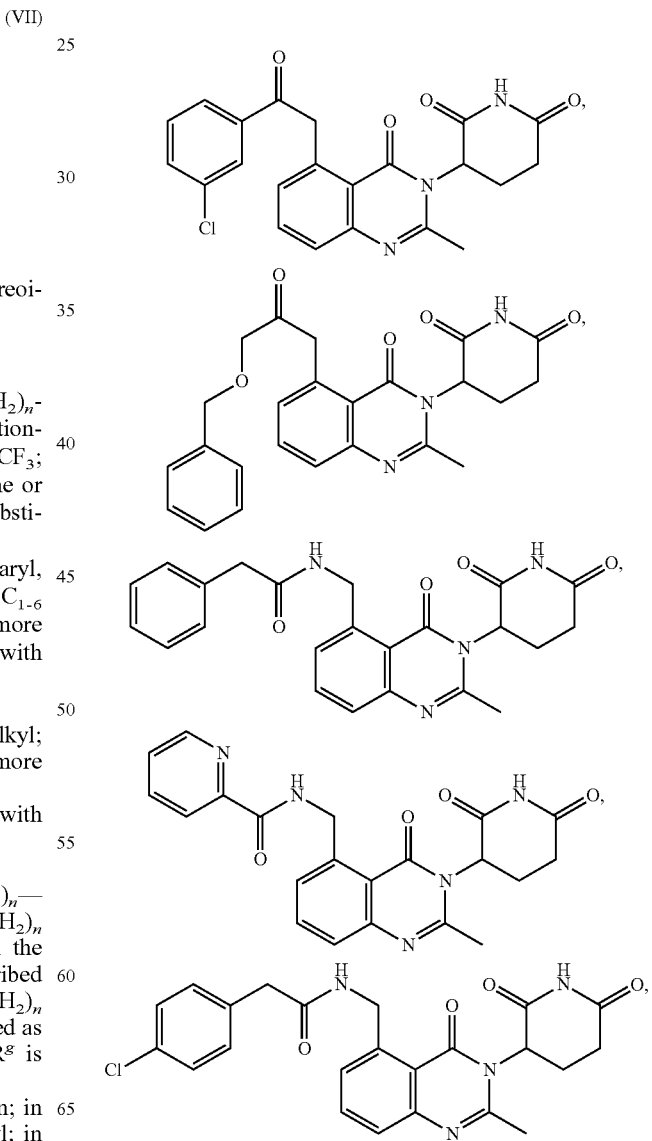

107
-continued
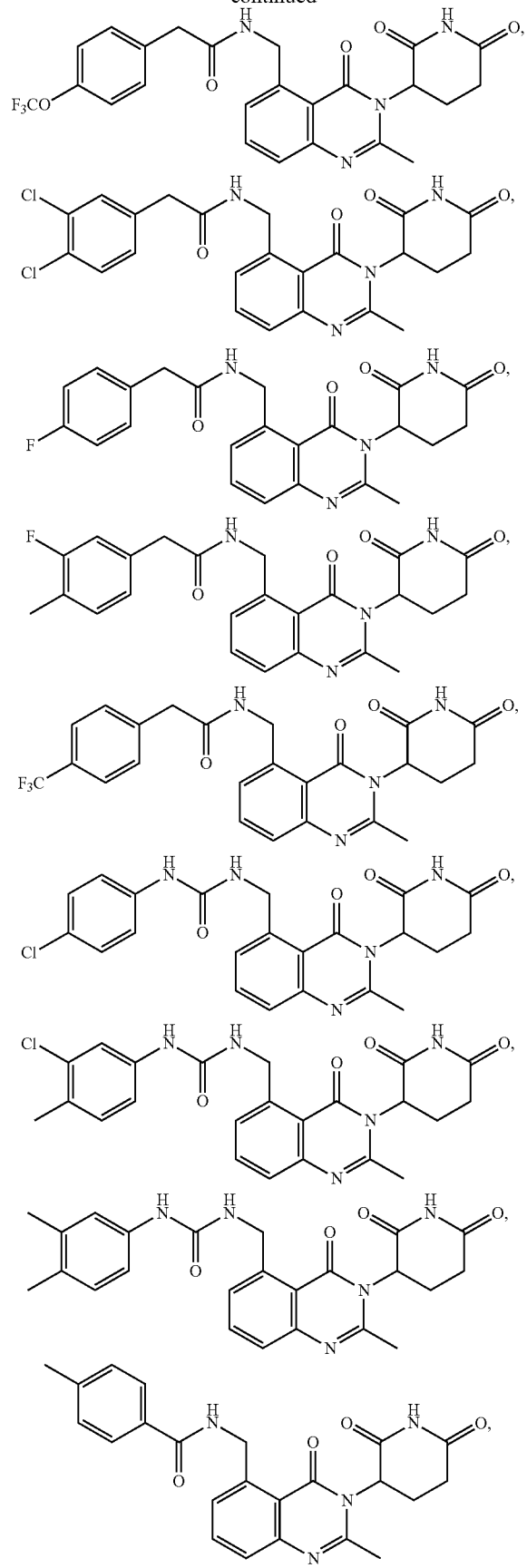
108
-continued
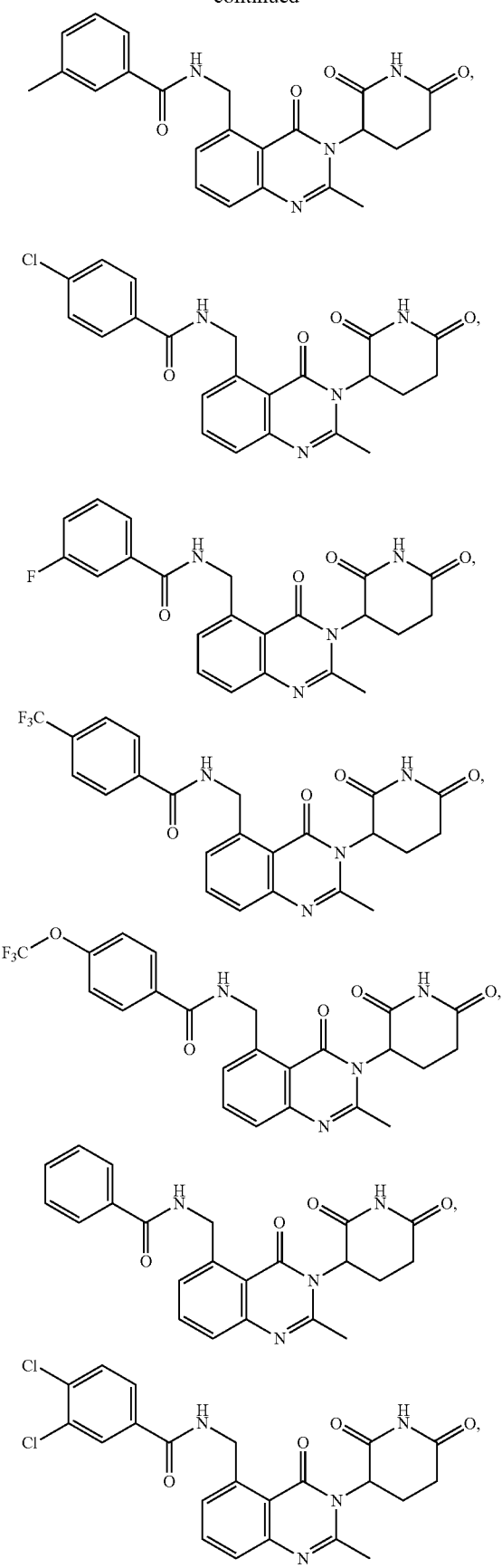

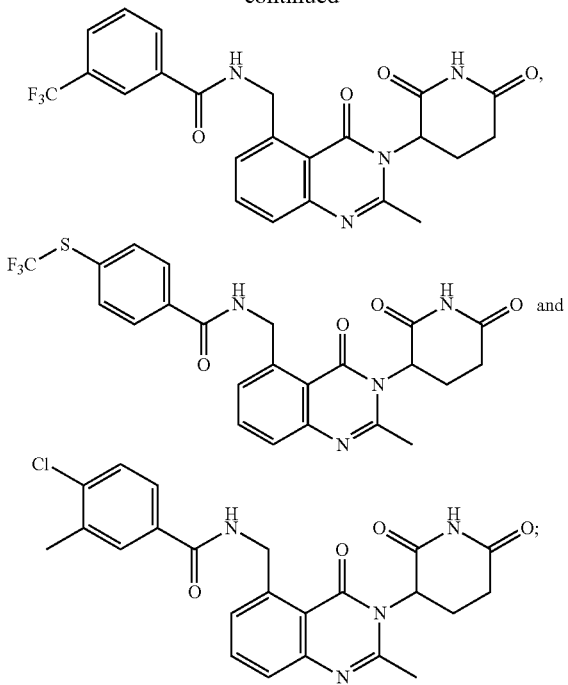

and pharmaceutically acceptable salts, solvates, and stereoisomers thereof.

In one embodiment, the immunomodulatory compound is a compound of Formula (VIII):

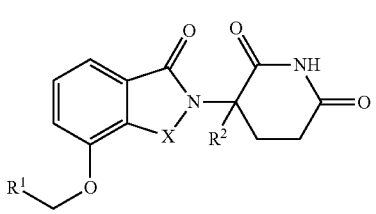

(VIII)

or a pharmaceutically acceptable salt, solvate or stereoisomer thereof, wherein:

X is C=O or $CH_2$;
$R^1$ is —Y—$R^3$;
$R^2$ is H or $C_{1-6}$ alkyl;
Y is $C_{6-14}$ aryl, heteroaryl or heterocyclyl, each of which is optionally substituted with one or more halogen; or a bond;
$R^3$ is —$(CH_2)_n$—$C_{6-14}$ aryl, —O—$(CH_2)_n$—$C_{6-14}$ aryl, or —$(CH_2)_n$—O—$C_{6-14}$ aryl, wherein the aryl is optionally substituted with one or more $C_{1-6}$ alkyl, itself optionally substituted with one or more halogen; $C_{1-6}$ alkoxy, itself substituted with one or more halogen; oxo; amino; carboxyl; cyano; hydroxyl; halogen; deuterium; $C_{6-14}$ aryl or heteroaryl, optionally substituted with one or more $C_{1-6}$ alkyl, $C_{1-6}$ alkoxy, or halogen; —$CONH_2$; or —COO—$C_{1-6}$ alkyl, wherein the alkyl is optionally substituted with one or more halogen;
—$(CH_2)_n$-heterocyclyl, —O—$(CH_2)_n$-heterocyclyl or —$(CH_2)_n$—O-heterocyclyl, wherein the heterocyclyl is optionally substituted with one or more $C_{1-6}$ alkyl, itself optionally substituted with one or more halogen; $C_{1-6}$ alkoxy, itself substituted with one or more halogen; oxo; amino; carboxyl; cyano; hydroxyl; halogen; deuterium; $C_{6-14}$ aryl or heteroaryl, optionally substituted with one or more $C_{1-6}$ alkyl, $C_{1-6}$ alkoxy or halogen; —$CONH_2$; or —COO—$C_{1-6}$ alkyl, wherein the alkyl is optionally substituted with one or more halogen; or —$(CH_2)_n$-heteroaryl, —O—$(CH_2)_n$-heteroaryl, or —$(CH_2)_n$—O-heteroaryl, wherein the heteroaryl is optionally substituted with one or more $C_{1-6}$ alkyl, itself optionally substituted with one or more halogen; $C_{1-6}$ alkoxy, itself substituted with one or more halogen; oxo; amino; carboxyl; cyano; hydroxyl; halogen; deuterium; $C_{6-14}$ aryl or heteroaryl, optionally substituted with one or more $C_{1-6}$ alkyl, $C_{1-6}$ alkoxy, or halogen; —$CONH_2$; or —COO—$C_{1-6}$ alkyl, wherein the alkyl is optionally substituted with one or more halogen; and n is 0, 1, 2 or 3.

In Formula VIII, in one embodiment, X is C=O; and in another embodiment, X is $CH_2$.

In Formula VIII, in one embodiment, $R^2$ is H; and in another embodiment, $R^2$ is $C_{1-6}$ alkyl.

In Formula VIII, in one embodiment, Y is $C_{6-14}$ aryl; in another embodiment, Y is heteroaryl; in yet another embodiment, Y is heterocyclyl; and in still another embodiment, Y is a bond.

In Formula VIII, in one embodiment, $R^3$ is unsubstituted —$(CH_2)_n$—$C_{6-14}$ aryl; in another embodiment, $R^3$ is —$(CH_2)_n$—$C_{6-14}$ aryl substituted with one or more $C_{1-6}$ alkyl, itself optionally substituted with one or more halogen; in yet another embodiment, $R^3$ is —$(CH_2)_n$—$C_{6-14}$ aryl substituted with one or more $C_{1-6}$ alkoxy, itself substituted with one or more halogen; in yet another embodiment, $R^3$ is —$(CH_2)_n$—$C_{6-14}$ aryl substituted with one or more oxo; in yet another embodiment, $R^3$ is —$(CH_2)_n$—$C_{6-14}$ aryl substituted with one or more amino; in yet another embodiment, $R^3$ is —$(CH_2)_n$—$C_{6-14}$ aryl substituted with one or more carboxyl; in yet another embodiment, $R^3$ is —$(CH_2)_n$—$C_{6-14}$ aryl substituted with one or more cyano; in yet another embodiment, $R^3$ is —$(CH_2)_n$—$C_{6-14}$ aryl substituted with one or more hydroxyl; in yet another embodiment, $R^3$ is —$(CH_2)_n$—$C_{6-14}$ aryl substituted with one or more halogen; in yet another embodiment, $R^3$ is —$(CH_2)_n$—$C_{6-14}$ aryl substituted with one or more deuterium; in yet another embodiment, $R^3$ is —$(CH_2)_n$—$C_{6-14}$ aryl substituted with one or more $C_{6-14}$ aryl, optionally substituted with one or more $C_{1-6}$ alkyl; in yet another embodiment, $R^3$ is —$(CH_2)_n$—$C_{6-14}$ aryl substituted with one or more heteroaryl, optionally substituted with one or more $C_{1-6}$ alkyl, $C_{1-6}$ alkoxy, or halogen; in yet another embodiment, $R^3$ is —$(CH_2)_n$—$C_{6-14}$ aryl substituted with one or more —$CONH_2$; and in still another embodiment, $R^3$ is —$(CH_2)_n$—$C_{6-14}$ aryl substituted with one or more —COO—$C_{1-6}$ alkyl, wherein the alkyl is optionally substituted with one or more halogen.

In Formula VIII, in one embodiment, $R^3$ is unsubstituted —O—$(CH_2)_n$—$C_{6-14}$ aryl; in another embodiment, $R^3$ is —O—$(CH_2)_n$—$C_{6-14}$ aryl substituted with one or more $C_{1-6}$ alkyl, itself optionally substituted with one or more halogen; in yet another embodiment, $R^3$ is —O—$(CH_2)_n$—$C_{6-14}$ aryl substituted with one or more $C_{1-6}$ alkoxy, itself substituted with one or more halogen; in yet another embodiment, $R^3$ is —O—$(CH_2)_n$—$C_{6-14}$ aryl substituted with one or more oxo; in yet another embodiment, $R^3$ is —O—$(CH_2)_n$—$C_{6-14}$ aryl substituted with one or more amino; in yet another embodiment, $R^3$ is —O—$(CH_2)_n$—$C_{6-14}$ aryl substituted with one or more carboxyl; in yet another embodiment, $R^3$ is —O—

$(CH_2)_n$—$C_{6-14}$ aryl substituted with one or more cyano; in yet another embodiment, $R^3$ is —$(CH_2)_n$—$C_{6-14}$ aryl substituted with one or more hydroxyl; in yet another embodiment, $R^3$ is —$(CH_2)_n$—$C_{6-14}$ aryl substituted with one or more halogen; in yet another embodiment, $R^3$ is —O—$(CH_2)_n$—$C_{6-14}$ aryl substituted with one or more deuterium; in yet another embodiment, $R^3$ is —O—$(CH_2)_n$—$C_{6-14}$ aryl substituted with one or more $C_{6-14}$ aryl, optionally substituted with one or more $C_{1-6}$ alkyl; in yet another embodiment, $R^3$ is —O—$(CH_2)_n$—$C_{6-14}$ aryl substituted with one or more heteroaryl, optionally substituted with one or more $C_{1-6}$ alkyl, $C_{1-6}$ alkoxy, or halogen; in yet another embodiment, $R^3$ is —O—$(CH_2)_n$—$C_{6-14}$ aryl substituted with one or more —$CONH_2$; and in still another embodiment, $R^3$ is —O—$(CH_2)_n$—$C_{6-14}$ aryl substituted with one or more —COO—$C_{1-6}$ alkyl, wherein the alkyl is optionally substituted with one or more halogen.

In Formula VIII, in one embodiment, $R^3$ is unsubstituted —$(CH_2)_n$—O—$C_{6-14}$ aryl; in another embodiment, $R^3$ is —$(CH_2)_n$—O—$C_{6-14}$ aryl substituted with one or more $C_{1-6}$ alkyl, itself optionally substituted with one or more halogen; in yet another embodiment, $R^3$ is —$(CH_2)_n$—O—$C_{6-14}$ aryl substituted with one or more $C_{1-6}$ alkoxy, itself substituted with one or more halogen; in yet another embodiment, $R^3$ is —$(CH_2)_n$—O—$C_{6-14}$ aryl substituted with one or more oxo; in yet another embodiment, $R^3$ is —$(CH_2)_n$—O—$C_{6-14}$ aryl substituted with one or more amino; in yet another embodiment, $R^3$ is —$(CH_2)_n$—O—$C_{6-14}$ aryl substituted with one or more carboxyl; in yet another embodiment, $R^3$ is —$(CH_2)_n$—O—$C_{6-14}$ aryl substituted with one or more cyano; in yet another embodiment, $R^3$ is —$(CH_2)_n$—O—$C_{6-14}$ aryl substituted with one or more hydroxyl; in yet another embodiment, $R^3$ is —$(CH_2)_n$—O—$C_{6-14}$ aryl substituted with one or more halogen; in yet another embodiment, $R^3$ is —$(CH_2)_n$—O—$C_{6-14}$ aryl substituted with one or more deuterium; in yet another embodiment, $R^3$ is —$(CH_2)_n$—O—$C_{6-14}$ aryl substituted with one or more $C_{6-14}$ aryl, optionally substituted with one or more $C_{1-6}$ alkyl; in yet another embodiment, $R^3$ is —$(CH_2)_n$—O—$C_{6-14}$ aryl substituted with one or more heteroaryl, optionally substituted with one or more $C_{1-6}$ alkyl, $C_{1-6}$ alkoxy, or halogen; in yet another embodiment, $R^3$ is —$(CH_2)_n$—O—$C_{6-14}$ aryl substituted with one or more —$CONH_2$; and in still another embodiment, $R^3$ is —$(CH_2)_n$—O—$C_{6-14}$ aryl substituted with one or more —COO—$C_{1-6}$ alkyl, wherein the alkyl is optionally substituted with one or more halogen.

In Formula VIII, in one embodiment, $R^3$ is unsubstituted —$(CH_2)_n$-heterocyclyl; in another embodiment, $R^3$ is —$(CH_2)_n$-heterocyclyl substituted with one or more $C_{1-6}$ alkyl, itself optionally substituted with one or more halogen; in yet another embodiment, $R^3$ is —$(CH_2)_n$-heterocyclyl substituted with one or more $C_{1-6}$ alkoxy, itself substituted with one or more halogen; in yet another embodiment, $R^3$ is —$(CH_2)_n$-heterocyclyl substituted with one or more oxo; in yet another embodiment, $R^3$ is —$(CH_2)_n$-heterocyclyl substituted with one or more amino; in yet another embodiment, $R^3$ is —$(CH_2)_n$-heterocyclyl substituted with one or more carboxyl; in yet another embodiment, $R^3$ is —$(CH_2)_n$-heterocyclyl substituted with one or more cyano; in yet another embodiment, $R^3$ is —$(CH_2)_n$-heterocyclyl substituted with one or more hydroxyl; in yet another embodiment, $R^3$ is —$(CH_2)_n$-heterocyclyl substituted with one or more halogen; in yet another embodiment, $R^3$ is —$(CH_2)_n$-heterocyclyl substituted with one or more deuterium; in yet another embodiment, $R^3$ is —$(CH_2)_n$-heterocyclyl substituted with one or more $C_{6-14}$ aryl, optionally substituted with one or more $C_{1-6}$ alkyl; in yet another embodiment, $R^3$ is —$(CH_2)_n$-heterocyclyl substituted with one or more heteroaryl, optionally substituted with one or more $C_{1-6}$ alkyl, $C_{1-6}$ alkoxy, or halogen; in yet another embodiment, $R^3$ is —$(CH_2)_n$-heterocyclyl substituted with one or more —$CONH_2$; and in still another embodiment, $R^3$ is —$(CH_2)_n$-heterocyclyl substituted with one or more —COO—$C_{1-6}$ alkyl, wherein the alkyl is optionally substituted with one or more halogen.

In Formula VIII, in one embodiment, $R^3$ is unsubstituted —O—$(CH_2)_n$-heterocyclyl; in another embodiment, $R^3$ is —O—$(CH_2)_n$-heterocyclyl substituted with one or more $C_{1-6}$ alkyl, itself optionally substituted with one or more halogen; in yet another embodiment, $R^3$ is —O—$(CH_2)_n$-heterocyclyl substituted with one or more $C_{1-6}$ alkoxy, itself substituted with one or more halogen; in yet another embodiment, $R^3$ is —O—$(CH_2)_n$-heterocyclyl substituted with one or more oxo; in yet another embodiment, $R^3$ is —O—$(CH_2)_n$-heterocyclyl substituted with one or more amino; in yet another embodiment, $R^3$ is —O—$(CH_2)_n$-heterocyclyl substituted with one or more carboxyl; in yet another embodiment, $R^3$ is —O—$(CH_2)_n$-heterocyclyl substituted with one or more cyano; in yet another embodiment, $R^3$ is —O—$(CH_2)_n$-heterocyclyl substituted with one or more hydroxyl; in yet another embodiment, $R^3$ is —O—$(CH_2)_n$-heterocyclyl substituted with one or more halogen; in yet another embodiment, $R^3$ is —O—$(CH_2)_n$-heterocyclyl substituted with one or more deuterium; in yet another embodiment, $R^3$ is —O—$(CH_2)_n$-heterocyclyl substituted with one or more $C_{6-14}$ aryl, optionally substituted with one or more $C_{1-6}$ alkyl; in yet another embodiment, $R^3$ is —O—$(CH_2)_n$-heterocyclyl substituted with one or more heteroaryl, optionally substituted with one or more $C_{1-6}$ alkyl, $C_{1-6}$ alkoxy, or halogen; in yet another embodiment, $R^3$ is —O—$(CH_2)_n$-heterocyclyl substituted with one or more —$CONH_2$; and in still another embodiment, $R^3$ is —O—$(CH_2)_n$-heterocyclyl substituted with one or more —COO—$C_{1-6}$ alkyl, wherein the alkyl is optionally substituted with one or more halogen.

In Formula VIII, in one embodiment, $R^3$ is unsubstituted —$(CH_2)_n$—O-heterocyclyl; in another embodiment, $R^3$ is —$(CH_2)_n$—O-heterocyclyl substituted with one or more $C_{1-6}$ alkyl, itself optionally substituted with one or more halogen; in yet another embodiment, $R^3$ is —$(CH_2)_n$—O-heterocyclyl substituted with one or more $C_{1-6}$ alkoxy, itself substituted with one or more halogen; in yet another embodiment, $R^3$ is —$(CH_2)_n$ O-heterocyclyl substituted with one or more oxo; in yet another embodiment, $R^3$ is —$(CH_2)_n$—O-heterocyclyl substituted with one or more amino; in yet another embodiment, $R^3$ is —$(CH_2)_n$—O-heterocyclyl substituted with one or more carboxyl; in yet another embodiment, $R^3$ is —$(CH_2)_n$—O-heterocyclyl substituted with one or more cyano; in yet another embodiment, $R^3$ is —$(CH_2)_n$—O-heterocyclyl substituted with one or more hydroxyl; in yet another embodiment, $R^3$ is —$(CH_2)_n$—O-heterocyclyl substituted with one or more halogen; in yet another embodiment, $R^3$ is —$(CH_2)_n$—O-heterocyclyl substituted with one or more deuterium; in yet another embodiment, $R^3$ is —$(CH_2)_n$—O-heterocyclyl substituted with one or more $C_{6-14}$ aryl, optionally substituted with one or more $C_{1-6}$ alkyl; in yet another embodiment, $R^3$ is —$(CH_2)_n$—O-heterocyclyl substituted with one or more heteroaryl, optionally substituted with one or more $C_{1-6}$ alkyl, $C_{1-6}$ alkoxy, or halogen; in yet another embodiment, $R^3$ is —$(CH_2)_n$—O-heterocyclyl substituted with one or more —$CONH_2$; and in still another embodiment, $R^3$ is —(CH$_2$)$_n$—O-heterocyclyl substituted with one or more —COO—C$_{1-6}$ alkyl, wherein the alkyl is optionally substituted with one or more halogen.

In Formula VIII, in one embodiment, R$^3$ is unsubstituted —(CH$_2$)$_n$-heteroaryl; in another embodiment, R$^3$ is —(CH$_2$)$_n$-heteroaryl substituted with one or more C$_{1-6}$ alkyl, itself optionally substituted with one or more halogen; in yet another embodiment, R$^3$ is —(CH$_2$)$_n$-heteroaryl substituted with one or more C$_{1-6}$ alkoxy, itself substituted with one or more halogen; in yet another embodiment, R$^3$ is —(CH$_2$)$_n$-heteroaryl substituted with one or more oxo; in yet another embodiment, R$^3$ is —(CH$_2$)$_n$-heteroaryl substituted with one or more amino; in yet another embodiment, R$^3$ is —(CH$_2$)$_n$-heteroaryl substituted with one or more carboxyl; in yet another embodiment, R$^3$ is —(CH$_2$)$_n$-heteroaryl substituted with one or more cyano; in yet another embodiment, R$^3$ is —(CH$_2$)$_n$-heteroaryl substituted with one or more hydroxyl; in yet another embodiment, R$^3$ is —(CH$_2$)$_n$-heteroaryl substituted with one or more halogen; in yet another embodiment, R$^3$ is —(CH$_2$)$_n$-heteroaryl substituted with one or more deuterium; in yet another embodiment, R$^3$ is —(CH$_2$)$_n$-heteroaryl substituted with one or more C$_{6-14}$ aryl, optionally substituted with one or more C$_{1-6}$ alkyl; in yet another embodiment, R$^3$ is —(CH$_2$)$_n$-heteroaryl substituted with one or more heteroaryl, optionally substituted with one or more C$_{1-6}$ alkyl, C$_{1-6}$ alkoxy, or halogen; in yet another embodiment, R$^3$ is —(CH$_2$)$_n$-heteroaryl substituted with one or more —CONH$_2$; and in still another embodiment, R$^3$ is —(CH$_2$)$_n$-heteroaryl substituted with one or more —COO—C$_{1-6}$ alkyl, wherein the alkyl is optionally substituted with one or more halogen.

In Formula VIII, in one embodiment, R$^3$ is unsubstituted —O—(CH$_2$)$_n$-heteroaryl; in another embodiment, R$^3$ is —O—(CH$_2$)$_n$-heteroaryl substituted with one or more C$_{1-6}$ alkyl, itself optionally substituted with one or more halogen; in yet another embodiment, R$^3$ is —O—(CH$_2$)$_n$-heteroaryl substituted with one or more C$_{1-6}$ alkoxy, itself substituted with one or more halogen; in yet another embodiment, R$^3$ is —O—(CH$_2$)$_n$-heteroaryl substituted with one or more oxo; in yet another embodiment, R$^3$ is —O—(CH$_2$)$_n$-heteroaryl substituted with one or more amino; in yet another embodiment, R$^3$ is —O—(CH$_2$)$_n$-heteroaryl substituted with one or more carboxyl; in yet another embodiment, R$^3$ is —O—(CH$_2$)$_n$-heteroaryl substituted with one or more cyano; in yet another embodiment, R$^3$ is —O—(CH$_2$)$_n$-heteroaryl substituted with one or more hydroxyl; in yet another embodiment, R$^3$ is —O—(CH$_2$)$_n$-heteroaryl substituted with one or more halogen; in yet another embodiment, R$^3$ is —O—(CH$_2$)$_n$-heteroaryl substituted with one or more deuterium; in yet another embodiment, R$^3$ is -O—(CH$_2$)$_n$-heteroaryl substituted with one or more C$_{6-14}$ aryl, optionally substituted with one or more C$_{1-6}$ alkyl; in yet another embodiment, R$^3$ is —O—(CH$_2$)$_n$-heteroaryl substituted with one or more heteroaryl, optionally substituted with one or more C$_{1-6}$ alkyl, C$_{1-6}$ alkoxy, or halogen; in yet another embodiment, R$^3$ is —O—(CH$_2$)$_n$-heteroaryl substituted with one or more —CONH$_2$; and in still another embodiment, R$^3$ is —O—(CH$_2$)$_n$-heteroaryl substituted with one or more —COO—C$_{1-6}$ alkyl, wherein the alkyl is optionally substituted with one or more halogen.

In Formula VIII, in one embodiment, R$^3$ is unsubstituted —(CH$_2$)$_n$—O-heteroaryl; in another embodiment, R$^3$ is —(CH$_2$)$_n$—O-heteroaryl substituted with one or more C$_{1-6}$ alkyl, itself optionally substituted with one or more halogen;

in yet another embodiment, R$^3$ is —(CH$_2$)$_n$—O-heteroaryl substituted with one or more C$_{1-6}$ alkoxy, itself substituted with one or more halogen; in yet another embodiment, R$^3$ is —(CH$_2$)$_n$ O-heteroaryl substituted with one or more oxo; in yet another embodiment, R$^3$ is —(CH$_2$)$_n$—O-heteroaryl substituted with one or more amino; in yet another embodiment, R$^3$ is —(CH$_2$)$_n$—O-heteroaryl substituted with one or more carboxyl; in yet another embodiment, R$^3$ is —(CH$_2$)$_n$—O-heteroaryl substituted with one or more cyano; in yet another embodiment, R$^3$ is —(CH$_2$)$_n$—O-heteroaryl substituted with one or more hydroxyl; in yet another embodiment, R$^3$ is —(CH$_2$)$_n$—O-heteroaryl substituted with one or more halogen; in yet another embodiment, R$^3$ is —(CH$_2$)$_n$—O-heteroaryl substituted with one or more deuterium; in yet another embodiment, R$^3$ is —(CH$_2$)$_n$—O-heteroaryl substituted with one or more C$_{6-14}$ aryl, optionally substituted with one or more C$_{1-6}$ alkyl; in yet another embodiment, R$^3$ is —(CH$_2$)$_n$—O-heteroaryl substituted with one or more heteroaryl, optionally substituted with one or more C$_{1-6}$ alkyl, C$_{1-6}$ alkoxy, or halogen; in yet another embodiment, R$^3$ is —(CH$_2$)$_n$—O-heteroaryl substituted with one or more —CONH$_2$; and in still another embodiment, R$^3$ is —(CH$_2$)$_n$—O-heteroaryl substituted with one or more —COO—C$_{1-6}$ alkyl, wherein the alkyl is optionally substituted with one or more halogen.

In Formula VIII, in one embodiment, n is 0; in another embodiment, n is 1; and in yet another embodiment, n is 2.

The immunomodulatory compounds of Formula VIII encompass any of the combinations of X, R$^1$, R$^2$, Y, R$^3$, and n as described herein.

In Formula VIII, in one embodiment, X is CH$_2$.

In Formula VIII, in one embodiment, Y is aryl; and in another embodiment, Y is phenyl.

In Formula VIII, in one embodiment, Y is phenyl, and R$^3$ is —(CH$_2$)$_n$-heterocyclyl; wherein, in one embodiment, the heterocyclyl is morpholinyl, piperidinyl, or pyrrolidinyl.

In Formula VIII, in one embodiment, Y is heteroaryl; in another embodiment, Y is 10-membered heteroaryl; in yet another embodiment, Y is benzo[d]thiazolyl; in yet another embodiment, Y is benzofuranyl; and in still another embodiment, Y is quinolinyl.

In Formula VIII, in one embodiment, Y is heteroaryl and R$^3$ is —(CH$_2$)$_n$-heterocyclyl, wherein, in one embodiment, the heterocyclyl is morpholinyl, piperidinyl, or pyrrolidinyl.

In Formula VIII, in one embodiment, Y is a bond; and in another embodiment, Y is a bond and R$^3$ is —(CH$_2$)$_n$-heterocyclyl or —(CH$_2$)$_n$-heteroaryl.

In certain embodiments, the immunomodulatory compound is selected from:

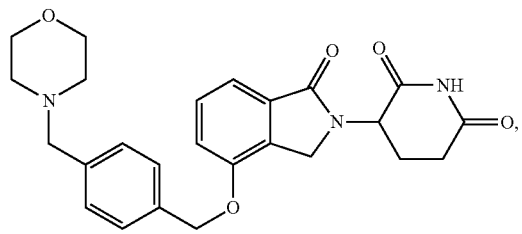

115
-continued
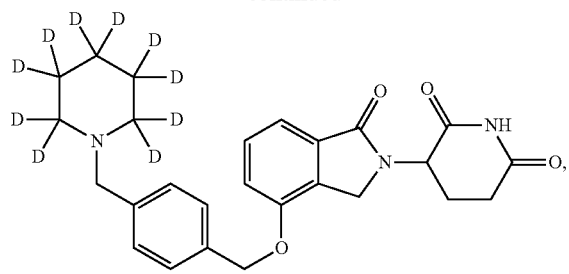
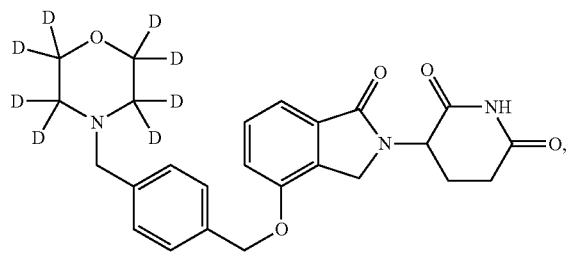
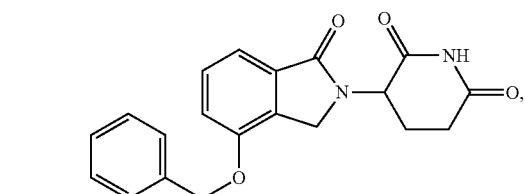
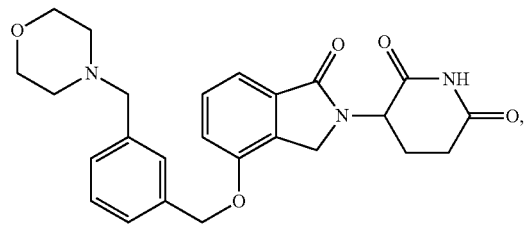
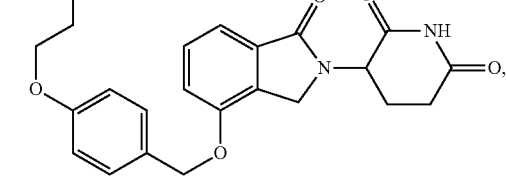
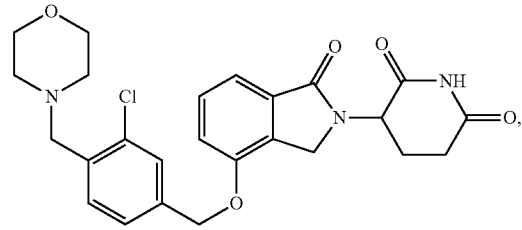
116
-continued
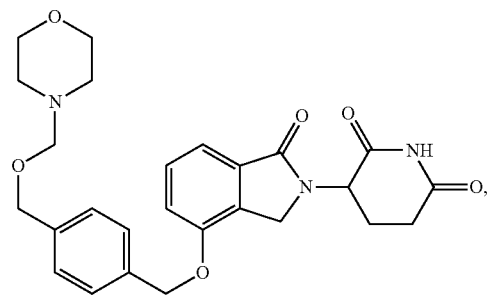
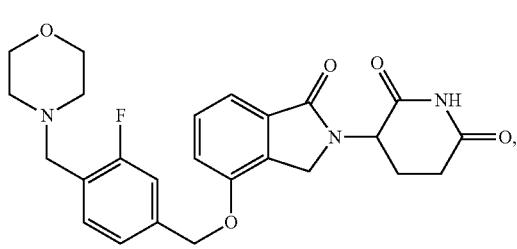
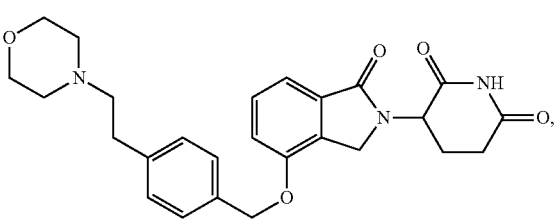
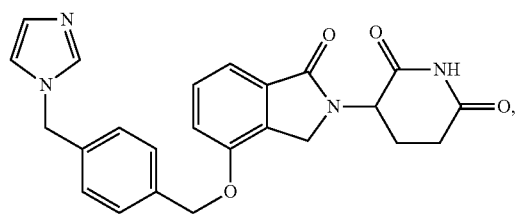
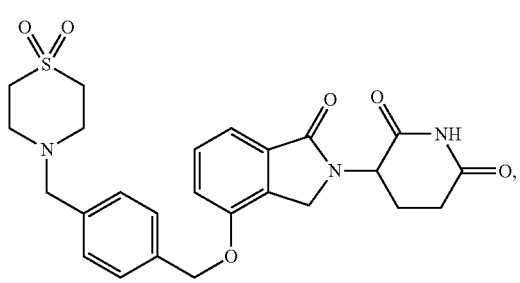
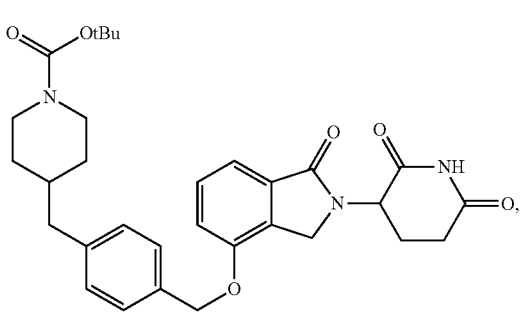

117
-continued
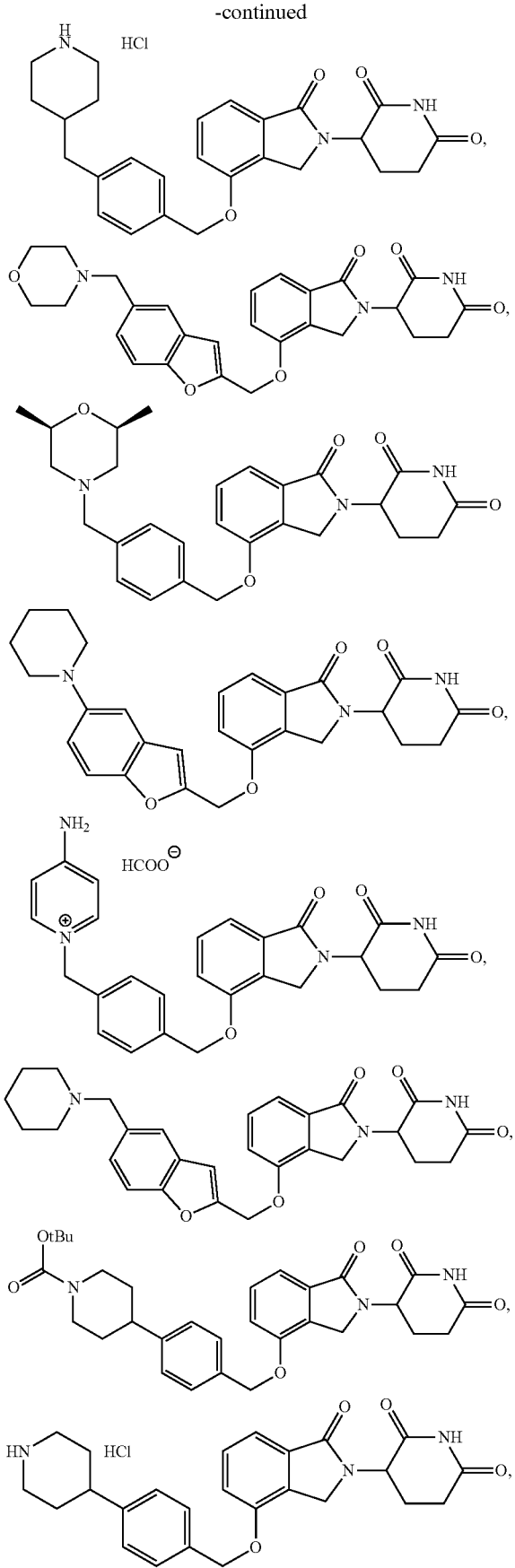
118
-continued
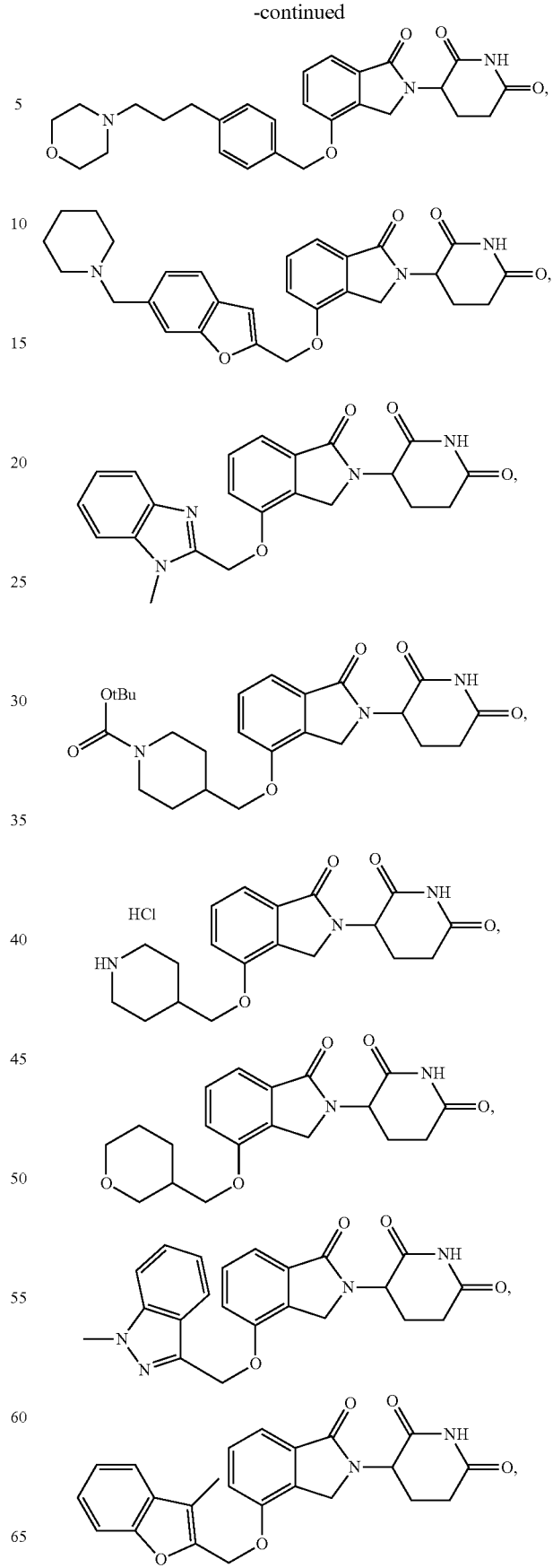

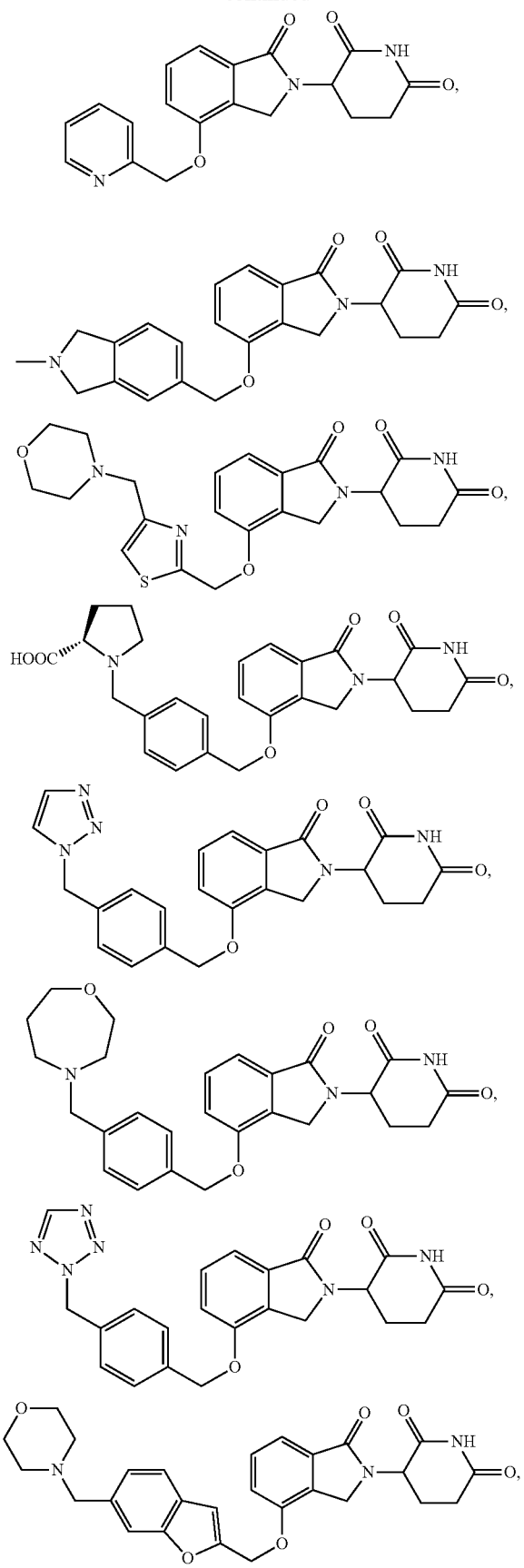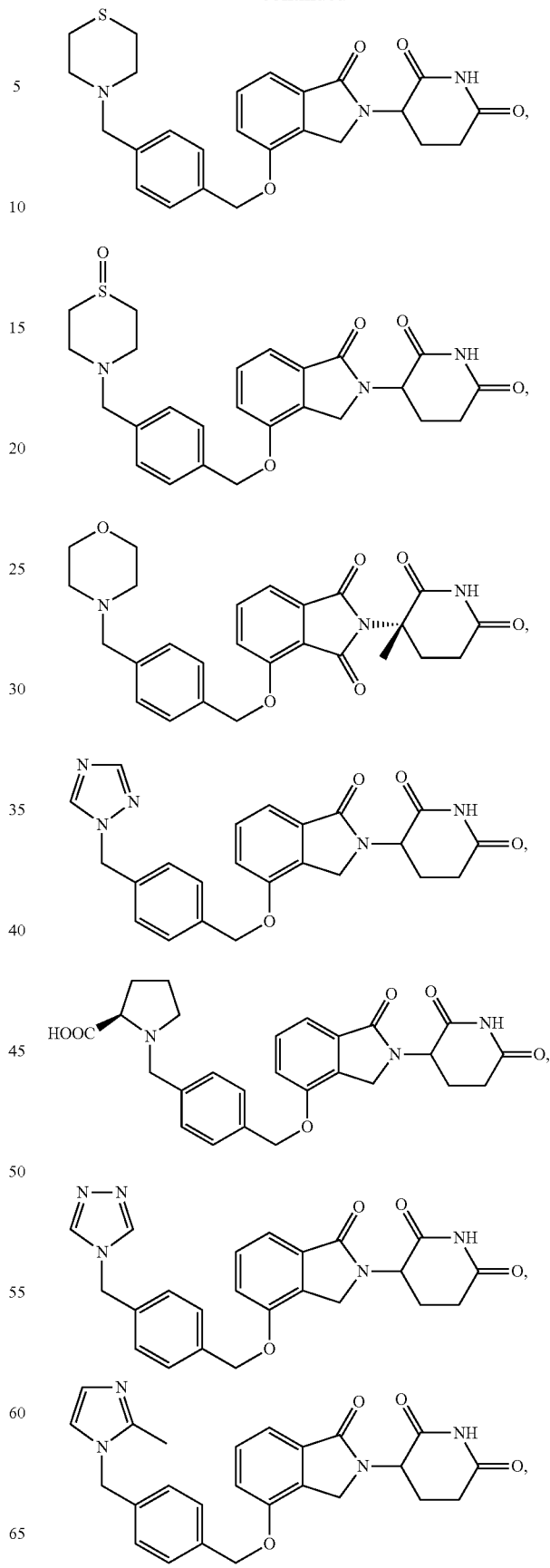

121
-continued
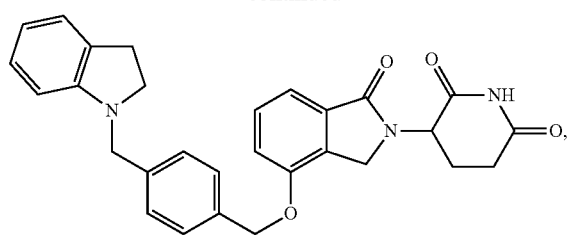
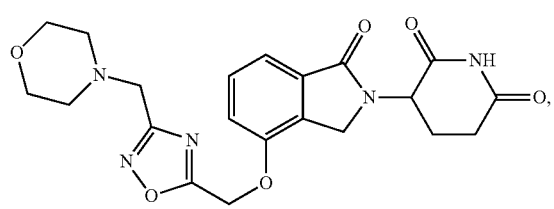
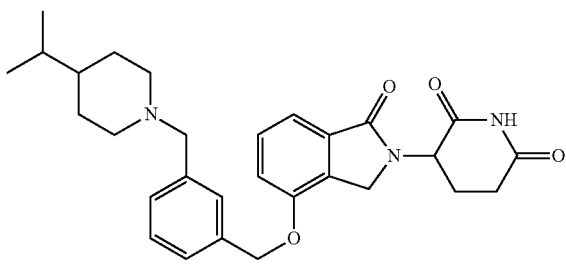
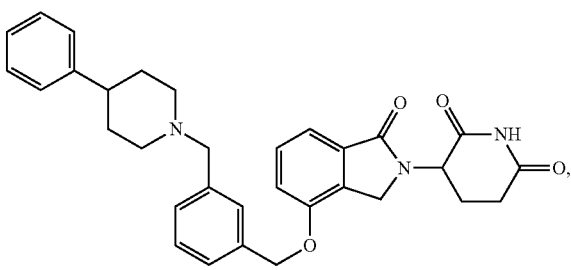
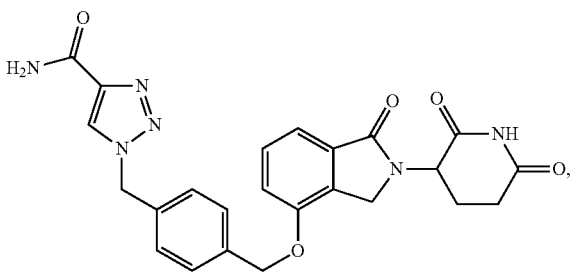
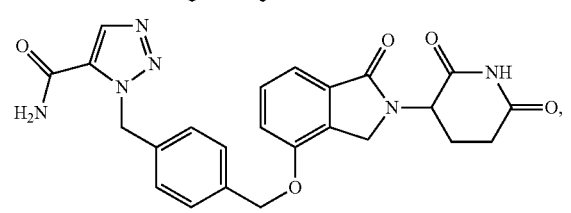
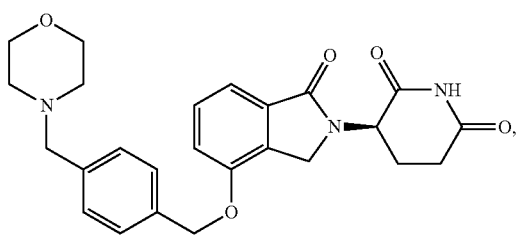
122
-continued
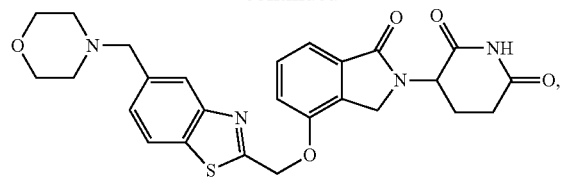
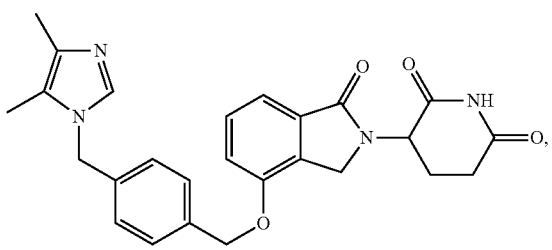
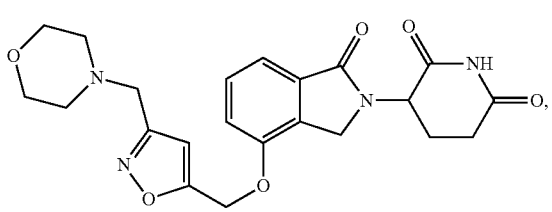
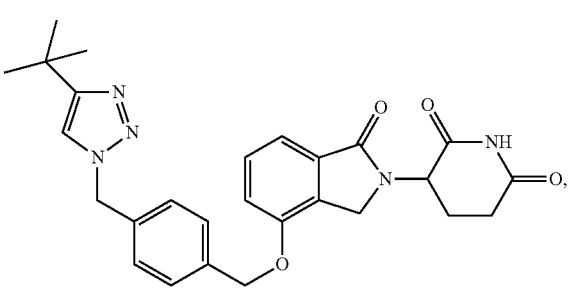
HCOOH
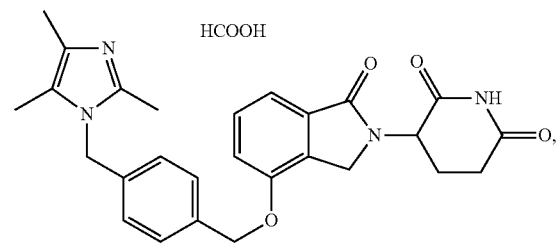
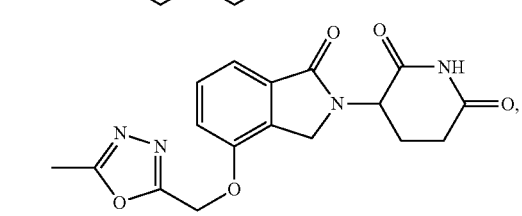
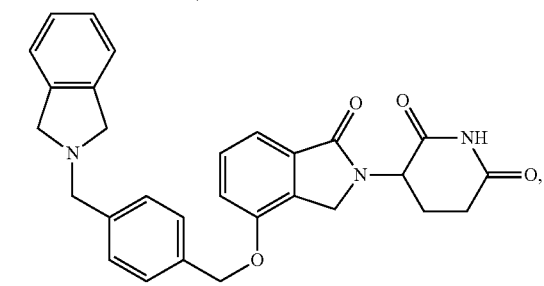

123
-continued
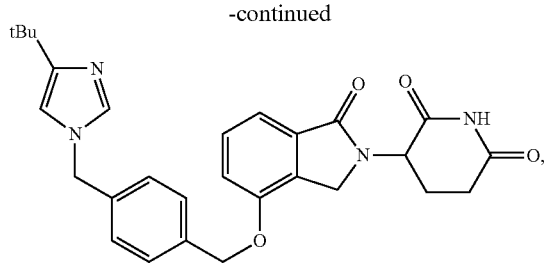
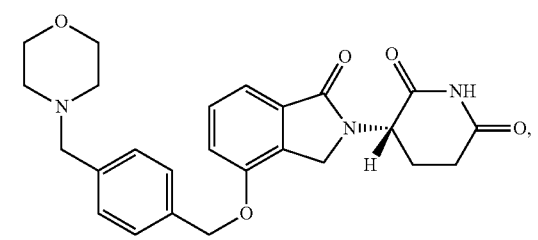
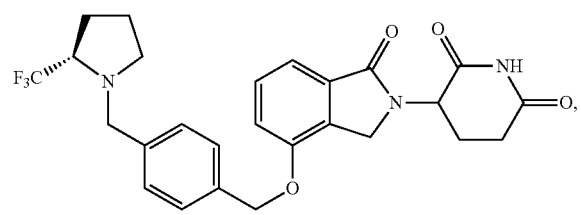
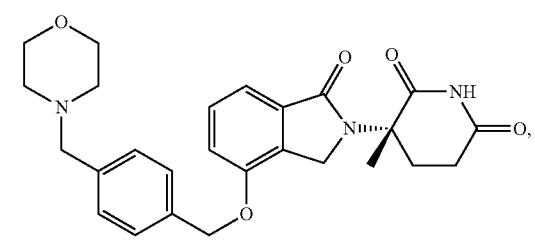
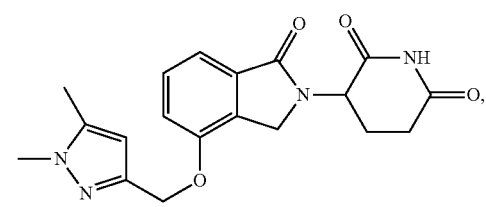
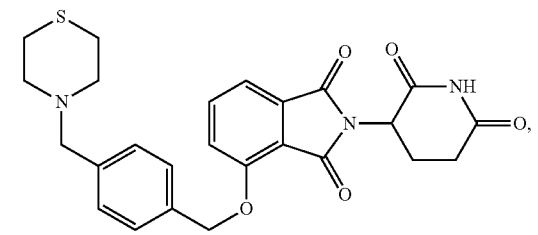
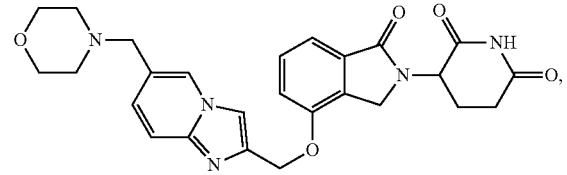
124
-continued
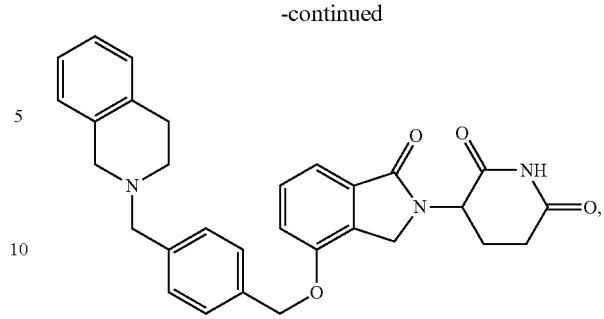
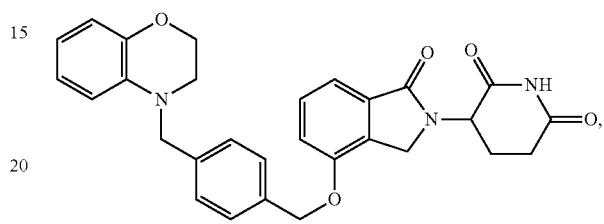
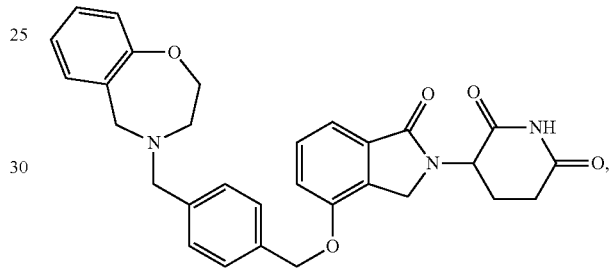
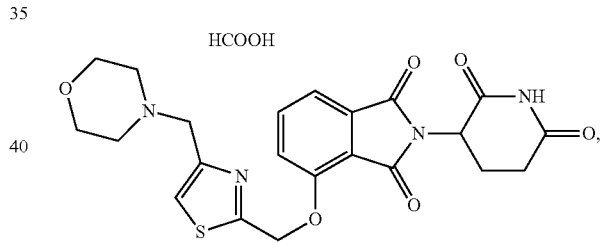
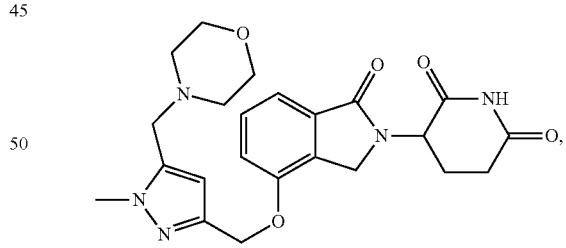
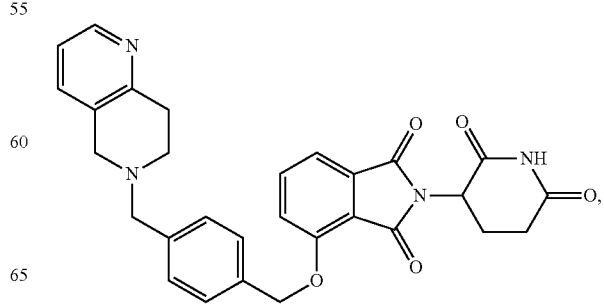

125
-continued
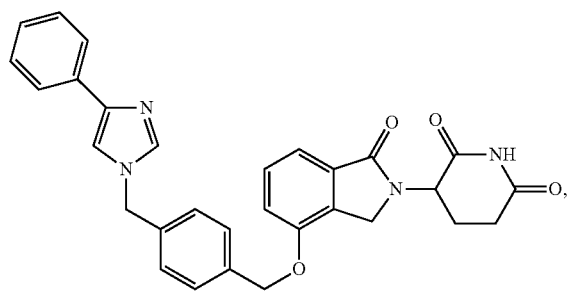
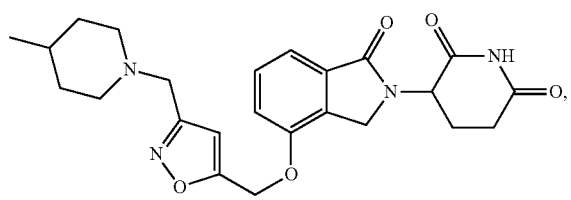
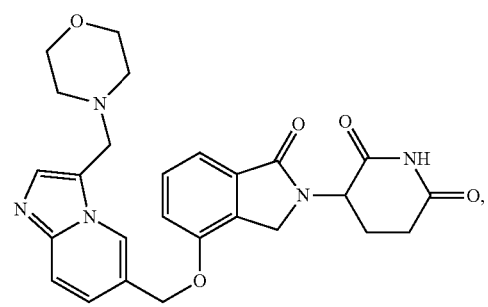
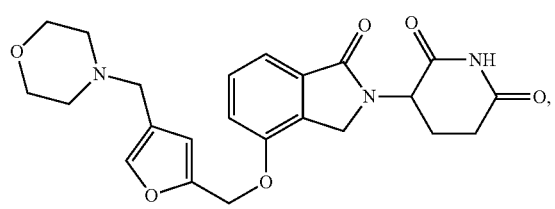
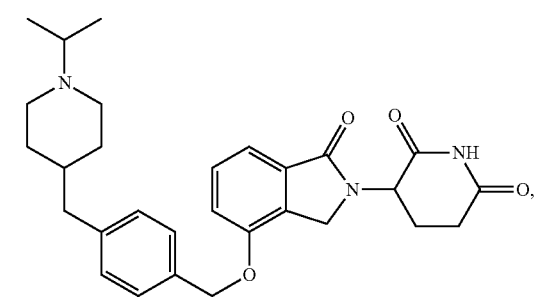
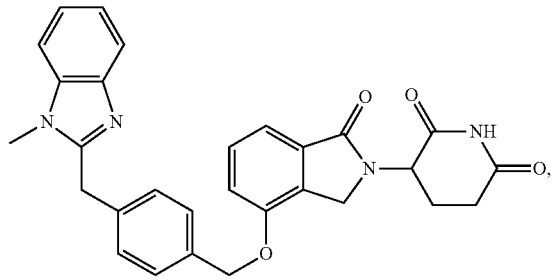
126
-continued
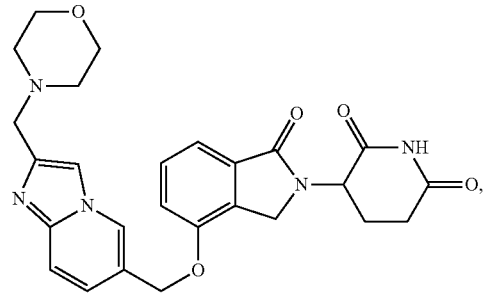
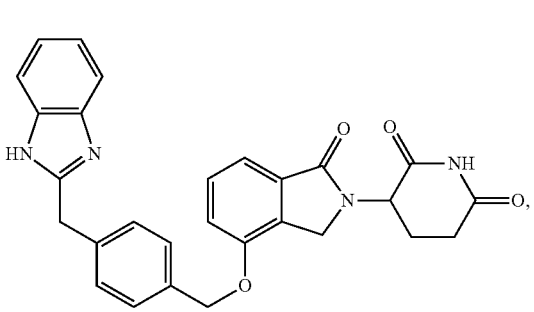
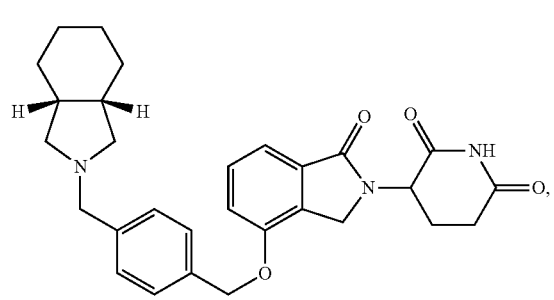
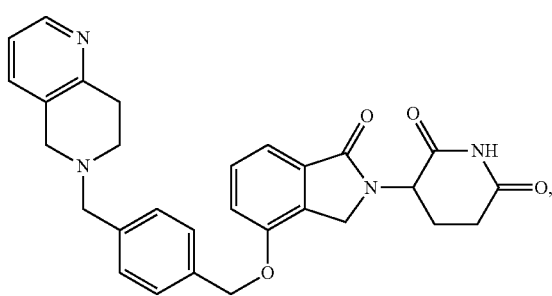
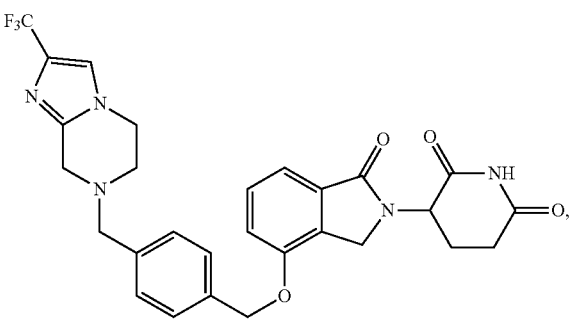

127
-continued
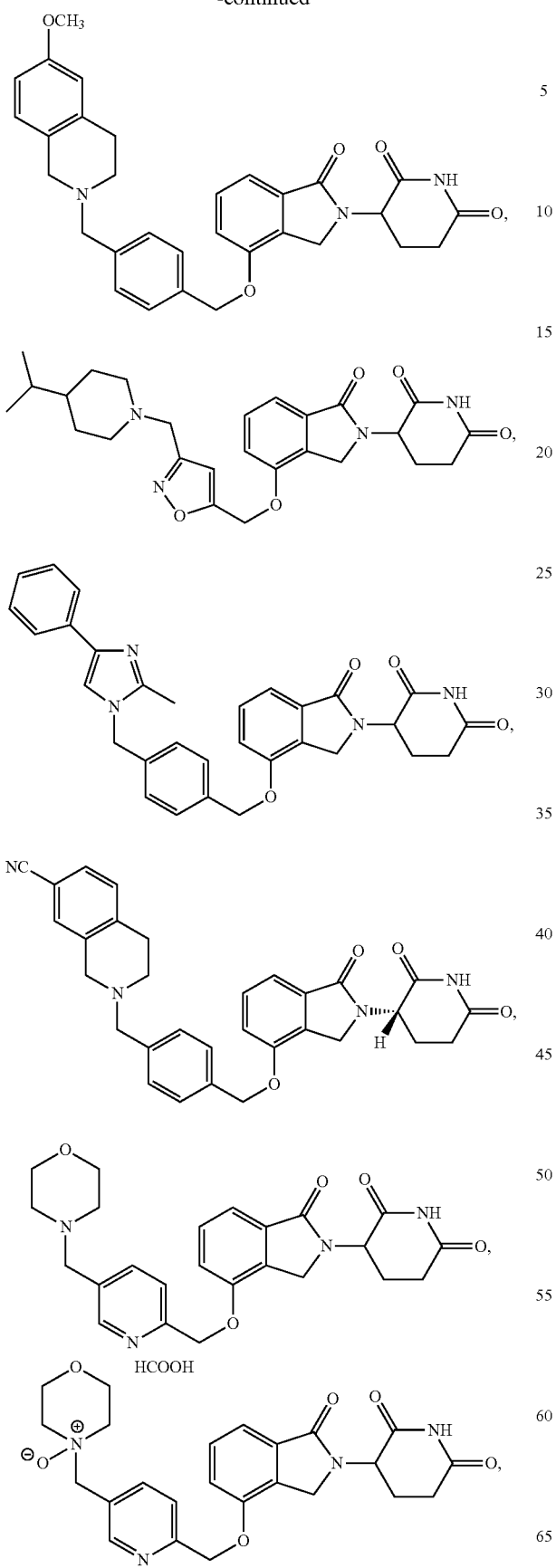
128
-continued
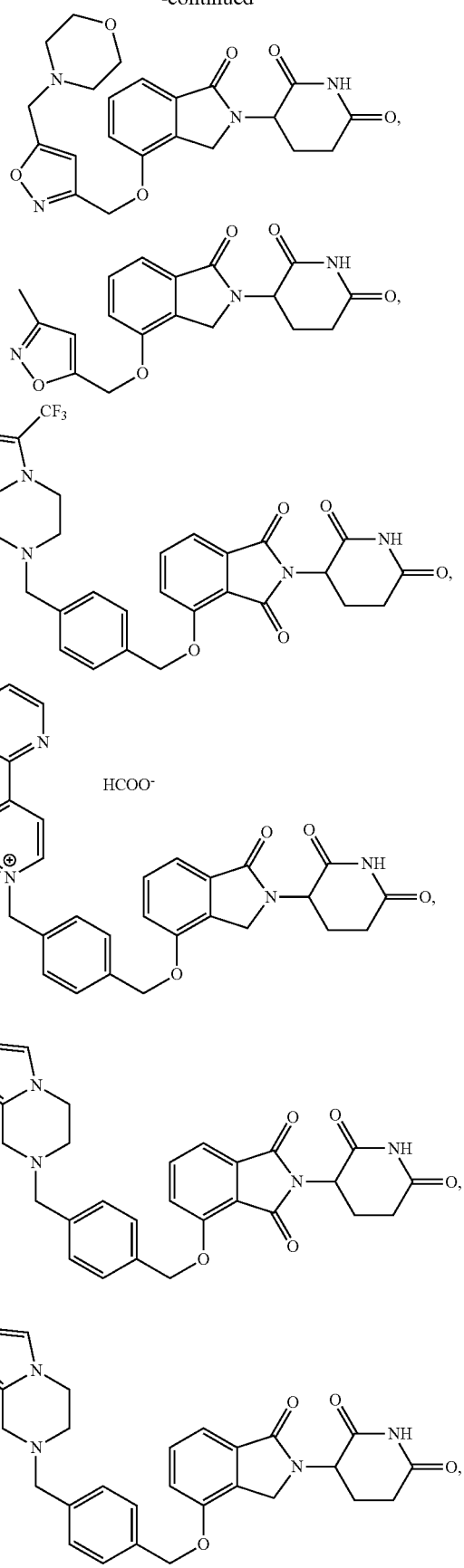

129
-continued
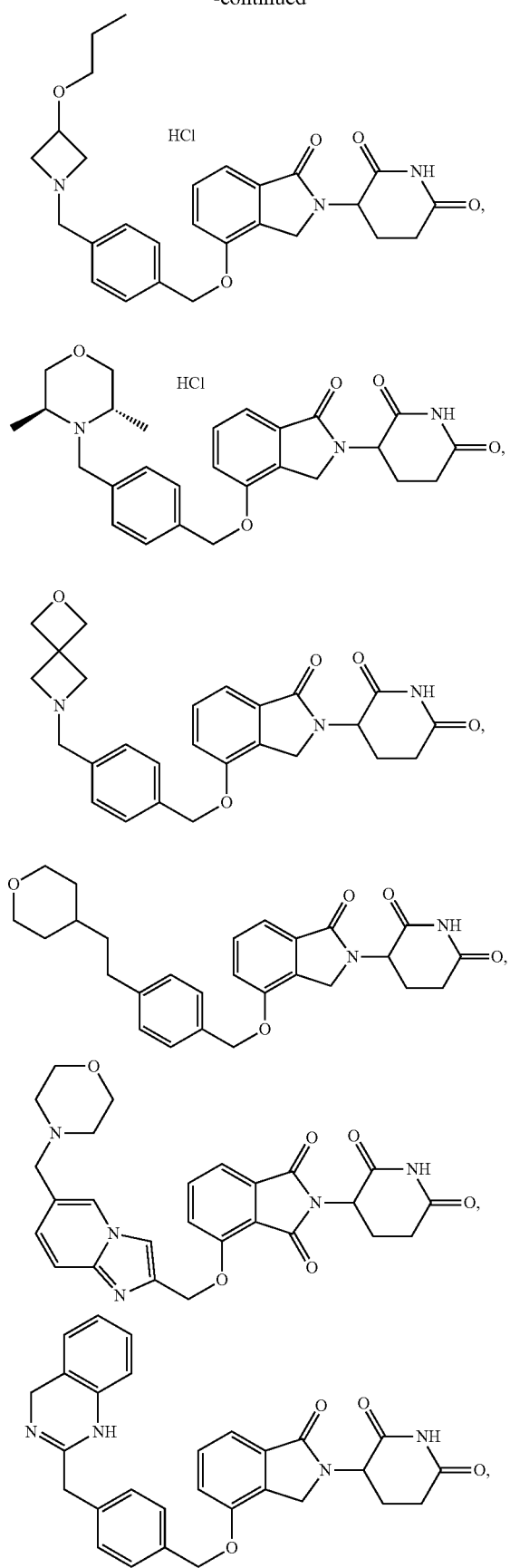
130
-continued
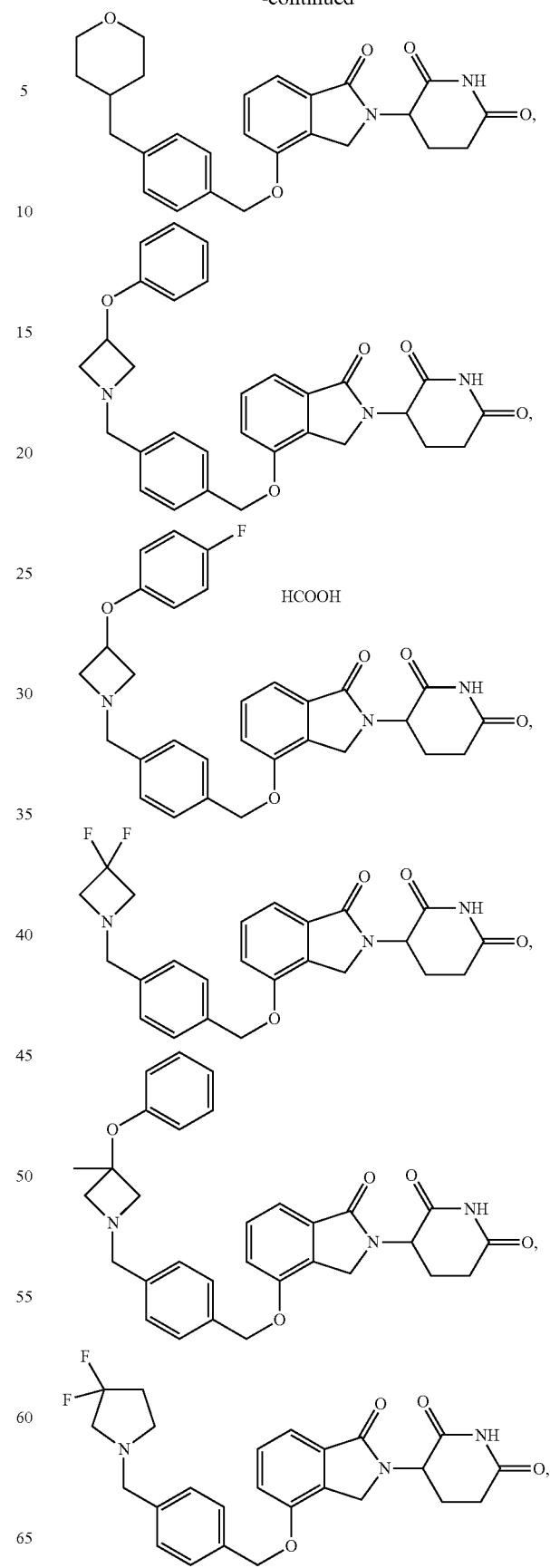

131
-continued
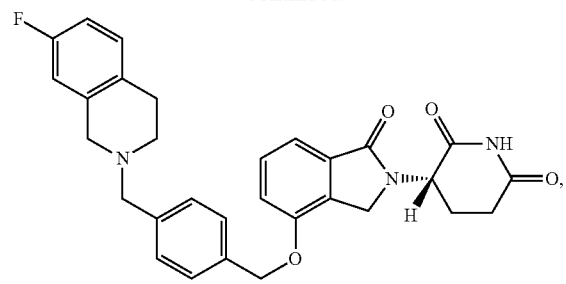
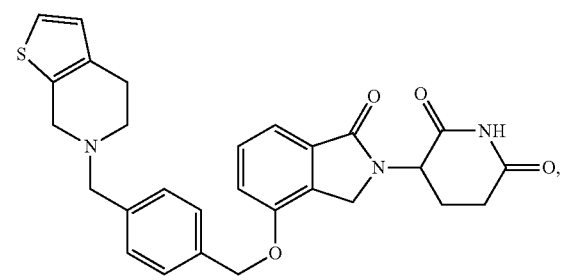
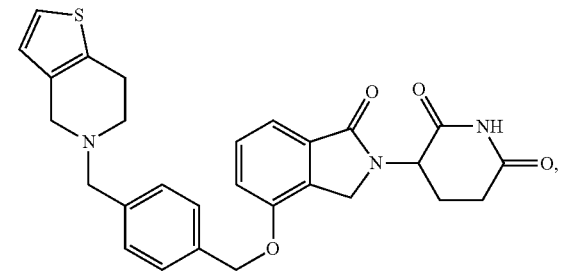
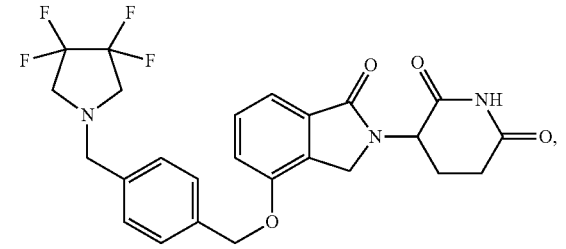
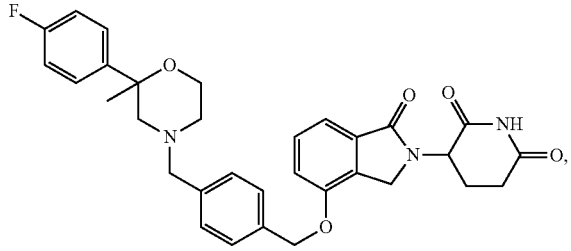
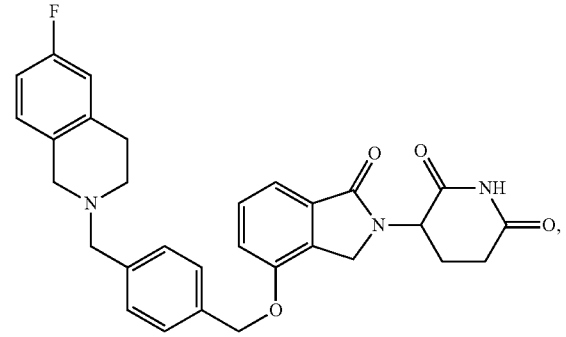
132
-continued
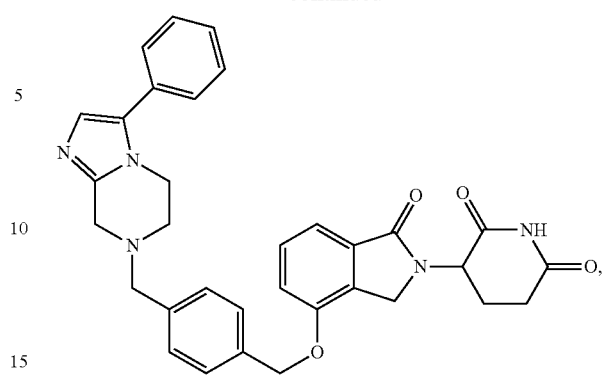
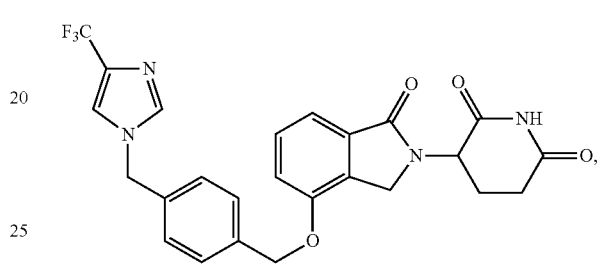
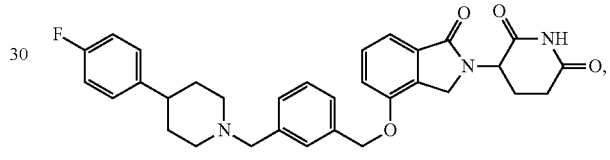
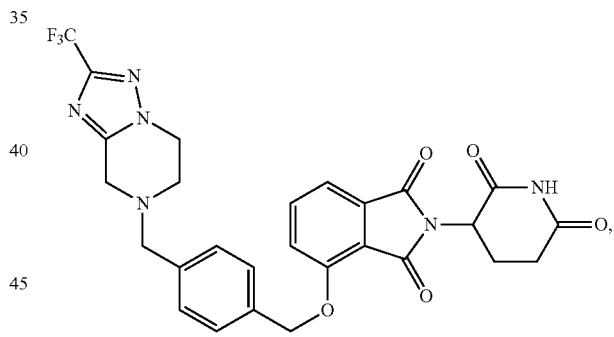
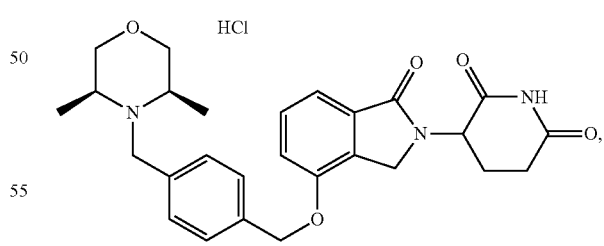
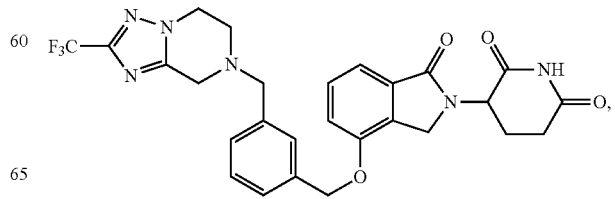

-continued

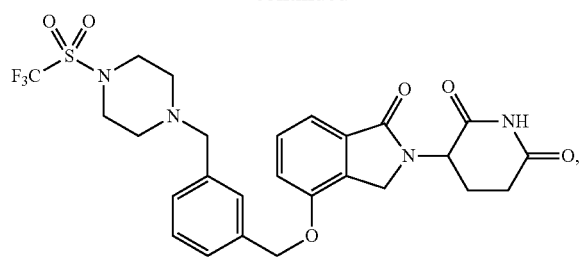

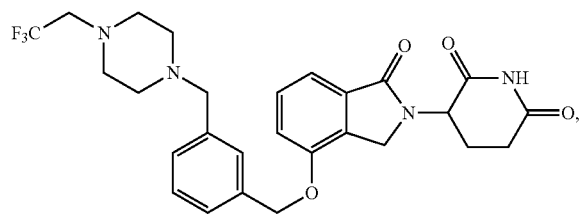

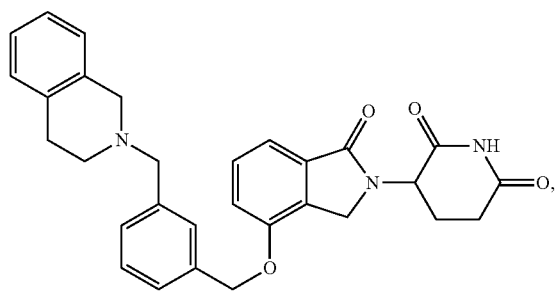

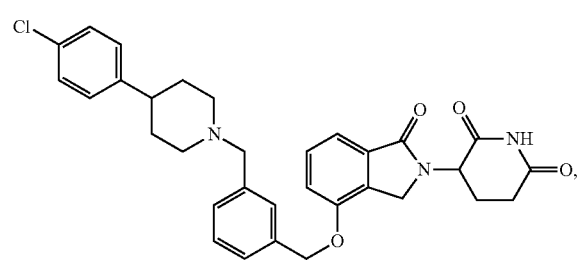

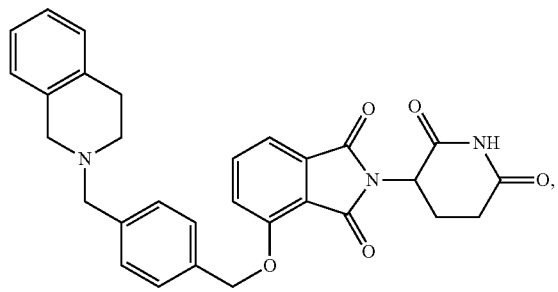

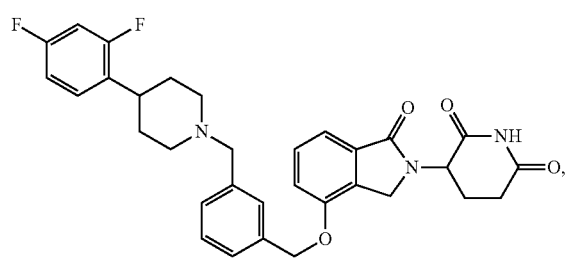

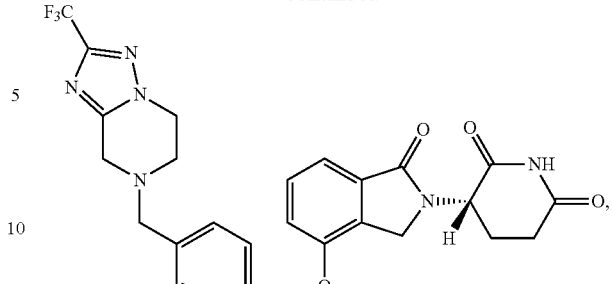

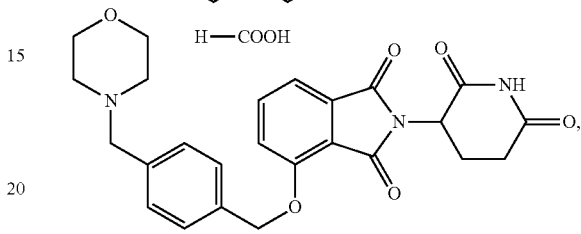

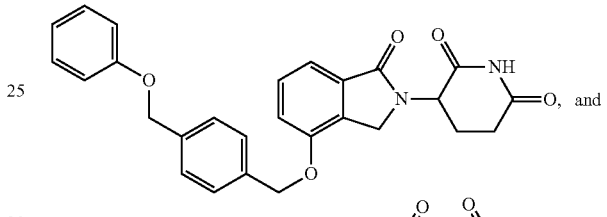

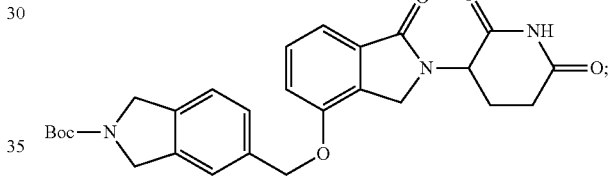

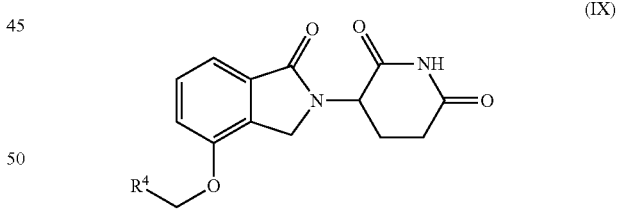

and pharmaceutically acceptable salts, solvates, and stereoisomers thereof.

In another embodiment, the immunomodulatory compound is a compound of Formula (IX):

(IX)

or a pharmaceutically acceptable salt, solvate, or stereoisomer thereof, wherein:

$R^4$ is benzothiazolyl, quinolinyl, isoquinolinyl, naphthyl, 2,3-dihydro-1H-indenyl, benzo[d][1,2,3]triazolyl, imidazo[1,2-a]pyridinyl, benzofuranyl, 2,3-dihydrobenzofuranyl, benzothienyl, benzo[d]oxazolyl, isoindolinyl, or chromanyl;

with the proviso that if the bicyclic ring is benzofuranyl or benzothienyl, then the ring is not connected to the isoindolyl ring through the 2-position.

In Formula IX, in one embodiment, $R^4$ is benzothiazolyl; in another embodiment, $R^4$ is quinolinyl; in yet another embodiment, $R^4$ is isoquinolinyl; in yet another embodiment, $R^4$ is naphthyl; in yet another embodiment, $R^4$ is 2,3-dihydro-1H-indenyl; in yet another embodiment, $R^4$ is benzo[d][1,2,3]triazolyl; in yet another embodiment, $R^4$ is imidazo[1,2-a]pyridinyl; in yet another embodiment, $R^4$ is benzofuranyl; in yet another embodiment, $R^4$ is 2,3-dihydrobenzofuranyl; in yet another embodiment, $R^4$ is benzothienyl; in yet another embodiment, $R^4$ is benzo[d]oxazolyl; in yet another embodiment, $R^4$ is isoindolinyl; and in still another embodiment, $R^4$ is chromanyl.

In certain embodiments, the immunomodulatory compound is selected from:

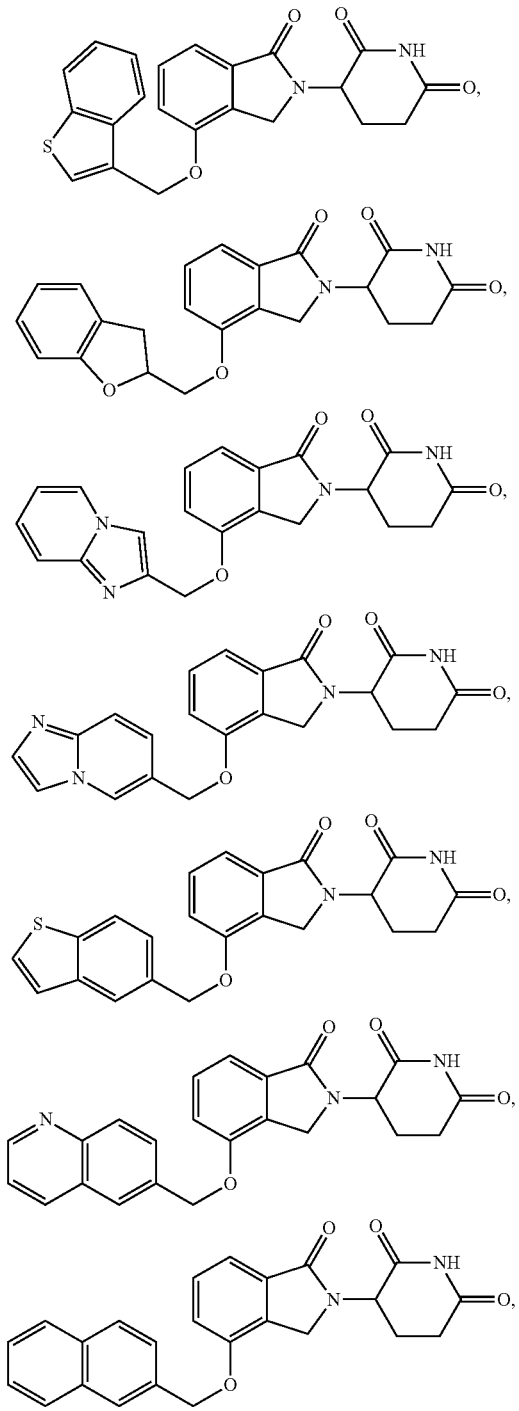

-continued

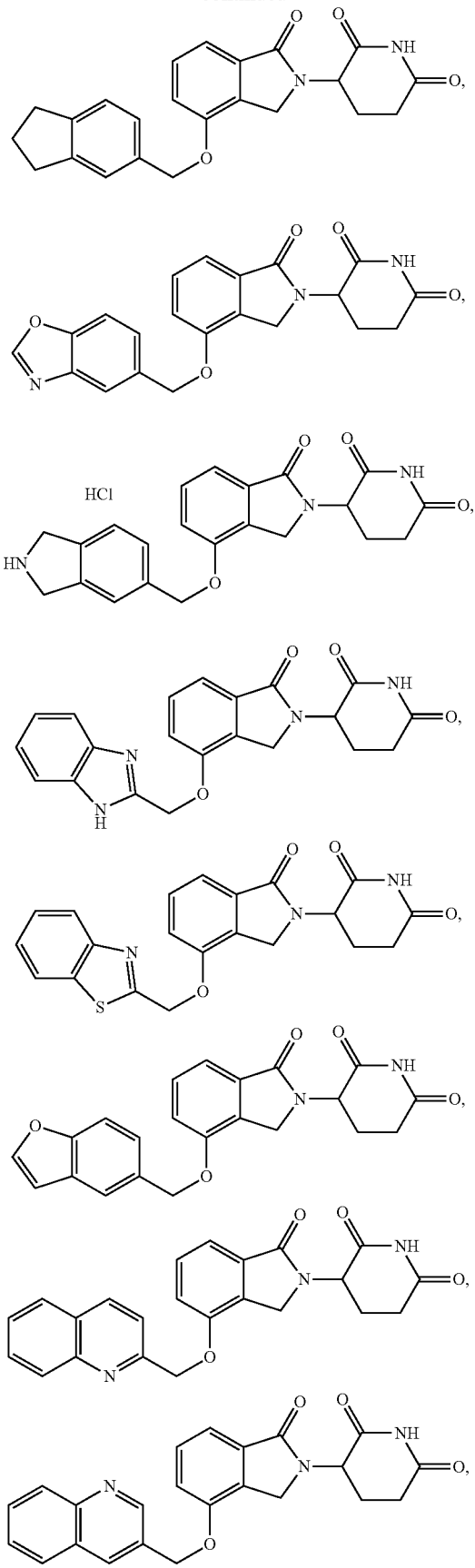

-continued

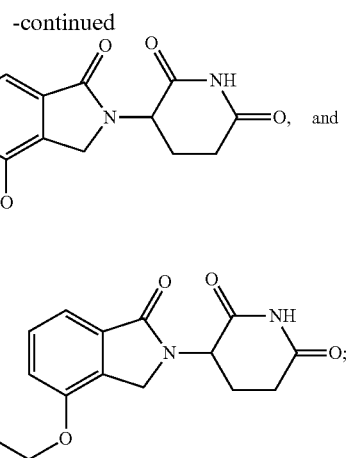

and pharmaceutically acceptable salts, solvates, and stereoisomers thereof.

In yet another embodiment, the immunomodulatory compound is a compound of Formula (X):

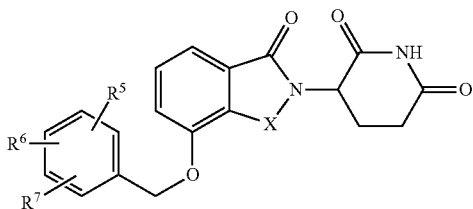

(X)

or a pharmaceutically acceptable salt, solvate, or stereoisomer thereof, wherein:

X is $CH_2$ or $C=O$;

$R^5$, $R^6$ and $R^7$ are each independently hydrogen, halogen, nitro, carbamoyl, amino, $-SO_2R^8$, $-CONR^9R^{10}$, $-C_{1-6}$ alkyl, or $-C_{1-6}$ alkoxy, where the alkyl or alkoxy is optionally substituted with one or more halogen, amino, hydroxyl, or $NR^9R^{10}$;

$R^8$ is: $C_{1-6}$ alkyl, optionally substituted with $C_{6-14}$ aryl; amino, optionally substituted with $C_{1-6}$ alkyl or $C_{6-14}$ aryl; or heterocyclyl, optionally substituted with $C_{1-6}$ alkyl or $C_{6-14}$ aryl;

$R^9$ and $R^{10}$ are each independently hydrogen, $C_{6-14}$ aryl, $-COO-C_{1-6}$ alkyl, $-C_{0-6}$ alkyl-CHO, $-C_{0-6}$ alkyl-COOH, $-C_{0-6}$ alkyl-$NR^{9'}R^{10'}$, $C_{0-6}$ alkyl-heterocyclyl, $-C_{1-6}$ alkyl-OH, $-C_{1-6}$ alkyl-O-$C_{1-6}$ alkyl, $C_{1-6}$ alkyl, or $C_{3-6}$ cycloalkyl; or $R^9$ and $R^{10}$ together form an optionally substituted 5- or 6-membered ring containing one or more heteroatoms; and $R^{9'}$ and $R^{10'}$ are each independently hydrogen or $C_{1-6}$ alkyl;

with the proviso that all of $R^5$-$R^7$ cannot be hydrogen; and with the proviso that if one of $R^5$-$R^7$ is hydrogen and the remaining two of $R^5$-$R^7$ are both chloride, then the two chloride atoms cannot be on the 3 and 4 positions of the phenyl ring.

In Formula X, in one embodiment, $R^5$ is hydrogen; in another embodiment, $R^5$ is halogen; in yet another embodiment, $R^5$ is nitro; in yet another embodiment, $R^5$ is carbamoyl; in yet another embodiment, $R^5$ is amino; in yet another embodiment, $R^5$ is $-SO_2R^8$; in yet another embodiment, $R^5$ is $-CONR^9R^{10}$; in yet another embodiment, $R^5$ is $-C_{1-6}$ alkyl, optionally substituted with one or more halogen, amino, hydroxyl, or $NR^9R^{10}$; and in still another embodiment, $R^5$ is $-C_{1-6}$ alkoxy, optionally substituted with one or more halogen, amino, hydroxyl or $NR^9R^{10}$.

In Formula X, in one embodiment, $R^6$ is hydrogen; in another embodiment, $R^6$ is halogen; in yet another embodiment, $R^6$ is nitro; in yet another embodiment, $R^6$ is carbamoyl; in yet another embodiment, $R^6$ is amino; in yet another embodiment, $R^6$ is $-SO_2R^8$; in yet another embodiment, $R^6$ is $-CONR^9R^{10}$; in yet another embodiment, $R^6$ is $-C_{1-6}$ alkyl, optionally substituted with one or more halogen, amino, hydroxyl, or $NR^9R^{10}$; and in still another embodiment, $R^6$ is $-C_{1-6}$ alkoxy, optionally substituted with one or more halogen, amino, hydroxyl or $NR^9R^{10}$.

In Formula X, in one embodiment, $R^7$ is hydrogen; in another embodiment, $R^7$ is halogen; in yet another embodiment, $R^7$ is nitro; in yet another embodiment, $R^7$ is carbamoyl; in yet another embodiment, $R^7$ is amino; in yet another embodiment, $R^7$ is $-SO_2R^8$; in yet another embodiment, $R^7$ is $-CONR^9R^{10}$; in yet another embodiment, $R^7$ is $-C_{1-6}$ alkyl, optionally substituted with one or more halogen, amino, hydroxyl, or $NR^9R^{10}$; and in still another embodiment, $R^7$ is $-C_{1-6}$ alkoxy, optionally substituted with one or more halogen, amino, hydroxyl or $NR^9R^{10}$.

In Formula X, in one embodiment, $R^8$ is $C_{1-6}$ alkyl, optionally substituted with $C_{6-14}$ aryl; in another embodiment, $R^8$ is amino, optionally substituted with $C_{1-6}$ alkyl or $C_{6-14}$ aryl; and in still another embodiment, $R^8$ is 6- to 10-membered heterocyclyl, optionally substituted with $C_{1-6}$ alkyl or $C_{6-14}$ aryl.

In Formula X, in one embodiment, $R^9$ is hydrogen; in another embodiment, $R^9$ is 6- to 10-membered aryl; in yet another embodiment, $R^9$ is $-COO-C_{1-6}$ alkyl; in yet another embodiment, $R^9$ is $-C_{0-6}$ alkyl-CHO; in yet another embodiment, $R^9$ is $-C_{0-6}$ alkyl-COOH; in yet another embodiment, $R^9$ is $-C_{0-6}$ alkyl-$NR^{9'}R^{10'}$; in yet another embodiment, $R^9$ is $-C_{0-6}$ alkyl-(5- to 10-membered heterocyclyl); in yet another embodiment, $R^9$ is $-C_{1-6}$ alkyl-OH; in yet another embodiment, $R^9$ is $-C_{1-6}$ alkyl-O-$C_{1-6}$ alkyl; in yet another embodiment, $R^9$ is $C_{1-6}$ alkyl; and in still another embodiment, $R^9$ is $C_{3-6}$ cycloalkyl.

In Formula X, in one embodiment, $R^{10}$ is hydrogen; in another embodiment, $R^{10}$ is 6- to 10-membered aryl; in yet another embodiment, $R^{10}$ is $-COO-C_{1-6}$ alkyl; in yet another embodiment, $R^{10}$ is $-C_{0-6}$ alkyl-CHO; in yet another embodiment, $R^{10}$ is $-C_{0-6}$ alkyl-COOH; in yet another embodiment, $R^{10}$ is $-C_{0-6}$ alkyl-$NR^{9'}R^{10'}$; in yet another embodiment, $R^{10}$ is $-C_{0-6}$ alkyl-(5- to 10-membered heterocyclyl); in yet another embodiment, $R^{10}$ is $-C_{1-6}$ alkyl-OH; in yet another embodiment, $R^{10}$ is $-C_{1-6}$ alkyl-O-$C_{1-6}$ alkyl; in yet another embodiment, $R^{10}$ is $C_{1-6}$ alkyl; and in still another embodiment, $R^{10}$ is $C_{3-6}$ cycloalkyl.

In Formula X, in one embodiment, $R^9$ and $R^{10}$ together form a 5- or 6-membered ring; in another embodiment, the ring contains one or more heteroatoms; and in still another embodiment, the heteroatoms are selected from the group consisting of N, S and O.

In Formula X, in one embodiment, $R^{9'}$ is hydrogen; and in another embodiment, $R^{9'}$ is $C_{1-6}$ alkyl.

In Formula X, in one embodiment, $R^{10'}$ is hydrogen; and in another embodiment, $R^{10'}$ is $C_{1-6}$ alkyl.

The immunomodulatory compounds of Formula X encompass any of the combinations of $R^5$-$R^{10}$ and $R^{9'}$-$R^{10'}$ as defined herein.

In Formula X, in one embodiment, one of $R^5$-$R^7$ is hydrogen and the remaining two of $R^5$-$R^7$ are halogen; in another embodiment, one of $R^5$-$R^7$ is hydrogen and the remaining two of $R^5$-$R^7$ are $C_{1-6}$ alkoxy; in yet another embodiment, one of $R^5$-$R^7$ is hydrogen and the remaining two of $R^5$-$R^7$ are $C_{1-6}$ alkyl; and in still another embodiment, $R^5$ is hydrogen, $R^6$ is halogen, and $R^7$ is $C_{1-6}$ alkoxy.

In Formula X, in one embodiment, two of $R^5$-$R^7$ are hydrogen and the remaining one of $R^5$-$R^7$ is halogen; in another embodiment, two of $R^5$-$R^7$ are hydrogen and the remaining one of $R^5$-$R^7$ is $C_{1-6}$ alkoxy; and in still another embodiment, two of $R^5$-$R^7$ are hydrogen and the remaining one of $R^5$-$R^7$ is $C_{1-6}$ alkyl.

In certain embodiments, the immunomodulatory compound is selected from:

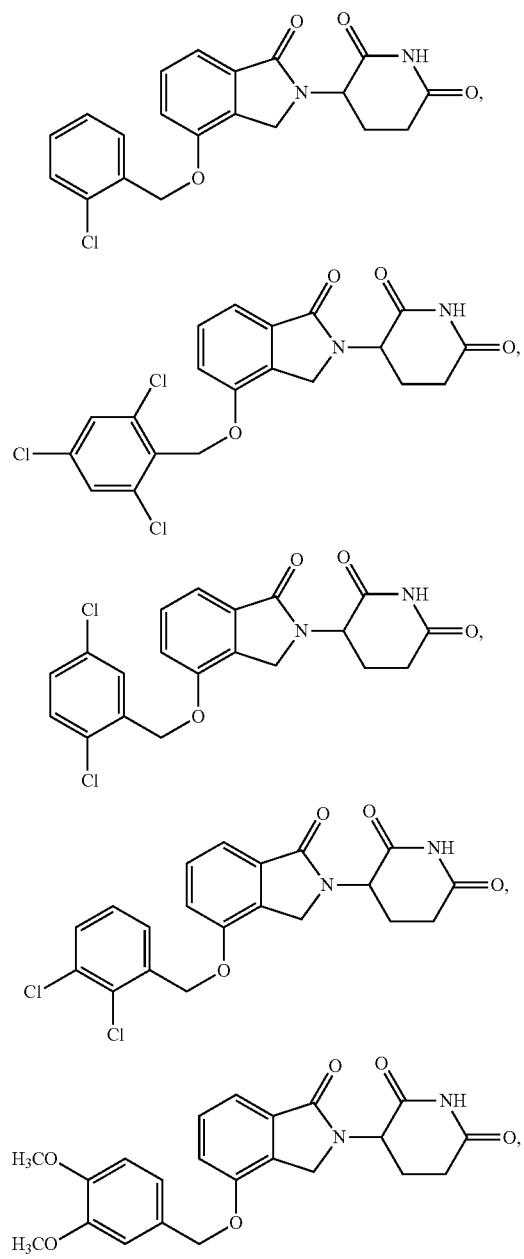

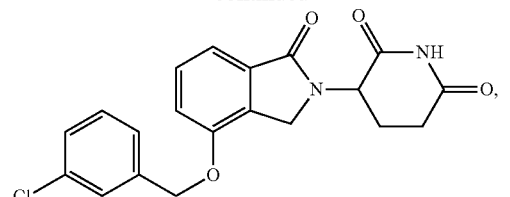

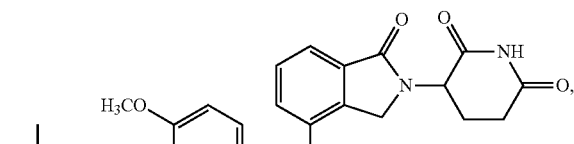

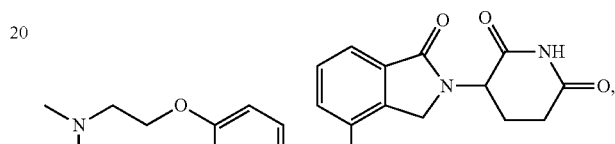

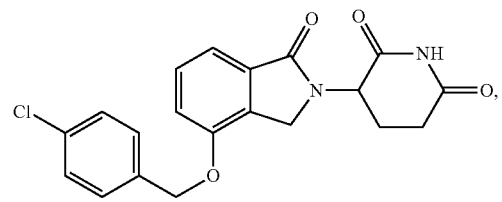

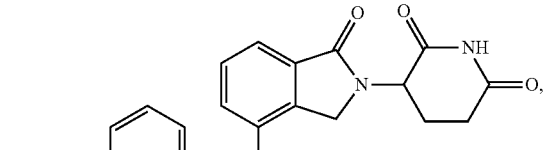

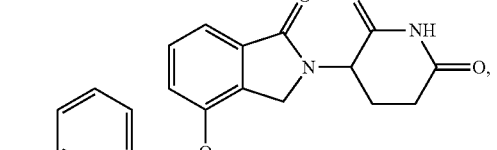

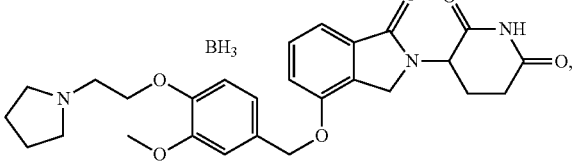

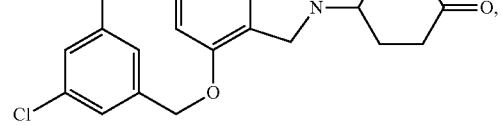

141
-continued
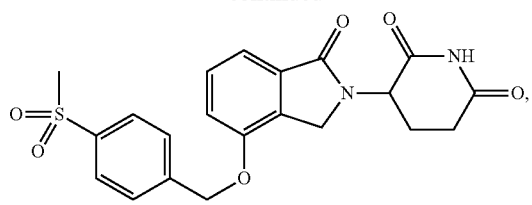
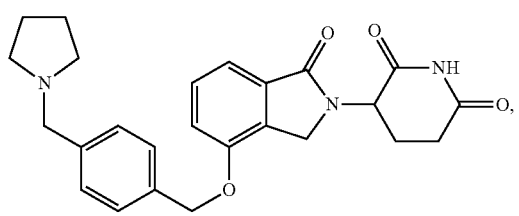
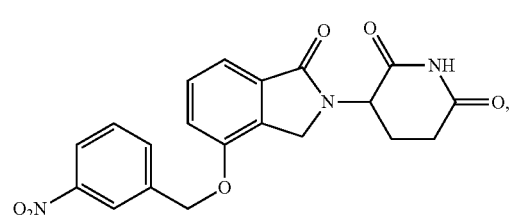
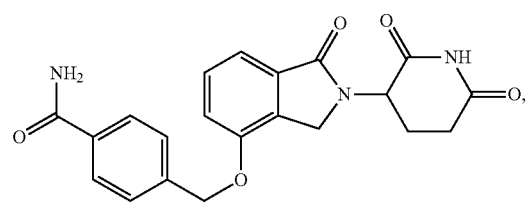
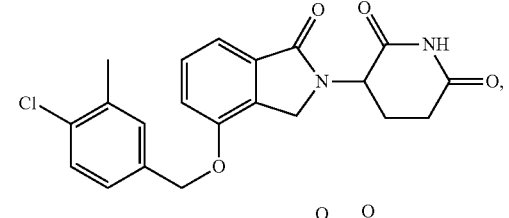
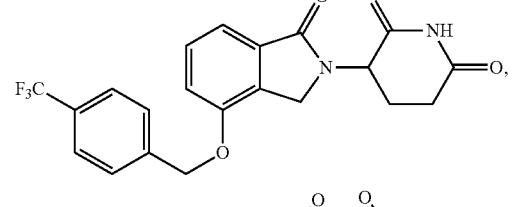
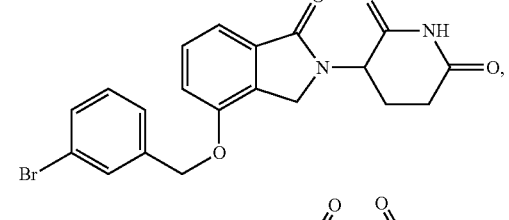
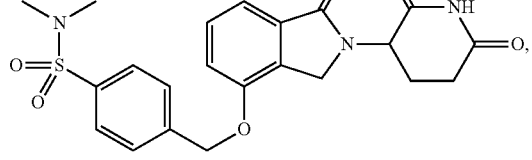
142
-continued
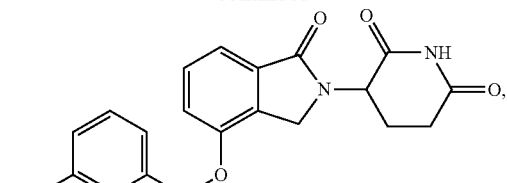
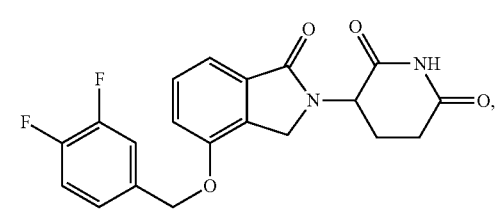
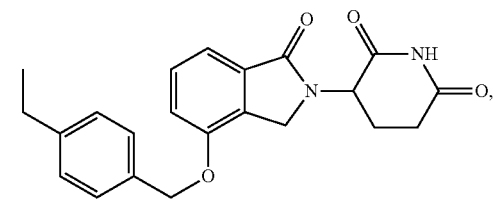
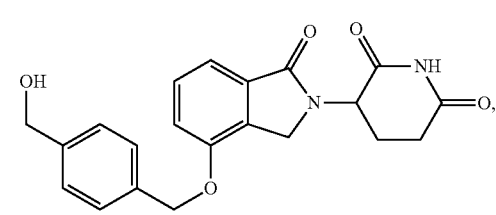
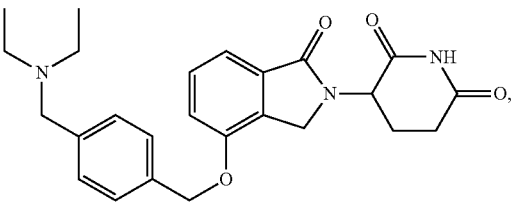
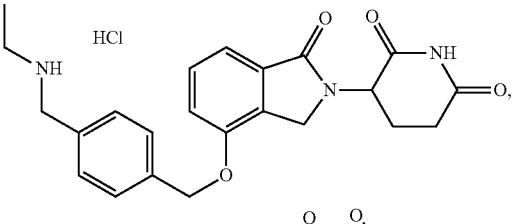
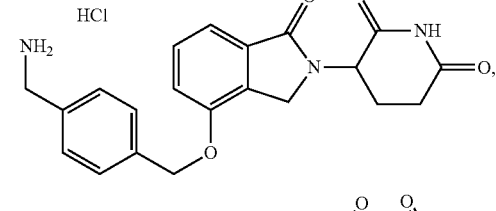
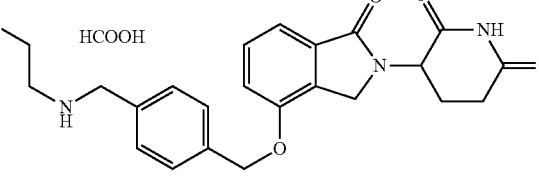

143
-continued
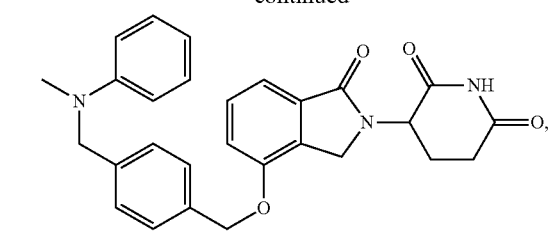
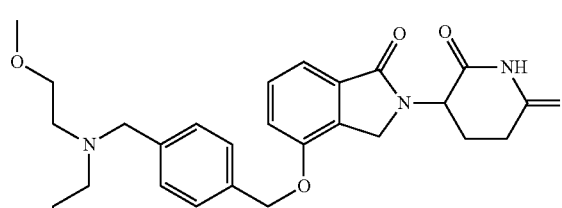
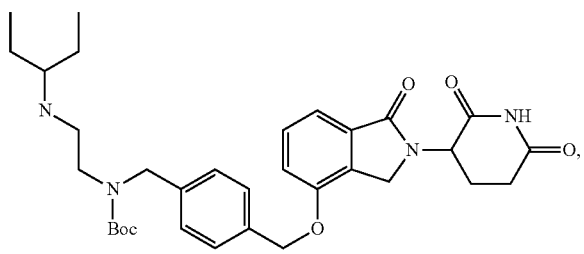
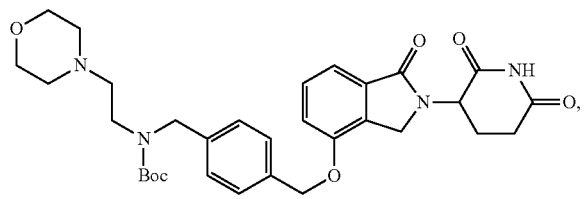
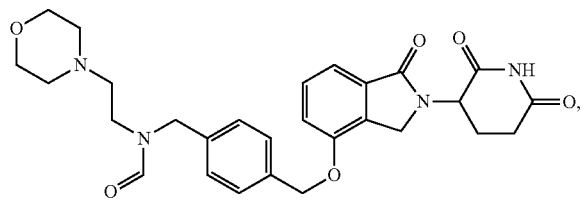
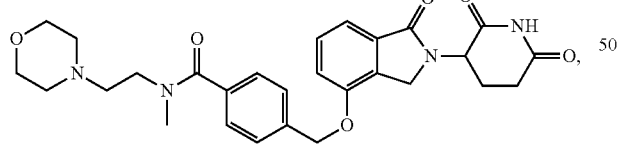
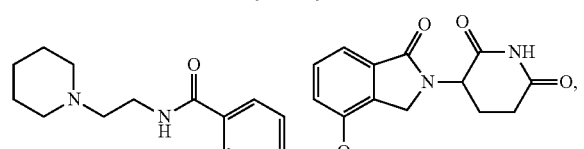
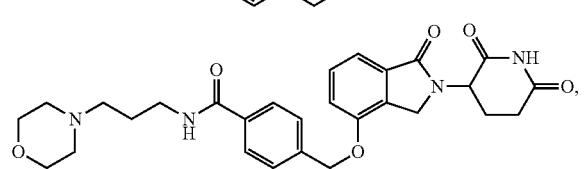
144
-continued
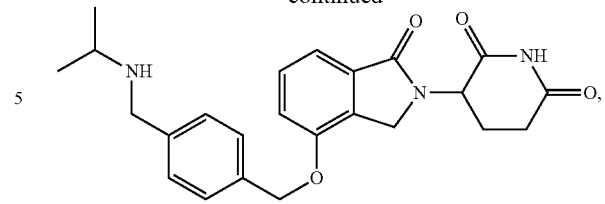
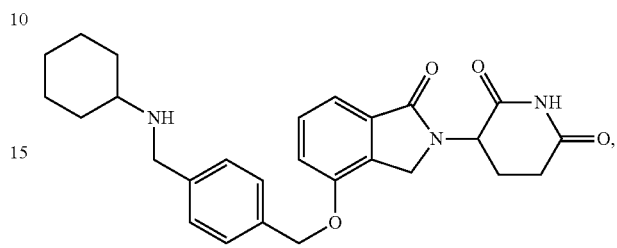
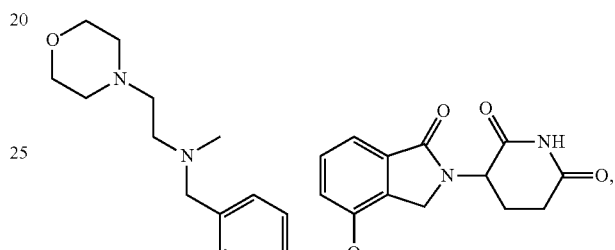
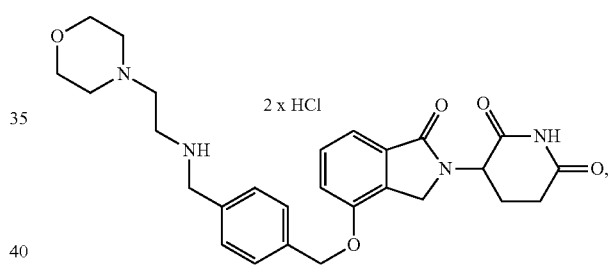
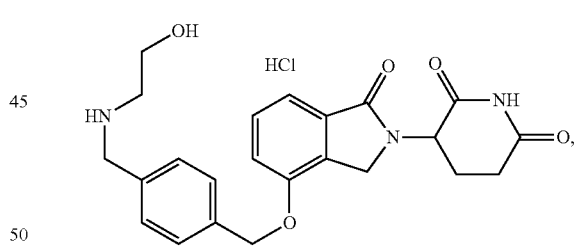
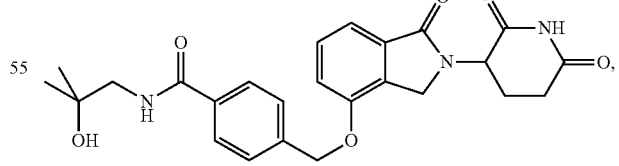
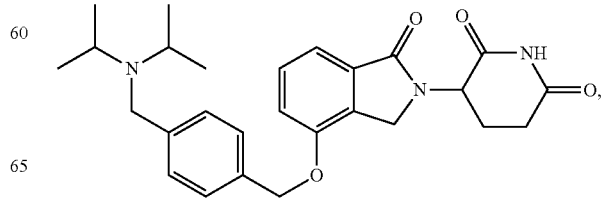

-continued
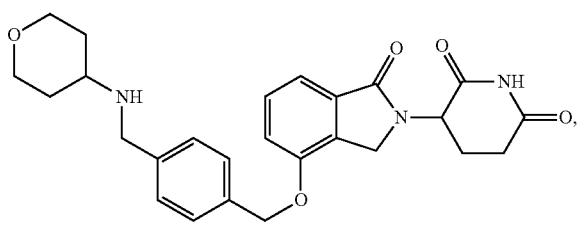
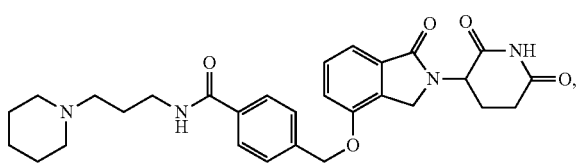
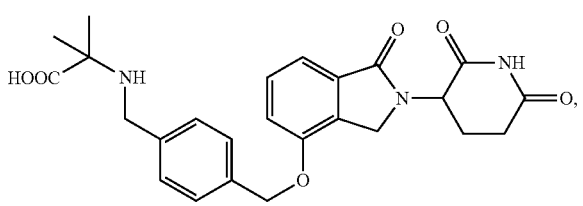
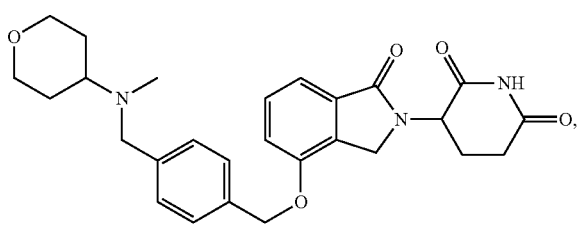
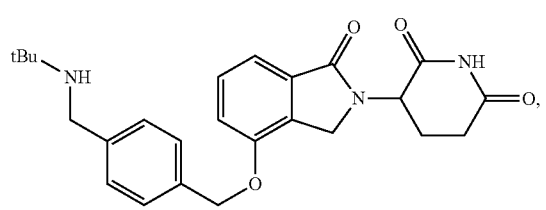
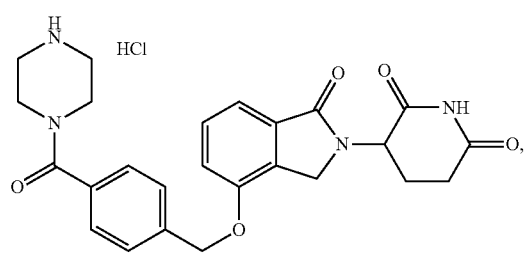
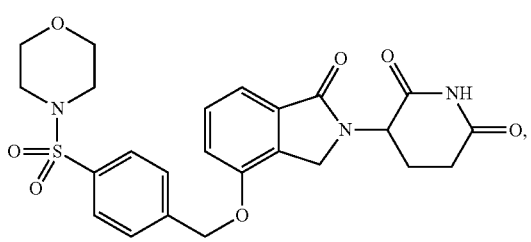
-continued
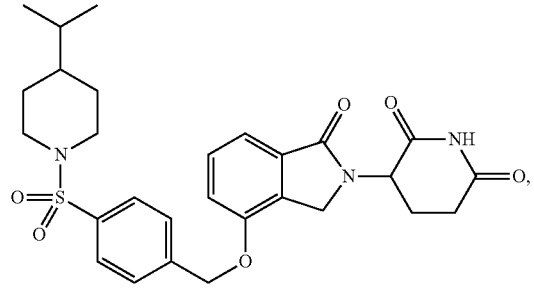
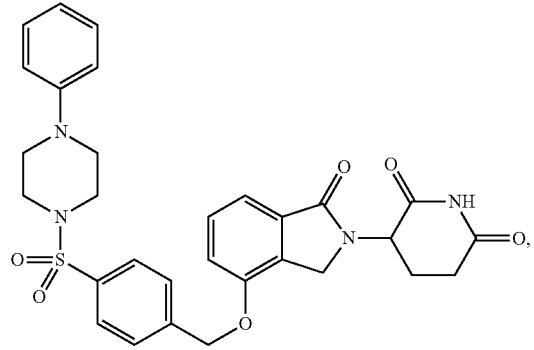
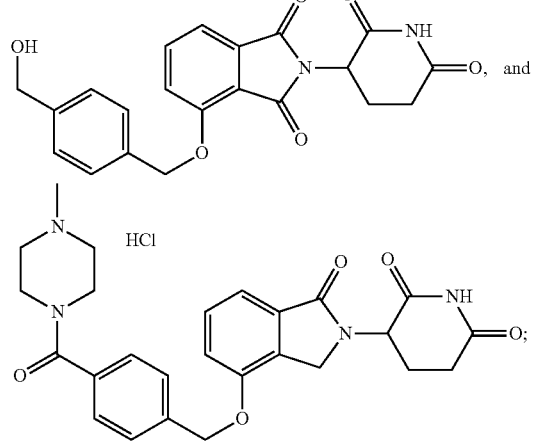
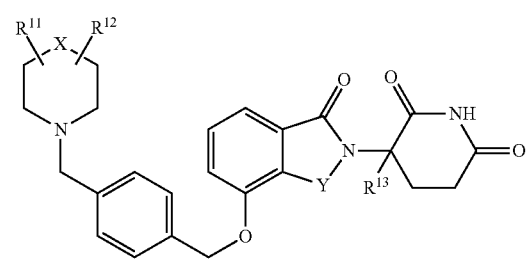
and pharmaceutically acceptable salts, solvates, and stereoisomers thereof.
In yet another embodiment, the immunomodulatory compound is a compound of Formula (XI):
(XI)
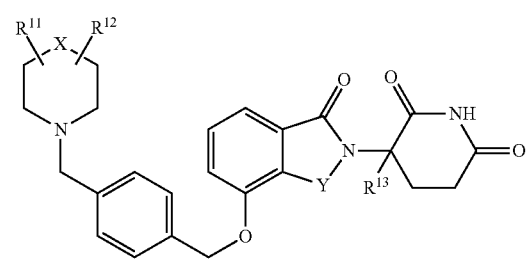
or a pharmaceutically acceptable salt, solvate, or stereoisomer thereof, wherein:
X is N or C;
Y is CH$_2$ or C=O;

$R^{11}$ and $R^{12}$ are each independently hydrogen, $C_{1-6}$ alkyl, —$C_{1-6}$ alkyl-$C_{3-6}$ cycloalkyl, $C_{1-6}$ alkoxy, —$C_{6-14}$ aryl, —CO—$C_{1-6}$ alkyl, —CO—$C_{3-6}$ cycloalkyl, —CO—$C_{6-14}$ aryl, —COO—$C_{1-6}$ alkyl, halogen, hydroxyl, oxo, 3- to 10-membered heterocyclyl, 6- to 10-membered heteroaryl, —NHCO—$C_{1-6}$ alkyl, —$(CH_2)_n$-phenyl, —$SO_2$—$C_{1-6}$ alkyl, —$SO_2$—$C_{3-6}$ cycloalkyl, —$SO_2$—$C_{6-14}$ aryl, or —$NR^{14}R^{15}$, wherein the alkyl, aryl or heteroaryl portion of each of the groups is optionally substituted with one or more halogen, hydroxyl, or —$C_{1-6}$ alkoxy;

$R^{13}$ is hydrogen or —$C_{1-6}$ alkyl;

$R^{14}$ and $R^{15}$ are each independently hydrogen or —$C_{1-6}$ alkyl; and n is 0, 1, 2 or 3.

In Formula XI, in one embodiment, X is N; and in another embodiment, X is C.

In Formula XI, in one embodiment, Y is $CH_2$; and in another embodiment, Y is C=O.

In Formula XI, in one embodiment, $R^{11}$ is hydrogen; in another embodiment, $R^{11}$ is $C_{1-6}$ alkyl; in yet another embodiment, $R^{11}$ is —$C_{1-6}$ alkyl-$C_{3-6}$ cycloalkyl; in yet another embodiment, $R^{11}$ is $C_{1-6}$ alkoxy; in yet another embodiment, $R^{11}$ is $C_{6-14}$ aryl; in yet another embodiment, $R^{11}$ is —CO—$C_{1-6}$ alkyl; in yet another embodiment, $R^{11}$ is —CO—$C_{3-6}$ cycloalkyl; in yet another embodiment, $R^{11}$ is —CO—$C_{6-14}$ aryl; in yet another embodiment, $R^{11}$ is —COO—$C_{1-6}$ alkyl; in yet another embodiment, $R^{11}$ is halogen; in yet another embodiment, $R^{11}$ is hydroxyl; in yet another embodiment, $R^{11}$ is oxo; in yet another embodiment, $R^{11}$ is 3- to 10-membered heterocyclyl; in yet another embodiment, $R^{11}$ is 6- to 10-membered heteroaryl; in yet another embodiment, $R^{11}$ is —NHCO—$C_{1-6}$ alkyl; in yet another embodiment, $R^{11}$ is —$(CH_2)_n$-phenyl; in yet another embodiment, $R^{11}$ is —$SO_2$—$C_{1-6}$ alkyl; in yet another embodiment, $R^{11}$ is —$SO_2$—$C_{3-6}$ cycloalkyl; in yet another embodiment, $R^{11}$ is —$SO_2$—$C_{6-14}$ aryl; in yet another embodiment, $R^{11}$ is —$NR^{14}R^{15}$; and in still another embodiment, the alkyl, aryl or heteroaryl portion of $R^{11}$ is substituted with one or more halogen, hydroxyl and/or —$C_{1-6}$ alkoxy.

In Formula XI, in one embodiment, $R^{12}$ is hydrogen; in another embodiment, $R^{12}$ is $C_{1-6}$ alkyl; in yet another embodiment, $R^{12}$ is —$C_{1-6}$ alkyl-$C_{3-6}$ cycloalkyl; in yet another embodiment, $R^{12}$ is $C_{1-6}$ alkoxy; in yet another embodiment, $R^{12}$ is $C_{6-14}$ aryl; in yet another embodiment, $R^{12}$ is —CO—$C_{1-6}$ alkyl; in yet another embodiment, $R^{12}$ is —CO—$C_{3-6}$ cycloalkyl; in yet another embodiment, $R^{12}$ is —CO—$C_{6-14}$ aryl; in yet another embodiment, $R^{12}$ is —COO—$C_{1-6}$ alkyl; in yet another embodiment, $R^{12}$ is halogen; in yet another embodiment, $R^{12}$ is hydroxyl; in yet another embodiment, $R^{12}$ is oxo; in yet another embodiment, $R^{12}$ is 3- to 10-membered heterocyclyl; in yet another embodiment, $R^{12}$ is 6- to 10-membered heteroaryl; in yet another embodiment, $R^{12}$ is —NHCO—$C_{1-6}$ alkyl; in yet another embodiment, $R^{12}$ is —$(CH_2)_n$-phenyl; in yet another embodiment, $R^{12}$ is —$SO_2$—$C_{1-6}$ alkyl; in yet another embodiment, $R^{12}$ is —$SO_2$—$C_{3-6}$ cycloalkyl; in yet another embodiment, $R^{12}$ is —$SO_2$—$C_{6-14}$ aryl; in yet another embodiment, $R^{12}$ is —$NR^{14}R^{15}$; and in still another embodiment, the alkyl, aryl or heteroaryl portion of $R^{12}$ is substituted with one or more halogen, hydroxyl and/or —$C_{1-6}$ alkoxy.

In Formula XI, in one embodiment, $R^{13}$ is hydrogen; and in another embodiment, $R^{13}$ is $C_{1-6}$ alkyl.

In Formula XI, in one embodiment, $R^{14}$ is hydrogen; and in another embodiment, $R^{14}$ is $C_{1-6}$ alkyl.

In Formula XI, in one embodiment, $R^{15}$ is hydrogen; and in another embodiment, $R^{15}$ is $C_{1-6}$ alkyl.

In Formula XI, in one embodiment, n is 0; in another embodiment, n is 1; in yet another embodiment, n is 2; and in still another embodiment, n is 3.

The immunomodulatory compounds of Formula XI encompass any of the combinations of X, Y, $R^{11}$-$R^{15}$ and n as defined herein.

In certain embodiments, the compound is selected from:

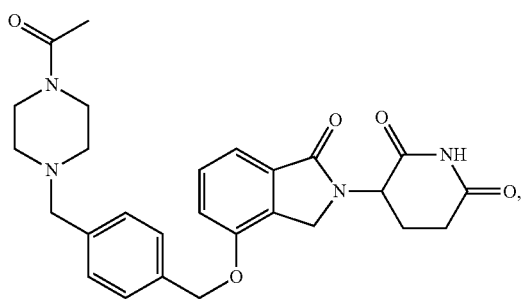

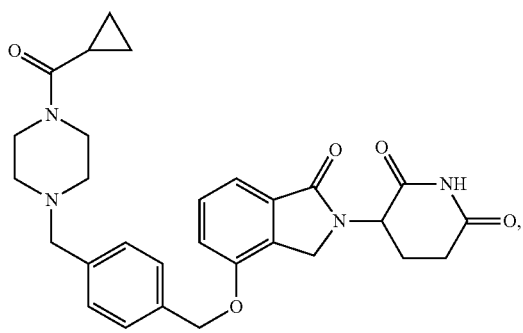

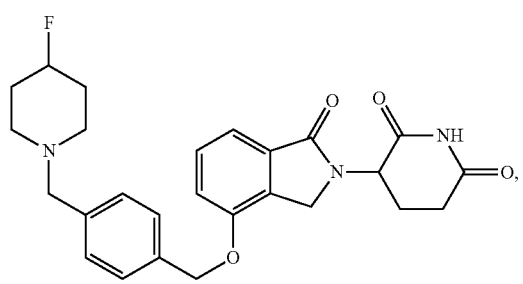

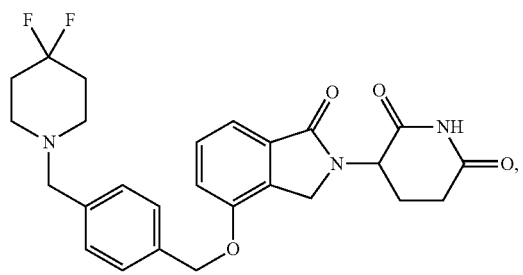

149
-continued
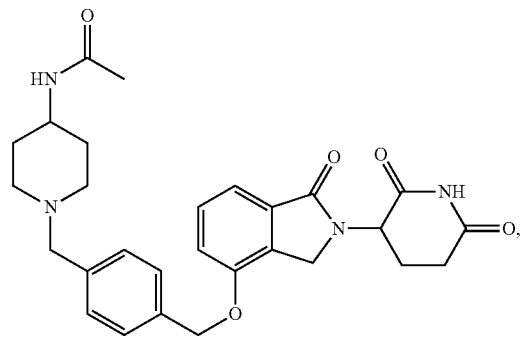
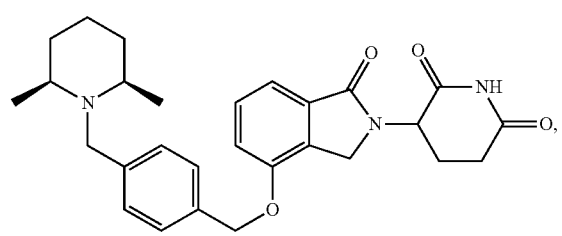
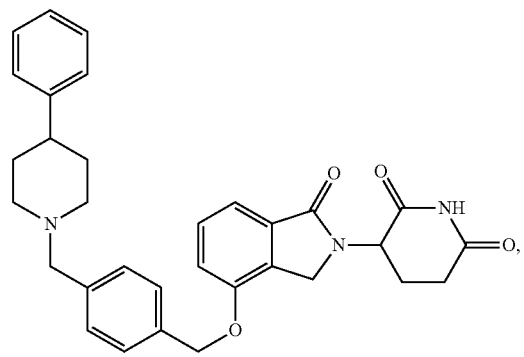
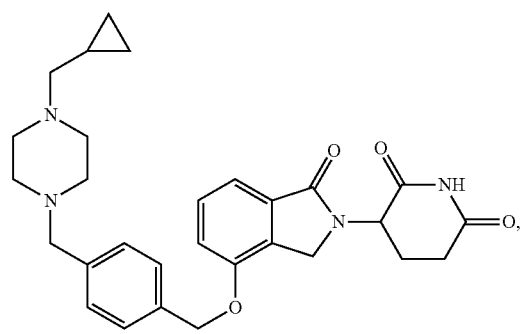
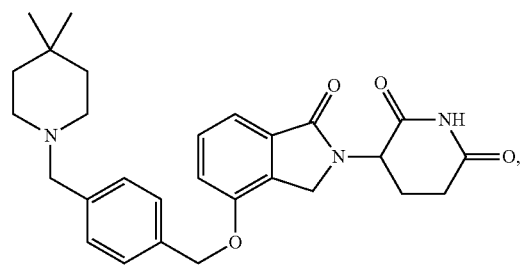
150
-continued
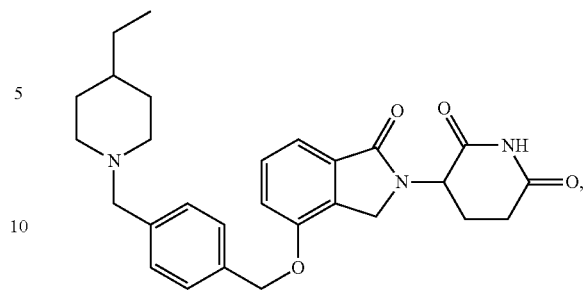
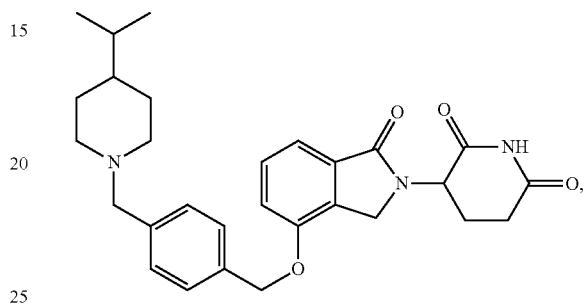
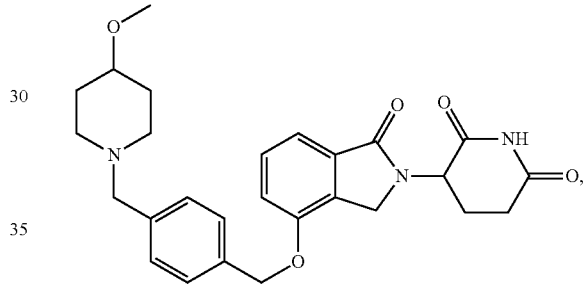
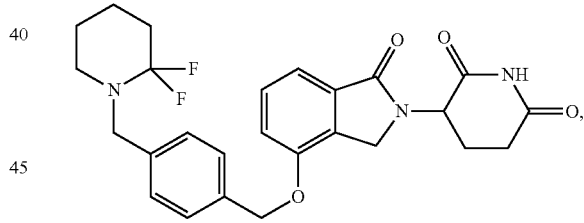
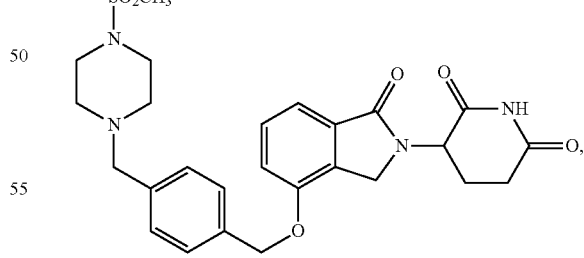
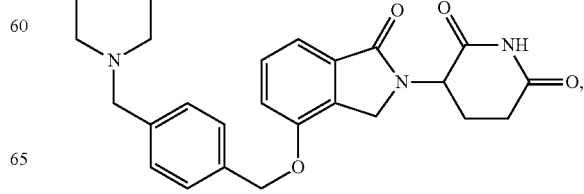

151
-continued
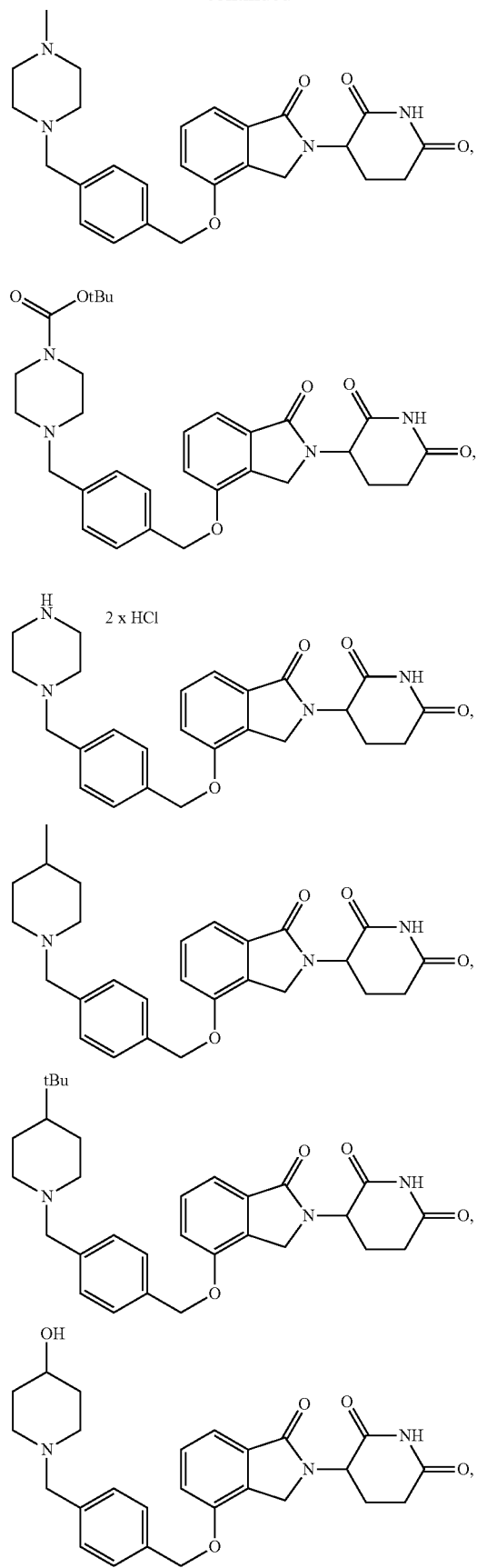
152
-continued
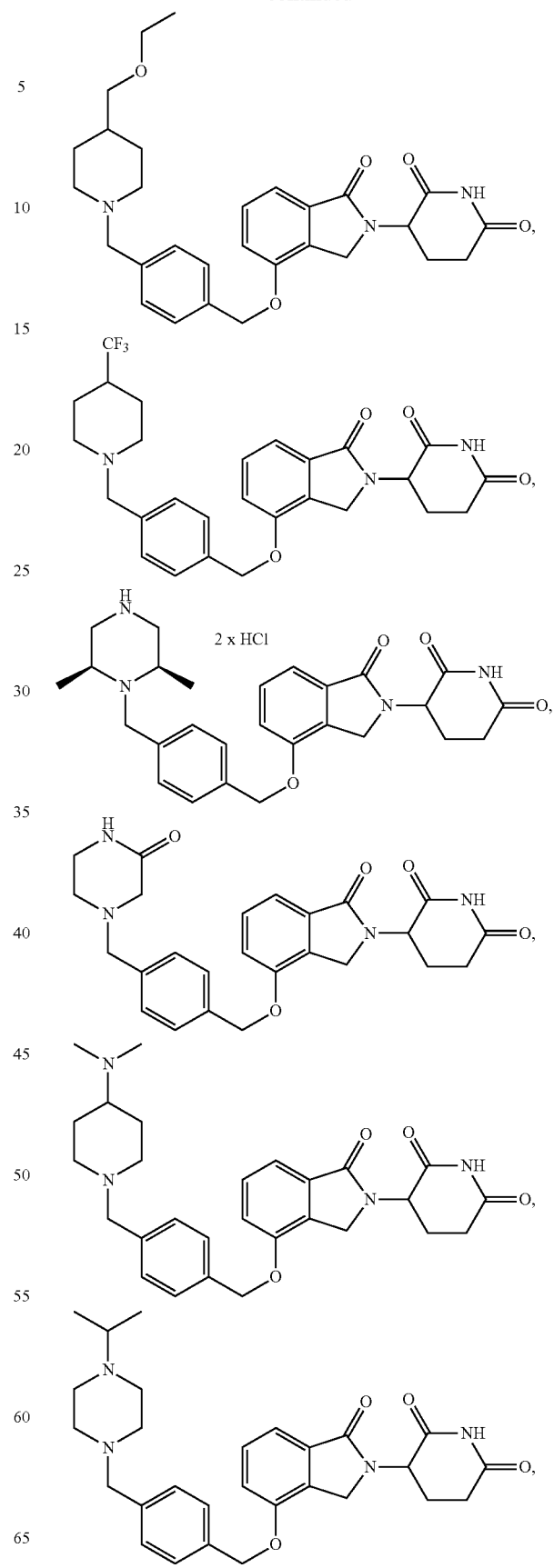

153
-continued
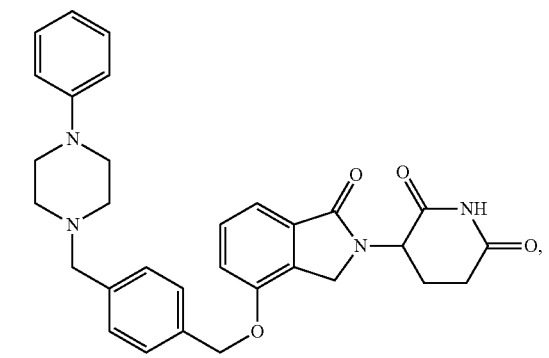
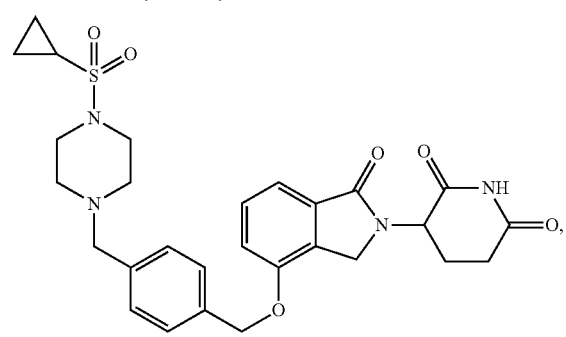
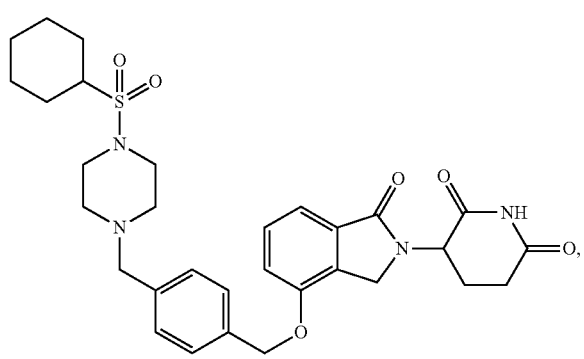
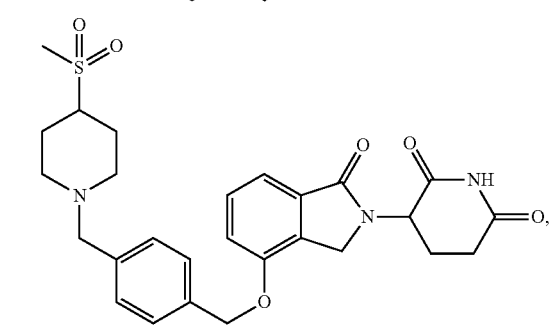
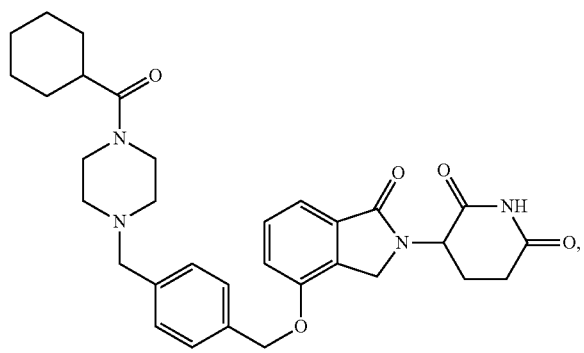
154
-continued
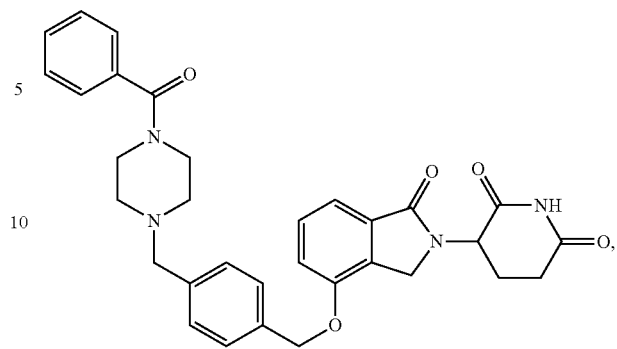
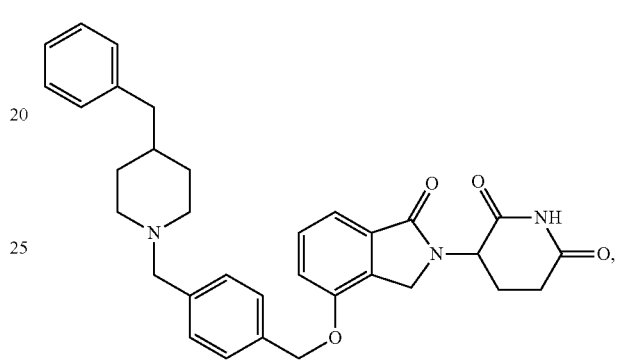
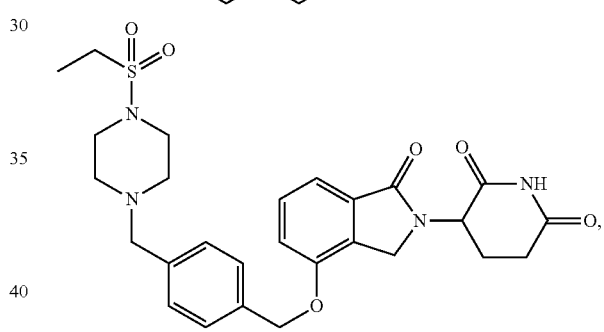
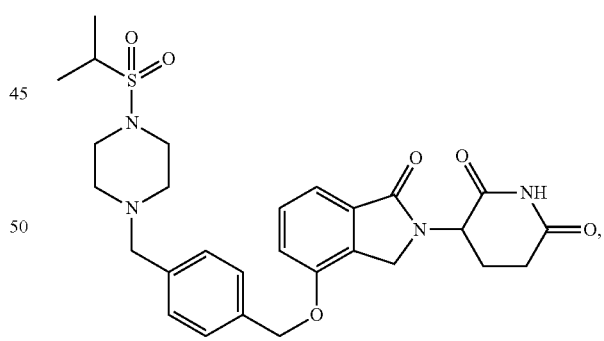
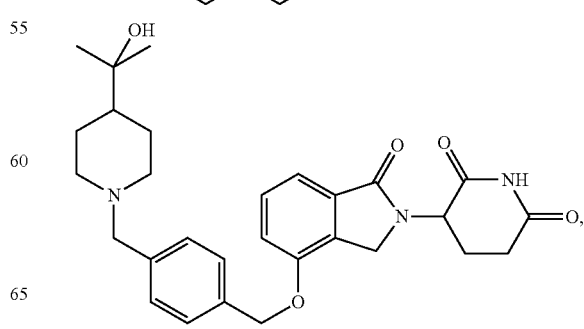

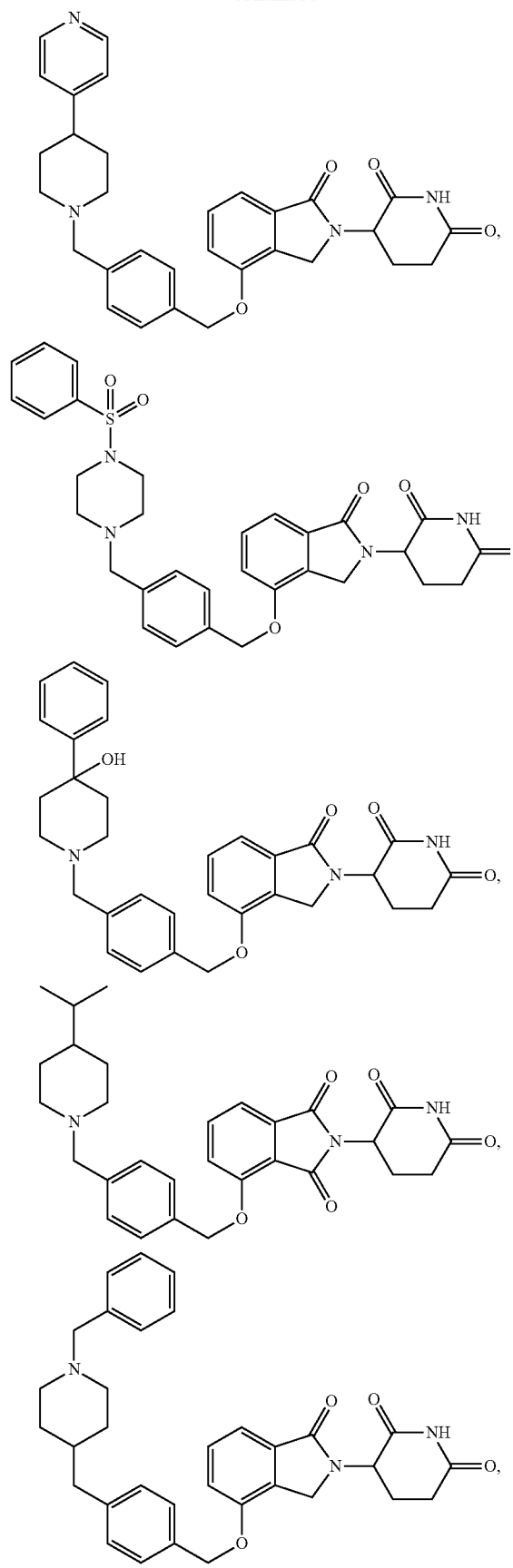
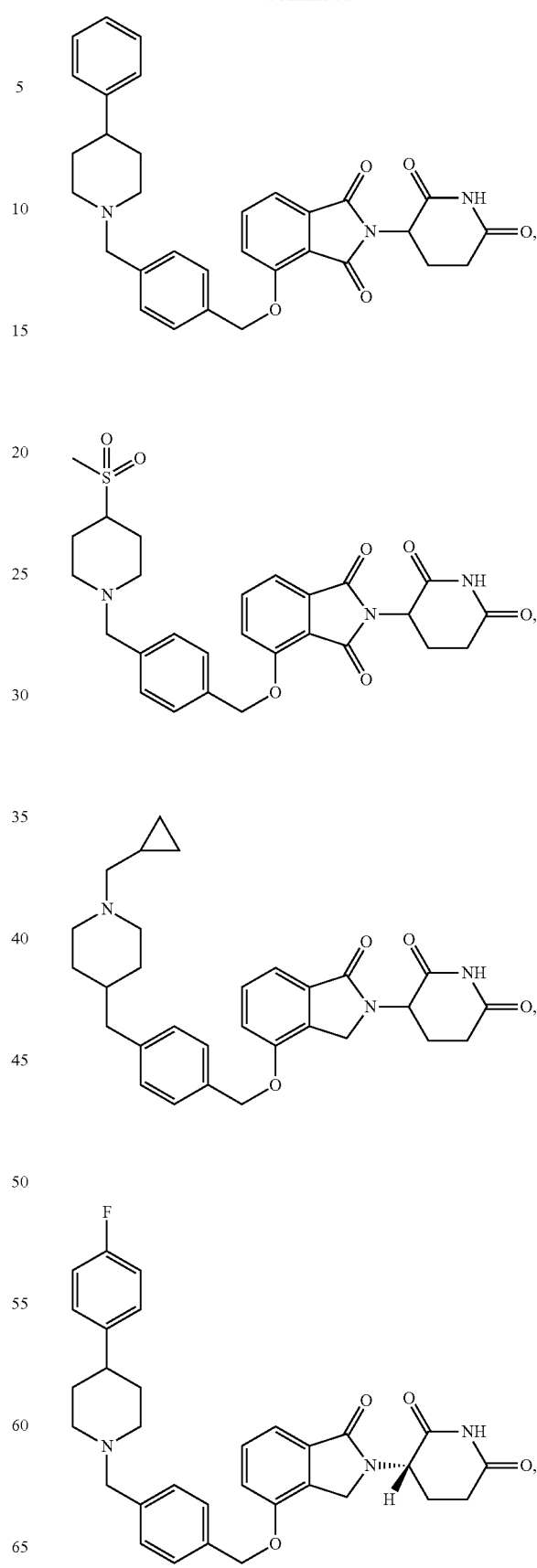

157
-continued
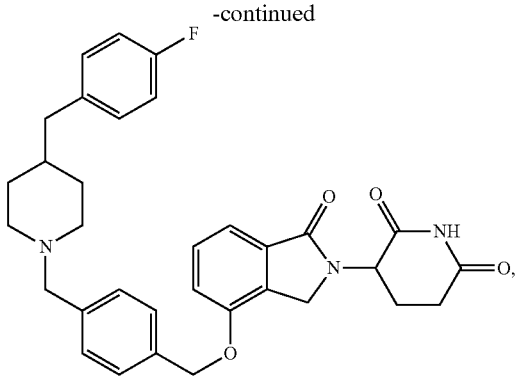
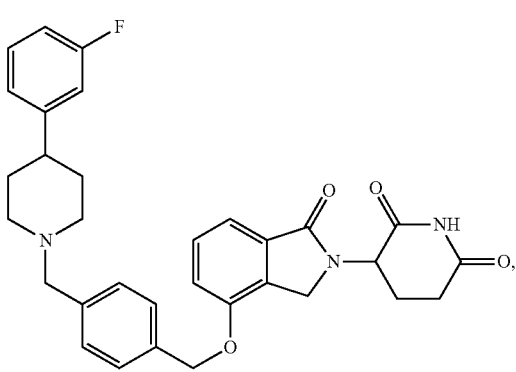
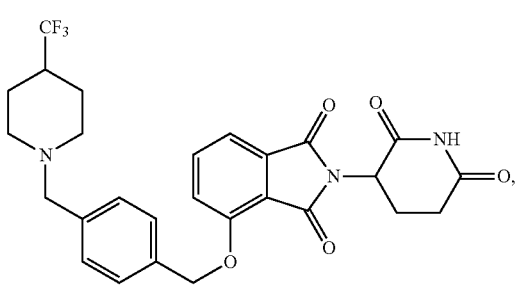
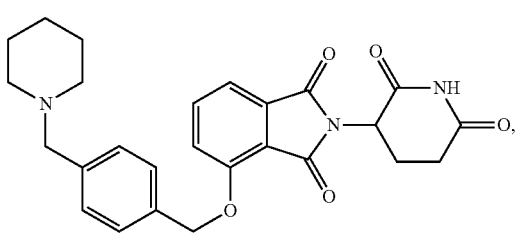
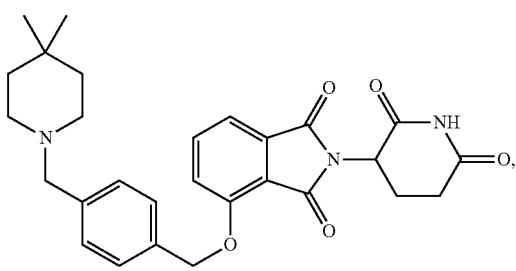
158
-continued
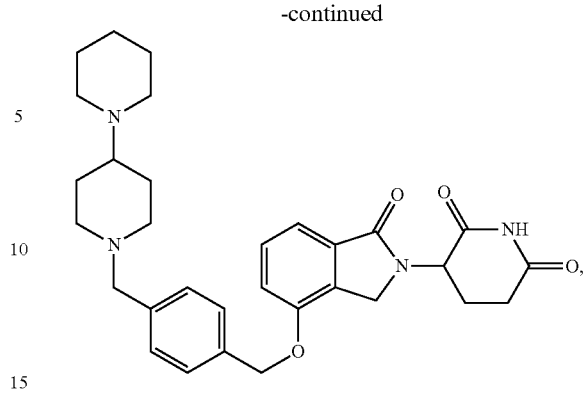
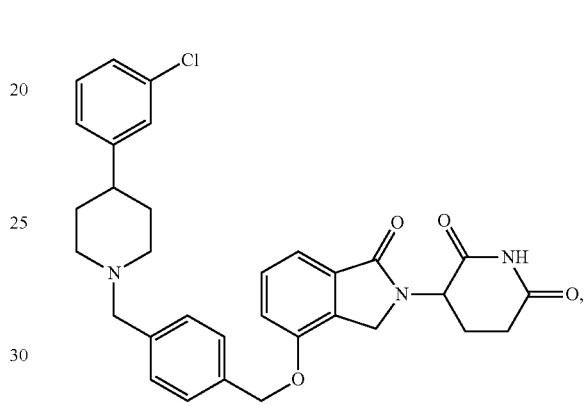
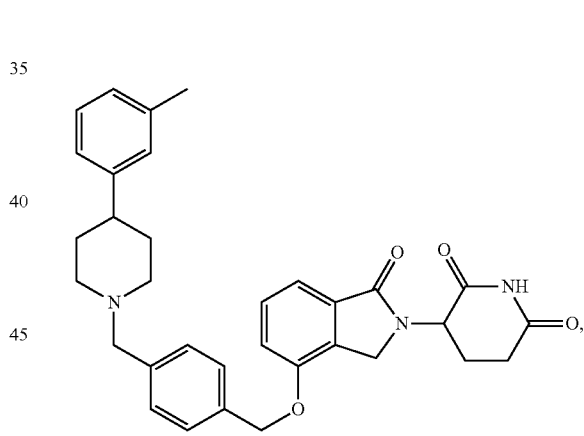
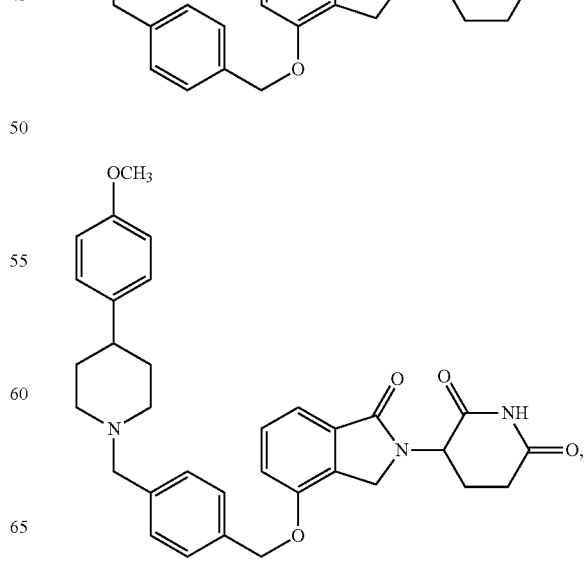

159
-continued
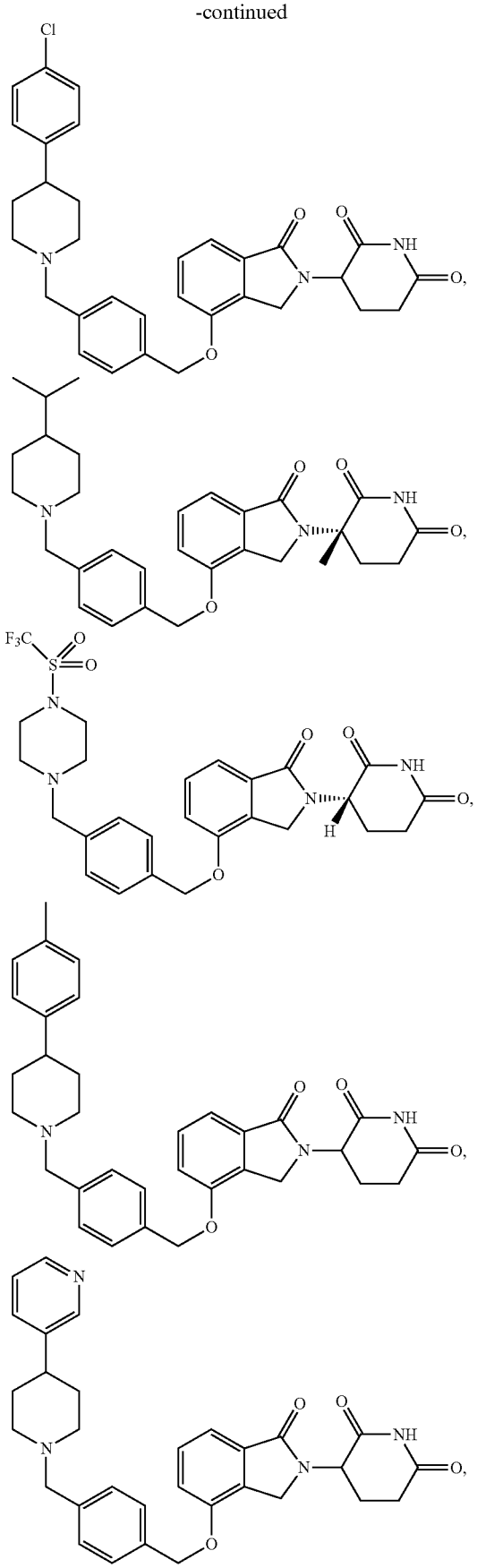
160
-continued
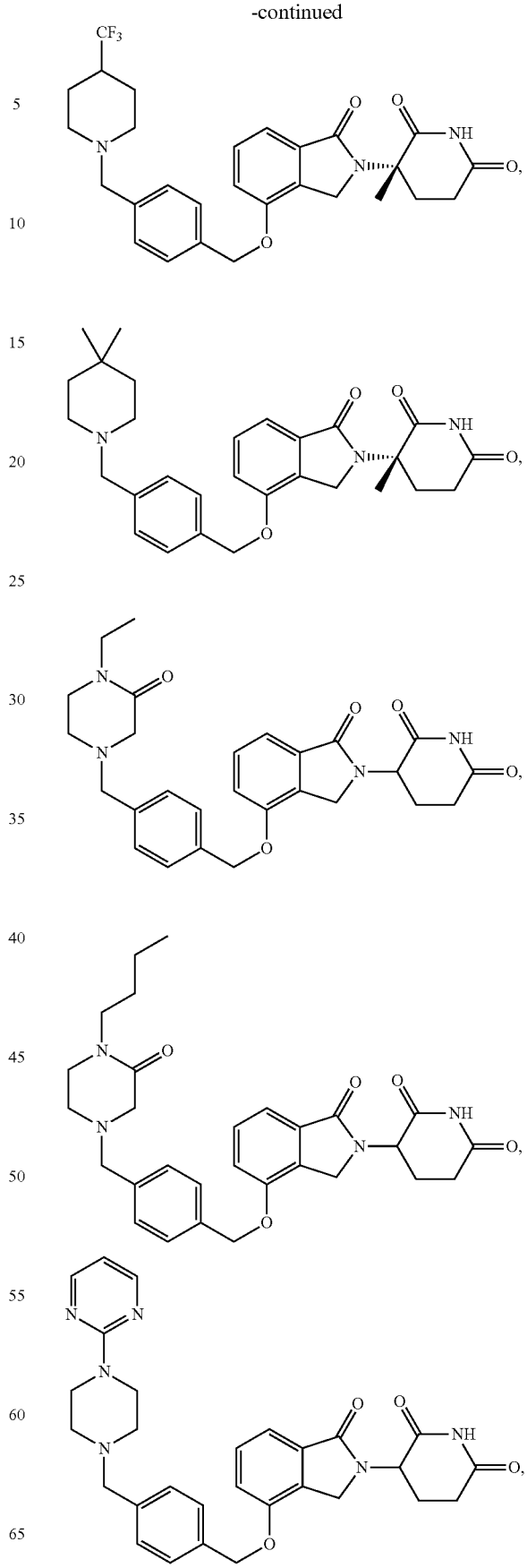

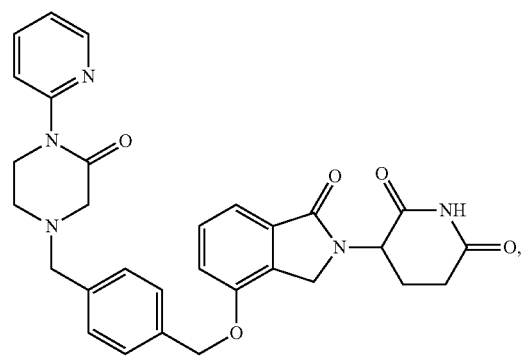
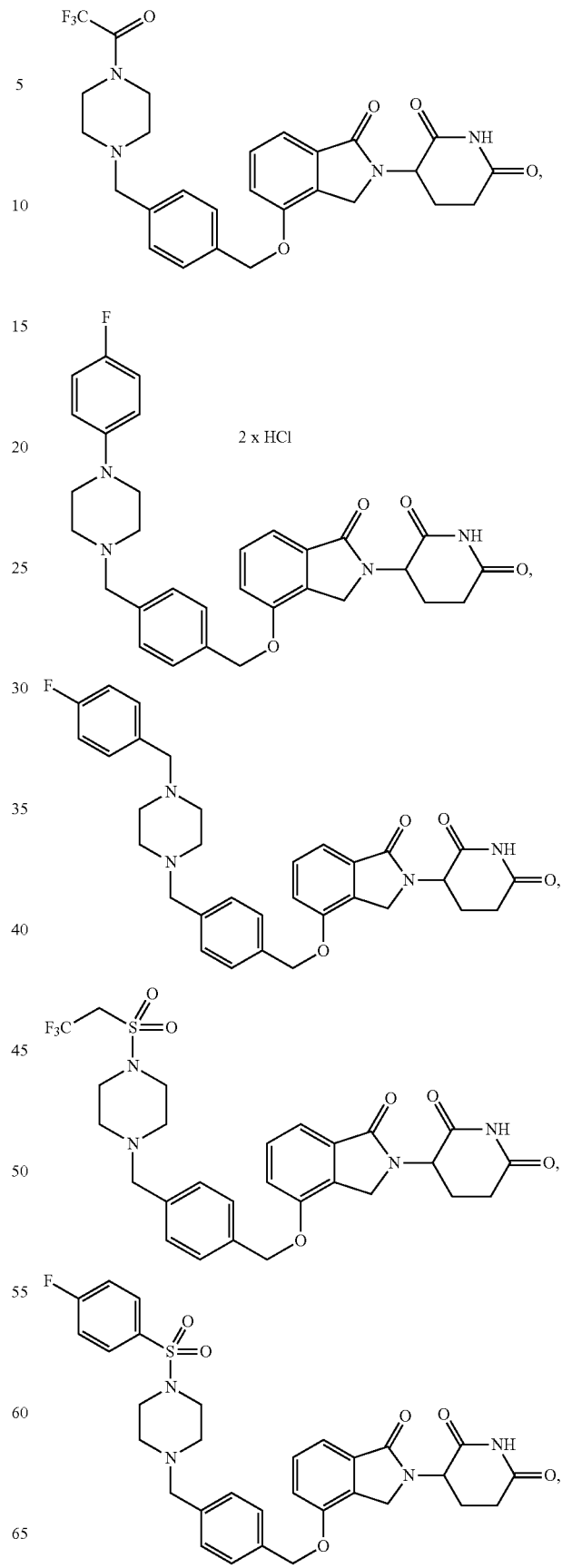

163
-continued
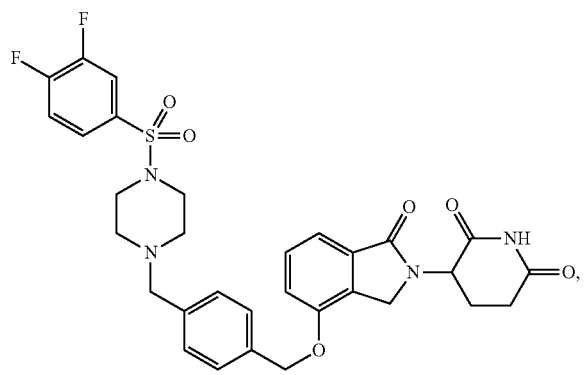
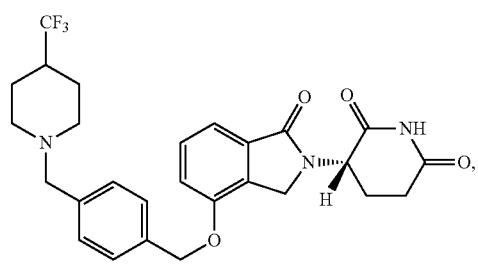
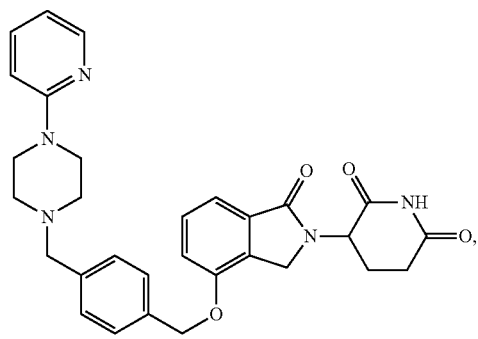
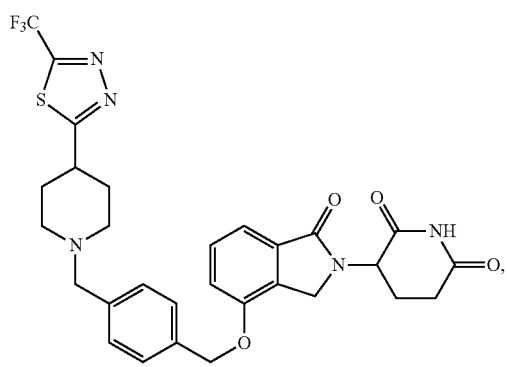
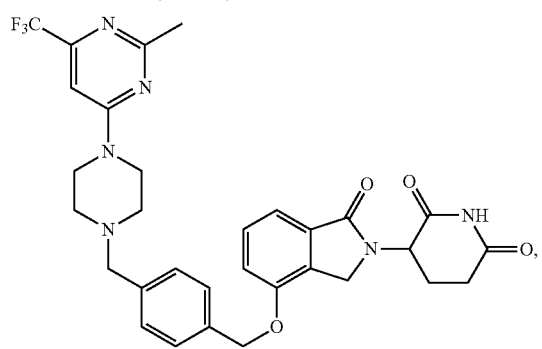
164
-continued
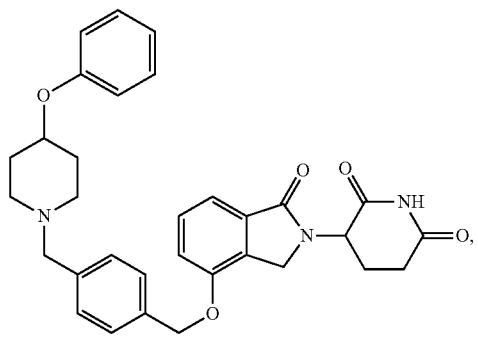
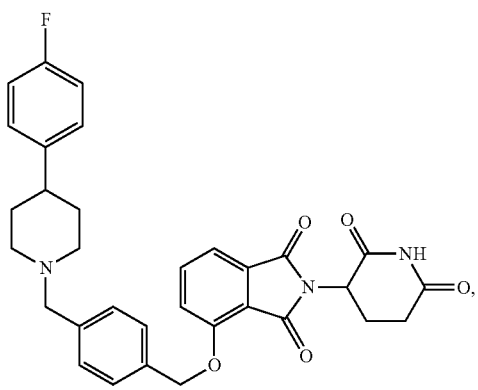
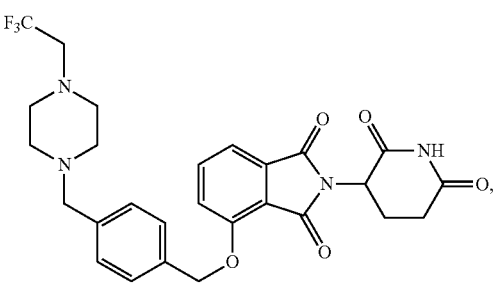
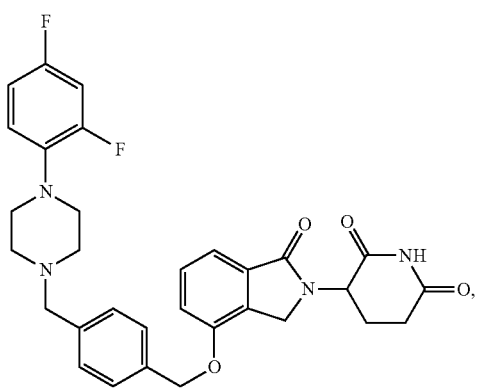

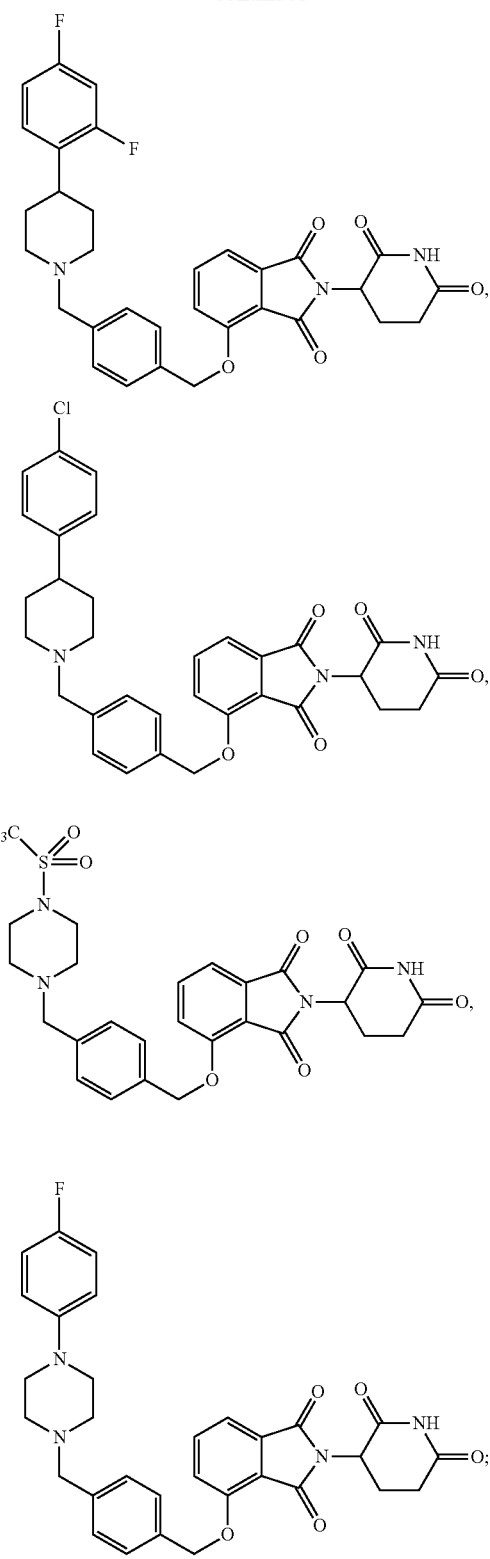
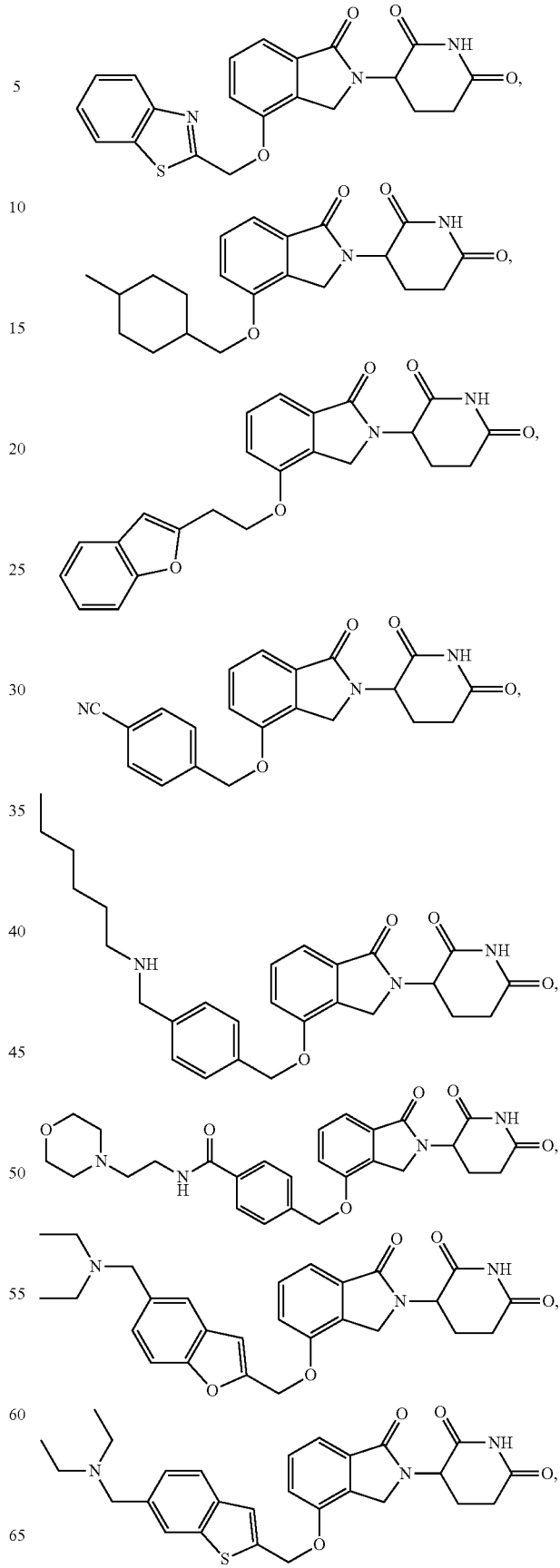
and pharmaceutically acceptable salts, solvates, and stereoisomers thereof.
In certain embodiments, the immunomodulatory compound is selected from:

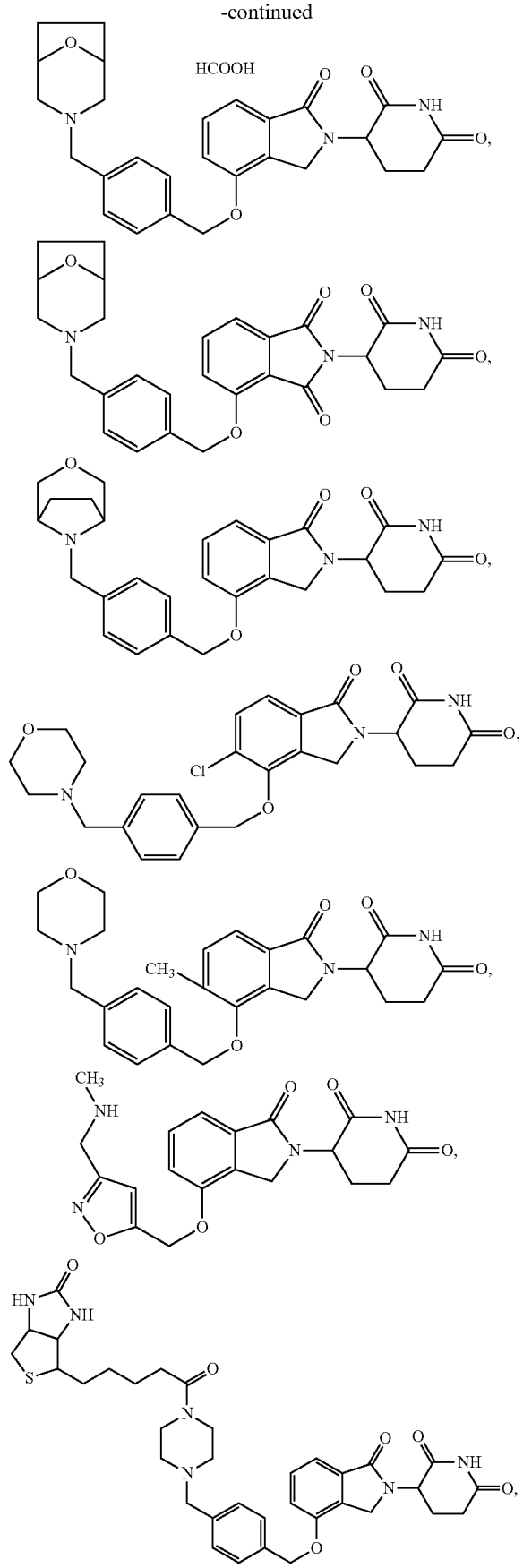
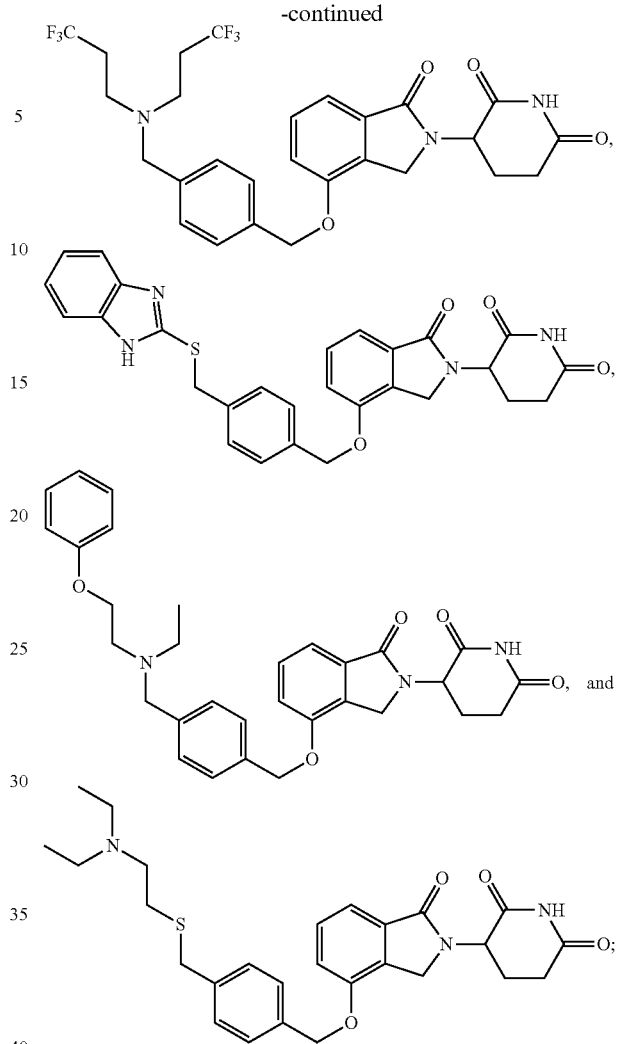

and pharmaceutically acceptable salts, solvates, and stereoisomers thereof.

In certain embodiments, the immunomodulatory compound is 3-(5-amino-2-methyl-4-oxoquinazolin-3(4H)-yl)piperidine-2,6-dione, or a pharmaceutically acceptable salt, solvate, or stereoisomer thereof. In certain embodiments, the immunomodulatory compound is 3-(4-((4-(morpholinomethyl)benzyl)oxy)-1-oxoisoindolin-2-yl)piperidine-2,6-dione, or a pharmaceutically acceptable salt, solvate, or stereoisomer thereof. In certain embodiments, the immunomodulatory compound is (S)-3-(4-((4-(morpholinomethyl)benzyl)oxy)-1-oxoisoindolin-2-yl)piperidine-2,6-dione, or a pharmaceutically acceptable salt or solvate thereof.

All of the compounds described herein are either commercially available or can be prepared according to the methods described in the patents or patent publications disclosed herein. Further, optically pure compounds can be asymmetrically synthesized or resolved using known resolving agents or chiral columns as well as other standard synthetic organic chemistry techniques. Additional information on immunomodulatory compounds, their preparation, and use can be found, for example, in U.S. Pat. No. 7,635,700, U.S. Pat. App. Pub. Nos. 2006/0188475, 2006/0205787, 2007/0049618, 2008/0161328, and 2011/

0196150, the disclosure of each of which is incorporated by reference herein in its entirety.

5.8 METHODS OF TREATMENT

In certain embodiments, provided herein is a method of treating, preventing, and/or managing an inflammatory disease, disorder, or condition, comprising administering to a subject a therapeutically effective amount of a treatment compound provided herein.

In certain embodiments, the disease is lupus, *scleroderma*, Sjögren syndrome, ANCA-induced vasculitis, anti-phospholipid syndrome, or myasthenia gravis. In certain embodiments, the disease is lupus or *scleroderma*.

In certain embodiments, provided herein is a method of treating, preventing, and/or managing *scleroderma* or a symptom thereof, comprising administering to a subject having *scleroderma* a therapeutically effective amount of a treatment compound provided herein. In certain embodiments, provided herein is a method of treating, preventing, and/or managing *scleroderma* or a symptom thereof, comprising administering to a subject having *scleroderma* or at risk of having *scleroderma* a therapeutically effective amount of a treatment provided herein.

In certain embodiments, the *scleroderma* is localized, systemic, limited, or diffuse *scleroderma*.

In certain embodiments, the systemic *scleroderma* comprises CREST syndrome (Calcinosis, Raynaud's syndrome, esophagaeal dysfunction or dysmotility, sclerodactyly, and telangiectasia). *Scleroderma* is also known as systemic sclerosis or progressive systemic sclerosis.

In certain embodiments, the disease is Raynaud's disease. In certain embodiments, systemic sclerosis comprises *scleroderma* lung disease, *scleroderma* renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life.

In certain embodiments, limited *scleroderma* is limited to the hands, the face, neck, or combinations thereof.

In certain embodiments, diffuse *scleroderma* comprises skin tightening and also occurs above the wrists (or elbows). In certain embodiments, the diffuse systemic sclerosis is sine *scleroderma*, comprising internal organ fibrosis, but no skin tightening; or familial progressive systemic sclerosis.

In one embodiment, *scleroderma* is not associated with wasting, such as disease-related wasting.

In one embodiment, provided herein is a method for the reduction, inhibition, or prevention of one or more of the following symptoms of *scleroderma*: (i) gradual hardening, thickening, and tightening of the skin (e.g., in extremities, such as hands, face, and feet); (ii) skin discoloration; (iii) numbness of extremities; (iv) shiny skin; (v) small white lumps under the surface of the skin that erupt into a chalky white fluid; (vi) Raynaud's esophagaeal dysfunction (pain, numbness, and/or color changes in the hands caused by spasm of the blood vessels upon exposure to cold or emotional stress); (vii) telangiectasia (red spots on, e.g., the hands, palms, forearms, face, and lips); (viii) pain and/or stiffness of the joints; (ix) swelling of the hands and feet; (x) itching of the skin; (xi) stiffening and curling of the fingers; (xii) ulcers (sores) on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; or (xx) digital autoamputation, comprising administering a therapeutically effective amount of a treatment provided herein to a subject in need thereof.

Without being bound to any particular theory, it is believed that the treatment provided herein compounds provided herein enhance Th1 immune response, and suppresses Th2 immune response, which may result in anti-fibrotic effects in the skin.

In certain embodiments, provided herein is a method for improving or reducing the skin thickness of a subject having *scleroderma*, comprising administering to the subject a therapeutically effective amount of a treatment compound provided herein. In one embodiment, the skin thickness is reduced by about 20%, about 25%, about 30%, about 40%, about 50%, about 60%, about 70% about 80%, about 90% or more.

In certain embodiments, provided herein is a method for achieving one or more clinical endpoints in treating a subject with *scleroderma*, comprising administering to the subject a therapeutically effective amount of a treatment compound provided herein.

In certain embodiments, provided herein is a method for increasing the overall survival, objective response rate, time to progression, progression-free survival and/or time-to-treatment failure of a subject having *scleroderma*, comprising administering to the subject a therapeutically effective amount of a treatment compound provided herein.

In certain embodiments, provided herein is a method for decreasing mortality, respiratory mortality and/or respiratory hospitalization of a subject having *scleroderma*, comprising administering to the subject a therapeutically effective amount of a treatment compound provided herein.

In certain embodiments, provided herein is a method for improving the modified Rodnan skin score of a subject having *scleroderma*, comprising administering to the subject a therapeutically effective amount of a treatment provided herein. In one embodiment, the improvement in modified Rodnan skin score is about 5, about 10, about 15, or about 20 points or more.

In certain embodiments, provided herein is a method for improving or reducing the skin thickness of a subject having *scleroderma*, comprising administering to the subject a therapeutically effective amount of a treatment compound provided herein. In one embodiment, the skin thickness is reduced by about 20%, about 25%, about 30%, about 40%, about 50%, about 60%, about 70% about 80%, about 90% or more.

In certain embodiments, provided herein is a method for improving or reducing skin induration of a subject having *scleroderma*, comprising administering to the subject a therapeutically effective amount of a treatment compound provided herein.

In certain embodiments, provided herein is a method for improving the dermatology quality of life index of a subject having *scleroderma*, comprising administering to the subject a therapeutically effective amount of a treatment compound provided herein.

In certain embodiments, provided herein is a method for improving the pulmonary function of a subject having *scleroderma*, comprising administering to the subject a therapeutically effective amount of a treatment compound provided herein.

In certain embodiments, provided herein is a method for improving the carbon monoxide diffusing capacity of a subject having *scleroderma*, comprising administering to the subject a therapeutically effective amount of a treatment compound provided herein. In one embodiment, the carbon monoxide diffusing capacity of a subject is improved by an improvement in the diffusing capacity of the lung for carbon monoxide ($D_Lco$) of about 10%, about 20%, about 25%, about 30%, about 40%, about 50%, about 60%, about 70% about 80%, about 90% or more.

In certain embodiments, provided herein is a method for improving the Mahler Dyspnea index of a subject having scleroderma, comprising administering to the subject a therapeutically effective amount of a treatment compound provided herein. In one embodiment, the improvement in Mahler Dyspnea index is about 4, about 5, about 6, about 7, about 8, about 9, or about 10 points or more.

In certain embodiments, provided herein is a method for improving the Saint George's Respiratory Questionnaire score of a subject having scleroderma, comprising administering to the subject a therapeutically effective amount of a treatment compound provided herein. In one embodiment, the improvement in Saint George's Respiratory Questionnaire score is about 4, about 8, about 12, about 16, about 20, about 24, about 28, about 32, about 36, about 40, about 44, about 48, about 52 points or more.

In certain embodiments, provided herein is a method for improving the UCLA scleroderma clinical trial consortium gastrointestinal tract score of a subject having scleroderma, comprising administering to the subject a therapeutically effective amount of a treatment compound provided herein.

In certain embodiments, provided herein is a method for treating or preventing digital ulcer of a subject having scleroderma, comprising administering to the subject a therapeutically effective amount of a treatment compound provided herein.

In certain embodiments, provided herein is a method for improving flow-mediated dilatation of a subject having scleroderma, comprising administering to the subject a therapeutically effective amount of a treatment compound provided herein.

In certain embodiments, provided herein is a method for improving or increasing the six minute walk distance of a subject having scleroderma, comprising administering to the subject a therapeutically effective amount of a treatment compound provided herein. In one embodiment, the improvement in the six minute walk distance is about 200 meters, about 250 meters, about 300 meters, about 350 meters, about 400 meters or more.

In certain embodiments, provided herein is a method of treating, preventing, and/or managing lupus erythematosus or a symptom thereof, comprising administering to a subject having lupus erythematosus a therapeutically effective amount of a treatment compound provided herein.

In certain embodiments, provided herein is a method of preventing lupus erythematosus or a symptom thereof, comprising administering to a subject at risk of having lupus erythematosus a therapeutically effective amount of a treatment compound provided herein.

In certain embodiments, the disease is systemic lupus erythematosus (SLE), cutaneous lupus erythematosus (CLE), or treatment compound-induced lupus.

The phrase "Systemic lupus erythematosus" is interchangeably used herein with SLE and lupus and refers to all manifestations of the disease as known in the art (including remissions and flares). In SLE, abnormal hyperactivity of B lymphocytes and massive abnormal production of immunoglobulin gamma (IgG) auto-antibodies play a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In: *Harrison's Principles of Internal Medicine* (16th edition); New York (US): McGraw-Hill; 2005. pp. 1960-1967).

Symptoms of SLE vary from person to person, and may come and go. In most subjects, the symptoms include joint pain and swelling. Frequently affected joints are the fingers, hands, wrists, and knees. Some subjects develop arthritis. Other common symptoms include: chest pain when taking a deep breath, fatigue, fever with no other cause, general discomfort, uneasiness, or ill feeling (malaise), hair loss, mouth sores, swollen lymph nodes, sensitivity to sunlight, skin rash-a "butterfly" rash over the cheeks and bridge of the nose affects about half of people with SLE, in some subjects, the rash gets worse in sunlight, and the rash may also be widespread.

Other symptoms depend on what part of the body is affected, and may include the following:
  Brain and nervous system: headaches, numbness, tingling, seizures, vision problems, personality changes,
  Digestive tract: abdominal pain, nausea, and vomiting,
  Heart: abnormal heart rhythms (arrhythmias),
  Lung: coughing up blood and difficulty breathing, and
  Skin: patchy skin color, fingers that change color when cold (Raynaud's phenomenon).

Some subjects only have skin symptoms. This is called discoid lupus.

In one embodiment, the disease is moderate, severe, or very severe SLE. The term "severe SLE" as used herein refers to an SLE condition where the subject has one or more severe or life-threatening symptoms (such as hemolytic anemia, extensive heart or lung involvement, kidney disease, or central nervous system involvement).

In certain embodiments, provided herein is a method for achieving one or more clinical endpoints in treating a subject with SLE, comprising administering to the subject a therapeutically effective amount of a treatment compound provided herein.

In certain embodiments, provided herein is a method for the overall survival, objective response rate, time to progression, progression-free survival and/or time-to-treatment failure of a subject having SLE, comprising administering to the subject a therapeutically effective amount of a treatment compound provided herein.

In certain embodiment, certain treatment compounds provided herein act as an inhibitor of primary human memory CD19+ B-cell differentiation to the plasmablast stage. Without being bound to any particular theory, it is believed that certain treatment compounds provided herein block cells at a premature stage thereby decreasing the numbers of plasmablasts that are capable of producing high levels of immunoglobulin. A functional consequence of this effect is reduced immunoglobulin G (IgG) and immunoglobulin M (IgM) production in these differentiation cultures.

In certain embodiments, provided herein is a method for treating, managing, or preventing an immune-related disease, disorder, or condition, comprising administering to a subject a therapeutically effective amount of a treatment compound provided herein.

In certain embodiments, provided herein is a method of treating a disease, disorder, or condition caused by, or is associated with, an inappropriate or undesirable immune response, comprising administering to a subject a therapeutically effective amount of a treatment compound provided herein.

In certain embodiments, provided herein is a method of treating a disease, disorder, or condition that can be treated beneficially by immunosuppression, comprising administering to a subject a therapeutically effective amount of a treatment compound provided herein.

In certain embodiments, the immune-related disease, i.e., a disease, disorder, or condition caused by, or is associated with, an inappropriate or undesirable immune response, is Sjögren syndrome, ANCA-induced vasculitis, anti-phospholipid syndrome, myasthenia gravis, Addison's disease, alopecia areata, ankylosing spondylitis, antiphospholipid antibody syndrome, antiphospholipid syndrome (primary or secondary), asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, degos disease, dermatitis hepatiformis, essential mixed cryoglobulinemia, Goodpasture's syndrome, Graves' disease, Guillain-Barre syndrome, Hashimoto's thyroiditis (Hashimoto's disease; autoimmune thyroditis), idiopathic pulmonary fibrosis, idiopathic thrombocytopenia purpura, IgA nephropathy, juvenile arthritis, lichen planus, Ménière disease, mixed connective tissue disease, morephea, narcolepsy, neuromyotonia, pediatric autoimmune neuropsychiatric disorders (PANDAs), *pemphigus vulgaris*, pernicious anemia, polyarteritis nodosa, polychondritis, polymyalgia rheumatica, primary agammaglobulinemia, primary biliary cirrhosis, Raynaud disease (Raynaud phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, or Wegener's granulomatosis.

In certain embodiments, provided herein is a method for treating and preventing cancer, comprising administering to a subject a therapeutically effective amount of a treatment compound provided herein.

In certain embodiments, provided herein is a method for managing cancer, comprising administering to a subject a therapeutically effective amount of a treatment compound provided herein.

In certain embodiments, provided herein is a method for treating or managing lymphoma, in one embodiment, non-Hodgkin's lymphoma, comprising administering to a subject a therapeutically effective amount of a treatment compound provided herein.

In certain embodiments, provided herein is a method for treating or managing non-Hodgkin's lymphoma (NHL), including but not limited to, diffuse large B-cell lymphoma (DLBCL), comprising administering to a subject a therapeutically effective amount of a treatment compound provided herein.

In certain embodiments, the subject is one who has been previously treated for cancer, but is non-responsive to a standard therapy. In certain embodiments, the subject is one who has not previously been treated.

As used herein, the term "cancer" includes, but is not limited to, solid tumors and blood born tumors. In certain embodiments, the term "cancer" refers to disease of skin tissues, organs, blood, and vessels, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus.

In certain embodiments, the term "cancer" refers to advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, *scleroderma*, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a blood borne tumor. In certain embodiments, the blood borne tumor is metastatic. In certain embodiments, the blood borne tumor is treatment compound resistant. In certain embodiments, the cancer is myeloma or lymphoma.

In certain embodiments, the cancer is a solid tumor. In certain embodiments, the solid tumor is metastatic. In certain embodiments, the solid tumor is treatment compound-resistant. In certain embodiments, the solid tumor is hepatocellular carcinoma, prostate cancer, ovarian cancer, or glioblastoma.

6. EXAMPLES

The examples below are carried out using standard techniques, which are well known and routine to those of skill in the art, except where otherwise described in detail. The examples are intended to be merely illustrative.

6.1 Analysis of CRBN Isoforms

CRBN isoform mapping was performed using a nested PCR approach and Sanger sequencing. Commercially available and newly generated rabbit anti-CRBN antibodies were characterized with recombinant human CRBN protein and MM cell line extracts via western blot analysis.

Figure 9:
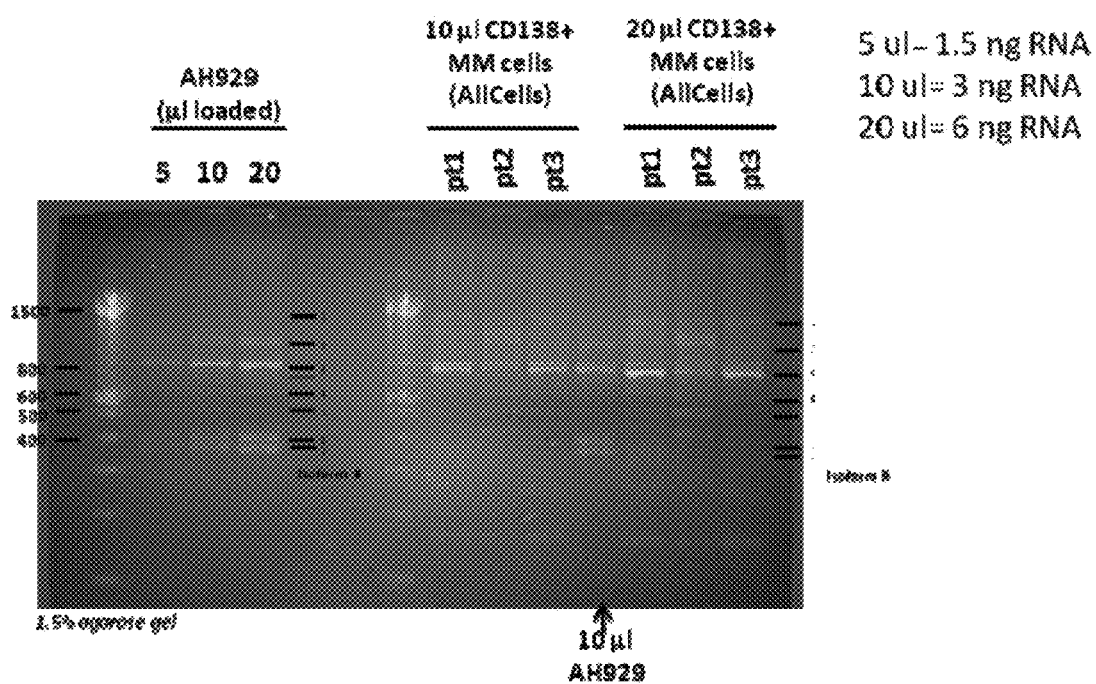
FIG. 9 shows the detection of the seven CRBN isoforms in AH929 and primary CD138+ isolated multiple myeloma (MM) cells.

CRBN RNA was first reverse transcribed (RT) using a pair of 5'-UTR (untranslated region) and 3'-UTR derived primers. A nested PCR reaction was then carried out using the RT reaction product as a template with primers designed to amplify the complete protein coding sequence (CDS). The PCR reaction product was loaded on an agarose gel to separate amplified DNA fragments. As shown in FIG. 9, seven distinct fragments were detected for MM cell line H929. The fragments were purified and inserted into a bacterial plasmid vector (e.g., Topo vector). Seven different inserts were derived from the fragments. DNA sequences from representative clones containing each insert were determined by the Sanger sequencing method. From the sequences of the fragments, their sizes were calculated to be 1329 bp, 1197 bp, 825 bp, 725 bp, 582 bp, 457 bp, and 331 bp, designated as Isoform 1, Isoform 2, Isoform 3, Isoform 4, Isoform 5, Isoform 6, and Isoform 7, respectively. Their sequences are shown in FIGS. 2 to 8.

6.2 RNA Sequencing

RNA was extracted from tumor cells and used to generate a sequencing library by the random hexamer method. 100 bp paired end RNA sequencing reactions were run in HiSeq (Illumina) platform and sequences were processed to develop mappable sequences to the CRBN gene in the human genome. For isoform detection, junction sequences from Isoform 2 to Isoform 7 were used as reference sequence, to which the entire RNA seq. sequences were aligned by using an alignment algorithm. Relative expression level of various isoforms was estimated by normalizing FPKM (fragment per kilobase per million reads) values of each isoform.

6.3 Detection of an Isoform of CRBN Comprising an Exon 6 Deletion Using PCR

Figure 12:
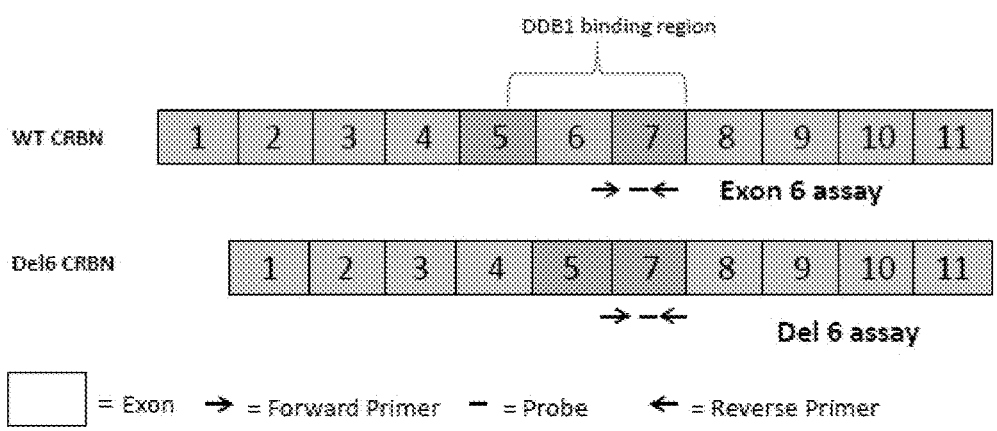
FIG. 12 illustrates an assay design for determining the presence or the level of an isoform of CRBN comprising an exon 6 deletion.
Figure 13:
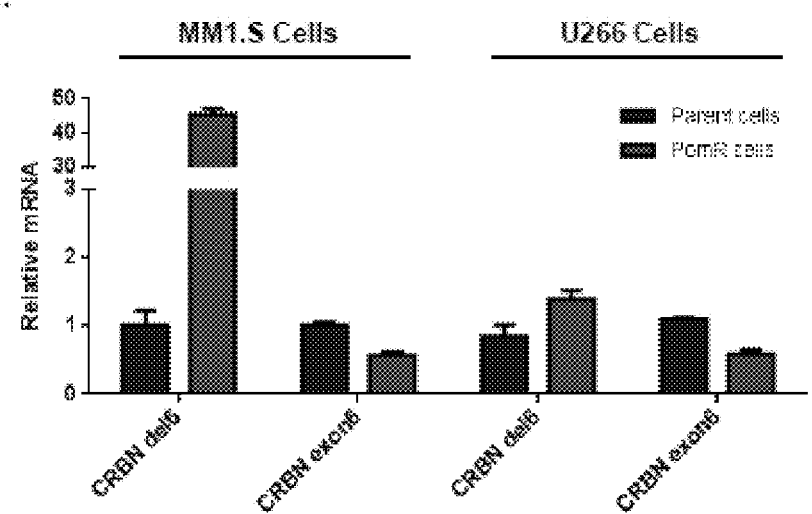
FIG. 13 shows a relative mRNA level using the assay design provided herein in MM1.S and U266 cells.

The mRNA was obtained from MM1.S parent cells, MM1.S Pomalidomide Resistant cells, U266 parent cells, and U266 Pomalidomide Resistant cells. A quantitative reverse transcriptase PCR (qRT-PCR) is used to quantify CRBN exon 6 deletion transcript first by creating cDNA from mRNA and then using the primers as designed in FIG. 12 and described above. In particular, in a first PCR reaction, one primer represented a sequence within exon 7 of CRBN, and a second PCR primer had a 5' portion and a 3' portion, the 5' portion representing a sequence within exon 6 of CRBN, the 3' portion presenting a sequence within exon 7 of CRBN. The presence of PCR products with proper size indicated the presence of exon 6 before exon 7. In a second PCR reaction, one primer represented a sequence within exon 7 of CRBN, and a second PCR primer had a 5' portion and a 3' portion, the 5' portion representing a sequence within exon 5 of CRBN, the 3' portion presenting a sequence within exon 7 of CRBN. The presence of PCR products with proper size indicates the presence of exon 5 right before exon 7 and absence of exon 6. The results were normalized to the level of PCR products in MM1.S parent cells. The results are shown in FIG. 13, as shown MM1.S Pomalidomide Resistant cells contain much higher level of CRBN transcripts with exon 6 deletion compared that in MM1.S parent cells. It is noted that there may be multiple mechanisms for resistance to Pomalidomide. Besides deletion of exon 6, downregulation of CRBN can also develop resistance to Pomalidomide, e.g., in certain U266 cells.

Figure 14:
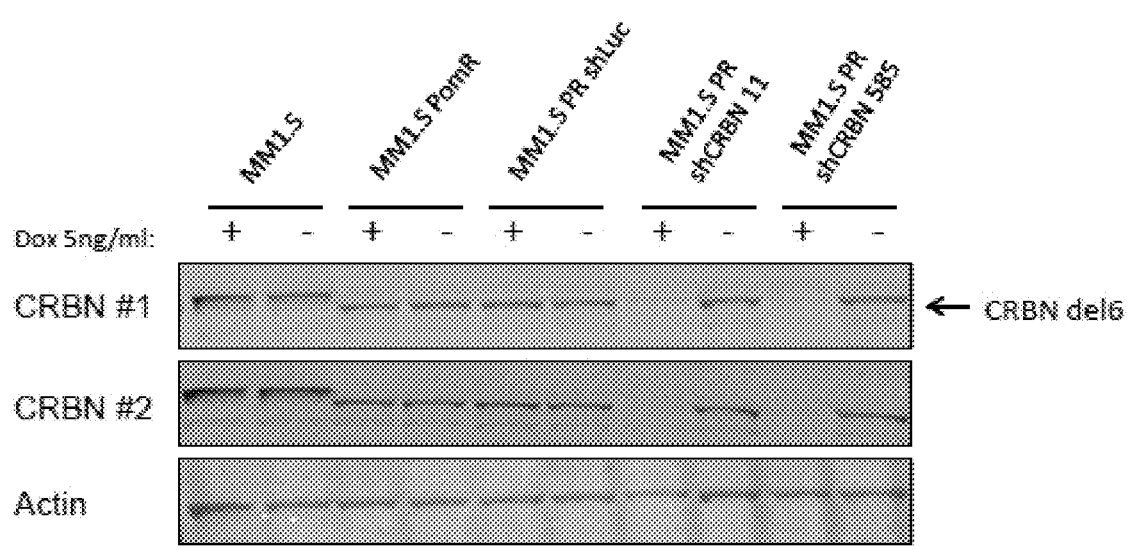
FIG. 14 shows detection of CRBN isoforms using anti-CRBN antibody in MM1.S and MM1.S Pomalidomide Resistant cells.

6.4 Detection of an Isoform of CRBN Comprising an Exon 6 Deletion Using Western Blot with Anti-CRBN Antibody Cell lysate was prepared from MM1.S parent cells, MM1.S Pomalidomide Resistant cells, MM1.S Pomalidomide Resistant cells transduced with 2 tetracycline inducible shRNA constructs targeting luciferase, MM1.S Pomalidomide Resistant cells transduced with 2 tetracycline inducible shRNA constructs targeting CRBN. Prior to preparing cell lysate from each sample, cells were grown in the presence of Doxycycline or PBS for 72 hours. Proteins in the cell lysate from each sample were separated using gel electrophoresis. The proteins were then transferred to a membrane, where they were stained with two different anti-CRBN antibodies. The results were shown in FIG. 14. As shown, a smaller size representing an isoform of CRBN comprising an exon 6 deletion was detected in MM1.S Pomalidomide Resistant cells, but not MM1.S parent cells.

Figure 15:
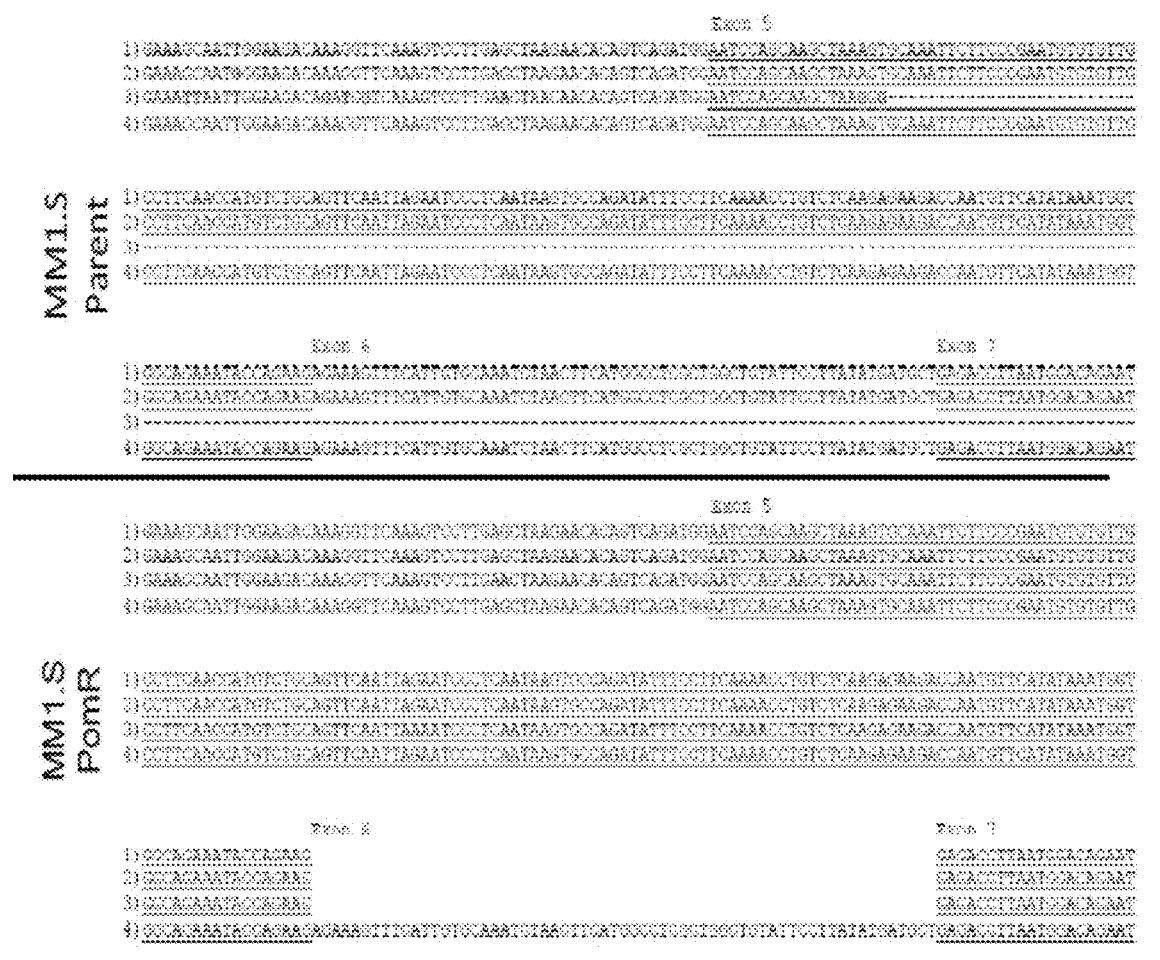

6.5 Sequencing PCR Products from MM1.S Parent Cells and MM1.S Pomalidomide Resistant cells The cDNA was prepared from mRNA of MM1.S parent cells and MM1.S Pomalidomide Resistant cells using an Oligo(dT) primer. PCR products were then sequenced using Sanger sequencing from three sets of primers designed to tile across the CRBN cDNA sequence. The three sequencing results (SEQ ID NOS:16-18 for MM1.S parent cell sequence result 1-3; SEQ ID NOS:20-22 for MM1.S Pomalidomide Resistance cell sequence result 1-3) were aligned with CRBN cDNA sequence (SEQ ID NO:19, the fourth sequence in both alignments), and the result was shown in FIG. 15. As shown, exon 6 was present in MM1.S parent cells but was absent from MM1.S Pomalidomide Resistant cells.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

7. SEQUENCE LISTING

The present specification is being filed with a computer readable form (CRF) copy of the Sequence Listing provided as a file entitled SEQLIST_12827-601-999.txt, which was created on Feb. 12, 2015 and is 25,852 bytes in size, and replaced by a file entitled SubstituteSEQLIST12827-601-999.txt created on Sep. 6, 2016 which is 29,195 bytes in size. The information in the CRF of the Sequence Listing is identical to the paper copy of the Sequence Listing and is incorporated herein by reference in its entirety.

What is claimed is:

1. A method for determining whether a subject having a multiple myeloma is sensitive to a treatment with pomalidomide or a pharmaceutically acceptable salt thereof, wherein said method comprises
   (a) obtaining a multiple myeloma sample from the subject;
   (b) determining the level of an isoform of CRBN in the multiple myeloma sample, the isoform of CRBN comprising a single exon 6 deletion and comprising exons 1-5 and 7-11;
   (c) diagnosing the subject as being sensitive to the treatment with pomalidomide or a pharmaceutically acceptable salt thereof if the isoform of CRBN was determined to be less than a baseline level in the multiple myeloma sample; and
   (d) administering an effective amount of pomalidomide or a pharmaceutically acceptable salt thereof to the subject diagnosed as being sensitive to the treatment with pomalidomide or a pharmaceutically acceptable salt thereof.

2. The method of claim 1, wherein the subject is diagnosed as being sensitive to the treatment with pomalidomide or a pharmaceutically acceptable salt thereof if the level of the isoform of CRBN in the multiple myeloma sample is determined to be less than 10%, 20%, 30%, 40%, 50%, 60%, 70%, 80% or 90% of the baseline level.

3. A method for treating a subject having or suspected of having a multiple myeloma, wherein said method comprising:
   (a) obtaining a multiple myeloma sample from the subject;

(b) determining the level of an isoform of CRBN in the multiple myeloma sample, the isoform of CRBN comprising a single exon 6 deletion and comprising exons 1-5 and 7-11;

(c) diagnosing the subject as being sensitive to a treatment with pomalidomide or a pharmaceutically acceptable salt thereof if the isoform of CRBN was determined to be less than a baseline level in the multiple myeloma sample; and (d) administering an effective amount of pomalidomide or a pharmaceutically acceptable salt thereof to the subject diagnosed as being sensitive to the treatment with pomalidomide or a pharmaceutically acceptable salt thereof.

4. The method of claim 3, wherein the subject is diagnosed as being sensitive to the treatment with pomalidomide or a pharmaceutically acceptable salt thereof if the level of the isoform of CRBN present in the multiple myeloma sample is determined to be less than 10%, 20%, 30%, 40%, 50%, 60%, 70%, 80% or 90% of the baseline level.

5. The method of claim 3, wherein the level of the isoform of CRBN is determined by contacting the sample with an isolated antibody that immunospecifically binds to an epitope in the CRBN, wherein the epitope has the amino acid sequence SEQ ID NO:8.

6. The method of claim 3, further comprising purifying CRBN protein and isoforms thereof from the sample.

7. The method of claim 6, further comprising measuring the size of the purified CRBN protein and isoforms thereof from the sample.

8. The method of claim 6, further comprising sequencing purified CRBN protein and isoforms thereof, and thereby determining presence or the level of the isoform of CRBN.

9. The method of claim 8, wherein the sequencing comprises use of mass spectrometry or an Edman degradation reaction.

10. The method of claim 3, further comprising extracting mRNA from the cancer sample.

11. The method of claim 10, wherein determining the level of the isoform of CRBN is performed by determining mRNA level of exon 6 of CRBN using a polymerase chain reaction (PCR).

12. The method of claim 11, wherein the PCR is a reverse transcriptase PCR (RT-PCR).

13. The method of claim 11, wherein one primer used in the PCR represents a sequence within exon 7 of CRBN.

14. The method of claim 11, wherein one primer used in the PCR has a 5' portion and a 3' portion, the 5' portion representing a sequence within exon 6 of CRBN, the 3' portion presenting a sequence within exon 7 of CRBN.

15. The method of claim 11, wherein one primer used in the PCR has a 5' portion and a 3' portion, the 5' portion representing a sequence within exon 5 of CRBN, the 3' portion presenting a sequence within exon 7 of CRBN.

16. The method of claim 10, further comprising generating cDNA from the mRNA.

17. The method of claim 16, wherein determining the level of the isoform of CRBN is performed by determining cDNA level of exon 6 of CRBN using a PCR.

18. The method of claim 17, wherein one primer used in the PCR represents a sequence within exon 7 of CRBN.

19. The method of claim 17, wherein one primer used in the PCR has a 5' portion and a 3' portion, the 5' portion representing a sequence within exon 6 of CRBN, the 3' portion presenting a sequence within exon 7 of CRBN.

20. The method of claim 17, wherein one primer used in the PCR has a 5' portion and a 3' portion, the 5' portion representing a sequence within exon 5 of CRBN, the 3' portion presenting a sequence within exon 7 of CRBN.

21. The method of claim 3, wherein determining the level of the isoform of CRBN is performed using a probe targeting a nucleic acid sequence presenting CRBN.

22. The method of claim 21, wherein the probe comprises a nucleic acid sequence complementary to a region representing exon 6 of CRBN.

23. The method of claim 21, wherein the probe comprises a nucleic acid sequence complementary to a sequence representing a junction region between exon 6 of CRBN and exon 7 of CRBN.

24. The method of claim 21, wherein the probe comprises a nucleic acid sequence complementary to a sequence representing a junction region between exon 5 of CRBN and exon 6 of CRBN.

25. The method of claim 3, further comprising enriching a target nucleic acid from the cancer sample, wherein the target nucleic acid represents CRBN or isoforms thereof.

26. The method of claim 25, wherein the target nucleic acid is a DNA.

27. The method of claim 25, wherein the target nucleic acid is a mRNA.

28. The method of claim 25, further comprising sequencing the target nucleic acid, and thereby determining the presence or the level of the isoform of CRBN with a single exon 6 deletion.

29. The method of claim 28, wherein the sequencing the target nucleic acid comprises use of sequencing by synthesis, sequencing by ligation, or sequencing by hybridization.

30. The method of claim 3, wherein the isoform of CRBN has an amino acid sequence of SEQ ID NO: 11.

31. The method of claim 3, wherein the isoform of CRBN has an amino acid sequence of SEQ ID NO: 12.

* * * * *

SEQUENCE LISTING

```
<160> NUMBER OF SEQ ID NOS: 22

<210> SEQ ID NO 1
<211> LENGTH: 1329
<212> TYPE: DNA
<213> ORGANISM: Artificial Sequence
<220> FEATURE:
<223> OTHER INFORMATION: CRBN isoform 1

<400> SEQUENCE: 1
atggccggcg aaggagatca gcaggacgct gcgcacaaca tgggcaacca cctgccgctc        60
ctgcctgcag agagtgagga agaagatgaa atggaagttg aagaccagga tagtaaagaa       120
```

-continued

| | |
|---|---|
| gccaaaaaac caaacatcat aaattttgac accagtctgc cgacatcaca tacatacccta | 180 |
| ggtgctgata tggaagaatt tcatggcagg actttgcacg atgacgacag ctgtcaggtg | 240 |
| attccagttc ttccacaagt gatgatgatc ctgattcccg acagacatt acctcttcag | 300 |
| cttttcacc ctcaagaagt cagtatggtg cggaatttaa ttcagaaaga tagaaccttt | 360 |
| gctgttcttg catacagcaa tgtacaggaa agggaagcac agtttggaac aacagcagag | 420 |
| atatatgcct atcgagaaga acaggatttt ggaattgaga tagtgaaagt gaaagcaatt | 480 |
| ggaagacaaa ggttcaaagt ccttgagcta agaacacagt cagatggaat ccagcaagct | 540 |
| aaagtgcaaa ttcttcccga atgtgtgttg ccttcaacca tgtctgcagt tcaattagaa | 600 |
| tccctcaata agtgccagat atttccttca aaacctgtct caagagaaga ccaatgttca | 660 |
| tataaatggt ggcagaaata ccagaagaga agtttcatt gtgcaaatct aacttcatgg | 720 |
| cctcgctggc tgtattcctt atatgatgct gagaccttaa tggacagaat caagaaacag | 780 |
| ctacgtgaat gggatgaaaa tctaaaagat gattctcttc cttcaaatcc aatagatttt | 840 |
| tcttacagag tagctgcttg tcttcctatt gatgatgtat tgagaattca gctccttaaa | 900 |
| attggcagtg ctatccagcg acttcgctgt gaattagaca ttatgaataa atgtacttcc | 960 |
| ctttgctgta acaatgtca agaaacagaa ataacaacca aaaatgaaat attcagttta | 1020 |
| tccttatgtg ggccgatggc agcttatgtg aatcctcatg gatatgtgca tgagacactt | 1080 |
| actgtgtata aggcttgcaa cttgaatctg ataggccggc cttctacaga acacagctgg | 1140 |
| tttcctgggt atgcctggac tgttgcccag tgtaagatct gtgcaagcca tattggatgg | 1200 |
| aagtttacgg ccaccaaaaa agacatgtca cctcaaaaat tttggggctt aacgcgatct | 1260 |
| gctctgttgc ccacgatccc agacactgaa gatgaaataa gtccagacaa agtaatactt | 1320 |
| tgcttgtaa | 1329 |

<210> SEQ ID NO 2
<211> LENGTH: 1197
<212> TYPE: DNA
<213> ORGANISM: Artificial Sequence
<220> FEATURE:
<223> OTHER INFORMATION: CRBN isoform 2

<400> SEQUENCE: 2

| | |
|---|---|
| atggccggcg aaggagatca gcaggacgct gcgcacaaca tgggcaacca cctgccgctc | 60 |
| ctgcctgcag agagtgagga agaagatgaa atggaagttg aagaccagga tagtaaagaa | 120 |
| gccaaaaaac caaacatcat aaattttgac accagtctgc cgacatcaca tacatacccta | 180 |
| ggtgctgata tggaagaatt tcatggcagg actttgcacg atgacgacag ctgtcaggtg | 240 |
| attccagttc ttccacaagt gatgatgatc ctgattcccg acagacatt acctcttcag | 300 |
| cttttcacc ctcaagaagt cagtatggtg cggaatttaa ttcagaaaga tagaaccttt | 360 |
| gctgttcttg catacagcaa tgtacaggaa agggaagcac agtttggaac aacagcagag | 420 |
| atatatgcct atcgagaaga acaggatttt ggaattgaga tagtgaaagt gaaagcaatt | 480 |
| ggaagacaaa ggttcaaagt ccttgagcta agaacacagt cagatggaat ccagcaagct | 540 |
| aaagtgcaaa ttcttcccga atgtgtgttg ccttcaacca tgtctgcagt tcaattagaa | 600 |
| tccctcaata agtgccagat atttccttca aaacctgtct caagagaaga ccaatgttca | 660 |
| tataaatggt ggcagaaata ccagaagaga agtttcatt gtgcaaatct aacttcatgg | 720 |
| cctcgctggc tgtattcctt atatgatgct gagaccttaa tggacagaat caagaaacag | 780 |
| ctacgtgaat gggatgaaaa tctaaaagat gattctcttc cttcaaatcc aatagatttt | 840 |

```
tcttacagag tagctgcttg tcttcctatt gatgatgtat tgagaattca gctccttaaa    900
attggcagtg ctatccagcg acttcgctgt gaattagaca ttatgaataa atgtacttcc    960
ctttgctgta aacaatgtca agaaacagaa ataacaacca aaaatgaaat attcaggtat   1020
gcctggactg ttgcccagtg taagatctgt gcaagccata ttggatggaa gtttacggcc   1080
accaaaaaag acatgtcacc tcaaaaattt tggggcttaa cgcgatctgc tctgttgccc   1140
acgatcccag acactgaaga tgaaataagt ccagacaaag taatactttg cttgtaa     1197

<210> SEQ ID NO 3
<211> LENGTH: 825
<212> TYPE: DNA
<213> ORGANISM: Artificial Sequence
<220> FEATURE:
<223> OTHER INFORMATION: CRBN isoform 3

<400> SEQUENCE: 3
atggccggcg aaggagatca gcaggacgct gcgcacaaca tgggcaacca cctgccgctc     60
ctgcctgcag agagtgagga agaagatgaa atggaagttg aagaccagga tagtaaagaa    120
gccaaaaaac ctgtctcaag agaagaccaa tgttcatata aatggtggca gaaataccag    180
aagagaaagt ttcattgtgc aaatctaact tcatggcctc gctggctgta ttccttatat    240
gatgctgaga ccttaatgga cagaatcaag aaacagctac gtgaatggga tgaaaatcta    300
aaagatgatt ctcttccttc aaatccaata gatttttctt acagagtagc tgcttgtctt    360
cctattgatg atgtattgag aattcagctc cttaaaattg gcagtgctat ccagcgactt    420
cgctgtgaat tagacattat gaataaatgt acttcccttt gctgtaaaca atgtcaagaa    480
acagaaataa caaccaaaaa tgaaatattc agtttatcct tatgtgggcc gatggcagct    540
tatgtgaatc tcatggata tgtgcatgag acacttactg tgtataaggc ttgcaacttg    600
aatctgatag gccggccttc tacagaacac agctggtttc tgggtatgc ctggactgtt    660 gcccagtgta agatctgtgc aagccatatt ggatggaagt ttacggccac caaaaaagac    720
atgtcacctc aaaaattttg gggcttaacg cgatctgctc tgttgcccac gatcccagac    780
actgaagatg aaataagtcc agacaaagta atactttgct tgtaa                   825

<210> SEQ ID NO 4
<211> LENGTH: 725
<212> TYPE: DNA
<213> ORGANISM: Artificial Sequence
<220> FEATURE:
<223> OTHER INFORMATION: CRBN isoform 4

<400> SEQUENCE: 4
atggccggcg aaggagatca gcaggacgct gcgcacaaca tgggcaacca cctgccgctc     60
ctgcctgcag agagtgagga agaagatgaa atggaagttg aagaccagga tagtaaagaa    120
gccaaaaaac caaacatcat aaattttgac accagtctgc cgacatcaca tataaccta    180 ggtgctgata tggaagaatt tcatggcagg actttgcacg atgacgacag ctgtcaggtg    240
attccagttc ttccacaagt gatgatgatc ctgattcccg gacagacatt acctcttcag    300 cttttttcacc ctcaagaagt cagtatggtg cggaatttaa ttcagaaaga tagaacccttt    360 gctgtaaaca atgtcaagaa acagaaataa caaccaaaaa tgaaatattc agtttatcct    420
tatgtgggcc gatggcagct tatgtgaatc tcatggata tgtgcatgag acacttactg    480
tgtataaggc ttgcaacttg aatctgatag gccggccttc tacagaacac agctggtttc    540
```

```
ctgggtatgc ctggactgtt gcccagtgta agatctgtgc aagccatatt ggatggaagt    600
ttacggccac caaaaaagac atgtcacctc aaaaattttg gggcttaacg cgatctgctc    660
tgttgcccac gatcccagac actgaagatg aaataagtcc agacaaagta atactttgct    720
tgtaa                                                                725

<210> SEQ ID NO 5
<211> LENGTH: 582
<212> TYPE: DNA
<213> ORGANISM: Artificial Sequence
<220> FEATURE:
<223> OTHER INFORMATION: CRBN isoform 5

<400> SEQUENCE: 5
atggccggcg aaggagatca gcaggacgct gcgcacaaca tgggcaacca cctgccgctc     60
ctgcctgcag agagtgagga agaagatgaa atggaagttg aagaccagga tagtaaagaa    120
gccaaaaaac caaacatcat aaattttgac accagtctgc cgacatcaca tacatacctg    180
ggtgctgata tggaagaatt tcatggcagg actttgcacg atgacgacag ctgtcaggtg    240
attccagttc ttccacaagt gatgatgatc ctgattcccg acagacatt  acctcttcag    300 cttttttcacc ctcaagaagt cagtatggtg cggaatttaa ttcagaaaga tagaaccttt    360
gctgttcttg catacagcaa tgtacaggaa agggaagcac agtttggaac aacagcagag    420
atatatgcct atcgagaaga acaggatttt ggaattgatg atgtattgag aaaagacatg    480
tcacctcaaa aattttgggg cttaacgcga tctgctctgt tgcccacgat cccagacact    540
gaagatgaaa taagtccaga caaagtaata ctttgcttgt aa                       582

<210> SEQ ID NO 6
<211> LENGTH: 457
<212> TYPE: DNA
<213> ORGANISM: Artificial Sequence
<220> FEATURE:
<223> OTHER INFORMATION: CRBN isoform 6

<400> SEQUENCE: 6
atggccggcg aaggagatca gcaggacgct gcgcacaaca tgggcaacca cctgccgctc     60
ctgcctgcag agagtgagga agaagatgaa atggaagttg aagaccagga tagtaaagaa    120
gccaaaaaac caaacatcat aaattttgac accagtctgc cgacatcaca tacatacctg    180
ggtgctgata tggaagaatt tcatggcagg actttgcacg atgacgacag ctgtcaggtg    240
attccagttc ttccacaagt gatgatgatc ctgattcccg acagacatt  acctcttcag    300 cttttttcacc ctcaagaagt cagtatggtg cggaatttaa ttcaaaaaag acatgtcacc    360
tcaaaaattt ggggcttaa cgcgatctgc tctgttgccc acgatcccag acactgaaga    420
tgaaataagt ccagacaaag taatactttg cttgtaa                              457

<210> SEQ ID NO 7
<211> LENGTH: 331
<212> TYPE: DNA
<213> ORGANISM: Artificial Sequence
<220> FEATURE:
<223> OTHER INFORMATION: CRBN isoform 7

<400> SEQUENCE: 7
atggccggcg aaggagatca gcaggacgct gcgcacaaca tgagcttatg tgaatcctca     60
tggatatgtg catgagacac ttactgtgta taaggcttgc aacttgaatc tgataggccg    120
gccttctaca gaacacagct ggtttcctgg gtatgcctgg actgttgccc agtgtaagat    180
```

```
ctgtgcaagc catattggat ggaagtttac ggccaccaaa aaagacatgt cacctcaaaa    240 attttgggc ttaacgcgat ctgctctgtt gcccacgatc ccagacactg aagatgaaat     300
aagtccagac aaagtaatac tttgcttgta a                                   331
```

```
<210> SEQ ID NO 8
<211> LENGTH: 21
<212> TYPE: PRT
<213> ORGANISM: Artificial Sequence
<220> FEATURE:
<223> OTHER INFORMATION: amino acid residues 229 to 249 encoded by exon
      6 of CRBN

<400> SEQUENCE: 8
```

```
Arg Lys Phe His Cys Ala Asn Leu Thr Ser Trp Pro Arg Trp Leu Tyr
1               5                   10                  15

Ser Leu Tyr Asp Ala
            20
```

```
<210> SEQ ID NO 9
<211> LENGTH: 441
<212> TYPE: PRT
<213> ORGANISM: Artificial Sequence
<220> FEATURE:
<223> OTHER INFORMATION: CRBN isoform containing 441 amino acids

<400> SEQUENCE: 9
```

```
Met Ala Gly Glu Gly Asp Gln Gln Asp Ala Ala His Asn Met Gly Asn
1               5                   10                  15

His Leu Pro Leu Leu Pro Glu Ser Glu Glu Asp Glu Met Glu Val
                20                  25                  30

Glu Asp Gln Asp Ser Lys Glu Ala Lys Lys Pro Asn Ile Ile Asn Phe
            35                  40                  45

Asp Thr Ser Leu Pro Thr Ser His Thr Tyr Leu Gly Ala Asp Met Glu
        50                  55                  60

Glu Phe His Gly Arg Thr Leu His Asp Asp Ser Cys Gln Val Ile
65              70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
            100                 105                 110

Ile Gln Lys Asp Arg Thr Phe Ala Val Leu Ala Tyr Ser Asn Val Gln
        115                 120                 125

Glu Arg Glu Ala Gln Phe Gly Thr Thr Ala Glu Ile Tyr Ala Tyr Arg
    130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
            180                 185                 190

Met Ser Ala Val Gln Leu Glu Ser Leu Asn Lys Cys Gln Ile Phe Pro
        195                 200                 205

Ser Lys Pro Val Ser Arg Glu Asp Gln Cys Ser Tyr Lys Trp Trp Gln
    210                 215                 220

Lys Tyr Gln Lys Arg Lys Phe His Cys Ala Asn Leu Thr Ser Trp Pro
225                 230                 235                 240
```

```
Arg Trp Leu Tyr Ser Leu Tyr Asp Ala Glu Thr Leu Met Asp Arg Ile
            245                 250                 255

Lys Lys Gln Leu Arg Glu Trp Asp Glu Asn Leu Lys Asp Ser Leu
        260                 265                 270

Pro Ser Asn Pro Ile Asp Phe Ser Tyr Arg Val Ala Ala Cys Leu Pro
            275                 280                 285

Ile Asp Asp Val Leu Arg Ile Gln Leu Leu Lys Ile Gly Ser Ala Ile
    290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
                325                 330                 335

Phe Ser Leu Ser Leu Cys Gly Pro Met Ala Ala Tyr Val Asn Pro His
            340                 345                 350

Gly Tyr Val His Glu Thr Leu Thr Val Tyr Lys Ala Cys Asn Leu Asn
                355                 360                 365

Leu Ile Gly Arg Pro Ser Thr Glu His Ser Trp Phe Pro Gly Tyr Ala
    370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
                405                 410                 415

Thr Arg Ser Ala Leu Leu Pro Thr Ile Pro Asp Thr Glu Asp Glu Ile
                420                 425                 430

Ser Pro Asp Lys Val Ile Leu Cys Leu
                435                 440

<210> SEQ ID NO 10
<211> LENGTH: 442
<212> TYPE: PRT
<213> ORGANISM: Artificial Sequence
<220> FEATURE:
<223> OTHER INFORMATION: CRBN isoform containing 442 amino acids

<400> SEQUENCE: 10

Met Ala Gly Glu Gly Asp Gln Gln Asp Ala Ala His Asn Met Gly Asn
1               5                   10                  15

His Leu Pro Leu Leu Pro Ala Glu Ser Glu Glu Glu Asp Glu Met Glu
            20                  25                  30

Val Glu Asp Gln Asp Ser Lys Glu Ala Lys Lys Pro Asn Ile Ile Asn
        35                  40                  45

Phe Asp Thr Ser Leu Pro Thr Ser His Thr Tyr Leu Gly Ala Asp Met
    50                  55                  60

Glu Glu Phe His Gly Arg Thr Leu His Asp Asp Asp Ser Cys Gln Val
65                  70                  75                  80

Ile Pro Val Leu Pro Gln Val Met Met Ile Leu Ile Pro Gly Gln Thr
                85                  90                  95

Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
    130                 135                 140

Arg Glu Glu Gln Asp Phe Gly Ile Glu Ile Val Lys Val Lys Ala Ile
145                 150                 155                 160
```

```
Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
        195                 200                 205

Pro Ser Lys Pro Val Ser Arg Glu Asp Gln Cys Ser Tyr Lys Trp Trp
    210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
    290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Lys Asn Glu
                325                 330                 335

Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
        355                 360                 365

Asn Leu Ile Gly Arg Pro Ser Thr Glu His Ser Trp Phe Pro Gly Tyr
    370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
            420                 425                 430

Ile Ser Pro Asp Lys Val Ile Leu Cys Leu
        435                 440

<210> SEQ ID NO 11
<211> LENGTH: 420
<212> TYPE: PRT
<213> ORGANISM: Artificial Sequence
<220> FEATURE:
<223> OTHER INFORMATION: sequence having a single exon 6 deletion from
      the full length sequence of CRBN (SEQ ID NO: 9)

<400> SEQUENCE: 11

Met Ala Gly Glu Gly Asp Gln Gln Asp Ala Ala His Asn Met Gly Asn
1               5                   10                  15

His Leu Pro Leu Leu Pro Glu Ser Glu Glu Glu Asp Glu Met Glu Val
                20                  25                  30

Glu Asp Gln Asp Ser Lys Glu Ala Lys Lys Pro Asn Ile Ile Asn Phe
            35                  40                  45

Asp Thr Ser Leu Pro Thr Ser His Thr Tyr Leu Gly Ala Asp Met Glu
        50                  55                  60

Glu Phe His Gly Arg Thr Leu His Asp Asp Ser Cys Gln Val Ile
65                  70                  75                  80
```

Pro Val Leu Pro Gln Val Met Met Ile Leu Ile Pro Gly Gln Thr Leu
            85                  90                  95

Pro Leu Gln Leu Phe His Pro Gln Glu Val Ser Met Val Arg Asn Leu
            100                 105                 110

Ile Gln Lys Asp Arg Thr Phe Ala Val Leu Ala Tyr Ser Asn Val Gln
            115                 120                 125

Glu Arg Glu Ala Gln Phe Gly Thr Thr Ala Glu Ile Tyr Ala Tyr Arg
            130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
            180                 185                 190

Met Ser Ala Val Gln Leu Glu Ser Leu Asn Lys Cys Gln Ile Phe Pro
            195                 200                 205

Ser Lys Pro Val Ser Arg Glu Asp Gln Cys Ser Tyr Lys Trp Trp Gln
            210                 215                 220

Lys Tyr Gln Lys Glu Thr Leu Met Asp Arg Ile Lys Lys Gln Leu Arg
225                 230                 235                 240

Glu Trp Asp Glu Asn Leu Lys Asp Asp Ser Leu Pro Ser Asn Pro Ile
                245                 250                 255

Asp Phe Ser Tyr Arg Val Ala Ala Cys Leu Pro Ile Asp Asp Val Leu
            260                 265                 270

Arg Ile Gln Leu Leu Lys Ile Gly Ser Ala Ile Gln Arg Leu Arg Cys
            275                 280                 285

Glu Leu Asp Ile Met Asn Lys Cys Thr Ser Leu Cys Cys Lys Gln Cys
            290                 295                 300

Gln Glu Thr Glu Ile Thr Thr Lys Asn Glu Ile Phe Ser Leu Ser Leu
305                 310                 315                 320

Cys Gly Pro Met Ala Ala Tyr Val Asn Pro His Gly Tyr Val His Glu
                325                 330                 335

Thr Leu Thr Val Tyr Lys Ala Cys Asn Leu Asn Leu Ile Gly Arg Pro
            340                 345                 350

Ser Thr Glu His Ser Trp Phe Pro Gly Tyr Ala Trp Thr Val Ala Gln
            355                 360                 365

Cys Lys Ile Cys Ala Ser His Ile Gly Trp Lys Phe Thr Ala Thr Lys
            370                 375                 380

Lys Asp Met Ser Pro Gln Lys Phe Trp Gly Leu Thr Arg Ser Ala Leu
385                 390                 395                 400

Leu Pro Thr Ile Pro Asp Thr Glu Asp Glu Ile Ser Pro Asp Lys Val
                405                 410                 415

Ile Leu Cys Leu
            420

<210> SEQ ID NO 12
<211> LENGTH: 421
<212> TYPE: PRT
<213> ORGANISM: Artificial Sequence
<220> FEATURE:
<223> OTHER INFORMATION: sequence having a single exon 6 deletion from
      the full length sequence of CRBN (SEQ ID NO: 10)

<400> SEQUENCE: 12

Met Ala Gly Glu Gly Asp Gln Gln Asp Ala Ala His Asn Met Gly Asn

-continued

```
1               5               10              15
His Leu Pro Leu Leu Pro Ala Glu Ser Glu Glu Glu Asp Glu Met Glu
            20                  25                  30
Val Glu Asp Gln Asp Ser Lys Glu Ala Lys Lys Pro Asn Ile Ile Asn
            35                  40                  45
Phe Asp Thr Ser Leu Pro Thr Ser His Thr Tyr Leu Gly Ala Asp Met
            50                  55                  60
Glu Glu Phe His Gly Arg Thr Leu His Asp Asp Ser Cys Gln Val
65                  70                  75                  80
Ile Pro Val Leu Pro Gln Val Met Met Ile Leu Ile Pro Gly Gln Thr
                    85                  90                  95
Leu Pro Leu Gln Leu Phe His Pro Gln Glu Val Ser Met Val Arg Asn
                    100                 105                 110
Leu Ile Gln Lys Asp Arg Thr Phe Ala Val Leu Ala Tyr Ser Asn Val
                    115                 120                 125
Gln Glu Arg Glu Ala Gln Phe Gly Thr Thr Ala Glu Ile Tyr Ala Tyr
                    130                 135                 140
Arg Glu Glu Gln Asp Phe Gly Ile Glu Ile Val Lys Val Lys Ala Ile
145                 150                 155                 160
Gly Arg Gln Arg Phe Lys Val Leu Glu Leu Arg Thr Gln Ser Asp Gly
                    165                 170                 175
Ile Gln Gln Ala Lys Val Gln Ile Leu Pro Glu Cys Val Leu Pro Ser
                    180                 185                 190
Thr Met Ser Ala Val Gln Leu Glu Ser Leu Asn Lys Cys Gln Ile Phe
                    195                 200                 205
Pro Ser Lys Pro Val Ser Arg Glu Asp Gln Cys Ser Tyr Lys Trp Trp
                    210                 215                 220
Gln Lys Tyr Gln Lys Glu Thr Leu Met Asp Arg Ile Lys Lys Gln Leu
225                 230                 235                 240
Arg Glu Trp Asp Glu Asn Leu Lys Asp Ser Leu Pro Ser Asn Pro
                    245                 250                 255
Ile Asp Phe Ser Tyr Arg Val Ala Ala Cys Leu Pro Ile Asp Asp Val
                    260                 265                 270
Leu Arg Ile Gln Leu Leu Lys Ile Gly Ser Ala Ile Gln Arg Leu Arg
                    275                 280                 285
Cys Glu Leu Asp Ile Met Asn Lys Cys Thr Ser Leu Cys Cys Lys Gln
                    290                 295                 300
Cys Gln Glu Thr Glu Ile Thr Thr Lys Asn Glu Ile Phe Ser Leu Ser
305                 310                 315                 320
Leu Cys Gly Pro Met Ala Ala Tyr Val Asn Pro His Gly Tyr Val His
                    325                 330                 335
Glu Thr Leu Thr Val Tyr Lys Ala Cys Asn Leu Asn Leu Ile Gly Arg
                    340                 345                 350
Pro Ser Thr Glu His Ser Trp Phe Pro Gly Tyr Ala Trp Thr Val Ala
                    355                 360                 365
Gln Cys Lys Ile Cys Ala Ser His Ile Gly Trp Lys Phe Thr Ala Thr
                    370                 375                 380
Lys Lys Asp Met Ser Pro Gln Lys Phe Trp Gly Leu Thr Arg Ser Ala
385                 390                 395                 400
Leu Leu Pro Thr Ile Pro Asp Thr Glu Asp Glu Ile Ser Pro Asp Lys
                    405                 410                 415
Val Ile Leu Cys Leu
                    420
```

<210> SEQ ID NO 13
<211> LENGTH: 1266
<212> TYPE: DNA
<213> ORGANISM: Artificial Sequence
<220> FEATURE:
<223> OTHER INFORMATION: coding sequence of an isoform of CRBN with a signle exon 6 deletion

<400> SEQUENCE: 13

```
atggccggcg aaggagatca gcaggacgct gcgcacaaca tgggcaacca cctgccgctc      60
ctgcctgcag agagtgagga agaagatgaa atggaagttg aagaccagga tagtaaagaa     120
gccaaaaaac caaacatcat aaattttgac accagtctgc cgacatcaca tacatacccta    180
ggtgctgata tggaagaatt tcatggcagg actttgcacg atgacgacag ctgtcaggtg     240
attccagttc ttccacaagt gatgatgatc ctgattcccg gacagacatt acctcttcag     300
cttttttcacc ctcaagaagt cagtatggtg cggaatttaa ttcagaaaga tagaaccttt    360
gctgttcttg catacagcaa tgtacaggaa agggaagcac agtttggaac aacagcagag     420
atatatgcct atcgagaaga acaggatttt ggaattgaga tagtgaaagt gaaagcaatt     480
ggaagacaaa ggttcaaagt ccttgagcta agaacacagt cagatggaat ccagcaagct     540
aaagtgcaaa ttcttcccga atgtgtgttg ccttcaacca tgtctgcagt tcaattagaa     600
tccctcaata agtgccagat atttccttca aaacctgtct caagagaaga ccaatgttca     660
tataaatggt ggcagaaata ccagaaggag accttaatgg acagaatcaa gaaacagcta    720
cgtgaatggg atgaaaatct aaaagatgat tctcttcctt caaatccaat agattttct    780
tacagagtag ctgcttgtct tcctattgat gatgtattga aattcagct ccttaaaatt     840
ggcagtgcta tccagcgact tcgctgtgaa ttagacatta tgaataaatg tacttccctt    900
tgctgtaaac aatgtcaaga aacagaaata acaaccaaaa atgaaatatt cagtttatcc    960
ttatgtgggc cgatggcagc ttatgtgaat cctcatggat atgtgcatga gacacttact   1020
gtgtataagg cttgcaactt gaatctgata ggccggcctt ctacagaaca gctggttt    1080
cctgggtatg cctggactgt tgcccagtgt aagatctgtg caagccatat tggatggaag   1140
tttacggcca ccaaaaaaga catgtcacct caaaaatttt ggggcttaac gcgatctgct   1200
ctgttgccca cgatcccaga cactgaagat gaaataagtc cagacaagt aatactttgc    1260
ttgtaa                                                                1266
```

<210> SEQ ID NO 14
<211> LENGTH: 25
<212> TYPE: DNA
<213> ORGANISM: Artificial Sequence
<220> FEATURE:
<223> OTHER INFORMATION: first PCR primer for determining the presence or the level of CRBN exon 6

<400> SEQUENCE: 14

```
gcagaaatac cagaaggaga cctta                                             25
```

<210> SEQ ID NO 15
<211> LENGTH: 19
<212> TYPE: DNA
<213> ORGANISM: Artificial Sequence
<220> FEATURE:
<223> OTHER INFORMATION: second PCR primer for determining the presence or the level of CRBN exon 6

<400> SEQUENCE: 15
gcgaagtcgc tggatagca                                             19

<210> SEQ ID NO 16
<211> LENGTH: 300
<212> TYPE: DNA
<213> ORGANISM: Artificial Sequence
<220> FEATURE:
<223> OTHER INFORMATION: partical CRBN cDNA sequence from MM1.S parent
      cell 1

<400> SEQUENCE: 16
gaaagcaatt ggaagacaaa ggttcaaagt ccttgagcta agaacacagt cagatggaat    60
ccagcaagct aaagtgcaaa ttcttcccga atgtgtgttg ccttcaacca tgtctgcagt   120
tcaattagaa tccctcaata agtgccagat atttccttca aaacctgtct caagagaaga   180
ccaatgttca tataaatggt ggcagaaata ccagaagaga aagtttcatt gtgcaaatct   240
aacttcatgg cctcgctggc tgtattcctt atatgatgct gagaccttaa tggacagaat   300

<210> SEQ ID NO 17
<211> LENGTH: 300
<212> TYPE: DNA
<213> ORGANISM: Artificial Sequence
<220> FEATURE:
<223> OTHER INFORMATION: partical CRBN cDNA sequence from MM1.S parent
      cell 2

<400> SEQUENCE: 17
gaaagcaatg ggaagacaaa ggttcaaagt ccttgagcta agaacacagt cagatggaat    60
ccagcaagct aaagtgcaaa ttcttcccga atgtgtgttg ccttcaacca tgtctgcagt   120
tcaattagaa tccctcaata agtgccagat atttccttca aaacctgtct caagagaaga   180
ccaatgttca tataaatggt ggcagaaata ccagaagaga aagtttcatt gtgcaaatct   240
aacttcatgg cctcgctggc tgtattcctt atatgatgct gagaccttaa tggacagaat   300

<210> SEQ ID NO 18
<211> LENGTH: 75
<212> TYPE: DNA
<213> ORGANISM: Artificial Sequence
<220> FEATURE:
<223> OTHER INFORMATION: partical CRBN cDNA sequence from MM1.S parent
      cell 3

<400> SEQUENCE: 18
gaaattaatt ggaagacaga tggtcaaagt ccttgaacta acaacacagt cagatggaat    60
ccagcaagct aaggg                                                    75

<210> SEQ ID NO 19
<211> LENGTH: 300
<212> TYPE: DNA
<213> ORGANISM: Artificial Sequence
<220> FEATURE:
<223> OTHER INFORMATION: partical CRBN cDNA sequence for alignment

<400> SEQUENCE: 19
gaaagcaatt ggaagacaaa ggttcaaagt ccttgagcta agaacacagt cagatggaat    60
ccagcaagct aaagtgcaaa ttcttcccga atgtgtgttg ccttcaacca tgtctgcagt   120
tcaattagaa tccctcaata agtgccagat atttccttca aaacctgtct caagagaaga   180
ccaatgttca tataaatggt ggcagaaata ccagaagaga aagtttcatt gtgcaaatct   240
aacttcatgg cctcgctggc tgtattcctt atatgatgct gagaccttaa tggacagaat   300

```
<210> SEQ ID NO 20
<211> LENGTH: 237
<212> TYPE: DNA
<213> ORGANISM: Artificial Sequence
<220> FEATURE:
<223> OTHER INFORMATION: partical CRBN cDNA from MM1.S pomalidomide
      resistant cell 1

<400> SEQUENCE: 20
gaaagcaatt ggaagacaaa ggttcaaagt ccttgagcta agaacacagt cagatggaat      60
ccagcaagct aaagtgcaaa ttcttcccga atgtgtgttg ccttcaacca tgtctgcagt     120
tcaattagaa tccctcaata agtgccagat atttccttca aaacctgtct caagagaaga    180
ccaatgttca tataaatggt ggcagaaata ccagaaggag accttaatgg acagaat        237

<210> SEQ ID NO 21
<211> LENGTH: 237
<212> TYPE: DNA
<213> ORGANISM: Artificial Sequence
<220> FEATURE:
<223> OTHER INFORMATION: partical CRBN cDNA from MM1.S pomalidomide
      resistant cell 2

<400> SEQUENCE: 21
gaaagcaatt ggaagacaaa ggttcaaagt ccttgagcta agaacacagt cagatggaat      60
ccagcaagct aaagtgcaaa ttcttcccga atgtgtgttg ccttcaacca tgtctgcagt     120
tcaattagaa tccctcaata agtgccagat atttccttca aaacctgtct caagagaaga    180
ccaatgttca tataaatggt ggcagaaata ccagaaggag accttaatgg acagaat        237

<210> SEQ ID NO 22
<211> LENGTH: 237
<212> TYPE: DNA
<213> ORGANISM: Artificial Sequence
<220> FEATURE:
<223> OTHER INFORMATION: partical CRBN cDNA from MM1.S pomalidomide
      resistant cell 3

<400> SEQUENCE: 22
gaaagcaatt ggaagacaaa ggttcaaagt ccttgaacta agaacacagt cagatggaat      60
ccagcaagct aaagtgcaaa ttcttcccga atgtgtgttg ccttcaacca tgtctgcagt     120
tcaattagaa tccctcaata agtgccagat atttccttca aaacctgtct caagagaaga    180
ccaatgttca tataaatggt ggcagaaata ccagaaggag accttaatgg acagaat        237
```